US012797516B2

(12) United States Patent
Kornfield et al.

(10) Patent No.: US 12,797,516 B2
(45) Date of Patent: Nov. 17, 2026

(54) BALLISTIC DELIVERY TO MULTILAYERED TISSUES AND RELATED PARTICLES, COMPOSITIONS, METHODS AND SYSTEMS

(71) Applicant: CALIFORNIA INSTITUTE OF TECHNOLOGY, Pasadena, CA (US)

(72) Inventors: Julia A. Kornfield, Pasadena, CA (US); Benjamin J. Laccetti, Pasadena, CA (US); Dennis L. Ko, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 747 days.

(21) Appl. No.: 18/061,997

(22) Filed: Dec. 5, 2022

(65) Prior Publication Data

US 2023/0173142 A1 Jun. 8, 2023

Related U.S. Application Data

(60) Provisional application No. 63/301,292, filed on Jan. 20, 2022, provisional application No. 63/301,432, filed on Jan. 20, 2022, provisional application No. 63/285,989, filed on Dec. 3, 2021, provisional application No. 63/285,993, filed on Dec. 3, 2021.

(51) Int. Cl.
*A61L 27/54* (2006.01)

(52) U.S. Cl.
CPC ......... *A61L 27/54* (2013.01); *A61L 2300/406* (2013.01); *A61L 2300/414* (2013.01)

(58) Field of Classification Search
None
See application file for complete search history.

(56) References Cited

U.S. PATENT DOCUMENTS

| | | | | |
|---|---|---|---|---|
| 7,892,836 | B2 | 2/2011 | Groisman et al. | |
| 12,375,130 | B2 | 7/2025 | Barton et al. | |
| 2005/0084537 | A1 | 4/2005 | Martyn et al. | |
| 2008/0206870 | A1* | 8/2008 | Groisman .............. | C12M 35/00 435/285.3 |
| 2009/0175949 | A1* | 7/2009 | Borovkov .............. | A61K 47/59 424/490 |
| 2019/0142864 | A1 | 5/2019 | Newman et al. | |
| 2021/0322462 | A1 | 10/2021 | Newman et al. | |
| 2022/0015943 | A1 | 1/2022 | Laccetti et al. | |
| 2022/0281859 | A1 | 9/2022 | Chakravarty et al. | |

OTHER PUBLICATIONS

Rinberg et al. "Pneumatic capillary gun for ballistic delivery of microparticles", Applied Physics Letters 87(1), Feb. 2005, 8 pages. (Year: 2005).*

Kendall et al., "Transdermal Ballistic Delivery of Micro-Particles: Investigation into Skin Penetration", Proceedings of the 22nd Annual EMBS International Conference, Jul. 2000, Chicago, IL, pp. 1621-1624, vol. 3. (Year: 2000).*

Adzick, N. Scott, Review of "Wound Healing: Biochemical and Clinical Aspects by Cohen, I.K. Diegelman, R.F and Lindblad, W.J. 656 pp. Philadelphia: W.B. Saunders, 1992", in Annals of Surgery, Nov. 1992; vol. 216, No. 5; p. 613.

Martins-Green, Chapter 2: Role of oxidants and antioxidants in diabetic wound healing. Wound Healing, Tissue Repair, and Regeneration in Diabetes. (2020), pp. 13-38. Website: doi.org/10.1016/B978-0-12-816413-6.00002-2.

Ter Riet, G., A.G. Kessels, and P.G. Knipschild, Randomized clinical trial of ascorbic acid in the treatment of pressure ulcers. Journal of clinical epidemiology, 1995. 48(12): p. 1453-1460.

Hemilii, H. and R.M. Douglas, Vitamin C and acute respiratory infections. The international journal of tuberculosis and lung disease, 1999. 3(9): p. 756-761.

Hemmila, M.R., "Topical Nanoemulsion Therapy Reduces Bacterial Wound Infection and Inflammation Following Burn Injury," *Surgery*, vol. 148, No. 3. Sep. 2010. pp. 499-509. 12 pages.

Hofmann, B., H.-J. Hecht, and L. Flohe, Peroxiredoxins. Biological chemistry, 2002. 383(3-4): p. 347-364.

Holsapple, J.S., et al., "Low Intensity Shockwave Treatment Modulates Macrophage Functions Beneficial to Healing Chronic Wounds," *Int. J. Mol. Sci.* 22, Jul. 22, 2021. 7844. 17 Pages. https://doi.org/10.3390/ijms22157844.

(Continued)

*Primary Examiner* — Sue X Liu
*Assistant Examiner* — Casey S Hagopian
(74) *Attorney, Agent, or Firm* — Steinfl + Bruno LLP

(57) ABSTRACT

Methods and systems and related devices particles and compositions are described for controlled ballistic delivery of particles to a target region of a multilayered tissue, the method comprising determining a velocity $v_{o,j}$ of the set of substantially spherical particles by iterating $$v_{o,i} = \sqrt{Y_a/\rho_p}\left((1/k)(d^*/D^m)(\mu_a^{m-1})\left(\sqrt{Y_a\rho_p}\right)^{1-m}(\rho_a/\rho_p)\right)^{1/n_t} \text{ from } i = 0 \text{ to } j,$$

$$\text{where } n_0 = 0.826 \text{ and } n_i = n_0 - q\left(v_{0,i-1}\sqrt{\rho_a/Y_a}\right),$$

$$\text{until } |(v_{0,i} - v_{0,i-1})/v_{0,i-1}| < 0.1;$$

selecting the $D_p$, $\rho_p$ and $v_{o,j}$ when $v_{o,j}$ is less than 1,500 m/sec; and ballistically delivering a set of substantially spherical therapeutic particles having the selected $D_p$ and $\rho_p$ at velocity $v_{o,j}$ to the accessible surface of the apical layer of the bilayer tissue to deliver into the target region at least 30% of the set of substantially spherical particles.

9 Claims, 52 Drawing Sheets

(56) References Cited

OTHER PUBLICATIONS

Hori, Kunilo et al. "Controlled-release of epidermal growth factor form cationized gelatin hydrogel enhances corneal epithelial wound healing". Journal of Controlled Release 118 (2007): 169-176.
Hussain, Z., et al., Exploring recent developments to improve antioxidant, anti-inflammatory and antimicrobial efficacy of curcumin: A review of new trends and future perspectives. Materials science and engineering C, 2017. 77: p. 1316-1326.
Huynh, J., "Factors governing photodynamic cross-linking of ocular coat," Thesis submitted to the California Institute of Technology. Defended May 6, 2011. 175 Pages.
IUPAC Periodic Table of the Elements dated Jun. 22, 2007. Downloaded on Dec 9, 2021, from https://old.iupac.org/reports/periodic_table/IUPAC_Periodic_Table-22Jun07b.pdf . 1 Page.
Jackson, C.M., et al., "Defining and measuring biological activity: applying the principles of metrology," *Accreditation and quality assurance*, Published Online Mar. 16, 2007. 12(6): p. 283-294. 13 Pages.
Jagetia, G.C. and G. Rajanikant, Role of curcumin, a naturally occurring phenolic compound of turmeric in accelerating the repair of excision wound, in mice whole-body exposed to various doses of y-radiation. Journal of Surgical Research, 2004. 120(1): p. 127-138.
James, Garth A., et al. "Biofilms in chronic wounds." Wound Repair and regeneration 16 (1) (2008): 37-44.
Jeon, Oju et al. "Affinity-based growth factor delivery using biodegradable, photocrosslinked heparin-alginate hydrogels". Journal of Controlled Release 154 (2011): 258-266.
Jeon, Oju et al. "Photocrosslinked alginate hydrogels with tunable biodegradation rates and mechanical properties". Biomaterials 30 (2009): 2724-2734.
Jia, H.Z., et al., "Efficacy of iontophoresis-assisted epithelium-on corneal crosslinking for keratoconus," *International journal of ophthalmology*, Apr. 18, 2018. 11(4): p. 687. 9 Pages.
Jiang, T., et al., Nrf2 suppresses lupus nephritis through inhibition of oxidative injury and the NF-KB-mediated inflammatory response. Kidney international, Feb. 2014. 85(2): p. 333-343. 19 pages.
Jimi, S. et al. "Sequential Delivery of Cryogel Released Growth Factors and Cytokines Accelerates Wound Healing and Improved Tissue Regeneration" Frontiers in Bioengineering and Biotechnology, Apr. 2020, vol. 8, Article 345, 14 pages. www.frontiersin.org.
Judith, R., et al., Application of a PDGF-containing novel gel for cutaneous wound healing. Life sciences, 2010. 87(1-2): p. 1-8.
Jull, A.B., et al., Honey as a topical treatment for wounds. Cochrane Database of Systematic Reviews, 2015 (3): p. Art. No. CD005083. 98 pages.
Jussila, J., "Preparing ballistic gelatine—review and proposal for a standard method," *Forensic science international*, 2004. 141(2-3): p. 91-98. 9 Pages.
Kasbekar, S.A., et al., "Corneal transplant surgery for keratoconus and the effect of surgeon experience on deep anterior lamellar keratoplasty outcomes," *Am J Ophthalmol*, 2014. 158(6): p. 1239-46. 9 Pages.
Kendall, M., et al., "Intradermal ballistic delivery of microparticles into excised human skin for pharmaceutical applications," *Journal of biomechanics*, 2004. 37(11): p. 1733-1741. 10 Pages.
Kendall, MAF, et al., "Transdermal ballistic delivery of microparticles: investigation into skin penetration," in *BS EMBS Int. Conf.*, Jul. 23-28, 2000. IEEE. 5 Pages.
Khan, R.U., S. Naz, and A.M. Abudabos, Towards a better understanding of the therapeutic applications and corresponding mechanisms of action of honey. Environmental Science and Pollution Research, 2017. 24(36): p. 27755-27766.
Kietzmann, M. and M. Braun, Effects of the zinc oxide and cod liver oil containing ointment Zincojecol in an animal model of wound healing. DTW. Deutsche tierarztliche Wochenschrift, 2006. 113(9): p. 331-334. German Original with English Summary.
Kim, J.H., et al., "Chlorate and Antibiotic Treatment Dismantle Pseudomonas Aeruginosa Biofilm and Lead to Healing of Chronic Wounds," *WHS Abstract Session List Key. Wound Rep Reg*, 29: A1-A53. 2021. Abstract Only. 2 Pages. https://doi.org/10.1111/wrr.12921.
King, M., "The Role of Mucus Viscoelasticity in Cough Clearance," *Biorheology*, vol. 24, No. 6, pp. 589-597, Jan. 1, 1987. DOI: 10.3233/BIR-1987-24611.12 Pages.
Klaesner, J.W. et al., Plantar Tissue Stiffness in Patients with Diabetes Mellitus and Peripheral Neuropathy. Arch Plys Med Rehabil, vol. 83, Dec. 2002, pp. 1796-1801.
Krasner, D., et al., The ABCs of wound care dressings. Wound management, 1993. pp. 66, 68-69, 72.
Kruger-Genge A. et al., "Vascular Endothelial Cell Biology: An Update." *Int J Mol Sci.* Sep. 7, 2019; 20(18):4411. doi: 10.3390/ijms20184411. PMID: 31500313; PMCID: PMC6769656. 22 pages.
Kumin, A., et al., Peroxiredoxin 6 is a potent cytoprotective enzyme in the epidermis. The American journal of pathology, 2006. 169(4): p. 1194-1205.
Kundukad, B., et al., Mechanistic action of weak acid drugs on biofilms. Scientific reports, Jul. 2017. 7(1): p. 1-12.
Kwon, J., et al., "Compressive strain rate sensitivity of ballistic gelatin," *Journal of Biomechanics* 43. 2010. pp. 420-425. 6 Pages.
Laccetti, B. and Kornfield J., "Ballistic delivery of compounds to inner layers of the cornea is limited by tough mechanical properties of stromal tissue," J Mech Behav Biomed Mater. Mar. 2021. 115:104246. doi: 10.1016/j.jmbbm.2020.104246. Epub Dec 5, 2020. Abstract ONLY. 1 Page.
Laccetti B., and Kornfield J., "Ballistic Delivery of Compounds to Inner Layers of the Cornea is Limited by Tough Mechanical Properties of Stromal Tissue," *Journal of the Mechanical Behavior of Biomedical Materials*, vol. 115, Mar. 2021, Journal Pre-Proof 23 Pages. 104246, ISSN 1751-6161.
Laccetti, B., "Therapeutic Microparticles and Biolistic Drug-Delivery to the Cornea," Dissertation (Ph.D.), California Institute of Technology. 2021. 226 Pages. doi: 10.7907/nf29-gy82. https://resolver.caltech.edu/CaltechTHESIS:10182020-133113205.
Lansdown, A.B., Metallothioneins: potential therapeutic aids for wound healing in the skin. Wound repair and regeneration, 2002. 10(3): p. 130-132.
Last, J.A., et al., "Compliance profile of the human cornea as measured by atomic force microscopy," *Micron*, 2012. 43(12): p. 1293-1298. 7 Pages.
Lavars, N., "World's smallest single-chip system can be injected into the body," News Atlas, Published May 11, 2021. Downloaded Dec 9, 2021, from https://newatlas.com/electronics/worlds-smallest-single-chip-system-injectable/ . 10 Pages.
Lazarus, G.S., et al., Definitions and guidelines for assessment of wounds and evaluation of healing. Arch Dermatol, 1994. 130(4): p. 489-493.
Lee, A.-R.C., et al., Reversal of silver sulfadiazine-impaired wound healing by epidermal growth factor. Biomaterials, 2005. 26(22): p. 4670-4676.
Lin, Y.-J., et al., Stimulation of wound healing by PU/hydrogel composites containing fibroblast growth factor-2. Journal of Materials Chemistry B, 2015. 3(9): p. 1931-1941.
Lindberg, T., et al., A systematic review and meta-analysis of dressings used for wound healing: the efficiency of honey compared to silver on burns. Contemporary nurse, 2015. 51(2-3): p. 121-134.
Lindblad, N.R., et al., "Production of uniform-sized liquid droplets," *Journal of Scientific Instruments*, 1965. 42(8): p. 635. 6 Pages.
Ling, Y., et al., "Tungsten carbide hollow microspheres with robust and stable electrocatalytic activity toward hydrogen evolution reaction," *ACS Omega*, Feb. 26, 2019. 4(2): p. 4185-4191. 8 Pages.
Long, D.W., et al., Controlled delivery of platelet-derived proteins enhances porcine wound healing. Journal of Controlled Release, 2017. 253: p. 73-81.
Long, M., et al., An essential role of NRF2 in diabetic wound healing. Diabetes, Mar. 2016. 65(3): p. 780-793.
Loo, A.E.K., et al., Effects of hydrogen peroxide on wound healing in mice in relation to oxidative damage. PloS One, 2012. 7(11): p. e49215. 13 pages.
Lord, M.S., et al., Perlecan and vascular endothelial growth factor-encoding DNA-loaded chitosan scaffolds promote angiogenesis and wound healing. Journal of Controlled Release, 2017. 250: p. 48-61.

(56) References Cited

OTHER PUBLICATIONS

Lu, J. and A. Holmgren, The thioredoxin antioxidant system. Free Radical Biology and Medicine, 2014. 66: p. 75-87.
Lu, WN. et al. 2003. Gene transfer into corneal endothelial cells by Helios gene gun. Nihon. Ganka Gakkai Zasshi 107, 189-195. Abstract only.
Ma, X., et al., "Cryopreservation: Organ Preservation, in Comprehensive Biotechnology," (Second Edition), *Academic Press*., 2011. p. 83-98. 17 Pages.
Mahmoud, M., et al., "Porous Glass Microspheres from Alkali-Activated Fiber Glass Waste." *Materials* 2022, 15, 1043. 9 pages. doi.org/10.3390/ma15031043.
Mandla, S., L. Davenport Huyer, and M. Radisic, Multimodal bioactive material approaches for wound healing. APL bioengineering, 2018. 2(2): p. 021503. 13 pages.
Mann, A., et al. Granulocyte-macrophage colony-stimulating factor is essential for normal wound healing. in Journal of Investigative Dermatology Symposium Proceedings. 2006. Elsevier. p. 87-92.
Marchese, A., et al., Effect of fosfomycin alone and in combination with N-acetylcysteine on *E. coli* biofilms. International journal of antimicrobial agents, 2003. 22: p. S95-S 100.
Marchini, M., et al., "Differences in the fibril structure of corneal and tendon collagen. An electron microscopy and X-ray diffraction investigation," *Connective tissue research*, 1986. 15(4): p. 269-281. 15 Pages.
Marczin, N., et al., Antioxidants in myocardial ischemia-reperfusion injury: therapeutic potential and basic mechanisms. Archives of Biochemistry and Biophysics, 2003. 420(2): p. 222-236.
Martin, P., Wound healing—aiming for perfect skin regeneration. Science, 1997. 276(5309): p. 75-81.
Mattson, M., et al., "Mechanical measurements of sclera for screening myopia treatments," *Investigative Ophthalmology & Visual Science*, May 2005. 46(13): p. 1991-1991. Abstract only. 3 Pages.
Mayet, N., et al., A comprehensive review of advanced biopolymeric wound healing systems. Journal of pharmaceutical sciences, 2014. 103(8): p. 2211-2230.
Mazzotta, C., et al., "Stromal haze after combined riboflavin-UVA corneal collagen crosslinking in keratoconus: in vivo confocal microscopic evaluation," *Clin Experiment Ophthalmol*, 2007. 35(6): p. 580-2. 6 Pages.
McKee, S. Renovo stock demolished by Justiva trial failure. PharmaTimes online, Feb. 15, 2011. 6 pages. Website: pharmatimes.com/news/renovo_stock_demolished_by_justiva_trial_failure_979597/.
Merediz, S.A.K. et al. 2000. Ballistic transfer of minimalistic immunologically defined expression constructs for IL4 and CTLA4 into the corneal epithelium in mice after orthotopic corneal allograft transplantation. Graef's Arch. Clin. Exp. Ophthalmol. 238, 701-707.
Miller, M.S., Use of topical recombinant human platelet-derived growth factor-BB (becaplermin) in healing of chronic mixed arteriovenous lower extremity diabetic ulcers. The Journal of foot and ankle surgery, 1999. 38(3): p. 227-231.
Mitchell, T. et al. 2003. A ballistic study of micro-particle penetration of the oral mucosa. Int. J. Impact Eng. 28, 581-599.
Mohanty, C. and S.K. Sahoo, Curcumin and its topical formulations for wound healing applications. Drug Discovery Today, 2017. 22(10): p. 1582-1592.
Mohsen, A., Khalaf, A., et al., Antibacterial, anti-biofilm activity of some non-steroidal anti-inflammatory drugs and N-acetyl cysteine against some biofilm producing uropathogens. American Journal of Epidemiology, 2015. 3(1): p. 1-9.
Moore, K., et al., Prediction and monitoring the therapeutic response of chronic dermal wounds. International wound journal, 2006. 3(2): p. 89-98.
Mo-Sci "Porous Silica" https://mo-sci.com/products/porous-silica/ Retrieved from the Wayback Machine for Dec 7, 2022.
Mudge, B.P., et al., Role of glutathione redox dysfunction in diabetic wounds. Wound Repair and Regeneration, 2002. 10(1): p. 52-58.
Mukai, K., et al., Effectiveness of Changing the Application of Japanese Honey to a Hydrocolloid Dressing in Between the Inflammatory and Proliferative Phases on Cutaneous Wound Healing in Male Mice. Wounds: a compendium of clinical research and practice, 2016. 29(1): p. 1-9.
Musalmah, M., et al., Comparative effects of palm vitamin E and a-tocopherol on healing and wound tissue antioxidant enzyme levels in diabetic rats. Lipids, 2005. 40(6): p. 575-580.
National Eye Institute, "How the Eyes Work," Updated Apr. 20, 2022. https://www.nei.nih.gov/learn-about-eye-health/healthy-vision/how-eyes-work.
Nery, R.A., et al., Uric acid and tissue repair. ABCD. Arquivos Brasileiros de Cirurgia Digestiva (Sao Paulo), 2015. 28(4): p. 290-292.
NetCE, "Disorders and Injuries of the Eye and Eyelid," Released Dec 1, 2023. https://www.netce.com/coursecontent.php?courseid=2715.
Niaz, K., et al., Health benefits of manuka honey as an essential constituent for tissue regeneration. Current drug metabolism, 2017. 18(10): p. 881-892.
Nickerson, C.S., et al., "A "cleat" geometry for suppressing wall slip," Journal of Rheology, 2005. 49(4): p. 865-874. 12 Pages.
Nurkesh, Ayan et al. "Recent advances in the controlled release of growth factors and cytokines for improving cutaneous wound healing". Frontiers in Cell and Development Biology 8 (2020): 638. p. 1-7.
Olivares Jimenez, J.L., et al., "Keratoconus: age of onset and natural history," *Optom Vis Sci*, Mar. 1997. 74(3): p. 147-51. 7 Pages.
Pailler-Mattei, C., S. Bec, and H. Zahouani. "In vivo measurements of the elastic mechanical properties of human skin by indentation tests." Medical Engineering &Pphysics, 30 (5) (2008): 599-606.
Panchatcharam, M., et al., Curcumin improves wound healing by modulating collagen and decreasing reactive oxygen species. Molecular and cellular biochemistry, 2006. 290(1): p. 87-96.
Papanas, N. et al. Benefit-risk assessment of becaplermin in the treatment of diabetic foot ulcers. Drug Safety: An International Journal of Medical Toxicology and Drug Experience, (2010), 33, pp. 455-461.
Park, Yoon Jeong et al. "Controlled release of platelet-derived growth factor from porous poly (L-lactide) membranes for guided tissue regeneration". Journal of Controlled Release 51.2-3 (1998): 201-211.
Pasumarthy, R.K.A., et al., "Mechanical and optical characterization of a tissue surrogate polymer gel," Polymer Testing 55. Available online Sep. 2, 2016. 219-229. 11 pages.
Patel, G.K., The role of nutrition in the management of lower extremity wounds. The international journal of lower extremity wounds, 2005. 4(1): p. 12-22.
Paterson, R.L., H.F. Galley, and N.R. Webster, The effect of N-acetylcysteine on nuclear factor-KB activation, interleukin-6, interleukin-8, and intercellular adhesion molecule-l expression in patients with sepsis. Critical care medicine, 2003. 31(11): p. 2574-2578.
Pelikan, E.W., Pharmacology Glossary. Boston University, Chobanian & Avedisian School of Medicine. 62 pages (2022).
Percival, N.J., Classification of wounds and their management. Surgery (Oxford), 2002. 20(5): p. 114-117.
Peshenko, I.V. and H. Shichi, Oxidation of active center cysteine of bovine 1-Cys peroxiredoxin to the cysteine sulfenic acid form by peroxide and peroxynitrite. Free Radical Biology and Medicine, 2001. 31(3): p. 292-303.
Petersen Shay, K., et al., Is a-lipoic acid a scavenger of reactive oxygen species in vivo? Evidence for its initiation of stress signaling pathways that promote endogenous antioxidant capacity. IUBMB life, 2008. 60(6): p. 362-367.
Phoenix Society for Burn Survivors, "Understanding the Healing Stages of a Burn Wound," Sep. 13, 2022. https://www.phoenix-society.org/resources/understanding-the-healing-stages-of-a-burn-wound.
Pierce, G., et al., Platelet-derived growth factor-BB and transforming growth factor beta 1 selectively modulate glycosaminoglycans, collagen, and myofibroblasts in excisional wounds. The American journal of pathology, 1991. 138(3): p. 629-646.

(56) References Cited

OTHER PUBLICATIONS

Pierce, G.F., et al., Transforming growth factor beta reverses the glucocorticoid-induced wound-healing deficit in rats: possible regulation in macrophages by platelet-derived growth factor. Proceedings of the National Academy of Sciences, 1989. 86(7): p. 2229-2233.
Pollard, A.M., et al., "Synthesis and stabilities of the basic copper (II) chlorides atacamite, paratacamite and botallackite," *Mineralogical magazine*, Dec 1989. 53(373): p. 557-563. 8 Pages.
Pugliese, Peter T. "The skin's antioxidant systems." Dermatology nursing, 10 (6)(Dec 1998): 401-416. 24 pages.
Raftos, J.E., et al., Kinetics of uptake and deacetylation of N-acetylcysteine by human erythrocytes. The international journal of biochemistry & cell biology, 2007. 39(9): p. 1698-1706.
Rago, T. et al., Elastography: New Developments in Ultrasound for Predicting Malignancy in Thyroid Nodules. The Journal of Clinical Endocrinology & Metabolism, 92 (8); 2917-2922. Published online Jun. 5, 2007.
Ram, M., et al., Antioxidant potential of bilirubin-accelerated wound healing in streptozotocin-induced diabetic rats. Naunyn-Schmiedeberg's archives of pharmacology, Jun. 2014. 387(10): p. 955-961. 10 pages.
Ram, M., et al., Bilirubin modulated cytokines, growth factors and angiogenesis to improve cutaneous wound healing process in diabetic rats. International immunopharmacology, 2016. 30:p. 137-149.
Rasik, A.M. and A. Shukla, Antioxidant status in delayed healing type of wounds. International journal of experimental pathology, 2000. 81(4): p. 257-263.
Abelson, M.B., et al., "Why Doesn't the Ocular Drug Work? A look at the various barriers and aids to the efficacy of ocular medications," *Review of Opthalmology*, Dec 22, 2009. 7 pages.
Abhari, S., et al., "Anatomic studies of the miniature swine cornea," *The Anatomical Record*, 2018. 301(11): p. 1955-1967. 14 Pges.
Adamson, B., et al., Delayed repair: the role of glutathione in a rat incisional wound model. Journal of Surgical Research, 1996. 62(2): p. 159-164.
Agren, M.S., et al., A randomized, double-blind, placebo-controlled multicenter trial evaluating topical zinc oxide for acute open wounds following pilonidal disease excision. Wound repair and regeneration, 2006. 14(5): p. 526-535.
Agren, M.S., Studies on zinc in wound healing. Acta Derm Venereal Suppl 1990. 154: p. 1-36.
Ahmed, I., "The noncorneal route in ocular drug delivery," in *Ophthalmic drug delivery systems*. 2003, CRC Press. p. 335-363. 31 Pages.
Aihara, M., et al., Effects of N-acetylcysteine and ambroxol on the production of IL-12 and IL-10 in human alveolar macrophages. Respiration, 2000. 67(6): p. 662-671.
Akers, B., et al., "Impact dynamics of a solid sphere falling into a viscoelastic micellar. Fluid," *Journal of Non-Newtonian Fluid Mechanics*, 2006. 135(2-3): p. 97-108. 13 Pages.
Alemrayat, B., et al., "Preparation and optimization of monodisperse polymeric microparticles using modified vibrating orifice aerosol generator for controlled delivery of letrozole in breast cancer therapy," *Drug development and industrial pharmacy*, 2018. 44(12): p. 1953-1965. 16 pages.
Alvarez-Suarez, J.M., et al., The composition and biological activity of honey: a focus on Manuka honey. Foods, Sep. 2014. 3(3): p. 420-432.
Amar, M. R.S., A Thesis: "Estimation of Mechanical Properties of Soft Tissue Subjected to Dynamic Impart", Dec 2010, Presented to the Faculty of The Graduate College at the University of Nebraska. 67 pages.
Armstrong, S. and C. Ruckley, Use of a fibrous dressing in exuding leg ulcers. Journal of Wound Care, 1997. 6(7): p. 322-324.
Arokoski, Jari P.A et al."Feasibility of the use of a novel soft tissue stiffness meter", PhysiologicaL Measurement, Institute of Physics Publishing, 2005, 26, pp. 215-228.
Aslan, N. et al., Fabrication of porous-Ti6Al4V alloy by using hot pressing technique and Mg space holder for hard-tissue biomedical applications. Journal of Materials Science: Materials in Medicine, vol. 32, Article No. 80, (2021), 12 pages.
Bao, P., et al., The role of vascular endothelial growth factor in wound healing. Journal of Surgical Research, 2009. 153(2): p. 347-358.
Baranano, D.E., et al., Biliverdin reductase: a major physiologic cytoprotectant. Proceedings of the national academy of sciences, 2002. 99(25): p. 16093-16098.
Bassett, D.C. et al., "Dissolution of copper mineral phases in biological fluids and the controlled release of copper ions from mineralized alginate hydrogels", Biomed Mater., Dec 29, 2014. 10(1); 015006. 24 pages. Doi: 10.1088/1748-6041/10/1/015006.
Baumann, L.S. and U.S. Md, The effects of topical vitamin Eon the cosmetic appearance of scars. Dermatologic Surgery, 1999. 25(4): p. 311-315.
Beck, L.S., et al., One systemic administration of transforming growth factor-beta 1 reverses age-or glucocorticoid-impaired wound healing. The Journal of clinical investigation, 1993. 92(6): p. 2841-2849.
Berglund, R.N., et al., "Generation of monodisperse aerosol standards," *Environmental Science & Technology*, Feb. 1973. 7(2): p. 147-153. 8 Pages.
Bernard, G., et al., Effect of N-acetylcysteine on the pulmonary response to endotoxin in the awake sheep and upon in vitro granulocyte function. The Journal of clinical investigation, 1984. 73(6): p. 1772-1784.
Biagio Manna, Phillip Nahirniak, Christopher A. Morrison, *Wound Debridement*,. StatPearls Publishing. Retrieved through the Wayback Machine for Dec. 7, 2022. https://web.archive.org/web/20221207131130/https://www.ncbi.nlm.nih.gov/books/NBK507882/.
Bidwell, G., et al., "A corneal penetrating drug delivery system based on elastin-like polypeptide (1053.4)," The FASEB Journal, Apr. 1, 2014. 28 (1) p. 1053.4. 1 Page. Abstract Only.
Blackburn, B.J., et al., "A review of structural and biomechanical changes in the cornea in aging, disease, and photochemical crosslinking," *Frontiers in bioengineering and biotechnology*, Mar. 29, 2019. 7: p. 1-16. 16 Pages.
Boateng J., et al., "Advanced Therapeutic Dressings for Effective Wound Healing," Journal of Pharmaceutical Sciences. 2015. 80 pages. DOI: 10.1002/JPS.24610.
Boateng, J.S., et al., Wound healing dressings and drug delivery systems: a review. Journal of pharmaceutical sciences, 2008. 97(8): p. 2892-2923.
Bolton, L. and L. Van Rijswijk, Wound dressings: meeting clinical and biological needs. Dermatology nursing, 1991. 3(3): p. 146-161.
Branski, L.K., et al., "Gene therapy in wound healing: present status and future directions," *Gene Therapy*, 14, 2007. pp. 1-10. 10 Pages. https://doi.org/10.1038/sj.gt.3302837.
Brown, GL, et al. "Enhancement of wound healing by topical treatment with epidermal growth factor". The New England Journal of Medicine, (1989), 321, pp. 76-79.
Bykhovskaya, Y., et al., "Variation in the lysyl oxidase (LOX) gene is associated with keratoconus in family-based and case-control studies," *Invest Ophthalmol Vis Sci*, Jun. 2012. 53(7): p. 4152-7. 7 Pages.
Calabrese, V., et al., Curcumin and the cellular stress response in free radical-related diseases. Molecular nutrition & food research, 2008. 52(9): p. 1062-1073.
Camodeca, A. et al. Last Updated: Apr. 17, 2023. Corneal foreign body. StatPearls 2024. 7 pages.
Campbell, L., "Under the hood: The physics of projectile ballistics," Downloaded on Dec 9, 2021 from http://panoptesv.com/RPGs/Equipment/Weapons/Projectile_physics.php . 11 Pages.
Cano Sanchez, M., et al., Targeting oxidative stress and mitochondrial dysfunction in the treatment of impaired wound healing: a systematic review. Antioxidants, 2018. 7(8): p. 98. 14 pages.
Caporossi, A., et al., "Long-term results of riboflavin ultraviolet a corneal collagen crosslinking for keratoconus in Italy: the Siena eye cross study," *Am J Ophthalmol*, 2010. 149(4): p. 585-93. 10 Pages.

(56) References Cited

OTHER PUBLICATIONS

Chedid, M., et al., Glucocorticoids inhibit keratinocyte growth factor production in primary dermal fibroblasts. Endocrinology, 1996. 137(6): p. 2232-2237.
Chen, J. et al. "Biomechanics of oral mucosa", J. R. Soc. Interface, (2015), 12: Mar. 25, 2015. 20 pages. Website: dx.doi.org/10/1098/rsif20115.0325.
Chen, W.J., A.A. Rogers, and M.J. Lydon, Characterization of biologic properties of wound fluid collected during early stages of wound healing. Journal of Investigative Dermatology, 1992. 99(5): p. 559-564.
Chen, X.H., et al., "Direct growth of hydroxy cupric phosphate heptahydrate monocrystal with honeycomb-like porous structures on copper surface mimicking lotus leaf," *Crystal Growth and Design*, 2009. 9(6): p. 2656-2661. 7 Pages.
Chigurupati, S., et al., A synthetic uric acid analog accelerates cutaneous wound healing in mice. PLoS One, Apr. 2010. 5(4): p. e10044. pp. 1-10.
Choi, S.M., et al., Development of stabilized growth factor-loaded hyaluronate-collagen dressing (HCD) matrix for impaired wound healing. Biomaterials Research, 2016. 20(9): p. 1-7.
Choi, S.M., et al., Effects of structurally stabilized EGF and bFGF on wound healing in type I and type II diabetic mice. Acta biomaterialia, 2018. 66: p. 325-334.
Cifariello, F., et al., "Epi-off versus epi-on corneal collagen cross-linking in keratoconus patients: a comparative study through 2-year follow-up," *Journal of ophthalmology*, 2018. 7 Pages.
Cooper, DM., Wound healing: New understandings. Nurs Pract Forum 1999. 10: p. 74-86.
Cornu, Christophe, et al. "Stiffness of Knee Extensors in Duchenne Muscular Dystrophy", Muscle and Nerve, Short Reports, Dec 1998, 21, pp. 1772-1774.
Corporation, M.-S. Porous Silica. Downloaded on Dec. 9, 2021, from website: mo-sci.com/products/porous-silica/ . 2021. 3 Pages.
Cotgreave, I., P. Moldeus, and I. Schuppe, The metabolism of N-acetylcysteine by human endothelial cells. Biochemical pharmacology, 1991. 42(1): p. 13-16.
Czerner, M., et al., "Determination of Elastic Modulus of Gelatin Gels by Indentation Experiments" *Procedia Materials Science* 8. 2015. pp. 287-296. 10 pages.
Da Rocha, R.P., et al., Effects of a vitamin pool (vitamins A, E, and C) on the tissue necrosis process: experimental study on rats. Aesthetic plastic surgery, 2002. 26(3): p. 197-202.
Daull, P., et al., "Novasorb® Cationic Nanoemulsion and Latanoprost: The ideal combination for glaucoma management," *J Eye Dis Disord*, Jan. 26, 2017. 2 (1). 5 Pages.
Dowd, Scot E., et al. "Polymicrobial nature of chronic diabetic foot ulcer biofilm infections determined using bacterial tag encoded FLX amplicon pyrosequencing (bTEFAP)." PloS one, vol. 3, Issue 10 (Oct. 2008): e3326. 7 pages.
Dowd, Scot E., et al. "Survey of bacterial diversity in chronic wounds using pyrosequencing, DGGE, and full ribosome shotgun sequencing." BMC microbiology 8 (43), (2008): 1-15.
Dudakova, L., et al., "The impairment of lysyl oxidase in keratoconus and in keratoconus-associate disorders," *J Neural Transm* (*Vienna*), 2013. 120(6): p. 977-82. 7 Pages.
Dwyer, T.J., et al., "Effects of treadmill exercise versus Flutter® on respiratory flow and sputum properties in adults with cystic fibrosis: a randomised, controlled, cross-over trial," *BMC Pulmonary Medicine*, 17:14. 2017. 8 Pages.
Eaglstein, W.H., et al., Optimal use of an occlusive dressing to enhance healing: Effect of delayed application and early removal on wound healing. Archives of dermatology, 1988. 124(3): p. 392-395.
Ehlers, N., et al., "The cornea: epithelium and stroma," *Advances in organ biology*, 2005. 10: p. 83-111. 30 Pages.
Ehrlich, H.P., H. Tarver, and T.K. Hunt, Effects of vitamin A and glucocorticoids upon inflammation and collagen synthesis. Annals of surgery, 1973. 177(2): p. 222-227.
Elcin, Y.M., V. Dixit, and G. Gitnick, Extensive in vivo angiogenesis following controlled release of human vascular endothelial cell growth factor: implications for tissue engineering and wound healing. Artificial organs, 2001. 25(7): p. 558-565.
Evans, N.D. et al., "Epithelial mechanobiology, skin would healing, and the stem cell niche", Journal of the Mechanical Behavior of Biomedical Materials, 28 (2013) pp. 397-409. http://www.sciencedirect.com/science/article/pii/S1751616113001550.
Fang, R.C. and R.D. Galiano, A review of becaplermin gel in the treatment of diabetic neuropathic foot ulcers. Biologics: targets & therapy, 2008. 2(1): p. 1-12.
Feng, X. et al., "In vivo stiffness measurement of epidermis, dermis, and hypodermis using broadband Rayleigh-wave optical coherence elastography," Acta Biomater. Jul. 1, 2022:146:295-305. doi: 10.1016/j.actbio.2022.04.030.
Ferguson, J.E., et al., "Wireless communication with implanted medical devices using the conductive properties of the body," *Expert Rev Med Devices*, 8(4). Jul. 2011. pp. 427-433. 14 Pages. doi: 10.1586/erd.11.16.
Ferguson, MW et al. Prophylactic administration of avotermin for improvement of skin scarring: three double-blinkd, placebo-controlled, phase I/II studies. Lancet, (2009), 373, pp. 1264-1274.
Ferreira, M.C., et al., Complex wounds. Clinics, 2006. 61(6): p. 571-578.
Fitzmaurice, S., R.K. Sivamani, and R.R. Isseroff, Antioxidant therapies for wound healing: a clinical guide to currently commercially available products. Skin pharmacology and physiology, 2011. 24(3): p. 113-126.
Flanigan, K.H., Nutritional aspects of wound healing. Advances in wound care: the journal for prevention and healing, 1997. 10(3): p. 48-52.
Gabriel, Allen, MD. "Wound Healing and Growth Factors". Overview, Types of Would Healing, Phases of Wound Healing. Medscape, Aug. 27, 2021, http://emedicine.medscape.com/article/1298196-overview#a3.
Garcia-Orue, I., et al., Novel nanofibrous dressings containing rhEGF and Aloe vera for wound healing applications. International journal of pharmaceutics, 2017. 523(2): p. 556-566.
Gardner, Sue E., Stephen L. Hillis, Kris Heilmann, Julia A. Segre, Elizabeth A. Grice; The Neuropathic Diabetic Foot Ulcer Microbiome is Associated With Clinical Factors. Diabetes, Mar. 2013; 62 (3): 923-930. Website: doi.org/10.2337/db12-0771.
Gaudana, R., et al., "Ocular drug delivery," *The AAPS Journal*, Sep. 2010. 12(3): p. 348-360. 14 Pages.
Gefen, A., et al., "Integration of plantar soft tissue stiffness measurements in routine MRI of the diabetic foot", Clinical Biomechanics, 16 (2001), pp. 921-925.
Gilbertson, M.W., et al., "Ergonomic control strategies for a hand-held force-controlled ultrasound probe", 2012 IEEE/RSJ International Conference on Intelligent Robots and Systems, Oct. 7-12, 2012. Vilamoura, Algarve, Portugal. pp. 1284-1291.
Gilbertson, M.W., et al., "Force and Position Control System for Freehand Ultrasound", IEEE Transactions on Robotics, vol. 31, No. 4, Aug. 2015, pp. 835-849.
Gilliland, E.L., et al., Bacterial colonisation of leg ulcers and its effect on the success rate of skin grafting. Annals of the Royal College of Surgeons of England, 1988. 70(2): p. 105-108.
Gjodsbol, Kristine, et al. "Multiple bacterial species reside in chronic wounds: a longitudinal study." International Wound Journal, vol. 3. No. 3 (2006): 225-231.
Gjodsbol, Kristine, et al. "No need for biopsies: comparison of three sample techniques for wound microbiota determination." International Wound Journal 9 (3) (2012): 295-302.
Godoy-Gallardo M, Portolés-Gil N, López-Periago AM, Domingo C, Hosta-Rigau L. Immobilization of BMP-2 and VEGF within Multilayered Polydopamine-Coated Scaffolds and the Resulting Osteogenic and Angiogenic Synergy of Co-Cultured Human Mesenchymal Stem Cells and Human Endothelial Progenitor Cells. International Journal of Molecular Sciences. 2020; 21(17):6418. https://doi.org/10.3390/ijms21176418.
Gomes, F., et al., Farnesol in combination with N-acetylcysteine against *Staphylococcus* epidermidis planktonic and biofilm cells. Brazilian Journal of Microbiology, 2012. 43(1): p. 235-242.

(56) References Cited

OTHER PUBLICATIONS

Gontcharova, Viktoria, et al. "A comparison of bacterial composition in diabetic ulcers and contralateral intact skin." The Open Microbiology Journal, 4 (2010): 8-19.

Gordon-Shaag, A., et al., "The genetic and environmental factors for keratoconus," *BioMed research international*, 2015. 795738, p. 24-32. 20 Pages.

Gore, D.M., et al., "New clinical pathways for keratoconus," *Eye* (*Lond*), 2013. 27(3): p. 329-39. 12 Pages.

Gouveia, S.M . . . et al., "Human tear viscosity: an interactive role for proteins and lipids," *Biochimica et Biophysica Acta* (*BBA*)-*Proteins and Proteomics*, 2005. 1753(2): p. 155-163. 10 Pages.

Grandjean, E.M., et al., Efficacy of oral long-term N-acetylcysteine in chronic bronchopulmonary disease: a meta-analysis of published double-blind, placebo-controlled clinical trials. Clinical therapeutics, 2000. 22(2): p. 209-221.

Greenhalgh, D.G., et al., PDGF and FGF stimulate wound healing in the genetically diabetic mouse. The American journal of pathology, 1990. 136(6): p. 1235-1246.

Greenhalgh, D.G., The role of growth factors in wound healing. Journal of Trauma and Acute Care Surgery, 1996. 41(1): p. 159-167.

Gu, D.-1., et al., Adenovirus encoding human platelet-derived growthfactor-B delivered in collagen exhibits safety, biodistribution, and immunogenicity profiles favorable for clinical use. Molecular therapy, 2004. 9(5): p. 699-711.

Gumus, K. et al. 2007. Corneal injury form a metallic foreign body: an occupational hazard. Eye Contact Lens 33, 259-260.

Guo, Q., et al., "Entanglement-based thermoplastic shape memory polymeric particles wit photothermal actuation for biomedical applications," *ACS applied materials & interfaces*, Mar. 30, 2018. 10(16): p. 13333-13341. 10 Pages.

Hanschmann, E.-M., et al., Thioredoxins, glutaredoxins, and peroxiredoxins-molecular mechanisms and health significance: from cofactors to antioxidants to redox signaling. Antioxidants & redox signaling, 2013. 19(13): p. 1539-1605.

Harding, K., H. Morris, and G. Patel, Clinical review Healing chronic wounds. Br Med J, 2002. 324: p. 160-163.

Hareendran, A., et al., Measuring the impact of venous leg ulcers on quality of life. Journal of Wound Care, 2005. 14(2): p. 53-57.

Hart, A., et al., Sensory neuroprotection, mitochondrial preservation, and therapeutic potential of N-acetyl-cysteine after nerve injury. Neuroscience, 2004. 125(1): p. 91-101.

Hedbys, B.O., et al., "The thickness-hydration relationship of the cornea," *Experimental eye research*, 1966. 5(3): p. 221-228. 9 Pages.

"Software estimates Chemical, Physical Properties," Chemical and Engineering News, 63(5), 1985. p. 27. 2 Pages.

"Types of Burns", 2018, from website: rnspeak.com/wp-content/uploads/2018/05/burn-classification-of-injuries.jpg.

Komarcevic, A., The modern approach to wound treatment. Medicinski pregled, 2000. 53(7-8): p. 363-368. Abstract Only.

Martins-Green, Chapter 2: Role of oxidants and antioxidants in diabetic wound healing. Wound Healing, Tissue Repair, and Regeneration in Diabetes. (2020), pp. 13-38. Abstract Only. Website: doi.org/10.1016/B978-0-12-816413-6.00002-2.

Rebenitsch, R.L., et al., "The lifetime economic burden of keratoconus: a decision analysis using a markov model," Am J Ophthalmol, 2011. 151(5): p. 768-773 e2. 9 p.

Ribeiro, M.D.M., et al., "The effect of adding oleic acid in the production of stearic acid lipid. Microparticles with a hydrophilic core by a spray-cooling process," *Food Research International*, 2012. 47(1): p. 38-44. 8 Pages.

Ringberg, D., et al., "Pneumatic capillary gun for ballistic delivery of microparticles," Applied Physics Letters 87(1), Feb. 2005. 8 Pages.

Rojas, A.I. and T.J. Phillips, Patients with chronic leg ulcers show diminished levels of vitamins A and E, carotenes, and zinc. Dermatologic Surgery, Aug. 1999. 25(8): p. 601-604.

Rothe, M. and V. Falanga, Growth factors: their biology and promise in dermatologic diseases and tissue repair. Archives of dermatology, Oct. 1989. 125(10): p. 1390-1398.

Russell, L., Understanding physiology of wound healing and how dressings help. British journal of nursing, 2000. 9(1): p. 10-21.

Sartelli M, et al., 2018 "WSES/SIS-E consensus conference: recommendations for the management of skin and soft-tissue infections", World Journal of Emergency Surgery, (2018) 13: 58. 24 pages. Website: doi.org/10.1186/s13017-018-0219-9.

Scales, B.S. and Huffnagle, G.B., "The microbiome in wound repair and tissue fibrosis." The Journal of Pathology, 229 (2), (2013): 323-331.

Schaefer, M. and S. Werner, Oxidative stress in normal and impaired wound repair. Pharmacological research, 2008. 58(2): p. 165-171.

Schreml, S., et al., Luminescent dual sensors reveal extracellular pH-gradients and hypoxia on chronic wounds that disrupt epidermal repair. Theranostics, 2014. 4(7): p. 721-735.

Scott, R. 2011. The injured eye. Philos. Trans. R. Soc. B Biol. Sci. 366, 251-260.

Segletes, S.B., "Modeling the penetration behavior of rigid spheres into ballistic gelatin," *Army Research Lab Aberdeen Proving Ground Md.*, Mar. 2008. 37 Pages.

Sen, C.K. and S. Roy, Redox signals in wound healing. Biochimica et Biophysica Acta (BBA)-General Subjects, Nov. 2008. 1780(11): p. 1348-1361. 23 pages.

Shakespeare, P., Burn wound healing and skin substitutes. Burns, 2001. 27(5): p. 517-522.

Shariati, A., et al., "The Effects of Davidson's Fixative Solution in Preserving the Rabbit Eye," *Investigative Ophthalmology & Visual Science*, May 2008. 49(13): p. 5207-5207. 2 Pages. Abstract Only.

Sharma, A., et al., "Strain-controlled criticality governs the nonlinear mechanics of fibre networks," *Nature Physics*, Jan. 25, 2016. 12(6): p. 584-587. 6 Pages.

Shetty, R., et al., "Attenuation of lysyl oxidase and collagen gene expression in keratoconus patient corneal epithelium corresponds to disease severity," *Mol Vis*, Jan. 12, 2015. 21: p. 12-25. 15 pages.

Shi, C., et al., "Application of a sub-0.1-mm3 implantable mote for in vivo real-time wireless temperature sensing," *Science Advances*, 7(19). May 7, 2021. 10 Pages. DOI: 10.1126/sciadv.abf6312.

Shukla, A., A.M. Rasik, and G.K. Patnaik, Depletion of reduced glutathione, ascorbic acid, vitamin E and antioxidant defence enzymes in a healing cutaneous wound. Free Radical Research, 1997. 26(2): p. 93-101.

Smiell, J.M., et al., Efficacy and safety of becaplermin (recombinant human platelet-derived growth factor-BB) in patients with nonhealing, lower extremity diabetic ulcers: a combined analysis of four randomized studies. Wound Repair and Regeneration, (Sep. 1999). 7(5): p. 335-346.

Smith, Karen, et al. "One step closer to understanding the role of bacteria in diabetic foot ulcers: characterising the microbiome of ulcers." BMC Microbiology, 16 (54), (2016): 1-12.

Spiller, Kara L. et al. "A novel method for the direct fabrication of growth factor-loaded microspheres within porous nondegradable hydrogels: controlled release for cartilage tissue engineering". Journal of Controlled Release 157.1 (2012): 39-45.

Steenfos, H.H., Growth factors and wound healing. Scandinavian journal of plastic and reconstructive surgery and hand surgery, 1994. 28(2): p. 95-105.

Strodtbeck, F., Physiology of wound healing. Newborn Infants Nurs Rev, Mar. 2001. 1: p. 43-52.

Suzuki, T. and M. Yamamoto, Stress-sensing mechanisms and the physiological roles of the Keap1-Nrf2 system during cellular stress. Journal of Biological Chemistry, Aug. 2017. 292(41): p. 16817-16824.

Swain, M., et al., "Projectile penetration into ballistic gelatin," *Journal of the mechanical behavior of biomedical materials*, 2014. 29: p. 385-392. 9 Pages.

Taeko, M., et al., "Wound Healing and Skin Regeneration", Cold Spring Harb Perspect Med 2015; 5:a023267; p. 1-12.

Tanelian, D.L., et al. Sep. 1997. Controlled gene gun delivery and expression of DNA within the cornea. Biotechniques 23, 484-488.

(56) References Cited

OTHER PUBLICATIONS

Taylor, R. and T. James, The role of oxidative stress in the development and persistence of pressure ulcers, in Pressure ulcer research. 2005, Springer. p. 205-232.
Taylor, T., et al., Ascorbic acid supplementation in the treatment of pressure-sores. The Lancet, Sep. 1974. 304(7880): p. 544-546.
Ten Dijke, P. and K.K. Iwata, Growth factors for wound healing. Bio/Technology, Aug. 1989. 7(8): p. 793-798.
Tenhunen, R., H.S. Marver, and R. Schmid, The enzymatic conversion of heme to bilirubin by microsomal heme oxygenase. Proceedings of the National Academy of Sciences of the United States of America, 1968. 61(2): p. 748-755.
Thomasy, S.M., et al., "Elastic modulus and collagen organization of the rabbit cornea: epithelium to endothelium," *Acta biomaterialia*, 2014. 10(2): p. 785-791. 8 Pages.
Tsai, M.-L., et al., Topical N-acetylcysteine accelerates wound healing in vitro and in vivo via the PKC/Stat3 pathway. International journal of molecular sciences, 2014. 15(5): p. 7563-7578.
UCSF Department of Surgery, "Debridement", 2024. 5 pages. surgery.ucsfedu/conditionsprocedures/debridement.asp.
Uruno, A., Y. Yagishita, and M. Yamamoto, The Keap1-Nrf2 system and diabetes mellitus. Archives of biochemistry and biophysics, Jan. 2015. 566: p. 76-84.
Vervaart, P. and K. Knight, Oxidative stress and the cell. Clinical Biochemist Reviews, Feb. 1996. 17: p. 3-16.
Veysset, D. et al. 2020. Laser-driven high-velocity microparticle launcher in atmosphere and under vacuum. Int. J. Impact Eng. 137. 8 pages.
Veysset, D., et al., "High-velocity micro-particle impact on gelatin and synthetic hydrogel," *Journal of the mechanical behavior of biomedical materials*, Published Online Jun. 14, 2018. 86: p. 71-76. 7 Pages.
Vinciguerra, P., et al., "Refractive, topographic, tomographic, and aberrometric analysis of keratoconic eyes undergoing corneal cross-linking," *Ophthalmology*, 2009. 116(3): p. 369-78.
Vinciguerra, R., et al., "Corneal cross-linking as a treatment for keratoconus: four-year morphologic and clinical outcomes with respect to patient age," *Ophthalmology*, 2013. 120(5): p. 908-16. 11 Pages.
VisionGain. Advanced wound care: world market prospects 2011-2021. Downloaded through the Wayback Machine, dated Aug. 17, 2012. 11 pages. (Website: www.visiongain.com/Report/716/Advanced-Wound-Care-World-Market-Prospects-2011-2021. Accessed Oct. 31, 2012).
Vogel, Benjamin et al. Determination of collagen content within picrosirius red stained paraffin-embedded tissue sections using fluorescence microscopy, MethodsX, (2015), 124-134.
Waasdorp, M. et al., "The Bigger Picture: Why Oral Mucosa Heals Better Than Skin", Biomolecules, (Aug. 6, 2021), 11, 1165. 22 pages. Website: doi.org/10.3390/biom11081165.
Wachter, K.C. et al., Muscle Damping Measured with a Modified Pendulum Test in Patients with Fibromyalgia, Lumbago, and Cervical Syndrome. Spine, (1996), vol. 21, No. 18, pp. 2137-2142.
Wallace, E., Feeding the wound: nutrition and wound care. British Journal of Nursing, 1994. 3(13): p. 662-667.
Warner, R.R., et al., "Electron probe analysis of human skin: determination of the water concentration profile," *Journal of Investigative Dermatology*, 1988. 90(2): p. 218-224. 8 Pages.
Webb, P.A., "Volume and density determinations for particle technologists," Micromeritics Instrument Corp. Downloaded on Dec 9, 2021 from https://www.micromeritics.com/Repository/Files/Volume_and_Density_determinations_for_Particle_Technologists.pdf, 2001: p. 1-16. 16 Pages.
Wellman, P.S., Howe, R.D., Dalton, E., and Kern K.A., Breast Tissue Stiffness in Compression is Correlated to Histological Diagnosis, (1999), 15 pages.
Wieman, TJ. Clinical efficacy of becaplermin (rhPDGF-BB) gel. Becaplermin gel studies group. American Journal of Surgery 176, 74S-79S (Aug. 1998).
Wieman, TJ, et al. Efficacy and safety of a topical gel formulation of recombinant human platelet-derived growth factor-bb (becaplermin) in patients with chronic neuropathic diabetic ulcers. A phase III randomized placebo-controlled double-blind study. Diabetes Care, (May 1998), 21, pp. 822-827.
Wikipedia. Ballistic gelatin, Downloaded on Dec. 9, 2021 from https://web.archive.org/web/20181222100214/https://en.wikipedia.org/wiki/Ballistic_gelatin 2018. 3 Pages.
Wikipedia. Epithelium. Downloaded on Dec. 9, 2021, from https://web.archive.org/web/20190325184737/https://en.wikipedia.org/wiki/Epithelium . 2019. 11 Pages.
Wikipedia. Polymer. Downloaded on Dec. 9, 2021, from: https://web.archive.org/web/20191212045342/https://en.wikipedia.org/wiki/Polymer . 2019. 14 pages.
Wikipedia. Porous glass. Downloaded on Dec. 9, 2021, from: https://web.archive.org/web/20200612145638/https://en.wikipedia.org/wiki/Porous_glass . 2020. 4 Pages.
Wikipedia. Steroid. Downloaded for Nov. 11, 2022. 20 pages. Website: web.archive.org/web/20221111004859/https://en.wikipedia.org/wiki/Steroid. 2022.
Wikipedia. Tissue (biology). Downloaded on Dec. 9, 2021 from https://web.archive.org/web/20191201005711/https://en.wikipedia.org/wiki/Tissue_(biology). 2019. 7 Pages.
Wiseman, H., Vitamin D is a membrane antioxidant. Ability to inhibit iron-dependent lipid peroxidation in liposomes compared to cholesterol, ergosterol and tamoxifen and relevance to anticancer action. FEES letters, Jul. 1993. 326(1-3): p. 285-288.
Wlaschek, M. and K. Scharffetter-Kochanek, Oxidative stress in chronic venous leg ulcers. Wound Repair and Regeneration, 2005. 13(5): p. 452-461.
Wolcott, R. et al., Microbiota is a primary cause of pathogenesis of chronic wounds. Journal of Wound Care, North American supplement, vol. 25, No. 10, Oct. 2016. S33-S43.
Wolcott, R.D., et al., Analysis of the chronic would microbiota of 2,963 patients by 16S rDNA pyrosequencing. Wound Repair and Regeneration. (2016), 24, 163-174.
Wood, Z.A., et al., Structure, mechanism and regulation of peroxiredoxins. Trends in biochemical sciences, Jan. 2003. 28(1): p. 32-40.
Xiong, C., et al., "Mass, size, and density measurements of microparticles in a quadrupole ion trap," *Analytical Chemistry*, 2019. 91(21): p. 13508-13513. 7 Pages.
Yang, C., et al., Rapamycin and mTOR inhibitors probably have therapeutic effects for post-operative cognitive dysfunction. Medical hypotheses, 2013. 81(3): p. 487-488.
Yang, H., J. Chai, and Z. Guo, Effect of improved topical agents on healing time of deep second-degree burn wound. Zhongguo xiu fu chong jian wai ke za zhi= Zhongguo xiufuchongjian waike zazhi= Chinese journal of reparative and reconstructive surgery, 2001. 15(3): p. 162-164. Chinese original with English Abstract.
Yang, Zhaoyang et al. "The effect of the dosage of NT-3/chitosan carriers on the proliferation and differentiation of neural stem cells". Biomaterials 31.18 (2010): 4846-4854.
Ye, S.J. et al. "Penetration dynamics of steel spheres into a ballistic gelatin: Experiments, nondimensional analysis, and finite element modeling", International Journal of Impact Engineering, vol. 162, (2022), 104144, 10 pages. ISSN 0734-743X, Website: doi.org/10.1016/j.ijimpeng.2021.104144.
Yoshida, T., et al., The involvement of thioredoxin and thioredoxin binding protein-2 on cellular proliferation and aging process. Annals-New York Academy of Sciences, 2005. 1055: p. 1-12.
Zamora, K.V., et al., "Polymicrobial keratitis after a collagen cross-linking procedure with postoperative use of a contact lens: a case report," *Cornea*, May 2009. 28(4): p. 474-6. 5 Pages.
Zayas, J.G., et al., "Bronchial Mucus Properties in Lung Cancer: Relationship with Site of Lesion," *Canadian respiratory journal: journal of the Canadian Thoracic Society* 6(3):246-52. 1999. 8 Pages DOI: 10.1155/1999/459084.
Zhai, Liang et al. "An Integrated Indenter-ARFI Imaging System for Tissue Stiffness Quantification", Ultrason Imaging, Apr. 2008, 30(2), pp. 95-111. 24 pages.

(56) References Cited

OTHER PUBLICATIONS

Zhang, Dongwei, Diganta B. Das, and Chris D. Rielly. "Potential of microneedle-assisted micro-particle delivery by gene guns: a review." Drug delivery 21 (8), (2014): 571-587.
Zhang, E.P. et al. 2002. Minimizing side effects of ballistic gene transfer into the murine corneal epithelium. Graefe's Arch. Clin. Exp. Ophthamol. 240, 114-119.
Zhang, W. et al. 2017. Experimental investigation on ballistic stability of high-speed projectile in sand. AIP Conf. Proc. 1793. 5 pages.
Zhang, Y. et al. "Drug-induced regeneration in adult mice". Science Translational Medicine, (Jun. 2015), 7 (290), 290ra92. 11 pages. Website: doi.org/10.1126/scitranslmed.3010228.
Zhao, Hai-yang et al. "Research Advances in Tissue Engineering Materials for Sustained Release of Growth Factors" BioMed Research International, vol. 2015, Article ID 808202, 7 pages, 2015. Website: doi.org/10.1155/2015/808202.
Zheng, H., et al., Therapeutic potential of Nrf2 activators in streptozotocin-induced diabetic nephropathy. Diabetes, Nov. 2011. 60(11): p. 3055-3066.
Zia, R.N., "Active and Passive Microrheology: Theory and Simulation," *Annu. Rev. Fluid Mech.* Jan. 2018. 50:371-405. 37 Pages.
Zilony, N., et al., "Bombarding cancer: biolistic delivery of therapeutics using porous Si carriers," *Scientific reports*, Aug. 26, 2013. 3(1): p. 1-6. 7 Pages.
Ziol, M. et al., Noninvasive Assessment of Liver Fibrosis by Measurement of Stiffness in Patients with Chronic Hepatitis C., Hepatology, vol. 41, No. 1, (Jan. 2005), pp. 48-54.
Ko, Dennis Lok, Thesis, "Design and Implementation of a Microparticle Delivery Device for the Cornea", California Institute of Technology, Pasadena, CA. (2024) 111 pages.
Non-Final Office Action for U.S. Appl. No. 17/376,024, filed Jul. 14, 2021 on behalf of California Institute of Technology. Mailed on Jun. 18, 2025. 33 pages.
Notice of Allowance for U.S. Appl. No. 17/376,024, filed Jul. 14, 2021 on behalf of California Institute of Technology. Mailed on Jan. 27, 2026. 9 pages.
Restriction Requirement for U.S. Appl. No. 17/376,024, filed Jul. 14, 2021 on behalf of California Institute of Technology. Mailed on Feb. 7, 2025. 10 pages.

* cited by examiner

CORNEA DATA:

GELATIN DATA:

B: blister
V: vein
C: capillaries
N: nerve
S: sweat gland
a: artery
R: sensory receptor
F: hair follicle
A: adipose
P: arrector pili muscle
E: epidermis
D: dermis
H: hypodermis
M: skeletal muscle

BALLISTIC DELIVERY TO MULTILAYERED TISSUES AND RELATED PARTICLES, COMPOSITIONS, METHODS AND SYSTEMS

CROSS-REFERENCE TO RELATED APPLICATIONS

This application claims priority to U.S. provisional application No. 63/285,989 entitled "Ballistic Wound Treatment and Related Particles Compositions Methods and Systems" filed on Dec. 3, 2021, to U.S. provisional application No. 63/285,993 entitled "Biolistic Wound Treatment and Related Particles Compositions Methods and Systems filed on Dec. 3, 2021, to U.S. provisional application No. 63/301,292 entitled "Ballistic Delivery for Wound healing" filed on January 20, to U.S. provisional application No. 63/301,432 entitled "Ballistic delivery for Wound healing" filed on Jan. 20, 2022, all of which herein enclosed for your prompt reference. The present application may also be related to U.S. application Ser. No. 17/376,024 entitled" Ballistic Delivery and related Particles, Composition Methods and Systems filed on Jul. 14, 2022 and to U.S. Provisional Application Ser. No. 63/051,677 entitled "Ballistic Delivery of Ocular Therapy" filed on Jul. 14, 2020 the contents of which is incorporated herein by reference in its entirety.

FIELD

The present disclosure generally relates to delivery of particles and related particles, compositions, methods and systems. In particular, the present disclosure relates to ballistic delivery of microparticles to a target organ of an individual for placing a cargo such as a drug or an implant in the tissue in controllable fashion.

BACKGROUND

Delivery of compounds to a target organ is at the center of various medical and research activities, often focused to delivery of drugs or implants to a tissue of an organ for a therapeutic goal.

Successful delivery of a cargo however is highly dependent on the features of the target tissue as will be understood by a skilled person and certain organs and related tissues, such as the eye and the corneal tissues have biophysical properties related to layered heterogeneity that complicate the uptake and controlled administration of drug species through traditional administration approaches to topical administration.

As a consequence, delivery of a drug to the eye and in particular to the cornea or other tissue with a layered heterogeneity remains challenging as will be understood by a skilled person.

SUMMARY

Provided herein, are methods and systems and related particles and compositions that can be used to deliver a cargo and in particular a biologically active cargo such as a drug to a target tissue having a layered heterogeneity, the delivery performed in a rapid, nonsurgical, and/or controllable fashion.

According to a first aspect, a method and a system, for controlled ballistic delivery of a biologically active cargo to a bilayer of multilayered tissue of an individual, is described, the method comprises providing a multilayered tissue, having a tissue Young's modulus E from 500 Pa to 50 MPa and a tissue density ρ from 850 kg/$m^3$ to 1200 kg/$m^3$. In the method, the provided multilayered tissue comprises a bilayer having a bilayer thickness L from 50 microns to 5000 microns, a bilayer width W at least 10 L. In the method, the bilayer comprises an apical layer and a basal layer underneath the apical layer, the apical layer having thickness $L_a \leq L$, and a compressive strength $Y_a$; and the basal layer having thickness $L_b=L-L_a$ and a compressive strength $Y_b$. In the method, the apical layer defined by an accessible surface facing an environment external to the tissue and an internal boundary facing the basal layer, the apical layer having an accessible surface area at least ten-times $L^2$.

The method of the first aspect further comprises selecting within the bilayer, a target region having a target region thickness Lt and comprising a portion of at least one of the apical layer and the basal layer the portion centered around a target penetration distance d from the accessible surface. In the target region, the thickness Lt and the target penetration distance d are selected from

- $L_t=L_a/2$, and $d=L_a/2$; when the portion consists of a portion of the apical layer
- $L_t$ equal to the lesser of $L_a/2$ or $(L_a+L_b)/4$, and $d=L_a$; when the portion comprises the internal boundary facing the basal layer; and
- Lt is the lesser of $L_a/2$ or $L_b/2$, and d is equal to the lesser of $5L_a/4$ or $(L_a+L_b/4)$; when the portion consists of a portion of the basal layer, The method of the first aspect also comprises determining an effective target penetration distance d* for the target region, wherein

- $d^*=d=L_a/2$ when the target region consists of a portion of the apical layer;
- $d^*=d^*(1+f)=L_a^*(1+f)$, where $$f = \arctan\left(\left|\log\left(\frac{Y_a}{Y_b}\right)\right|\right)$$

when the target region consists of the internal boundary facing the basal layer; and

- $d^*=d^*(1+f)+(d-L_a)(\sqrt{Y_b/Y_a})=L_a^*(1+f)+\min\ (L_a/4,L_b/4)^*(\sqrt{Y_b/Y_a})$ when the target region consists of a portion of the basal layer The method of the first aspect additionally comprises providing a set of substantially spherical particles each comprising the biologically active cargo, the set of substantially spherical particles having

- an average density $\rho_p$ from 1400 kg/$m^3$ to 20000 kg/$m^3$,
- an average diameter $D_p$ greater than 1 micron and less than the least of 1000 micron, $D_p$ being $L_a/2$ or $L_b/2$, and
- a dispersity index PDI from 1 to 2, The method of the first aspect further comprising determining a velocity $v_{o,j}$ of the set of substantially spherical particles by iterating $$v_{o,i} = \sqrt{Y_a/\rho_p}\left((1/k)(d^*/D^m)(\mu_a^{m-1})\left(\sqrt{Y_a\rho_p}\right)^{1-m}(\rho_a/\rho_p)\right)^{1/n_t} \text{ from } i=0 \text{ to } j,$$

$$\text{where } n_0 = 0.826 \text{ and } n_i = n_0 - q\left(v_{0,i-1}\sqrt{\rho_a/Y_a}\right),$$

$$\text{until } \left|(v_{0,i}-v_{0,i-1})/v_{0,i-1}\right| < 0.1;$$

and selecting the $D_p$, $\rho_p$ and $v_{o,j}$ when $v_{o,j}$ is less than 1,500 m/sec; and The method of the first aspect also comprises ballistically delivering a set of particle which can be substantially spherical particles having the selected $D_p$ and $\rho_p$ at velocity $v_{o,j}$ to the accessible surface of the apical layer of the bilayer tissue to deliver into the target region at least 30% of the set of particles.

The system according to the first aspect comprises a set of particles each comprising the biologically active cargo, and a device configured to ballistically deliver to the multilayered tissue the set of particles. In the system according to the first aspect the set of particles has an average density $\rho_p$ from 1400 kg/m$^3$ to 20000 kg/m$^3$, an average diameter $D_p$ greater than 1 micron and less than the least of 1000 micron, $D_p$ being $L_a/2$ or $L_b/2$, and a dispersity index PDI from 1 to 2. In the system according to the first aspect and the device can be used for controlled ballistic delivery of a biologically active cargo to the multilayered tissue of an individual according to methods herein described.

According to a second aspect, a capillary gun and related methods are described for delivery of ballistic particles into a target, the capillary gun comprising:

- an outer housing;
- a capillary tube inside the outer housing configured to direct a flow of gas and particles from a source to the target, the capillary tube having an inner diameter and having a major axis along the capillary tube and having an exit end to be directed to the target when in use;
- a set of two or more disks that would be positioned between the exit end of the capillary tube and the target when in use, each of the two or more disks having an orifice positioned to allow particles from the capillary tubes to pass through the orifice, the orifice being smaller in diameter than the inner diameter of the capillary tube;
- an insert for holding the set of two or more disks in the outer housing;
- a vacuum chamber surrounding the insert, the vacuum chamber having an outlet configured to be attached to a vacuum generator;
- a plurality of vacuum channels in the insert, the plurality of vacuum channels connecting the vacuum chamber to a space between two of the two or more disks, the plurality of vacuum channels being evenly spaced around the insert.

The method according to the second aspect is a method of delivery ballistic particles to a target by using the device of claim 1, including applying a vacuum to the outlet and injecting a jet of a gas and the ballistic particles into the capillary tube.

Methods and systems herein described and related devices, particles and compositions, in several embodiments can be used to deliver a biologically active cargo such as drugs and implants to controlled target regions of a bilayer within multilayered tissues and in particular to deliver microparticles to a target layer of the multilayered tissue with controlled spatial distribution.

Methods and systems herein described and related devices, particles and compositions, in several embodiments can be used to deliver a biologically active cargo such as drugs and implants to inner layers of a multilayered tissues such as the corneal tissues, and in particular of epithelium and the upper layers of the corneal stroma without the need of surgery.

Methods and systems herein described and related devices, particles and compositions, in several embodiments where the carrier material is dissolvable, can be used to embed a biologically active cargo such as drugs and implants, in controlled target region of a multilayered tissues such as cornea, wherein following dissolution of the carrier material the biologically active cargo stays in place.

Accordingly, methods and systems herein described and related devices, particles and compositions, in several embodiments can be used to efficiently deliver a controlled amount of a biologically active cargo such as drugs to controlled target regions of a multilayered tissue such as the corneal tissues.

In particular in embodiments of methods and systems herein described and related particles and compositions applied to corneal tissue, the methods and systems of the present disclosure can thus overcome the biological barrier to mass-transfer that limits existing methods such as administration of solutions and other topical preparations for drug delivery to the cornea are washed away within just 15-30 s after instillation. [1]

Accordingly methods and systems herein described and related devices, particles and compositions, in several embodiments can also be used to obtain a sustained action of the biologically active cargo over a period of time (e.g. several days) which requires patient compliance to apply the topical formulation on a precise schedule. This effect would particularly be advantageous for patient populations, such as children and elderly patients, who may have difficulty complying with topical administration schedules.

Methods and systems herein described and related devices, particles and compositions, in several embodiments can thus be used to increase bioavailability of a biologically active drug delivered to a multilayered tissue such as the corneal tissues compared to existing methods and preparations such as suspension, emulsions, ointments, gels and polymeric inserts used to deliver drugs to the eye.

Methods and systems herein described and related devices, particles and compositions, in several embodiments can also be used to control the spatial distribution of a drug by using a ballistic microparticle mass transfer modality. In particular, with precision microparticle technology, particles can be delivered in rings or in other patterns to affect tissues disproportionally in 2D space.

The methods and systems herein described and related devices, particles and compositions can be used in connection with various applications wherein controlled delivery of a biologically active cargo to the corneal tissue of the eye or other multilayered target tissue having a layered heterogeneity in the sense of the disclosure, is desired. For example, methods and systems herein described and related composition can be used in application to that are useful in ophthalmology, dermatology, dentistry, cardiology, gastroenterology and wound healing concerning multilayered tissues of an individual, with particular reference to medical and research applications such as therapeutic treatments of the cornea and other soft tissues. Additional exemplary applications include delivery to mucosal tissue layers, soft tissues in any portion of the digestive tract and in particular in the gut, delivery to soft tissues the brain, delivery in wounds and in general in any tissue which has an apical layer and a basal layer with the features of the disclosure, for medical (e.g. therapeutic, prophylactic and/or diagnostic) and research field as well as in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 8 Panel B shows droplets from an aerosol excited at 60 kHz, outside of the monodisperse regime. Water was used as opposed to ethanol, which is used in later sections.

Solid intercept lines show average measured penetration depths of barium titanate spheres embedded in 5% w/w and 10% w/w gelatin. Dotted lines show one standard deviation above and below the mean. Dash intercept line shows the penetration depth and the corresponding impact velocity of a microparticle embedding at the maximum recorded normalized penetration.

Figure 45:
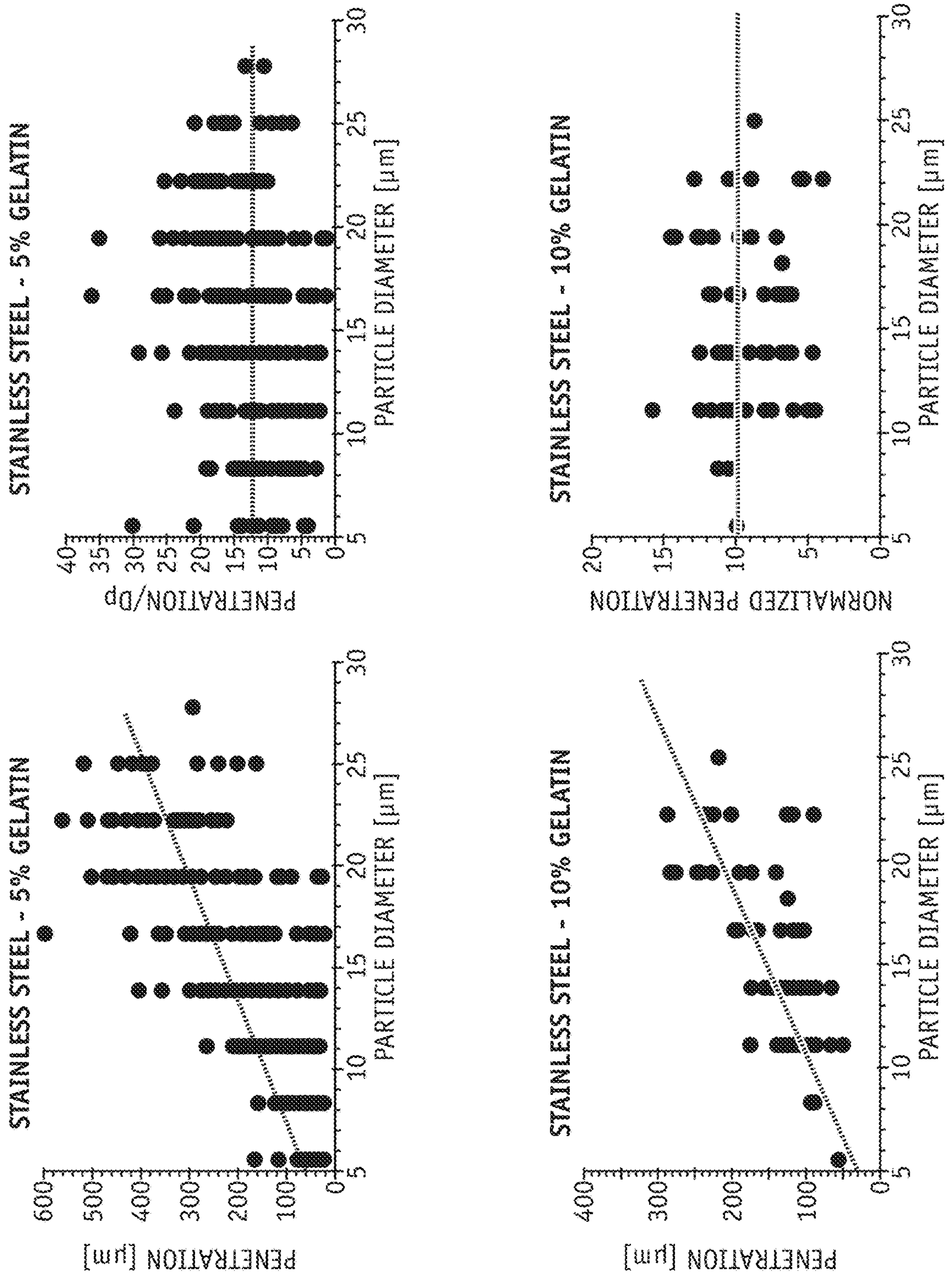

FIG. 45 shows charts illustrating actual penetration in left panels and normalized penetration in right panels of stainless-steel particles delivered to 5% w/w ballistic gelatin in top panels and 10% w/w ballistic gelatin in bottom panels, wherein the data for 10% w/w ballistic gelatin are collected from images of 75 particles embedded in gelatin in total.

Figure 46:
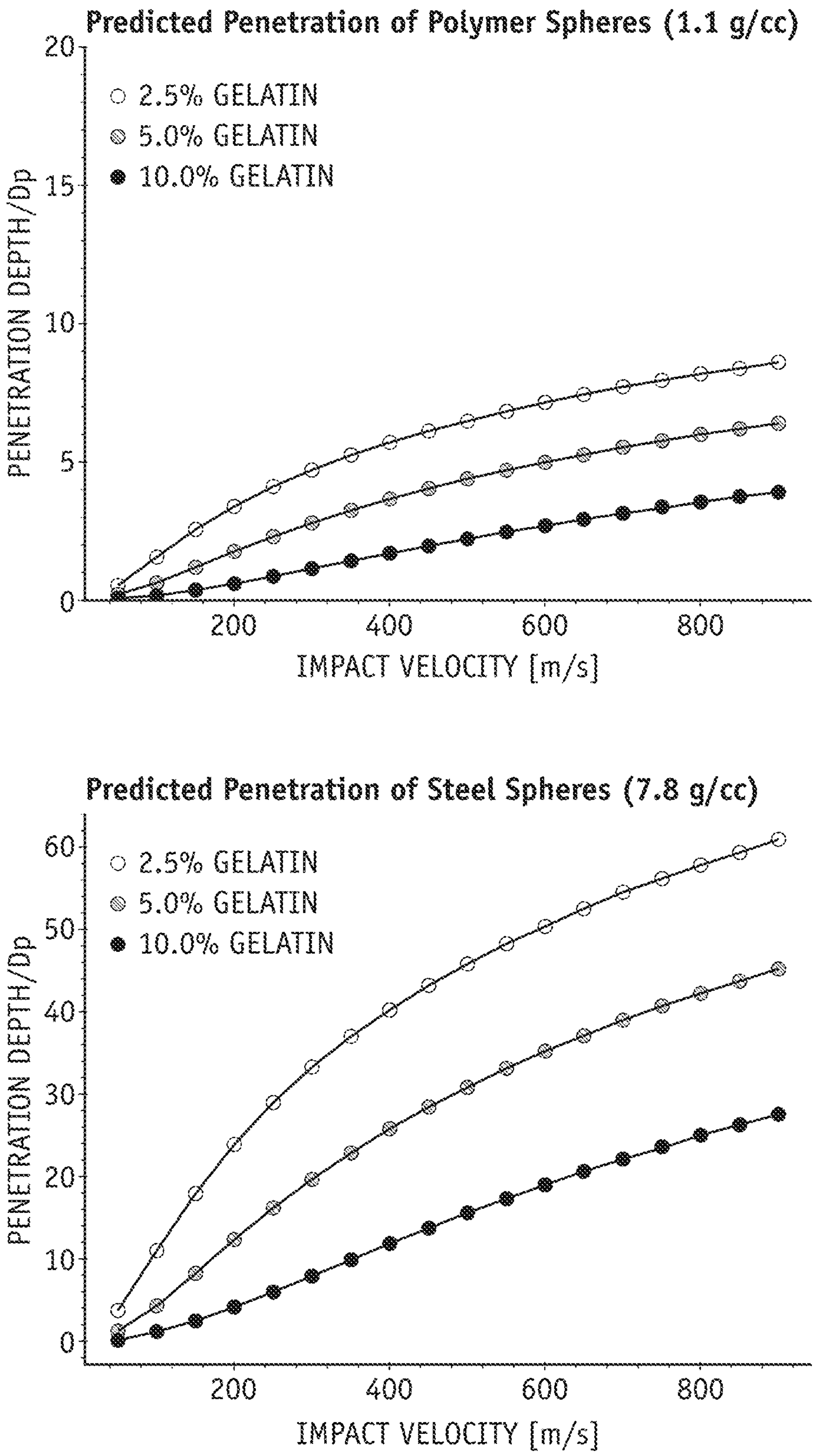

FIG. 46 shows a chart illustrating the penetration depth of two different particle compositions in gelatin predicted by the Poncelét Model. Low density polyethylene in top panel and stainless steel in bottom panel each in 2.5% (upper curve), 5% (middle curve), and 10% (lower curve) w/w ballistic gelatin. Data calculated using resistance parameters and model from Veysset et al.

Figure 47:
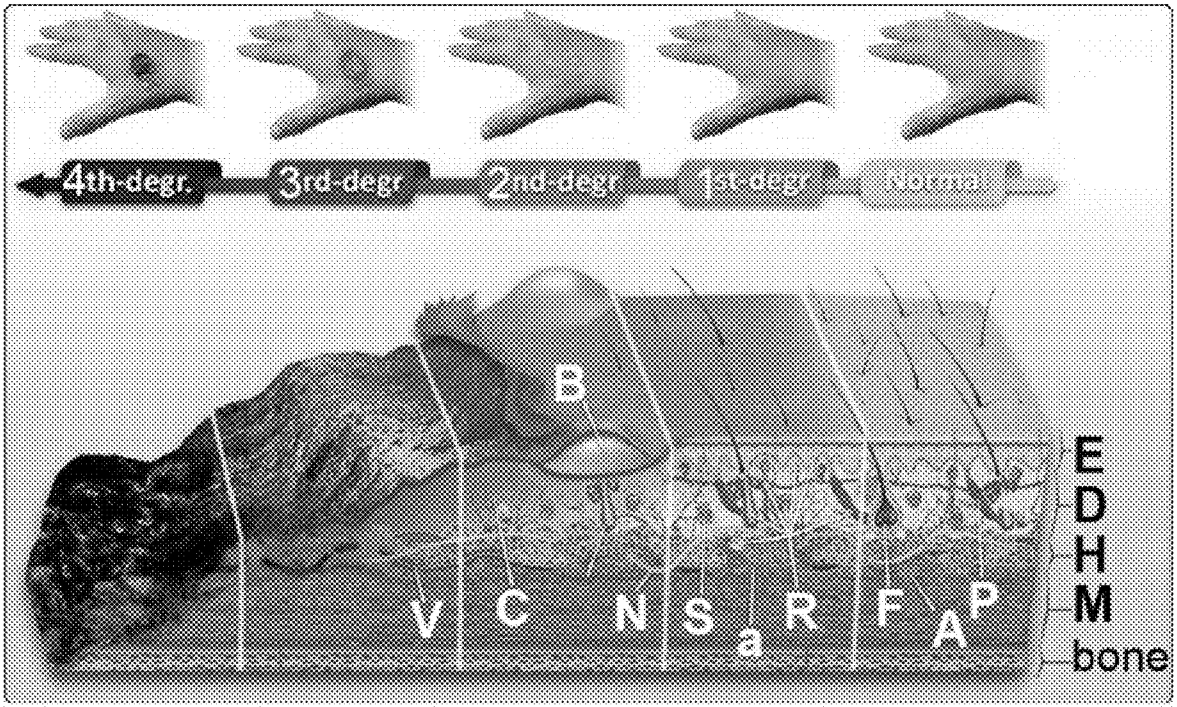

FIG. 47 shows a schematic representation of different types of skin wounds adapted from (Ref https://rnspeak-.com/wp-content/uploads/2018/05/burn-classification-of-injuries.jpg.]

Figure 48A:
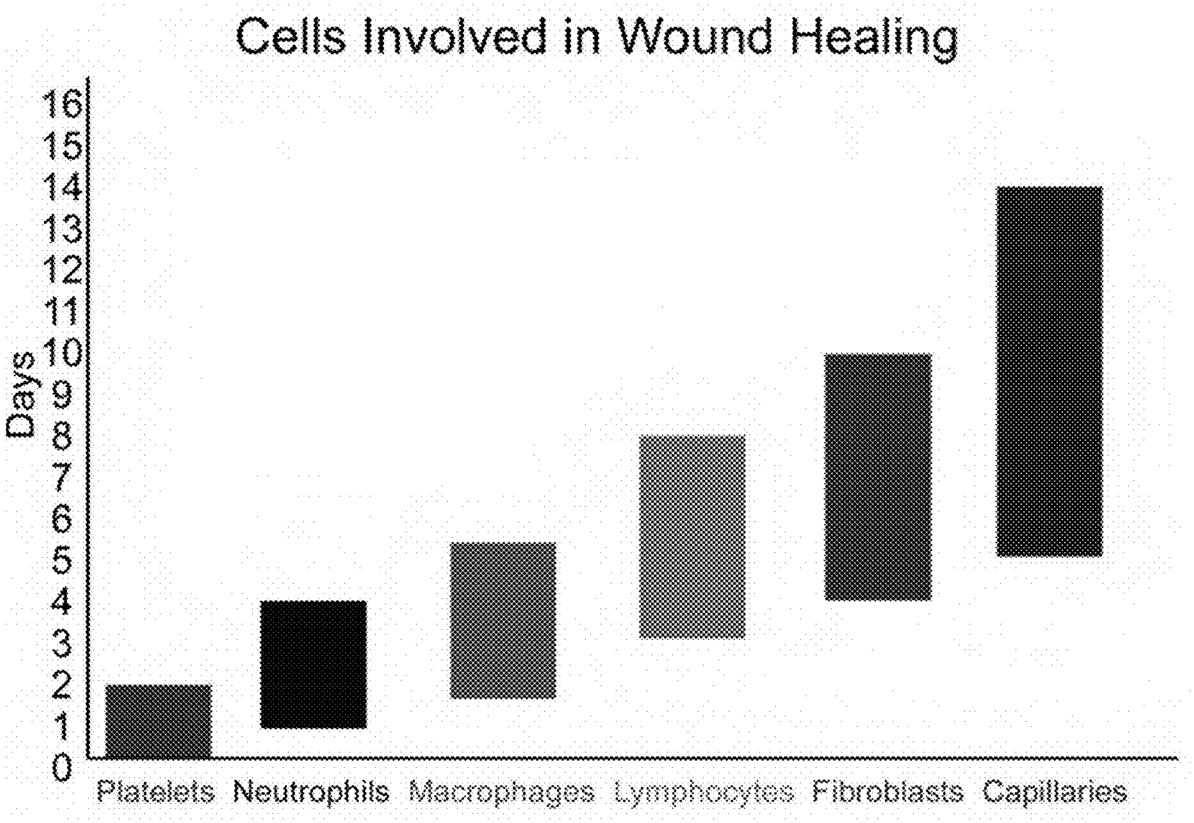
Figure 48B:
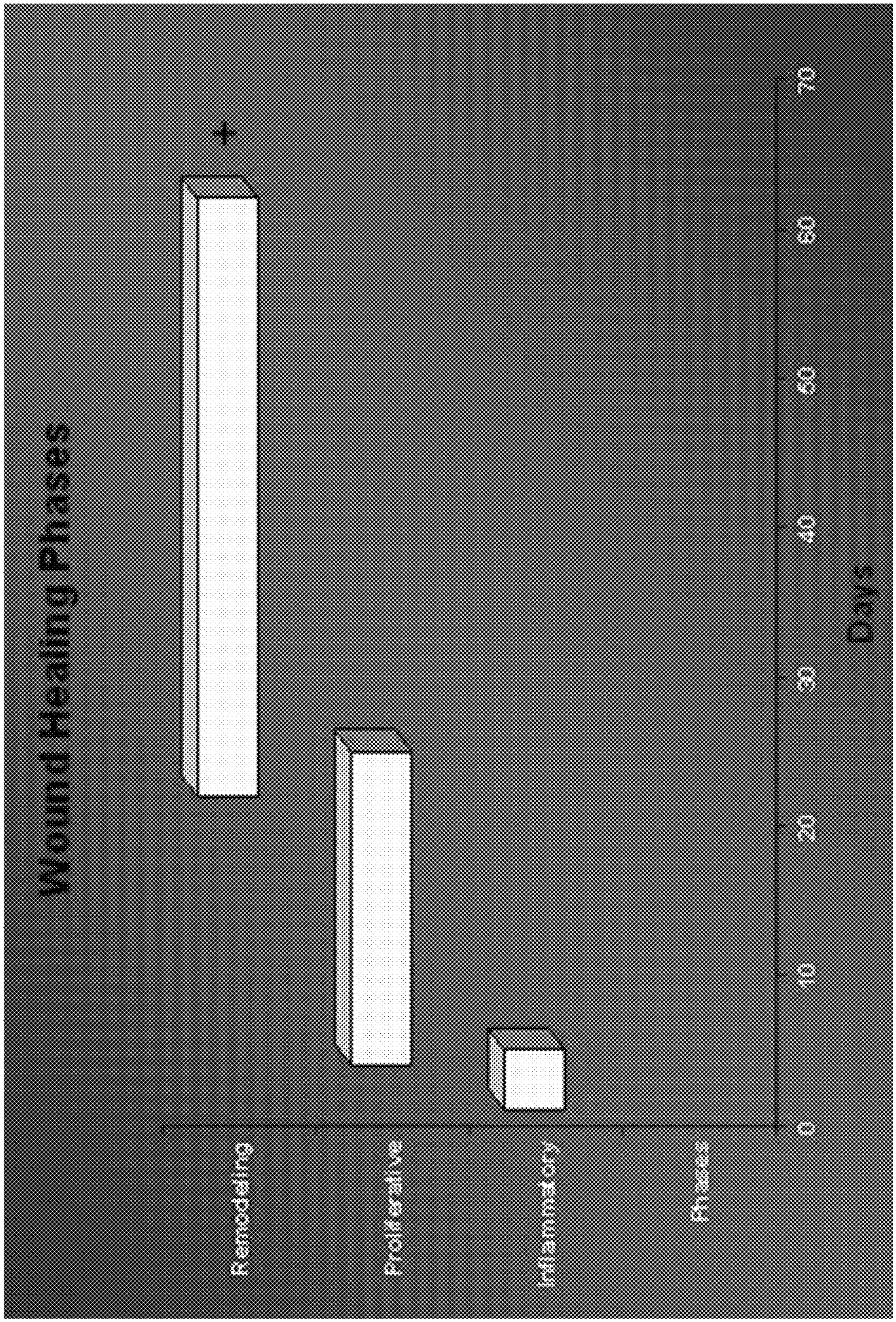

FIG. 48A shows a chart from "Wound healing and growth factors. (Ref https://emedicine.medscape.com/article/1298196-overview?reg=1&icd=login_success_email_match_norm illustrating Cells involved in wound healing. The cells appearing in a wound are depicted in sequence from left to right, and the color bars represent the range of days each cell type is in the wound platelet FIG. 48B shows a chart from the link "Wound healing phase" https://emedicine.medscape.com/article/1298196-overview?reg=1&icd=login_success_email_match_norm at the fling date of the present disclosure, illustrating timing of the various phases of wound healing. in particular the illustration show that the inflammatory phase begins at the time of injury and lasts 2-4 days. The proliferative phase begins on approximately day 3; it overlaps with the inflammatory phase. The remodeling phase including Increased collagen production and breakdown continue for 6 months to 1 year after injury.

Figure 49A:
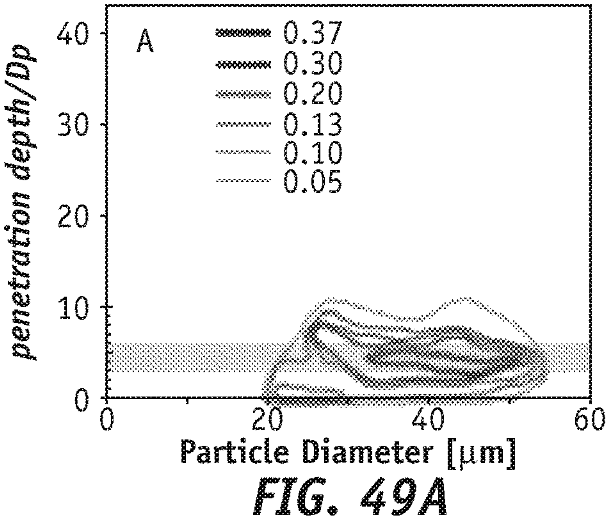

FIG. 49A shows a chart illustrating the results of a first set of exemplary experiments that can be performed in gelatin with particles having dimensions, density and velocity determined with the method and systems and related device of the disclosure.

Figure 49B:
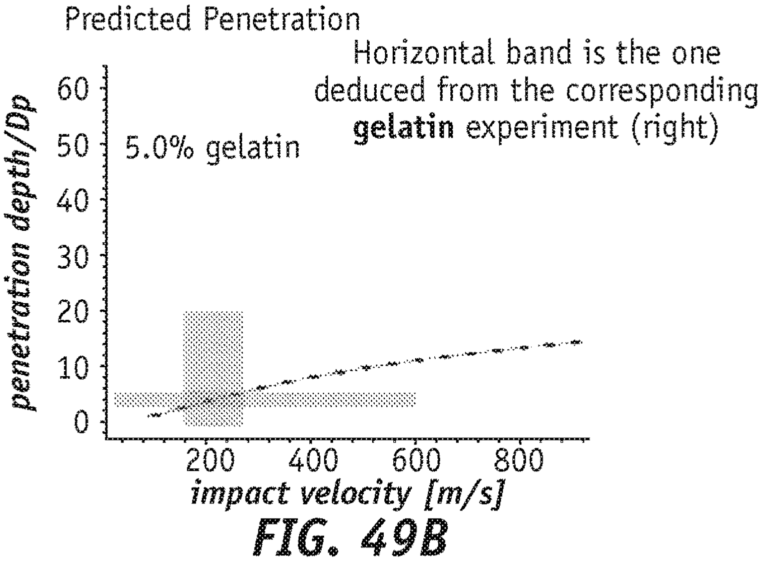

FIG. 49B shows a chart illustrating the results of a second set of exemplary experiments that can be performed in gelatin with particles having dimensions, density and velocity determined with the method and systems and related device of the disclosure.

Figure 49C:
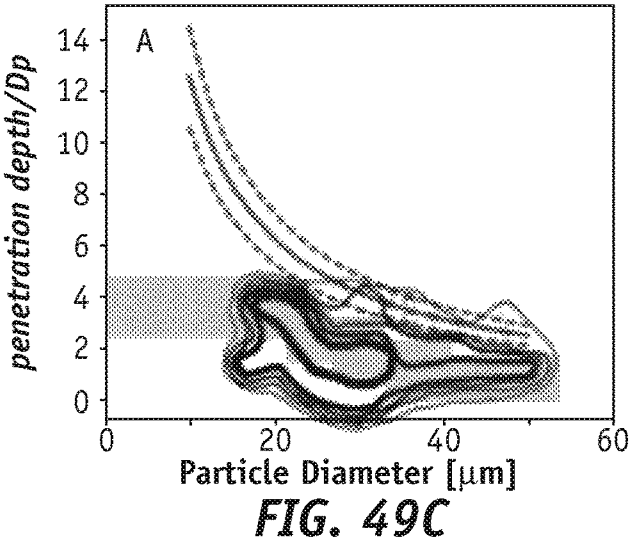
Figure 50:
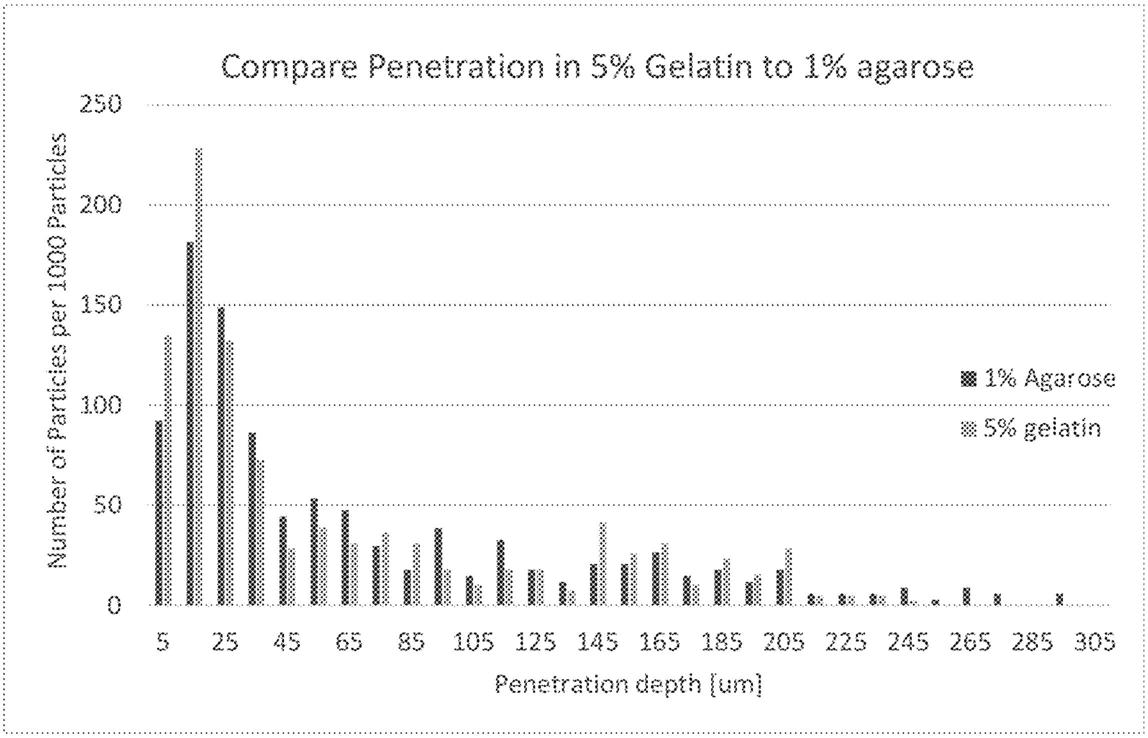

FIG. 49C shows a chart illustrating the results of a third set of exemplary experiments that can be performed in gelatin with particles having dimensions, density and velocity determined with the method and systems and related device of the disclosure FIG. 50 shows a histogram of particle penetration depths on a 1000 particle basis. In particular FIG. 50 shows a histogram of number of particles delivered to a given penetration depth in single layer gels of both 1% agarose (blue) and 5% gelatin (red). For the range up to approximately 220 um, the penetration depths of both are relatively similar. Silver coated soda lime glass particles (2.8 g/cc) with size 5-22 um were delivered using our delivery device with 100 psi Helium air.

Figure 51:
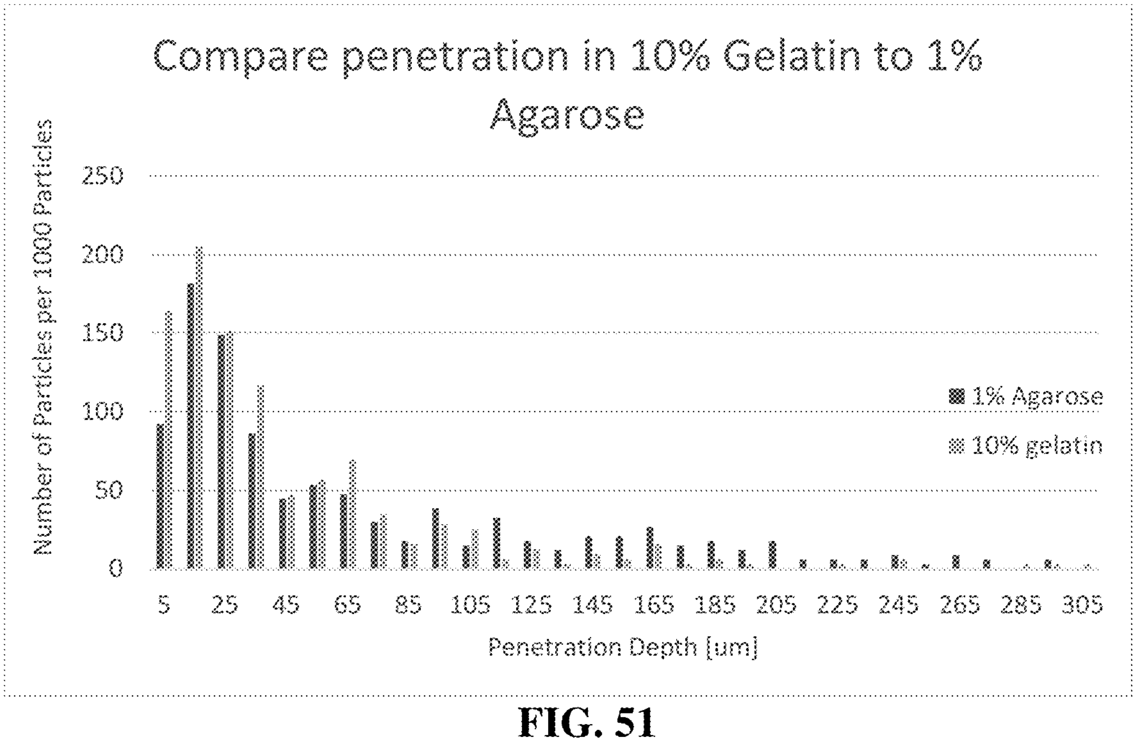

FIG. 51 shows a histogram of particle penetration depths on a 1000 particle basis. In particular, FIG. 51 shows a histogram of number of particles delivered to a given penetration depth in single layer gels of both 1% agarose (blue) and 10% gelatin (red). For shorter ranges, up to approximate 40 um, the 10% gelatin contains far more particles near the surface. In other words, fewer particles have enough penetrating power to reach depths of 100 μm or more. Silver coated soda lime glass particles (2.8 g/cc) with size 5-22 um were delivered using our delivery device with 100 psi Helium air.

Figure 52:
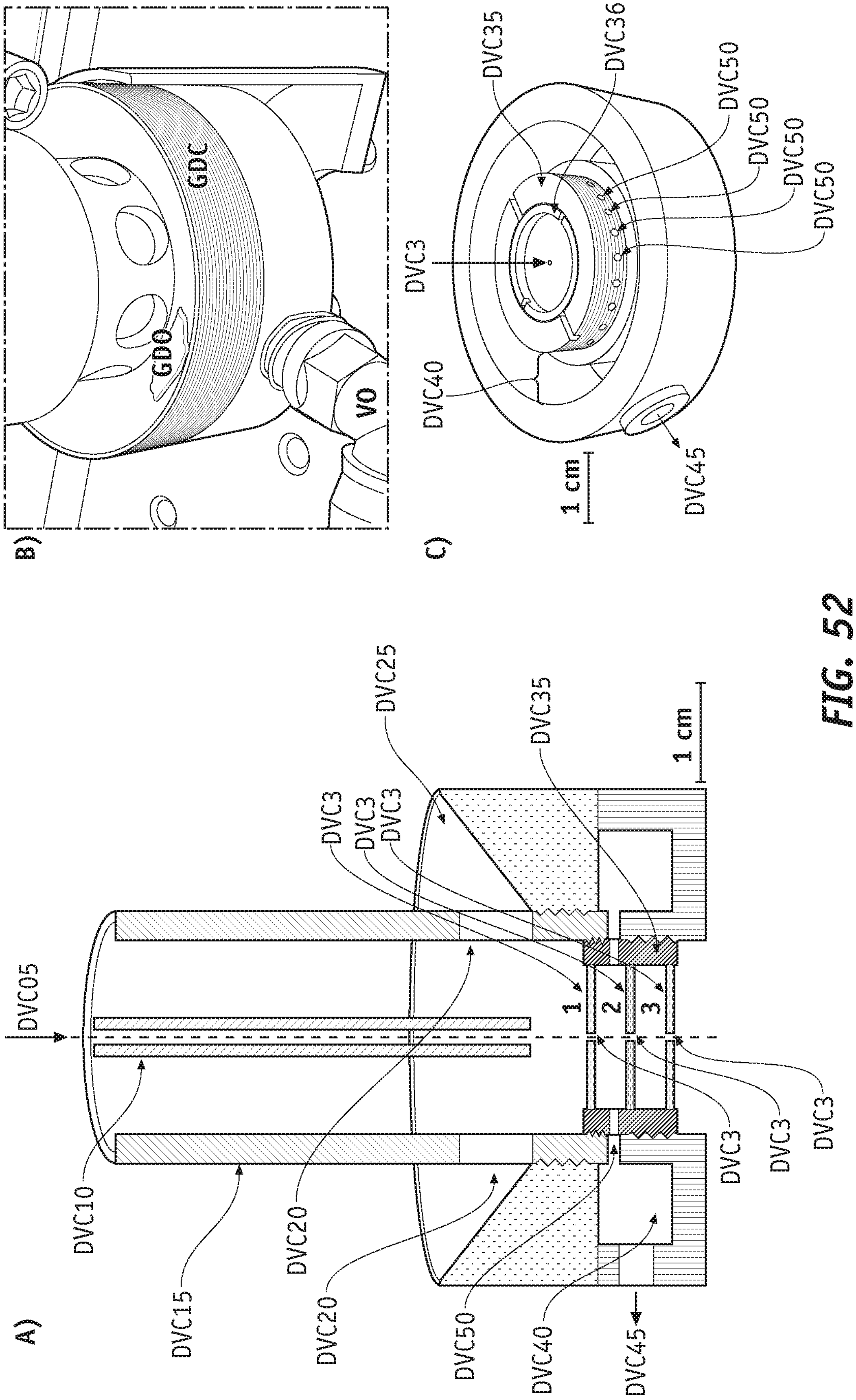
Figure 53:
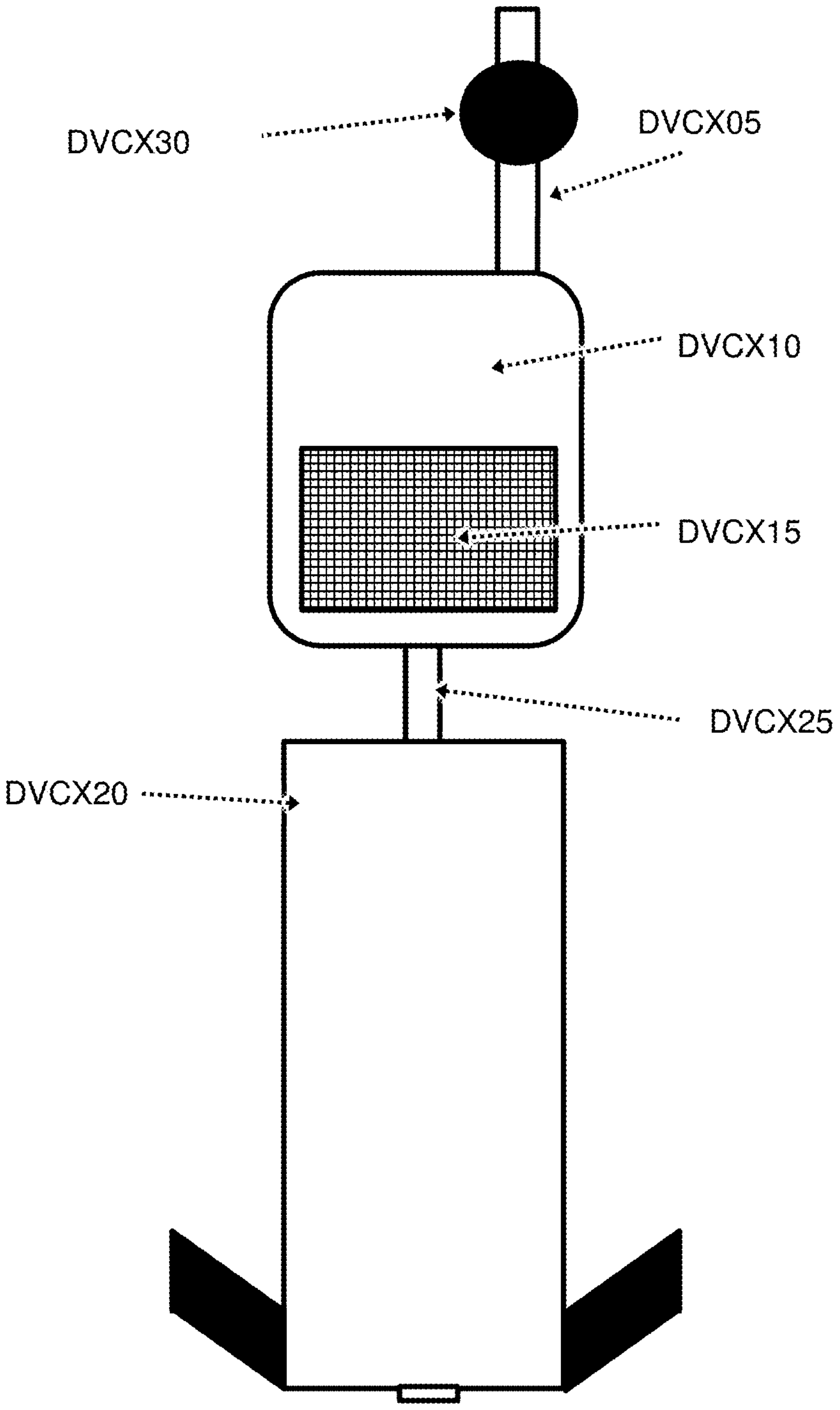
Figure 54:
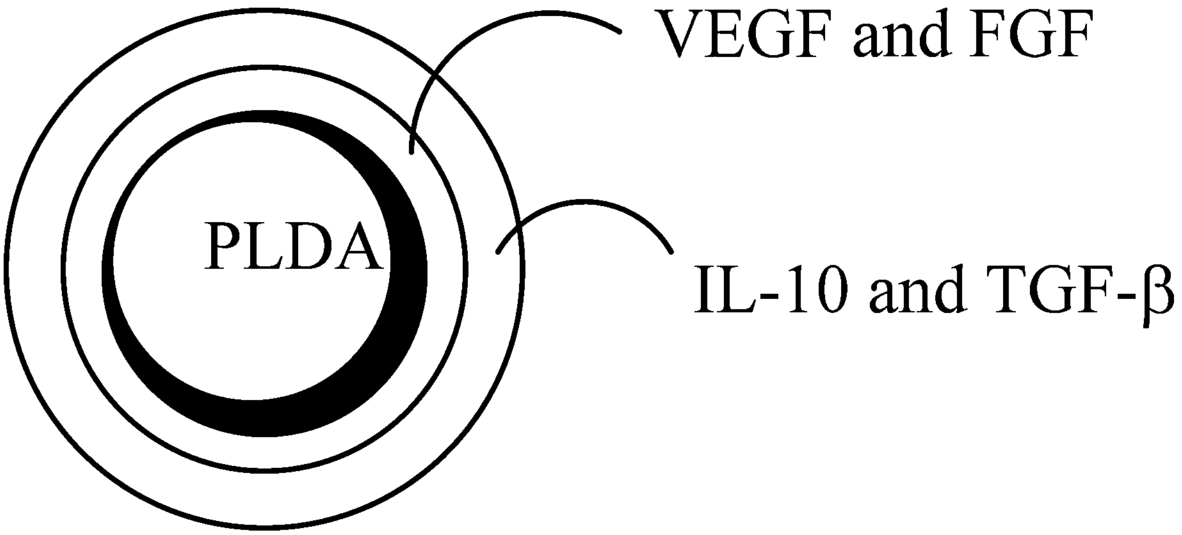

FIG. 52 shows a schematic representation of a ballistic device which can be used in methods and systems of the disclosure FIG. 53 shows a schematic representation of a ballistic device configured for delivery in multilayered tissue which can be used in methods and systems of the disclosure FIG. 54 shows a schematic representation of the structure of particle which can be ballistically delivered with methods, systems and devices of the present disclosure.

DETAILED DESCRIPTION

Provided herein, are methods and systems and related particles and compositions that can be used to deliver a cargo and, in particular, a biologically active cargo such as a drug to a target tissue having a layered heterogeneity, such as the cornea of an individual.

The term "biologically active" is used herein indicate capability to have an effect on or respond to living matter such as an effect on a plant, animal or another microorganism which changes the living matter physiology. Accordingly, the term biologically active identify an item capable of influence the physiology of a living matter. In particular, biologically active molecular entities are capable to have an effect on the living matter following contact with the living matter. Compounds capable of interact with the living matter and microscopic devices that respond to living matter in which they are embedded (e.g. to release a compound and/or transmit information that is needed to appropriately care for the living matter) are examples of biological activity as will be understood by a skilled person. Biological activity is a result of the combined effect of location and concentration of a referenced item as will also be understood by a skilled person. Accordingly a biologically active molecular entity is capable to achieve a defined biological effect of on living matter [4] and the related biological activity can be measured in terms of potency or the concentration of the molecular entity needed to produce the effect [5].

The term "cargo" as used herein indicates a load of materials being transported by a carrier for delivery to a target organ or tissue of an individual. A cargo in the sense of the disclosure comprises any materials that can be configured for delivery in microparticles in the sense of the disclosure and comprise compounds, in which atoms are linked by covalent bonds ionic bonds and/or metallic bonds, as well as material that can be implanted to replace a missing biological structure, support a damaged biological structure, or enhance an existing biological structure. Cargos in the sense of the disclosure can be hydrophilic or hydrophobic, can be electrically charged in all or portions therefore, or have no electrical charge. Cargos in the sense of the disclosure are typically solid at room temperature Exemplary cargo compounds for molecular delivery comprise drugs and genetic material inclusive in this context not only of DNA exogenous to the individual (such as transgenes) but also RNA and/or proteins and additional compounds identifiable by a skilled person. Additional exemplary cargos comprise implants which can interact with the surrounding tissue to provide a detectable effect in the tissue.

The term "drug" as used herein indicated is any substance that causes a change in an organism's physiology (intended as functions and mechanisms in the organism as a living system when contacted with the organism Accordingly a drug is a chemical substance, typically of known structure, which, when administered to a living organism, produces a biological effect and is used to treat, cure, prevent, or diagnose a condition or to promote well-being. Pharmaceutical drugs are often classified into drug classes—groups of related drugs that have similar chemical structures, the same mechanism of action (binding to the same biological target), a related mode of action, and that are used to treat the same disease. Exemplary drugs comprise steroid, antimicrobials and in particular antibiotic and antifungal, as well as additional biologically active cargos as will be understood by a skilled person The term "steroid" as used herein refers to biologically active organic compound having core structure is typically composed of seventeen carbon atoms, bonded in four "fused" rings: three six-member cyclohexane rings (rings A, B and C in the first illustration) and one five-member cyclopentane ring (the D ring), will be understood by a skilled person. Steroids vary by the functional groups attached to this four-ring core and by the oxidation state of the rings. Sterols are forms of steroids with a hydroxy group at position three and a skeleton derived from cholestane. Steroids can also be more radically modified, such as by changes to the ring structure, for example, cutting one of the rings. (Ref. from https://en.wikipedia.org/wiki/Steroid at the fling date of the present disclosure)

The term "antimicrobial" as used herein indicates a substance that kills or inhibits the growth of microorganisms such as bacteria, fungi, or protozoans. Antimicrobial either kills microbes (microbiocidal) or prevent the growth of microbes (microbiostatic).

The term "antibiotics" as used herein refers to a type of antimicrobial used in the treatment and prevention of bacterial infection. Some antibiotics can either kill or inhibit the growth of bacteria. Others can be effective against fungi and protozoans. The term "antibiotics" can be used to refer to any substance used against microbes. Antibiotics are commonly classified based on their mechanism of action, chemical structure, or spectrum of activity. Most antibiotics target bacterial functions or growth processes. Antibiotics having bactericidal activities target the bacterial cell wall, such as penicillins and cephalosporins, or target the cell membrane, such as polymyxins, or interfere with essential bacterial enzymes, such as rifamycins, lipiarmycins, quinolones and sulfonamides. Antibiotics having bacteriostatic properties target protein synthesis, such as macrolides, lincosamides and tetracyclines. Antibiotics can be further categorized based on their target specificity. "Narrow-spectrum" antibacterial antibiotics target specific types of bacteria, such as Gram-negative or Gram-positive bacteria. "Broad-spectrum" antibiotics affect a wide range of bacteria The term "antifungal" as used herein refers to an antimicrobial used to treat and prevent mycosis such as athlete's foot, ringworm, candidiasis (thrush), serious systemic infections such as cryptococcal meningitis.

The term "corticoid" or "corticosteroid" refers to a steroid produced in the adrenal cortex of vertebrates, as well as the synthetic analogues of those natural steroid hormones. Exemplary corticosteroid in the particle as described herein includes cortisone, hydrocortisone, fludrocortisone acetate, prednisolone, prednisone, methylprednisolone, triamcinolone, Dexamethasone Sodium phosphate (Decadron™), betamethasone, triamcinolone acetonide, and fluorometholone. Glucocorticosteroids inhibit prostaglandin, bradykinin, histamine and leukotrienes production thereby decreasing inflammation.

Exemplary additional biologically active cargos, comprise NSAID and growth factors.

The term "non-steroid anti-inflammatory drug" or "NSAID" refers to an active agent or a biologically active cargo which is a class of compounds that are free of any steroid moieties yet are capable of providing anti-inflammatory effects. Exemplary NSAIDs in the particle as described herein includes Celebrex™ (that is celecoxib), refecoxib (commonly known as Vioxx™), etoricoxib, valdecoxib, parecoxib, aspirin, diflunisal, ibuprofen, dexibuprofen, naproxen, fenoprofen, ketoprofen, indomethacin, tolmetin, diclofenac, sulindac, etodolac, ketorolac, piroxicam, meloxicam, tenoxicam, droxicam, mefenanmic acid, meclofenanmic acid, clonixin, and licofelone.

The term "Cox inhibitor" refers to NSAID which blocks the action of, cyclooxygenase-1, and/or cyclooxygenase-2. Exemplary Cox inhibitor in the particle as described herein includes Celebrex™ (that is celecoxib), refecoxib (commonly known as Vioxx™), etoricoxib, valdecoxib, parecoxib, aspirin, diflunisal, ibuprofen, dexibuprofen, naproxen, fenoprofen, ketoprofen, indomethacin, tolmetin, diclofenac, sulindac, etodolac, ketorolac, piroxicam, mobic (meloxicam), tenoxicam, droxicam, mefenanmic acid, meclofenanmic acid, clonixin, licofelone, and paracetamol (acetaminophen).

The wording "growth factor" in the sense of the disclosure indicates a substance capable of stimulating cell proliferation, wound healing, and/or cellular differentiation and/or cellular processes as will be understood by a skilled person. Generally a growth factor includes a secreted protein or a steroid hormone produced by an individual. Exemplary growth factors that can be included in the particles of the disclosure include Endothelial Growth Factor (EGF), Transforming Growth Factor (TGF), TGF-β1, TGF-β3, Fibroblast Growth Factor (FGF), Platelet-Derived Growth Factor (PDGF), elastin-like peptide (ELP), keratinocyte GF (KGF), Vascular Endothelial Growth Factor (VEGF), Interleukins (IL), IL-10, EGF-like growth factor, ELP-KGF, ELP-ARA290, Substance-P, granulocyte colony-stimulating factor (G-CSF), and stromal cell-derived factor-1 (SDF-1).

The term. "implant" as used herein indicates medical implants manufactured to replace a missing biological structure, support a damaged biological structure, or enhance an existing biological structure. An exemplary, biologically active microscopic device can transduce chemical changes in the living matter, such as changes in the concentrations of dissolved gases such as oxygen or carbon dioxide, changes in concentrations of metabolites such as glucose or lactic acid. and/or a change in concentrations biological signals such as a hormone or a cytokine. Additionally exemplary biologically active implants, comprise microscopic devices that can transduce physical and/or chemical changes in the living matter. In particular physical changes comprise changes in temperature or pH or osmolarity as will be understood by a skilled person. For example, a biologically active microscopic device can wirelessly transmit information to a monitoring system that guides appropriate action to care for the living matter. A biologically active microscopic device can autonomously respond to take a desired action based on the change in conditions of the living matter. In some cases, the spatial arrangement of a plurality of microscopic devices can provide important details regarding changes in the living matter as will be understood by a skilled person.

In methods and systems of the disclosure biologically active cargos can be provided within a convex particle alone or in combination with combined with a carrier material.

The term "carrier material" as used herein indicates any material that can be combined with a biologically active cargo in the sense of the disclosure to improve the selectivity, effectiveness, and/or safety of the cargo administration to an individual. Suitable carrier materials comprise polymers, glass, metal and alloys as well as additional material identifiable by a skilled person.

The term a "polymer" as used herein indicates molecule whose structure is composed of multiple repeating units. Polymers in the sense of the disclosure can be organic or inorganic, synthetic or naturally occurring as will be understood by a skilled person. Exemplary polymers comprise synthetic plastics such as polystyrene to natural biopolymers such as polysaccharide and proteins. Polymers, both natural and synthetic, are created via polymerization of many small molecules, known as monomers. Their consequently large molecular mass, relative to small molecule compounds, produces unique physical properties including toughness, high elasticity, viscoelasticity, and a tendency to form amorphous and semicrystalline structures rather than crystal as will be understood by a skilled person (Ref. https://en.wikipedia.org/wiki/Polymer)

The term "glass" refers to a any non-crystalline (amorphous) solid that has a density of at least 1 g/cc and that exhibits a glass transition at a temperature of at least 100° C. when heated towards the liquid state. Although the atomic-scale structure of glass shares characteristics of the structure of a supercooled liquid, glass exhibits all the mechanical properties of a solid. As in other amorphous solids, the atomic structure of a glass lacks the long-range periodicity observed in crystalline solids. Due to chemical bonding constraints, glasses do possess a high degree of short-range order with respect to local atomic polyhedra. Glass can be formed by rapid cooling (quenching) of the molten form. Exemplary glass includes soda-lime glass, borosilicate glass, and barium titanate glass. Glass can be made porous to provide cavities for holding a drug as described herein. Porous glasses having an average pore size (diameter) of 40 to 200 Å can be generated by an acidic extraction of phase separated alkaliborosilica glasses, or by a sol-gel-process. By regulating the manufacturing parameters, it is possible to produce a porous glass with a pore size of between 0.4 and 1000 nm in a very narrow pore size distribution. (Ref. https://en.wikipedia.org/wiki/Porous_glass).

The wording "carrier metal" as used herein refers to a any solid metal in the periodic table that is substantially stable in water under ambient or physiological conditions. The term "Periodic Table" refers to the version of IUPAC Periodic Table of the Elements dated Jun. 22, 2007, and the numbering scheme for the Periodic Table Groups is as described in Chemical and Engineering News, 63(5), 27 (1985).

In some embodiments, the particle as described comprise a bio-derived material or a synthetic material as carrier for an active agent. Exemplary bio-derived materials include but is not limited to gelatin-based hydrogels, alginic acid, hyaluronic acid, photo-crosslinked alginic acid, photo-crosslinked hyaluronic acid and chitosan. Exemplary synthetic materials include but is not limited to Poly(D,L-lactic acid) (PDLLA), Poly(L-lactic acid) (PLLA), Poly(D-lactic acid) (PDLA), poly(lactic-co-glycolic acid) (PLGA), Polycaprolactone (PCL), poly-3-hydroxybutyrate (P3HB), poly-4-hydroxybutyrate (P4HB), polyhydroxyvalerate (PHV), polyhydroxyhexanoate (PHH), and polyhydroxyoctanoate (PHO).

As used herein, the term "alloy" refers to a metal alloy and in particular to any solid metallic particle comprising at least two metal elements in the periodic table that is substantially stable in water under ambient or physiological conditions.

Alloy carrier material of the present disclosure includes be any alloy that is biologically compatible. In some embodiments, alloy of the particles as described herein includes at least two of the metal elements select from the group comprising aluminum, titanium, vanadium, chromium, iron, nickel, copper, zinc, tungsten, lead, silver, gold, and platinum and optionally nonmetallic elements such as carbon and silicon. Examples of alloys include red gold (gold and copper) white gold (gold and silver), sterling silver (silver and copper), steel (containing carbon) or silicon steel (containing silicon).

In some embodiments, the biologically active cargo can be delivered in absence of any carrier materials. In those embodiments, the cargo has a density higher than the density of the target region where the cargo is to be delivered with methods and systems of the disclosure (e.g. about 1 g/cc if the target layer is a layer of the cornea), Exemplary cargos that can be delivered without carrier material can be identified by a skilled person upon reading of the present disclosure.

In some embodiments where the cargo has a density lower than the target layer where the cargo is to be delivered with methods and systems of the disclosure, the active cargo can be delivered in combination with any carrier materials In some embodiments, the cargo can be formulated with a polymer carrier to form the microparticles. In general, carrier polymer for the microparticle as described herein are pharmaceutically acceptable and/or biodegradable.

In some embodiments, the carrier polymer for the microparticle as described can be represented by Formula (I):

$$[B_1\text{-}co\text{-}(B_2)_{b2} \ldots co\text{-}(B_m)_{bm}][X_1]_{r1} \ldots [X_p]_{rp} \quad (I)$$

in which

- $B_1$ to $B_m$ each refers to a block polymer moiety which are copolymerized to form copolymer $B_1$-co-$B_2$ . . . co-$B_m$, wherein m ranges from 1 to 9,
- b2 to bm each refers to a molar fractional number of block polymer moiety B2 to Bm relative to B1, wherein b2 to bm are each equal to or less than 1 and a sum of b2 to bm is equal to or less than 5,
- $X_1$ to $X_p$ each refers to a cross-linker moiety, each of which cross-links at least two polymer moieties,
- r1 to rp each refers a molar fractional number of cross-linker $L_1$ to $L_p$ per block copolymer $[B_1\text{-co-}(B_2)_{b2} \ldots \text{co-}(B_m)_{bm}]$, wherein a sum of r1 to rp is equal to or less than 0.5,
- wherein the molecular weight of the carrier particle ranges from 5000 Daltons to 5,000,000 Daltons.

In some embodiments, a polymer of Formula (I) includes poly-N-2-dimethylamino ethyl-methacrylamide (PDMAEMAm), poly-N-2-dimethylamino ethyl-acrylamide (PDMAEAAm), poly-N-2-dimethylamino ethyl-methacrylate (PDMAEMA), poly-N-2-dimethylamino ethylacrylate (PDMAEA), poly methacrylamide (PMAAm), poly N,N-dimethyl methacrylamide (PDMMAAm), polymethyl methacrylate (PMMA), polyacrylamide (PAAm), polyacrylic acid (PAA), poly dimethylaminoethylmethacrylate (PDEAEMA), polyisopropylacrylamide (PNIPAAm), poly(N-isopropyl-3-butenamide) (PNIPBAm), alpha-aminoomegamethyl-poly ethylene glycol (AMPEG), poly (epsilon-caprolactone-co-lactide-polyethylene glycol) copolymer, cross-linked copolymers of polyethyleneglycol and methyacrylic acid, block copolymer poly(methacrylic acid-co-ethylene glycol), block copolymer poly(2-hydroxythyl methacrylate-co-N,N-dimethylaminoethyl methacrylate), poly(hydroxyethyl methacrylamide) (poly-HEMAm), copolymer poly(HEMA-co-DMAEMA) poly(hydroxylethyl methacrylate-co-N,N-dimethylaminoethylmethacrylate), copolymer of gelatin and PVA (polyvinyl alcohol), copolymer of poly-PNIPA and poly-PNIPA-Co-AA (poly N-isopropyl acrylamide and poly N-isopropyl acrylamide-co-acrylic acid), poly organophosphazene with a-amino omegamethylpolyethylene glycol, polyepsilon caprolactone-co-lactide-polyethylene glycol, poly(NIPAAm-co-AAm) (N-isopropylacrylamide-co-acrylamide), poly (methacrylamide-co-N-vinyl-2-pyrrolidone-co-itaconic acid), poly(2-(N-ethylperfluorooctanesulfonamido)ethylacrylate), a cross-linked polymer thereof or a cross-linked any combination of polymers thereof.

In some embodiments, when the carrier polymer of Formula (I) does not contain copolymer moiety and crosslinker moiety, the carrier polymer of Formula (I) as described herein can be reduced to a homopolymer and can be represented by Formula (II):

$$-[M]_n- \quad (II)$$

wherein M is a monomeric moiety, n is the degree of polymerization ranging from 50 to 500,000, M is a monomeric moiety formed by a polymerized monomer.

In some embodiments, a polymer of Formula (II) includes poly(N-vinylpyrrolidone), poly(acrylic acid), poly(methacrylic acid), poly(2-hydroxyethyl methacrylate), poly(2-hydroxyethyl methacrylic acid), poly(2-hydroxypropyl methacrylate), poly(2-ethyl-2-oxazoline), polymethacrylamide, polyacrylamide, poly(N-iso-propylacrylamide), poly (2-vinylpyridine), poly(2-vinylpyridine N-oxide), poly(4-vinylpyridine), poly(2-vinylpyridine N-oxide), poly(2-vinyl-1-methylpyridinium bromide), poly(ethylene oxide), poly(propylene oxide), poly(styrenesulfonic acid), poly(styrenesulfonate sodium), poly(vinylsulfonic acid), poly(vinylsulfonate sodium), poly(vinyl phosphoric acid), poly (vinyl phosphorate sodium), poly(vinyl alcohol), poly(allyl amine), poly(2-methacryloxyethyltrimethylammonium bromide), poly(N-vinylpyrrolidone), poly(vinyl acetate) or any one of combinations thereof.

In some embodiments, the monomeric moiety M contains a chemical bond that is hydrolysable under biological environment and thus the polymer is biodegradable. In such biodegradable polymer, the monomeric moiety contains an amide bond (—CO—NH—), carboxylic ester bond (—CO—O—), or an ether or a glycosidic bond (—O—).

In some embodiments, the carrier polymer is selected from the group consisting of poly(ethylene glycol) (PEG), poly(D-lactic acid) (PDLA), poly(L-lactic acid) (PLLA), poly(D-lactic acid-co-L-lactic acid) (PDLLA) and poly(ethylene glycol), polyglycolic acid (PGA) or any combination thereof.

In some embodiments, the carrier polymer comprises poly(D-lactic acid-co-L-lactic acid) (PDLLA) wherein the molar ratio of D-lactic acid to L-lactic acid moieties ranges from 10:1 to 1:10.

In some embodiments, the carrier polymer comprises poly(L-lactic acid) (PLLA) and/or poly(D-lactic acid) (PDLA/PLLA).

In some embodiments, the carrier polymer comprises poly(L-lactic acid) (PLLA) and poly(D-lactic acid) (PDLA) wherein the poly(L-lactic acid) (PLLA) and poly(D-lactic acid) (PDLA) has a weight ratio of 10:1 to 1:10.

In some embodiments, the carrier polymer comprises poly(L-lactide-co-caprolactone) of Formula (IXa), wherein m and n each ranges from 50 to 50,000, optionally the ratio of m to n ranges from 10:1 to 1:10.

Formula (IXa)

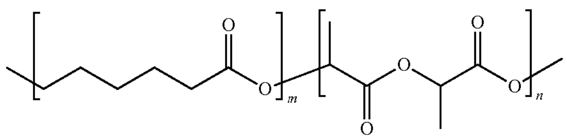

In some embodiments, the carrier polymer comprises poly(D-lactide-co-caprolactone) of Formula (IXb), wherein m and n each ranges from 50 to 50,000, optionally the ratio of m to n ranges from 10:1 to 1:10.

Formula (IXb)

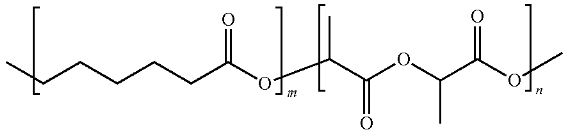

In some embodiments, the microparticle as described herein further comprise additive, wherein the additive facilitates crosslinking of collagen fibrils.

In some embodiments, the microparticle as described herein further comprise additive, wherein the additive comprises copper (II) ion.

The term "monoscaccharide" refers to a carbohydrate unit that is not decomposable into simpler carbohydrate units by hydrolysis, is classed as either an aldose or ketose, and contains one or more hydroxyl groups per molecule. Exemplary monosaccharides comprise glucose, fructose, or ribose. Additionally, exemplary amino monosaccharide includes but is not limited to N-acetylglucosamine, sialic acids such as neuraminic acid, D-galactosamine. Monosacchardides can occur naturally or be chemically synthesized. Monosaccharide monomers can be bound one to another by glycosidic bond which can be an alpha or a beta glycosidic bond. For example, cellobiose, Formula (Xa), consists of two glucose moieties linked by a beta (1→4) glycosidic bond.

Formula (Xa)

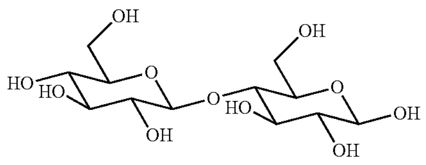

In another example, alpha-maltose, Formula (Xb) consists of two glucose moieties linked by an alpha (1→4) glycosidic bond.

Formula (Xb)

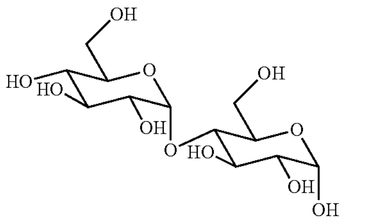

In some embodiments, a polymer includes at least two monosaccharide moieties linked by at least one glycosidic bond. Exemplary neutral monosaccharide includes but is not limited to D-glucose, D-mannose, D-galactose, D-xylose, D-apiose, L-rhamnose, D-galactose, D-fructose, L-fucose, D-ribose, and L-arabinose. Exemplary carboxylic acid monosaccharide includes but is not limited to L-iduronic acid, 2-O-sulfo-L-iduronic acid (IdoA2S), D-glucopyranuronic acid, D-galacturonic acid.

In some embodiments, biodegradable polysaccharides for the microparticle composition includes cellulose acetate phthalate (CAP) agarose, amylose, chitin, chitosan, any of the derivative thereof, or any of the combinations thereof, wherein n ranges from 10 to 1,000.

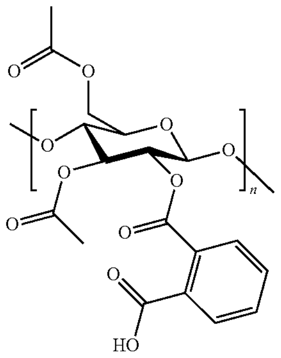

Cellulose acetate phthalate (CAP)

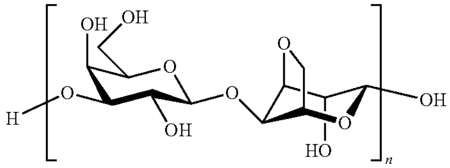

Agarose

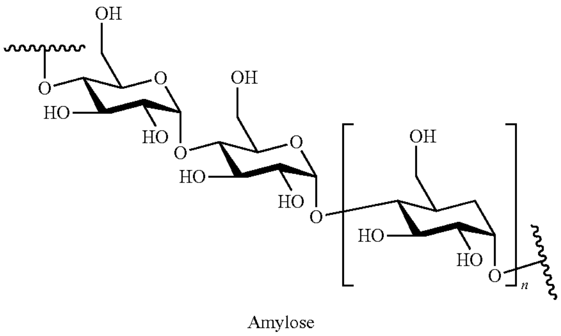

Amylose

-continued

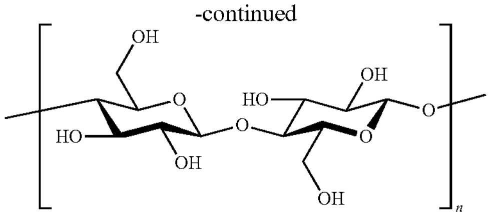

Cellulose

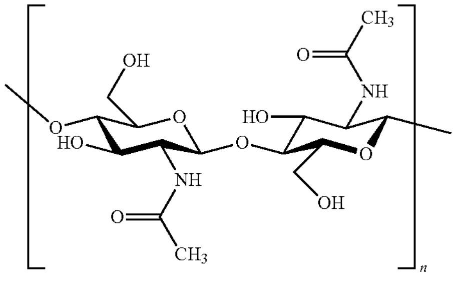

Chitin

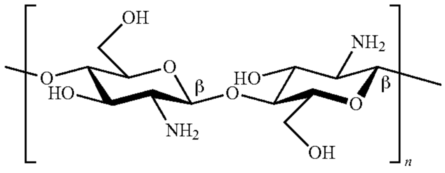

Chitosan

In embodiments where the carrier material comprises a polymer carrier material, a microparticle can be formed by mixing the cargo with the carrier in a suspension or a solution of a solvent. The mixture can be aerosolized to form small droplets, for example, through a pinhole of a vibrating orifice aerosol generator. Evaporation of solvent provides the microparticle with the cargo.

In some embodiments, a carrier can be selected from one of the group comprising hydrogel, nanofiber, biofilm, fibrin matrix, collagen matrix, lyotropic liquid crystal, and cryogel.

In some embodiments, the carrier material can comprise a glass carrier be prepared in microparticle form. In particular suitable glass carrier comprise silicate glasses based on the chemical compound silica (silicon dioxide, or quartz), such as borosilicate glasses, and silica-free glasses as will be understood by a skilled person. Suitable glasses can be porous glass includes pores, usually in the nanometer- or micrometer-range, Exemplary glasses can comprise SiO2 and/or B2O3, Soda-Lime glass and barium titanate glass.

In embodiments wherein the carrier material comprises a glass carrier, a cargo can be dissolved in a suitable solvent. The drug cargo solution can then be mixed with a porous glass of 1 to 100 microns, preferably 10 to 50 microns, and fills the cavity of the porous glass with the solution. Evaporation of the solvent leaves the drug in the cavity having an average pore size (diameter) of 40 to 200 Å and provides a glass microparticle comprising a cargo. Additional methods to prepare a microparticle identifiable by a skilled person.

A microparticle as described herein can have a porosity ranging from 1% to 50%, or 5 to 20%. A porosity as used herein refers to the volume of the pores relative to the total volume of the particle. In some embodiments, the pore in the microparticle are open pores. Open pores in a particle are fluidically connected to the environment of the particle such as solvents and tissue where the particle embeds.

In embodiments wherein the carrier material comprises a carrier of alloy as described herein, a cargo can be dissolved in a suitable solvent. The drug cargo solution can then be mixed with a porous alloy particle of 1 to 100 microns, preferably 10 to 50 microns, and fills the cavity of the porous alloy particle with the solution. Evaporation of the solvent leaves the drug in the cavity having an average pore size (diameter) of 40 to 200 Å and provides a glass microparticle comprising a cargo. Additional methods to prepare a microparticle identifiable by a skilled person.

In some embodiment, a carrier glass can comprise any one of soda-lime glass, borosilicate glass, aluminosilicate glass. In some embodiment, the carrier glass can have a spherical shape having a diameter of 5 to 30 μm. In some embodiments, the carrier glass can be porous having an average pore size (diameter) of 40 to 200 Å, preferably 80 to 150 Å. The porosity of the glass can be used in connection with the loading of the cargo and in particular to increase loading of on or more cargos loaded on a particle.

In some embodiment, a glass microsphere can be formed using $SiO_2$ and $B_2O_3$ that can contain up to 45% porosity. The porosity makes the material suitable to include cargos and accordingly these "thirsty glass" materials can be made to carry drug of interest. Due to the density of $SiO_2$ (2.65 g/$cm^3$), these carriers can be considered particles of interest for ballistic drug delivery applications. (Ref: https://mo-sci.com/products/porous-silica/). Aspherical porous silica has already been demonstrated as a highly effective ballistic drug delivery carrier (Ref https://www.nature.com/articles/srep02499).

In some embodiment, fiber glass waste was subjected to alkali activation in an aqueous solution with different concentrations of sodium/potassium hydroxide. The activated materials were fed into a methane-oxygen flame with a temperature of around 1600° C. Pore formation was favored by using highly concentrated activating alkali solutions to produce porous glass microparticle. (Ref Mokhtar Mahmoud et al. Materials 2022, 15(3), 1043; https://doi.org/10.3390/ma15031043)

In some embodiments, the carrier material can comprise a carrier metal. In particular, in some embodiments, a carrier metal can be a transition metal including Group 3 to Group 12 elements. In some embodiments, a carrier metal can be a main group metal including metal elements in Group 13 to Group 14.

In some embodiments, a metal elemental can be made porous, for example, by space-holder method. In these methods, a metal microparticle is made to contain a filler material in the powder form. Ammonium bicarbonate particles for example can be used as the space holders. The ammonium bicarbonate particles can be removed by decomposition at a temperature below 200° C. to produce a porous metal microparticle.

In some embodiments, porous metal microparticles having an average pore size (diameter) of 40 to 200 Å can be generated by space-holder method.

In embodiments wherein the microparticle comprise a carrier metal or alloy, a cargo as described in can dissolved in a suitable solvent. The cargo solution is then mixed with a porous metal microparticle of 5 to 30 μm in diameter and fills the cavity of the porous glass with the solution. Evaporation of the solvent leaves the drug in the cavity having an average pore size (diameter) of 40 to 200 Å and provides a metal microparticle comprising a drug cargo.

In some embodiment, a carrier metal can comprise to any one of metal titanium, iron, copper, silver, gold, tungsten. In some embodiment, the carrier metal can have a spherical shape having a diameter of 5 to 30 μm. In some embodiments, the carrier metal can be porous having an average pore size (diameter) of 40 to 200 Å, preferably 80 to 150 Å. Similarly, to what indicated for glass carriers the porosity of the metal can be used in connection with the loading of the cargo and in particular to increase loading of one or more cargos loaded on a particle according to the disclosure.

In some embodiment, a metal carrier can be or comprise a metal oxide which can comprise iron oxide Fe3O4. In some embodiment, the carrier metal oxide can have a spherical shape having a diameter of 5 to 30 μm. In some embodiments, the carrier metal oxide can be porous having an average pore size (diameter) of 40 to 200 Å, preferably 80 to 150 Å. The porosity of the metal oxide can be used to provide particles with a set density and loading amount of a desired cargo.

In some embodiment, a metal carrier can be or comprise tungsten and tungsten carbide microspheres can be prepared with hollow or porous morphologies, and can be used as a carrier material in connection with providing microparticles with high densities (over 7.8 g/cc) (Ref https://pubs.acs.org/doi/10.1021/acsomega.8b03449

In some embodiments the carrier material can comprise a carrier alloy. In particular in some embodiments, a carrier metal alloy comprises at least a transition metal including Group 3 to Group 12 elements. In some embodiments, a carrier metal alloy comprises at least a main group metal including metal elements in Group 1, Group 2, Group 13 or Group 14. In some embodiments, a carrier metal alloy comprises at least a transition metal including Group 3 to Group 12 elements and at least one main group metal element in Group 1, Group 2, Group 13 or Group 14.

In some embodiments, metal alloy microparticles can be made porous, for example, by space-holder method. In these methods, a metal alloy microparticle is made to contain a filler material in the powder form. Ammonium bicarbonate particles for example can be used as the space holders. The ammonium bicarbonate particles can be removed by decomposition at a temperature below 200° C. to produce a porous metal alloy microparticle.

In some embodiments, porous metal alloy microparticles having an average pore size (diameter) of 40 to 200 Å can be generated by space-holder method.

In some embodiments, a cargo as described in can dissolved in a suitable solvent. The cargo solution is then mixed with a porous metal alloy microparticle of 5 to 30 μm in diameter and fills the cavity of the porous metal alloy microparticle with the solution. Evaporation of the solvent leaves the drug in the cavity having an average pore size (diameter) of 40 to 200 Å and provides a metal alloy microparticle comprising a drug cargo.

In some embodiment, porous alloy microparticle can be made using hot pressing technique and Mg space. Alloy microparticles can be in an appropriate amount ranging from 1% to 50% by volume of spherical magnesium (Mg) powder with of predetermined particle sizes such as 0.1 micron to 10 microns as spacers and evaporating magnesium via the atmosphere-controlled sintering. The obtained porous structures were characterized by SEM, XRD and EDS. Furthermore, the strength and elastic modulus were evaluated by performing compression tests. (Ref. N. Aslan et al., Journal of Materials Science: Materials in Medicine volume 32, Article number: 80 (2021))

In some embodiments, a carrier alloy can comprise to any one of metal alloys comprising titanium, iron, copper, silver, gold, or tungsten. In some embodiment, the carrier alloy can have a spherical shape having a diameter of 5 to 30 μm. In some embodiments, the carrier metal alloy can be porous having an average pore size (diameter) of 40 Å to 10 microns, 0.1 micron to 5 microns, 40 to 200 Å, 80 to 150 Å. The porosity of the metal alloy helps can be used in connection with the loading of the cargo and in particular to increase loading of on or more cargos loaded on a particle in accordance with the disclosure.

In general, porous microparticles as described herein can carry sufficient amount of active agent or cargo drugs by physically containing the active agents or cargo drugs. In some embodiments, active agent or cargo drugs can be dissolved in a suitable solvent which will fill the cavities of the porous particle. The solvent can be evaporated leaving the active agent or cargo drugs in dry form. Alternatively, the active agent or cargo drugs can stay in solution in the microparticle as described.

In some embodiments, porous steel or other alloys can be prepared using mechanical pulverization and sieving In some embodiments, the biologically active cargo as described herein comprises an active pharmaceutical ingredient. An active pharmaceutical ingredient refers to any substance or mixture of substances intended to be used in the manufacture of a drug product and that, when used in the production of a drug, becomes an active ingredient in the drug product.

In some embodiments, the microparticle as described herein comprises an ophthalmic medicine selected from the group consisting of prostaglandin analog, α-adrenoreceptor agonist, β-adrenoreceptor antagonist, carbonic anhydrase inhibitor, and parasympathomimetic agents or any combination thereof.

In some embodiments, ophthalmic prostaglandin analog as described herein attenuates intraocular pressure (IOP) by improving the outflow of aqueous humor. Prostaglandin analogs exhibit agonistic activity on FP prostanoid receptors, which promotes uveoscleral outflow. Medications within this class include latanoprost, travoprost, bimatoprost, tafluprost, and unoprostone isopropyl.

In some embodiments, ophthalmic α-adrenoreceptor agonists as described herein can decrease production of aqueous humor. Ophthalmic α2 agonists include brimonidine and apraclonidine. By activating α2 receptors in the ciliary epithelium, adenylyl cyclase becomes inhibited and cyclic adenosine monophosphate (cAMP) is no longer formed. This hinders ion transport and, thus, fluid production. Over time, these medications can improve fluid outflow as well.

In some embodiments, ophthalmic β-adrenoreceptor antagonist as described herein can reduce intraocular pressure (IOP) by decreasing aqueous humor production. Beta-blockers antagonize the effects of sympathetic neurotransmitters by inhibiting β1 and β2 receptors. Exemplary ophthalmic β-adrenoreceptor antagonist include timolol, betaxolol, carteolol, and levobunolol.

In some embodiments, ophthalmic carbonic anhydrase inhibitors (CAIs) as described herein works by decreasing production of aqueous humor. Carbonic anhydrase is an enzyme that catalyzes the formation of bicarbonate from carbon dioxide and water (and vice-versa), with the most active isoform being carbonic anhydrase II. Inhibition of this isoenzyme within the ciliary epithelium slows the formation of bicarbonate ions; decreasing the extracellular transport of water necessary for aqueous humor production. Exemplary ophthalmic carbonic anhydrase inhibitors (CAIs) includes dorzolamide, brinzolamide and acetazolamide.

In some embodiments, ophthalmic parasympathomimetic agents as described herein are cholinergic agonists that reduce IOP by improving fluid outflow through the trabecular meshwork. Activation of muscarinic (M3) receptors allows for contraction of ciliary muscle fibers, which expands the pores of the trabecular meshwork to enhance outflow. Ophthalmic agents within this class include carbachol and pilocarpine.

In some embodiment, the ophthalmic medicine includes anti-inflammatory agent selected from the group consisting of dexamethasone, cyclosporine, bromfenac, nepafenac, ketorolac, suprofen, flurbiprofen or any combinations thereof.

In some embodiment, the ophthalmic medicine includes an anti-angiogenic ophthalmic agent selected from the group consisting of aflibercept, ranibizumab, pegaptanib, and brolucizumab, or any combinations thereof.

In some embodiment, the ophthalmic medicine includes a mydriatics selected from the group consisting of homatropine, cyclopentolate, tropicamide, phenylephrine, scopolamine, atropine or any combinations thereof.

In some embodiment, the ophthalmic medicine includes an anesthetic selected from the group consisting of tetracaine, proparacaine, lidocaine, or any combinations thereof.

In some embodiment, the ophthalmic medicine includes an anti-infective selected from the group consisting of moxifloxacin, gatifloxacin, ganciclovir, azithromycin, polymyxin b/trimethoprim, besifloxacin, tobramycin, trifluridine, vidarabine, oxytetracycline/polymyxin b, sulfacetamide sodium, erythromycin, levofloxacin, ofloxacin, gentamicin, chloramphenicol, gramicidin/neomycin/polymyxin b, bacitracin/neomycin/polymyxin b, idoxuridine, ciprofloxacin, chloramphenicol, or any combinations thereof.

In some embodiment, the ophthalmic medicine includes an antihistamines and/or decongestant selected from the group consisting of tetrahydrozoline/zinc sulfate, olopatadine, naphazoline/pheniramine, bepotastine, alcaftadine, ketotifen, epinastine, phenylephrine, azelastine, pemirolast, naphazoline/zinc sulfate, nedocromil, cetirizine, oxymetazoline, levocabastine, emedastine, cromolyn, lodoxamide, or any combinations thereof.

In some embodiment, the ophthalmic medicine includes a glaucoma agent selected from the group consisting of brimonidine/brinzolamide, netarsudil, bimatoprost, brimonidine/timolol, latanoprost/netarsudil, latanoprost, tafluprost, latanoprostene bunod, travoprost, dorzolamide/timolol, brimonidine, dorzolamide, brinzolamide, echothiophate iodide, timolol, unoprostone, dipivefrin, pilocarpine, metipranolol, carteolol, acetylcholine, carbacholor, apraclonidine, physostigmine, epinephrine, bimatoprost, betaxolol, and levobunolol, or any combinations thereof.

In some embodiment, the ophthalmic medicine includes a steroid selected from the group consisting of difluprednate, loteprednol, dexamethasone, fluocinolone, triamcinolone, rimexolone, fluorometholone, and prednisolone or any combinations thereof.

In some embodiment, the ophthalmic medicine can comprise a photosensitizing agent that can induce corneal cross-linking. In response to light exposure with specific wavelengths, photosensitizing agents generate reactive oxygen singles that participate in photochemical reactions to form advanced glycan endproducts, covalent cross-links between amino acids in collagen chains. In addition, species that are not photsensitizing, including metal ions, can be delivered which act as enzymatic cofactors in cross-linking reactions In some embodiment, the ophthalmic medicine can comprise a compound which participates in the cross-linking of collagen in the cornea. Riboflavin and Eosin Y have been demonstrated as compounds that when irradiated with the correct wavelength of light, will generate oxygen singlets that participate in the formation of advanced glycan end-product crosslinks. Copper ions have also been shown to be able to crosslink collagen in the presence of lysyl oxidase enzymes.

In embodiments, herein described biologically active cargo in the sense of the disclosure form a microparticle The term "particle" in the sense of the disclosure, indicates particles with a dimension from 1 and 1000 μm and in particular with dimension of less than 300 μm and a density from 1.4 g/cc to 20 g/cc. Size of microparticles can be effectively measured using scanning electron microscopy. Standard light transmission microscopy can be used as well in combination with reference standard objects to measure size. Size, mass, and density measurement can be achieved using a quadrupole ion trap[6]. Another way to measure particle density includes measuring the settling velocity of particles in water by using a microscope focused on a vertical capillary. Several microparticles are commercially available in a wide variety of materials, including ceramics, glass, polymers, and metals.

Microparticle in the sense of the disclosure are convex microparticles having an average density $\rho_p$ from 1.4 g/cc to less than 20 g/cc and an average diameter $D_p$ from 1 μm to 1,000 μm.

The term "convex" when used in connection with microparticles indicates a particle which has a having a surface of the particle curved such as the exterior of sphere or ellipsoid. Convex microparticle comprises spherical, substantially spherical discs, subs rods, and other shapes as will be understood by a skilled person [6]. "As used herein, "substantially spherical" refers to an shape that is symmetrically circularly convex in all radial directions and having a maximum diameter within 10% of the minimum diameter.

The term "average density" of a particle as used herein indicates the total mass of particles divided by the total volume of those particles. The "density" of a particle is equal to the particle volumetric mass density as will be understood by a skilled person. Average density of the particles can be measured in several ways known to the person skilled in the art, such as: measurement of total mass of the particles divided by total volume of the particles, obtained through techniques including but not limited to spectroscopy, buoyancy, frequency shifting and so on. See, for example, "Volume and density determinations for particle technologists", Paul A. Webb (February 2001), micromeritics.com/Repository/Files/Volume_and_Density_determinations_for_Particle_Technologists.pdf, incorporated herein by reference in its entirety. mass divided by the particle volume particle.

For example, to measure the density of the microparticles, the microparticles are placed inside a pycnometer of known volume and weighed. The Pycnometer is then filled with a fluid of known density, in which the microparticle is not soluble. The volume of the microparticles is determined by the difference between the volume as shown by the pycnometer, and the volume of liquid added (the volume of air displaced). Division of weight of the microparticle by the measured volume gives the density of the microparticles. When all the particles are the same, the result gives the density of individual microparticle. When particles have different density, the result is the average density of all particles that are involved in the measurement.

In particular, the average density can be measured using a statistically significant sample of n particles and measuring the total mass $n\langle m_p\rangle$ and displaced volume $n\langle V_p\rangle$, then computing the ratio of mass to volume, $\rho_p=(n\langle m_p\rangle)/(n\langle V_p\rangle)=\langle m_p\rangle/\langle V_p\rangle$. In the present disclosure, particles have an average density $\rho_p$ that is at least 1 g/cc and equal to or less than 20 g/cc.

The term "average dimension" as used herein indicates is the summation of dimension of all particles divided by the number of particles. The dimension of a single particle indicates the diameter of a particle if the particle is spherical or the diameter of a representative sphere is the particle is non spherical wherein the diameter of the representative sphere is calculated based on the volume or the area of the non-spherical particle.

In particular a volume-based particle size equals the diameter of the sphere that has the same volume as a given particle. Typically used in sieve analysis, as shape hypothesis (sieve's mesh size as the sphere diameter).

$$D = 2\sqrt[3]{\frac{3V}{4\pi}}$$

Where D: is the diameter of representative sphere and V is volume of particle

An area-based particle size equals the diameter of the sphere that has the same surface area as a given particle. Typically used in optical granulometry techniques.

$$D = \sqrt[2]{\frac{4A}{\pi}}$$

Where D is the diameter of representative sphere and A: surface area of particle In some embodiments, where the convex microparticle of the disclosure to be delivered have different dimensions, the distribution of particle sizes can be narrow, by which it is meant that 90% of the biological cargo is contained in particles that have individual diameter $D_{pi}$ from $0.9\langle D_{pi}\rangle$ to $1.1\langle D_p\rangle$. In some embodiments, where the convex microparticle of the disclosure have different dimensions the distribution of particles can be moderately broad, by which we mean 80% of the biologically active cargo is contained in particles having individual diameter $D_{pi}$ from $0.75\langle D_{pi}\rangle$ to $2\langle D_{pi}\rangle$.

In exemplary embodiments, two different batches of convex microparticles both have diameter $\langle D_p\rangle=15$ microns and have very different size distributions. When a statistically significant number of particles is examined under the microscope, one sample shows no particles having effective dimension less than 13.5 microns and no particles having effective diameter greater than 16.5 microns. For particles that carry biological cargo in proportion to their volume, such an observation indicates that more than 90% of the biological cargo is contained in particles that have individual effective diameters $D_{pi}$ from $0.9\langle D_{pi}\rangle$ to $1.1\langle D_{pi}\rangle$. For the other sample of particles such as substantially spherical particles with $\langle D_p\rangle=15$ microns, examination of a statistically significant number n of particles shows that 10 of 100 particles have $D_p<5$ microns, and 5 of 100 particles have $D_p>30$ microns (representing >125-times the mass of the particles with $D_p<5$ microns); and 10 of 100 have Dp from 5 to 7.5 microns. The n individual effective diameter values are used to estimate the volume of each particle; the sum of the n particle volumes gives the total volume of the n particles; starting from the smallest particle detected, individual particle volumes are summed until the cumulative volume equals 10% of the total volume, the $D_p$ of the last small particle in the sequence is taken as the cutoff diameter at small particles size, $D_{small}$; repeat the process starting from the largest particle detected and sum the volume until the cumulative volume equals 10% of the total; the Dp of the last large particle in the sequence is taken as the cutoff size for large particles that account for 10% of the total volume, $D_{large}$. A particular batch of substantially spherical particles having $<D_p>=15$ microns and prepared such that the biologically active cargo is loaded in proportion to particle volume, is found to have $D_{small}=11$ microns and $D_{large}=35$ microns. The range of effective particle diameters starts below 0.75<Dp> and extends beyond $2<D_p>$; such a distribution would be regarded as broad.

In some embodiments, a convex particle can be substantially spherical, where the term substantially spherical refers to irregular convex particles having a sphericity index value from 0.9 to 1.0. The sphericity is taken to be the minimum of two different expressions, each of which individually proved adequate for efficiently identifying a useful point in the operating space of particle size, particle density and particle velocity for a specified the tissue of interest, target layer, tissue properties and particle accelerating device. The first of the methods of evaluating the sphericity is: the cube root of the ratio of the average particle volume $<V_p>$ to the average volume of the smallest sphere that circumscribes a particle. In which the volume displaced by a statistically significant sample of n particles is used as $n<V_p>$ to evaluate $<V_p>$ and the average volume of the smallest circumscribing sphere $<V_{cs}>$ is computed by analyzing a micrograph of the set of n particles spread apart such that the silhouette of each particle is visible, the particles tend to have their long axis approximately parallel to the microscope slide and the n values of the length of the long axis $a_{la}$ of the n particle silhouettes in the micrograph are used to compute the n volumes of the individual circumscribing spheres $V_{cs}=(\pi/6) a_{la}^3$. The second method uses the micrograph to determine the n pairs of values of $a_{la}$ and minor axis length $b_{la}$ in the direction orthogonal to the long axis of a given particle's silhouette and the sphericity is evaluated as the cube root of $(a_{la}^3)/(a_{la}b_{la}^2)=(a_{la}/b_{la})^2$.

In some embodiments a substantially spherical particle tends to lie down with their thinnest axis orthogonal to the microscope slide, and is identified as platelet-like particles. because they seen through the microscope to be platelets, In those embodiments the first method The first of the methods of evaluating the sphericity should be used.

In embodiments wherein substantially spherical particles are used, the average particle diameter can be evaluated using a micrograph of a statistically significant number of particles n as the average of the n values of the effective particle diameter, calculated as square root of the area of a particle silhouette in the micrograph. Particles carrying biologically active cargo can have internal variations of density and their effective density is equal to the particle mass divided by the particle volume particle.

In some embodiments, a convex microparticle in the sense of the disclosure can be an irregularly shaped convex particle having a major axis, a minor axis and an intermediate axis as will be understood by a skilled person. The major axis refers to the longest line that connects two points on the surface of the particle. The coordinates of one of the endpoints is taken as the origin and the opposite end point is (x,y,z) the length of the major axis denoted by $a_{major}$, is the square root of the sum of squares x,y,z, $sqrt(x^2+y^2+z^2)$. The intermediate axis is the longest line that is orthogonal to the major axis and connects two points on the surface of the particle. The length of the line connecting the two end points of the intermediate axis is denoted $a_{interned}$. When the major and intermediate axes are known, the minor axis is the longest line between two points on the surface of the particle and is orthogonal to both the major and intermediate axes. The minor axis length is denoted $a_{minor}$. The methods used to characterize particle shape determine average values over a large number of particles. The most common techniques to determine particle size distribution are dynamic image analysis (DIA), static laser light scattering (SLS, also called laser diffraction), dynamic light scattering (DLS) and sieve analysis. The most sophisticated techniques for evaluating the size and shape is tomography as will be understood by a skilled person. Depending on the size range and optical properties of the particles, confocal optical microscopy (particle axis lengths of at least 5 microns; particle surface fluorescently labeled) and/or optical coherence tomography (particle axis lengths of at least 20 microns and particle surface that strongly scatters light). For detailed characterization of particles that have a dimension that is less than 5 microns can be performed using scanning electron microscope micro-computed tomography or x-ray micro-computed tomography. Tomographic images are used to evaluate all three of the principle axes of each particle and the compute desired average quantities from them.

An irregularly shaped convex particle can be produced as the result of a process used to load a particular biologically active agent into particles. For example, when a macroscopic block of materials is pulverized to create a powder of irregularly shaped convex particles from which, according to the disclosure, the desired range of particle size is obtained. Alternatively, regularly-shaped non-spherical particles can be produced by a variety of established methods, including but not limited to 3D printing, micro-molding, and extrusion with pelletization.

In in some embodiments of the disclosure, preferred irregularly shaped particles have $a_{interned}/a_{major}$, between ½ and 1⁄10 and have $a_{minor}/a_{interned}$ between ½ and 1.

In some embodiment microparticles of the present disclosure can comprise more than one cargo and more than one carrier materials that can be combined to allow coupling of the carrier with the cargo and/or to obtain a desired density as will be understood by a skilled person.

Microparticles comprising a cargo and optionally a carrier material in the sense of the disclosure can be prepared with methods identifiable by a skilled person upon reading of the present disclosure which depend on the specific cargo and specific carrier material as will be understood by a skilled person. Additional, preparation of a microparticle with set density and amounts of cargo can also be identified by a skilled person.

Methods to prepare micropoarticles in the sense of the disclosure include mechanical pulverization, spray-drying, spray chilling, and emulsion-drying techniques as well as additional methods identifiable by a skilled person (Ref (https://pubs.acs.org/doi/abs/10.1021/acsami.8b01582). (Ref (https://pubmed.ncbi.nlm.nih.gov/30035646/). (Ref (haps://www.sciencedirect.com/science/article/abs/pii/S0963996912000415).

In some embodiments, the convex microparticle of the disclosure can be monodisperse in some embodiments the convex microparticle of the disclosure can be polydisperse The dispersity is a measure of the heterogeneity of particles in a mixture. A collection of objects is called uniform if the objects have the same size, shape, or mass. A measure of the dispersity is provided by the Polydispersity index (PDI) which is a measure of the breadth of the molecular weight distribution for a polymer as described herein. PDI is defined as Mw/Mn where Mw and Mn are the weight average and number average molecular weight, respectively. For a perfectly uniform ("monodisperse") sample consisting of exactly one and only one molecular weight, both the Mw and the Mn would be the same value. Gel Permeation Chromatography (GPC), Size Exclusion Chromatography (SEC) or Dynamic Light Scattering (DLS) can be used to measure polydispersity index (PDI). A narrow, moderate and broad polydisperse particle has PDI in the ranges of 1.0-1.1, 1.1-2.0, and greater than 2.0, respectively.

In some embodiments, preparation of microparticles can be performed using a vibrating orifice aerosol generator (VOAG) to prepare a microparticle with a set density and diameter.

In particular, a VOAG can be used incorporate density boosting metal nanoparticles. For example, gold or tungsten nanoparticles with size less than 100 nm have settling velocities low enough such that they will stay dispersed in a liquid. Accordingly, inclusion of these metal nanoparticles together with a suitable cargo in the liquid used to prepare microspheres using the VOAG will include the metal within carrier materials used to form to microspheres. In particular, in some embodiments, I=incorporating one or more carriers formed by high density materials can impart mass needed to increase momentum that contributes to particle embedding energy as will also be understood by a skilled person. For example tungsten nanoparticles can be added to an ethanol/polymer solution further including a cargo to prepare a microparticle with a density higher than 7.8 g/cc as will be understood by a skilled person.

In additional exemplary embodiments a VOAG can be used with a carrier polymer such as poly(ethylene glycol) dissolved in suitable solvent (such as ethanol) and a drying column, to provide microparticles in the sense of the present disclosure using a spray drying technique. In those embodiments, the solution is ejected from the VOAG and is converted into a droplet train that has low polydispersity. The droplets can then then fed into a drying column (e.g. 1-meter-tall) with nitrogen fed at 30 standard cubic feet per minute. As particles settle to the bottom of the column, which is heated to a suitable temperature (e.g. 120° C.), ethanol is evaporated from the droplets until a solid particle is left over at the bottom. From empirical research, it was found that droplets had to be prepared that were 70-90 μm in diameter in order to become fully solid at the bottom of the column.

In embodiments, wherein spray drying technique are performed with a VOAG it is possible to obtain a precise control of the size of droplets produced and include additives with polymers or other carrier materials to change the composition and physical properties of the microparticle. Droplet size can be changed using different precision pinholes in the VOAG as will be understood by a skilled person (see Examples section). Additional size control can be achieved by modulating the vibration of piezoelectric excitation The resulting dry particle that can be produced is proportional to the size of the droplet emitted by the VOAG (see Examples section).

In addition to providing control over the size of the dry particles produced by spray drying technique, the VOAG allows customization of particle composition and properties. For example, Incorporating charged species (e.g. lysine) will result in a hollow particle morphology. Methods have already been discussed to alter particle density using metal nanoparticles.

In embodiments, where a VOAG is used a precise control over the polydispersity of the droplets emitted from the device can also be achieved as will be understood by a skilled person. By exciting the VOAG piezoelectric ceramic with appropriate frequencies, monodisperse droplet trains can be emitted from the device. As long as particles are effectively dispersed in a drying column, preventing coagulation, the resulting fully dried particles will be monodisperse as well. If a polydisperse size distribution is desired, excitational frequencies can simply be turned off. Monodisperse particles, assuming they have the same impact velocities, will be found at similar penetration depths within a soft, homogeneous target substrate. Polydisperse particles will result in a more varied penetration depth distribution as will be understood by a skilled person.

In some embodiments, microparticles with set characteristics can be commercially sourced, as will be understood by a skilled person. Manufacturers comprises Spherotech and Cospheric and additional manufacturer identifiable by a skilled person In some embodiments, microparticles of the disclosure can be used for delivery to multilayered tissues of an individual comprising mechanically heterogenous layers.

The term "tissue" as used herein indicates an association of cells of a multicellular organism, with a similar structure and function which usually have a with a common embryological origin. (Ref. X.MaY.LiuW.FanZ.Cui Comprehensive Biotechnology (Second Edition) Volume 5, 2011, Pages 83-98 https://doi.org/10.1016/B978-0-08-088504-9.00437-2). Accordingly tissue is an ensemble of similar cells and their extracellular matrix from the same origin that together carry out a specific function as will be understood by a skilled person. Organs are then formed by the functional grouping together of multiple tissues as will also be understood by a skilled person.

In particular, animal tissues are grouped into four basic types: connective, muscle, nervous, and epithelia. In particular, an epithelial tissue is formed by cells that cover an organ surface, such as the surface of eye, skin, the airways, surfaces of soft organs, the reproductive tract, and the inner lining of the digestive tract. The cells comprising an epithelial layer are typically linked via semi-permeable, tight junctions; hence, this tissue provides a barrier between the external environment and the organ it covers. In addition to this protective function, epithelial tissue may also be specialized to function in secretion, excretion and absorption. Epithelial tissue helps to protect organs from microorganisms, injury, and fluid loss. (source Ref https://en.wikipedia.org/wiki/Tissue_(biology))

Three principal shapes associated with epithelial cells are squamous, cuboidal, and columnar. Squamous epithelium has cells that are wider than their height (flat and scale-like). This is found as the lining of the mouth, oesophagus, and including blood vessels and in the alveoli of the lungs. Cuboidal epithelium has cells whose height and width are approximately the same (cube shaped). Columnar epithelium has cells taller than they are wide (column-shaped). Columnar epithelium can be further classified into ciliated columnar epithelium and glandular columnar epithelium. (Source Ref. https://en.wikipedia.org/wiki/Epithelium)

In embodiments herein described the tissue are "multilayered" and thus include at least two layers. The term "layer" in the sense of the disclosure when mention in reference to a biological tissue refers to a structure of the tissue that has thickness in the range from 10 microns to 10 mm, and having continuum properties in at least one of the following attributes: mass fraction of non-volatile solids (lipids, protein, polysaccharide or polynucleotide), volume fraction of cells averaged over 10 microns in the thickness direction and 1000 microns in the lateral directions within the layer. Accordingly, within a layer the continuum density varies less than 10% and the continuum Youngs modulus varies less than 10% and boundaries that on each side with the eternal environment and/or with another structure in the tissue that differs by 10% in at least one of the following attributes: mass fraction of non-volatile solids (lipids, protein, polysaccharide or polynucleotide), volume fraction of cells, Youngs modulus and density. A tissue layer can have a thickness greater than 10 microns, preferably greater than 20 microns, and most preferably greater than 50 microns thick. These property of a tissue layer can be observed also in connection with corresponding properties of the multi-layered tissue by using at least one of ultrasound (US) imaging, optical coherence tomography (OCT) or magnetic resonance imaging (MRI) as will be understood by a skilled person.

In particular, a multilayered tissue in the sense of the disclosure, has a tissue thickness L ranging from 50 microns and 5000 microns, a width W in at least one lateral direction that is at least ten-times greater than the tissue thickness L, an accessible surface of an apical layer that has area at least ten-times the tissue thickness L squared.

A tissue layer within the multilayers tissue can have a thickness greater than 5 microns, preferably greater than 20 microns, and most preferably greater than 100 microns thick based on the spatial resolution of the selected imaging techniques (see e.g. OCT having resolution of 5 to 20 microns; or MRI having a resolution ranging from 20 microns to 80 microns as will be understood ay a skilled person). A tissue layer can include "sublayer" which indicates a structures that may not be observable by the skilled person. For example, if an anatomical structure in a layered soft tissue is less than 5 microns thick, it is difficult to observe and the skilled person might not be able to measure its thickness. A tissue layer can include an "overlying layers" which are layers that are near the accessible surface of the apical layer and lie between the accessible surface and the target layer. The term "underlying layers" as used herein refers to layers of a soft tissue that are farther from the accessible surface of the apical layer than the target region.

Multilayered tissues in the sense of the disclosure can be imaged with proper instrumentation as will be understood by a skilled person. In preferred embodiments of the disclosure properties of the tissues or portions therefore can be detected by ultrasound in view of the ability to observe a tissue boundary via "echogenicity" is related to the acoustic impedance mismatch between adjacent materials, as is described in textbooks on ultrasound imaging, such as *Diagnostic Ultrasound*, by C. M. Rumack and D. Levine M D. For example, skin has been imaged in vivo with US instruments operating at frequencies in the range from 20 MHz to 50 MHz that have resolutions in the range from 20 microns to 100 microns in the vertical direction.

A multilayered tissue in the sense of the disclosure further has a tissue density ρ from 850 kg/m$^3$ to 1200 kg/m$^3$ [a] and a Young's modulus Y from 500 Pa to 50,000,000 Pa, and a density from 850 kg/m$^3$ to 1200 kg/m$^3$ and.

The term "density" with reference to a tissue or a portion thereof, refers to the volumetric mass density or specific mass, which is the substance's mass per unit of volume herein identified with symbol ρ. Mathematically, density is defined as mass divided by volume:[1]

$$\rho = \frac{m}{V}$$

where ρ is the density, m is the mass, and V is the volume. Density of exemplary tissues are shown in the following Table 1

TABLE 1

| | Density ρ(Kg/m$^3$) |
|---|---|
| Air (25° C.) | 1.16 |
| Water (22° C.) | 998 |
| Blood | 1,060 |
| Skeletal Muscle | 1,041 |
| Liver | 105.0 |
| Kidney | 1,050 |
| Fat | 928 |
| Bone | 1,600 |

As used herein, the "Young's modulus" indicates a parameter that quantifies the relationship between stress and axial strain in the linear elastic region of a material. Young's modulus is sometimes referred to as the elastic modulus or modulus of elasticity. Also identified as modus of elasticity or compression, Young's modulus is a mechanical property that measures the tensile or compressive stiffness of a solid material when the force is applied along an axis. The Young's modulus of layered tissue specimens is measured by preparing a specimen with a dog-bone shape that has a substantially rectangular middle portion of width that is greater than 10-times the thickness and a length that is approximately 10-times its width and had a wider portion at each end. The wider portions are clamped into a tensile testing apparatus capable of imposing a tensile force and measuring the displacement of the grips. From these the engineering stress and strain are calculated. Additional corrections may be incorporated to provide values of the true stress and true strain. For the purposes of the present disclosure, Young's modulus values based on engineering stress and strain or true stress and strain may be used, particularly if only one or the other is available.

In embodiments herein described, the multilayered tissue is a soft tissue. As used herein, the term "soft tissue" refers to a biological tissue that has Young's modulus, E, less than or approximately 200 MPa. In contrast, cortical bone has a Young's modulus of approximately 15 GPa and trabecular bone has Young's modulus of approximately 350 MPa. The symbol kPa refers to $10^3$ Pa, MPa refers to $10^6$ Pa and GPa refers to $10^9$ Pa.

Soft tissues in the sense of the disclosure have the potential to undergo large deformations and still return to the initial configuration when unloaded and their stress-strain curve is nonlinear. For example, skin can respond reversibly up to an engineering strain of 30% and its modulus increases by an order of magnitude when the strain exceeds a threshold that is typically between 5% and 20% strain depending on age and other factors. Soft tissues are also viscoelastic (e.g., showing significant hysteresis during cyclic loading), approximately incompressible, and usually anisotropic.

Exemplary layers of multilayered tissue in the scope of the disclosure can have mechanical properties similar to 1.0 w/v % agarose or 5.0 w/w % gelatin, in particular, the materials can have bulk storage modulus is less than 20 kPa, as will be understood by a skilled person upon reading of the disclosure. While this testing does not reflect the high strain-rate behavior of corneal tissue, oscillatory shear rheology has identified these gel materials to be the most similar to corneal tissue.

Soft tissue in the sense of the disclosure comprises biological cells and an extracellular matrix that comprises collagen, elastin and ground substance. Ground substance is primarily composed of water and large organic molecules, such as glycosaminoglycans (GAGs), proteoglycans, and glycoproteins. GAGs are polysaccharides, including hyaluronic acid, heparan sulfate, dermatan sulfate, and chondroitin sulfate. With the exception of hyaluronic acid, GAGs are bound to proteins called proteoglycans, with one or more glycosaminoglycan chains attached to the protein. GAGs trap water, giving the ground substance a gel-like texture. Glycoproteins, comprising oligosaccharides attached to protein, are mainly located in cell membranes. Glycoproteins attach components of the ground substance to one another and to the surfaces of cells.

Exemplary soft tissues include ocular tissue, oral soft tissue, mucosa and skin as well as vascular tissue.

The term "ocular soft tissues" in the sense of the disclosure comprises the corneal and scleral tissues which are part of the outer tunic of the eye. Each is a connective tissue containing collagen fibrils embedded in a proteoglycan-rich extrafibrillar matrix. Both tissues require strength to maintain a stable shape despite the excess pressure within the eye. This mechanical strength is provided by the deposition of collagen in a lamellar structure, where the lamellae run parallel to the surface of the tissue rather than through its thickness.

The term cornea as used herein indicates the transparent front part of the eye (a sense organ that reacts to light and allows vision) of an individual.

When referred to as a noun, the term "individual" as used herein in the context of treatment refers to a single biological organism, including animals having a sense organ that reacts to light and allows vision and in particular higher animals and in particular vertebrates such as mammals and in particular human beings.

Figure 1A:
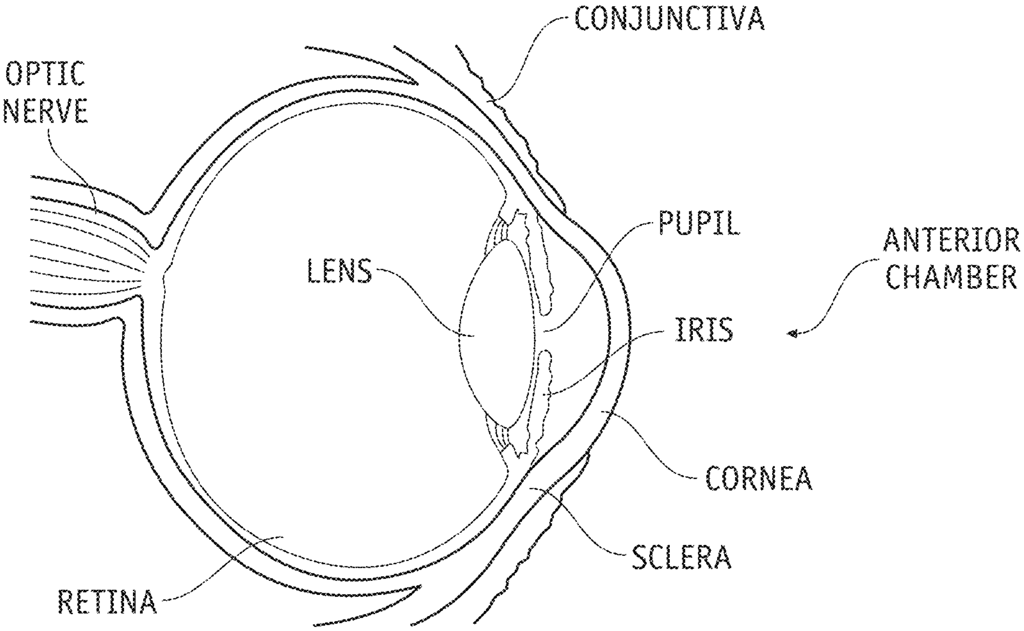
FIG. 1A shows a schematic representation of the anatomy of the eye and positioning of basic optical elements. Reproduced from the National Eye Institute. National Institutes of Health.

The cornea of the eye of a human being indicates the parts that covers the iris, pupil, and anterior chamber. The cornea, with the anterior chamber and lens, refracts light, with the cornea accounting for approximately two-thirds of the eye's total optical power. The related position with respect is schematically illustrated in FIG. 1A.

Corneal tissue has biophysical properties related to layered heterogeneity that prevent the uptake of drug species.

Figure 1B:
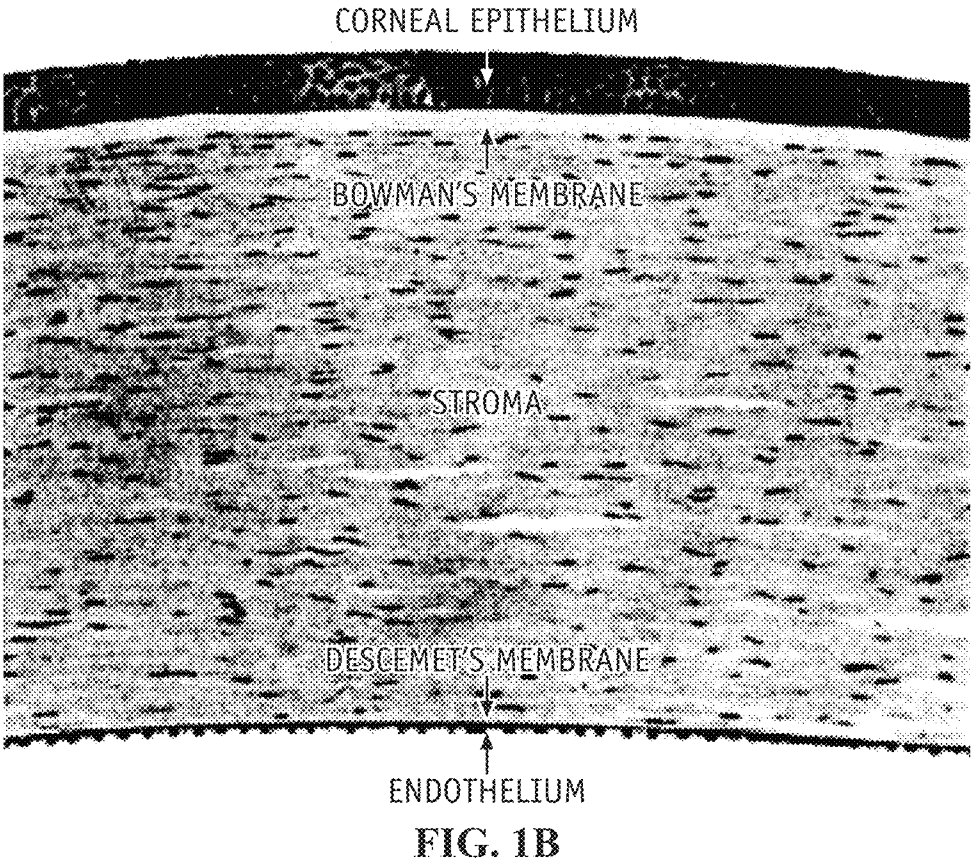
FIG. 1B shows a representation of the major layers of the cornea shown in H&E stained tissue section. Image reprinted from Ehlers and Hjortdal. [2]

The cornea is comprised of five main layers in the order of the epithelium, Bowman's Layer, the stroma, Descemet's Membrane, and the endothelium (identified in FIG. 1B).

The epithelium is on average 53 μm thick and sits on a 0.3-μm-thick basement membrane, which consists of collagen fibrils and laminin proteins. Beneath this, Bowman's Layer is a sheet of randomly oriented collagen fibrils that provides an outward toughness to the cornea. Next, the stroma constitutes most of the corneas' thickness. It is mainly acellular (1 keratocyte per 50,000 $\mu m^3$) and contains 200 collagen lamellae containing fibrils that radiate outwards at precise angles to give the cornea its transparency. The extracellular matrix consists of a mixture of peptidoglycans, glycosaminoglycans, fibronectins, and laminins [7]. The high content of peptidoglycans and glycosaminoglycans in the stroma gives the tissue a net negative charge. Finally, Descemet's Membrane is an acellular fibrous layer secreted by the endothelium monolayer below. The biomechanical strength of the cornea can be attributed to its inner stromal layer, since epithelial and endothelial cell layers lack any contiguous protein network. The interlamellar spacing between collagen fibrils and constitutive properties between protein and peptidoglycan is what gives rise to a transparent tissue, similar in structure to tendon, that has considerable mechanical strength (Table 2). [8]

As shown in Table 2 below, the cornea has significant stiffness, especially in Bowman's Layer and the stroma.

TABLE 2

Mechanical properties of individual layers of the cornea. Data from Last et al. unless otherwise specified*.

| Structure | Mechanical Properties Reported in Literature |
|---|---|
| Tear Film | Loss modulus (viscosity): 2.33 mPa [Human; Rheometry]** |
| Epithelium | Elastic Modulus: 0.57 kPa [Rabbit; AFM] |
| Epithelial Basement Membrane | Elastic Modulus: 7.5 kPa [Human: AFM] |
| Bowman's Layer | Elastic Modulus: 108.9 kPa [Human; AFM] |
| Stroma | Elastic Modulus: 33.1 kPa [Human; AFM] |
| Descemet's Membrane | Elastic Modulus: 50 kPa [Human; AFM] |
| Endothelium | Elastic Modulus: 4.1 kPa [Rabbit; AFM]*** |

*From Last et al.; 2012[9]
**From Gouveia et al.; 2005 [10]
***From Thomasy et al.; 2014 [11]

Additionally tear film with dissolved mucin forms a hydrophilic, negatively charged barrier, blocking hydrophobic materials or anions. Superficial epithelial cells are joined to one another by desmosomes and tight-junction complexes (zonula occludens). These structural elements stitch the anterior surface of the eye together and prevent the infiltration of bacteria and viruses, but also medicinal compounds. Corneal epithelial cells express an array of ATP-binding cassette efflux transporter pumps, which actively remove lipophilic molecules and organic anions from epithelial cytoplasm [12]. The corneal epithelium is lipophilic in nature—hydrophilic compounds that are delivered topically have low uptake rates. These characteristics impair the ability to deliver drugs to the cornea, and especially to underlying stromal tissue. Furthermore, precorneal barriers to drug delivery include solution drainage, blinking, and induced lacrimation.

The cornea transmits over 90% of the incident light at visible wavelengths because, at the nanoscopic level, the corneal collagen fibrils have uniform diameter much less than visible wavelengths and are oriented and positioned in a highly ordered way. The cornea has a layered structure comprising epithelium, Bowman's layer, stroma, Descemet's membrane, and endothelium.

The sclera (the white part of the eye) constitutes the rest of the globe. Scleral collagen has similar composition and arrangement to that in skin, with wider fibrils and a more interwoven structure than in the cornea. The sclera comprises three layers, from the outside to the inside: Episclera—clear, thin tissue; Stroma—white, opaque layer comprising fibroblasts and collagen fibers; and *Lamina fusca*—an elastic, transitional layer between the sclera and the choroid.

The wording "oral soft tissues" in the sense of the disclosure include the soft tissues of the oral cavity of an individual, such as to the lips, soft palate, tonsils, uvula, tongue, gingiva (gums), buccal mucosa (the inner lining of the lips and cheeks), and floor of the mouth under the tongue. The oral mucosa is composed of two layers, the surface stratified squamous epithelium and the deeper lamina propria. The stratified squamous epithelium comprises four sublayers: Stratum basale, Stratum spinosum, Stratum granulosum and Stratum corneum (keratinized layer). The lamina propria comprises two sublayers: papillary and dense.

In general, "mucosa" in the sense of the disclosure indicates the soft tissue that lines the body's canals and organs in the digestive, respiratory and reproductive systems. The oral mucosa is the mucous membrane lining inside of the mouth, including cheeks and lips (buccal mucosa). Mucosa comprise two or more layers, depending on their function and location in the body.

In some embodiments, the methods of the disclosure can be used to deliver of microparticles to mucosal tissue layers, soft tissues in the gut, in the brain, and in other areas of the body should require lower velocities and particle density to achieve considerable penetration depth and therapeutic delivery.

The term "skin" in the sense of the disclosure indicates a complex organ of an individual comprised of three layers of tissue: Epidermis, the top layer. Dermis, the middle layer. Hypodermis, the bottom or fatty layer. The skin of an individual also contain skin appendages, including the hair follicle and sebaceous gland.

The epidermis layer has a Young's modulus value of approximately 4 MPa. The dermal layer in human skin and has a Young's modulus of 40 kPa, while the bottom layer hypodermis is very soft (Young's modulus of 15 kPa), playing the role of the hypodermal adipose layer of skin. (Ref. X. Feng, G-Y Li, A. Ramier, A. M. Eltony, S-H Yun. In vivo stiffness measurement of epidermis, dermis, and hypodermis. Acta Biomaterialia 146 (2022) 295305. doi: 10.1016/j.actbio.2022.04.030.)

The epidermis keeps bacteria and germs from entering the body. The epidermis continually makes new skin cells. Langerhans cells in the epidermis are part of the body's immune system. The epidermis contains pigments that give skin its color. The epidermis comprises five sublayers (top to bottom): Stratum corneum—dead keratinized cells that slough off; Stratum lucidum—several layers of clear, transparent cells; Stratum granulosum—composed of flattened granular cells; Stratum spinosum—flattened cells with short spinous processes; and Stratum basale—basal cell layer comprising keratinocytes that are the dividing and differentiating cells that continually produce new skin cells. The keratinocytes also produce cytokines, which may help induce inflammatory response.

The dermis makes up 90% of skin's thickness. This middle layer of skin contains collagen and elastin that provide strength and resilience. Collagen fibers are the major components of the dermis (77% of the fat-free dry weight) and form an irregular network of wavy fibers that are oriented preferentially parallel to skin surface. The roots of hair follicles attach to the dermis. Nerves in the dermis provide sense of touch. Oil glands in the dermis support the proper hydrophobicity of the skin. Sweat glands in the dermis release sweat through skin pores. Blood vessels in the dermis provide nutrients to the epidermis. Accordingly, in the dermis layer of the multilayered skin tissue, the lateral averaging would include hair follicles, oil glands, sweat glands, nerves and blood vessels averaged into a continuum representation of the material.

The bottom layer of skin, or hypodermis, is the fatty layer. The hypodermis provides a protective cushion over muscles and bones. The hypodermis comprises connectives tissue that connects layers of skin to muscles and bones. Nerves and blood vessels in the dermis (middle layer) are connected to larger nerves and blood vessels in the hypodermis. These nerves and blood vessels connect the hypodermis to the rest of the body.

Together, the skin and mucosae form the barrier immune system. These structures form physical barriers to infection that prevent pathogens from entering the body. The stratified epithelium is supported by a subsurface layer of connective tissues (dermis for skin and lamina propria for oral mucosa) that contains fibroblasts, macrophages, mast cells, blood vessels, and nerve endings embedded in the extracellular matrix (ECM), that provides the epithelium with structural support and nutrients.

The wording "vascular tissue" in the sense of the disclosure refer to multilayer tissue of arteries, capillaries and veins. Layers of the vascular multilayered tissue comprise endothelium cells formed by endothelial cells (EC) which anchor to an 80-nm-thick basal lamina (BL). Both endothelium and basal constitute the vascular intima, establishing a hemocompatible surface, of the vascular tissue of an individual estimated to provide a total combined surface area of 3000-6000 $m^2$ in the human body, comprising 1 to $6\times10^{13}$ EC (Ref. Krüger-Genge A, Blocki A, Franke R P, Jung F. Vascular Endothelial Cell Biology: An Update. Int J Mol Sci. 2019 Sep. 7; 20(18):4411. doi: 10.3390/ijms20184411. PMID: 31500313; PMCID: PMC6769656.

Methods and systems of the present disclosure are based on the discovery that preferential placement of convex and in particular substantially spherical particles within a multilayered tissue can be achieved without distinguishing structures that are less than 5 microns thick. Accordingly, methods and systems of the present disclosure does not require knowledge of the thickness or properties of anatomical layers on a scale of 5 microns. In many implementations, knowledge of features that have thickness of 100 microns or more is sufficient to achieve a beneficial distribution of penetration depths of the convex and preferably substantially spherical particles.

In methods and systems of the present disclosure, the upper bound of 5 mm on layer thickness can be chosen to avoid impact energies that would cause harm to the tissue. The chose layer thickness can be use in mathematical expression and/or for in creating a tissue surrogate for efficiently identifying particle size and particle delivery conditions that preferentially place particles in a target region within a bilayer of the multilayered tissue.

In methods and systems of the present disclosure, a bilayer is identified within the multilayered tissue which comprises an apical layer and an underlying basal layer. An apical layer has a surface facing an environment external to the multilayered tissue and a surface facing the basal layer herein also identified as internal boundary.

In some embodiments the bilayer is comprised in an intact tissue. In some embodiments the bilayer is comprised in a tissue which is injured and in which a layer included within the intact multilayered tissue, in the injured multilayered tissue becomes an apical layer in the sense of the disclosure. Accordingly for example in skin dermis can become am apical layer and the hypodermis can be a basal layer in multilayered tissues formed by injured skin.

Multilayered tissue in the sense of the disclosure comprises a tissue which is injured and presents wounds as described in application for U.S. Ser. No. 17/634,656 incorporated herein by reference in its entirety.

Accordingly, the term "wound" as used herein indicates the result of a disruption of normal anatomic structure and function of a layered soft tissue ([13] [14]. Accordingly, wounds in the sense of the disclosure encompass a wide range of a defects or breaks in a tissue and/or organs of an individual, resulting from physical, chemical and/or thermal damage, and/or as a result of the presence of an underlying medical or physiological condition" as will be understood by a skilled person [15]).

Exemplary wounds comprise abrasions and tears of a tissue of an organ of an individual (e.g. skin) which can be caused by blunt and/or frictional contact with hard surfaces, such as when the an organ is torn, cut, or punctured (an open wound), when the organ is contused (a closed wound), as well as when the organ lesioned and comprise a region in an organ or tissue having abnormal structural change, e.g. following damage through injury or disease. Boateng 2008 [15]).

Exemplary wounds comprise ulcers, like decubitus ulcers (bedsores or pressure sores) and leg ulcers (venous, ischemic or of traumatic origin). [16]) [17]) [18], abscesses such as lesions caused by foreign bodies at the time of an injury, or by infections and tumors [15].

In particular wounds comprise abnormal structures in the body of an individual caused by mechanical forces (such as knives and guns but also surgical treatment), thermal sources, chemical agents, radiation, electricity and/or other sources identifiable by a skilled person [15] [19]. Wounds also comprise abnormal anatomic structure and function of organs and/or tissues in an individual resulting from conditions such as autoimmune diseases or disorders, infections such as viral infections, cancer, as well as chronic diseases such as diabetes.

Exemplary wounds comprise superficial wounds (affecting only a surface epithelium of the organ, e.g. epidermal skin), partial thickness wounds (also affecting a connective tissues, of the organ such as skin's deep dermal layers) and full thickness wound (further affecting deeper tissues of the organ such as subcutaneous fat in addition to the epidermis and dermal layers) [15]; [20] [21].)

Exemplary wounds also comprise lesions in multilayered tissues in eyes, ears, scalp, vasculature, airways, reproductive tract, stomach, intestine and additional portions of the gastrointestinal tract.

Wounds in the sense of the present disclosure can be categorized based on the related characteristics in connection with the wound healing process in the individual.

The term "wound healing" as used herein indicates a biological process directed to growth and tissue regeneration in the individual [15] In particular, during the wound healing process cellular and extracellular components of the injured tissue or organ interact to restore the integrity of the organ or tissue in interdependent and overlapping stages will be understood by a skilled person [22] [23] [24] [25] [26], and [27]).

In particular, a wound heling process in the sense of the disclosure comprises hemostasis, inflammation, migration, proliferation and maturation phases [25] [28]).

The term "hemostasis" in the sense of the disclosure indicates a stage of wound healing characterized by the presence of by exudate (blood without cells and platelets), exudate components such as clotting factors, coagulation of the exudate, formation of a fibrin network, and production of a clot in the wound causing bleeding to stop [15] [29].

The term "inflammation" in the sense of the disclosure indicates a stage of wound healing process characterized by release of protein-rich exudate, vasodilation through release of histamine and serotonin, presence of phagocytes and engulfdead cells forming necrotic tissue in the wound, sloughy (yellowish colored mass), and platelets aggregate as will be understood by a skilled person [15]). The inflammatory phase occurs almost simultaneously with hemostasis, sometimes from within a few minutes of injury to 24 h and lasts for about 3 days as also understood by a skilled person. [15]).

The term "migration" in the sense of the disclosure indicates a stage of wound healing process characterized by movement of epithelial cells and fibroblasts to the injured area, regeneration and growth of fibroblast and epithelial cells accompanied by epithelial thickening. [15]).

The term "proliferation" in the sense of the disclosure indicates a stage of wound healing process characterized by formation of granulation tissue, collagen synthesis and ingrowth of capillaries and lymphatic vessels into the wound, formation of blood vessels, fibroblast proliferation and collagen thickening blood vessels decrease and oedema recedes, as will be understood by a skilled person. [15]). The proliferative phase occurs almost simultaneously or just after the migration phase (Day 3 onwards) and basal cell proliferation, which lasts for between 2 and 3 days, and continues for up to 2 weeks by which time blood vessels decrease and oedema recedes as will also be understood by a skilled person. [15])

The term "maturation" or "remodeling" in the sense of the disclosure indicates a stage of wound healing process characterized by formation of cellular connective tissue and strengthening of the new epithelium which determines the nature of the final scar. [15]) Cellular granular tissue is changed to an acellular mass from several months up to about 2 years.

A description of appearance of wound in connection with the wound heling process can be found in Table 1 of [15]) enclosed, as Appendix III in U.S. provisional 63/012,036 incorporated herein by reference in its entirety, Wounds in the sense of the disclosure can be categorized in connection with the related progression and repairs in the healing process, in acute wounds and chronic wounds.

"Acute wounds" in the sense of the disclosure are "tissue injuries that heal completely, with minimal scarring, within the expected time frame, usually 8-12 weeks" [15],) (see also [30]).

Conversely, a "chronic wound" or a "complex wound" in the sense of the disclosure indicates wounds that fail to proceed through the normal phases of wound healing in an orderly and timely manner and often stall in the inflammation phase of healing. In particular, the wording "chronic wound" refers a wound subjected to a disruption of the orderly sequence of events during the wound healing process which slows down or prevent healing of the wound [31] [32]).

Typically, a chronic wound is wound not healed in 4 weeks and in some cases over 4 weeks, beyond, 12 weeks or later [31]) typically following repeated tissue insults, underlying physiological conditions, pathological conditions (e.g. persistent infections) treatment of the individual and/or other patient related factors [15]). If healed, a chronic wound can often reoccur. [32])

Typically a chronic wound is a characterized by a high level of oxidative stress compared with non-chronic wounds and with tissue and organs with no lesions, Oxidative stress (OS) is present in tissues and cells when there is an imbalance between the levels of reactive oxygen species (ROS) and the ability of antioxidants in the tissues and cells to remove these species and repair the damage they cause, as will be understood by a skilled person (see [33]enclosed as Appendix VI in U.S. provisional 63/012,036 incorporated herein by reference in its entirety.

Oxidative stress can be detected by detecting expression levels of enzymes that produce ROS, e.g. XCT or Slc7a11, which can have up to an 8.6 fold increase, Nox4 which can have up to 2.1.3 fold increase and Hmox1 which can have up to 4.5 fold increase, in chronic wounds determined by Nanostring analysis during the first 48 hrs of chronicity initiation. Additional methods to detect oxidative stress comprise measuring the levels of DNA/RNA damage, lipid peroxidation, and protein oxidation/nitration, directed to measure reactive oxygen species indirectly, as well as additional methods identifiable by a skilled person, Typically, a chronic would is also characterized by hypoxic or anoxic conditions. In particular, in a chronic wound the pO2 is typically halved compared to a non-chronic wounds. For example, chronic wound surfaces on skin have been identified to be hypoxic at ~37 mmHg, with a mean pH of ~6.8 even in absence of an epidermal barrier absent in most areas. Additionally, it has been shown that one day after wounding pH is above 8 and pO2 is ~60 mmHg, and that both parameters decrease during epidermal barrier restoration in physiological healing [34].

Exemplary chronic wounds in the sense of the disclosure comprise wounds presenting an extensive loss of the integument (skin, hair, and associated glands), wounds presenting tissue death and/or signs of circulation impairment and, as well as wounds resulting from a pathology [15]; [35]).

Exemplary chronic wounds further comprise wounds presenting an excess exudate which typically is more corrosive as it includes a relatively higher levels of tissue destructive proteinase enzymes [15] [36]; [18]. Accordingly, chronic wounds comprise oedema caused by inflammation, reduced mobility and venous or lymphatic insufficiency and additional wounds presenting an excess exudate as will be understood by a skilled person [15]; [17]).

Exemplary chronic wounds also comprise wounds including foreign bodies and possibly presenting granuloma or abscess formation, and wounds presenting keloid (raised) scars resulting from excess collagen production in the latter part of the wound healing process. [15]; [29]).

Exemplary chronic wounds also comprise wounds presenting a persistent infection (e.g. Fournier's gangrene), and in particular infection of one of more pathogenic bacteria such as *Staphylococcus aureus, Pseudomonas aeruginosa, Streptococcus pyrogenes* and some *Proteus, Clostridium* and a Coliform. Typically, chronic wounds presenting persistent infections are infected with *P. aeruginosa* and/or *S. aureus* which significantly reduce skin graft healing [15]; [16]).

Exemplary chronic wounds also comprise wounds of individuals in poor nutritional status (e.g. protein, vitamin (e.g. vitamin C) and mineral deficiencies) and/or of old age [37] [38].

Exemplary chronic wounds further comprise wounds of individuals with underlying conditions such as diabetes and anemia [15] [39].) and/or under treatment of drugs such as glucocorticoids or other steroids capable of suppressing the body's inflammatory responses and thereby impede the inflammatory stage of wound healing [40]; [41] [42]).

Exemplary chronic wounds include diabetic foot ulcers, venous leg ulcers, pressure ulcers, decubitus ulcers (bedsores or pressure sores) and leg ulcers (venous, ischemic or of traumatic origin) and others identifiable to a person skilled in the art.

Exemplary current treatment of a hyperkeratotic, infected, and nonviable (necrotic or dead) soft tissue is usually aggressive and begins with removal of the tissue. The process is known as debridement, which is considered a standard in wound management. It provides the benefits of removing nonviable tissue, bacteria, and senescent cells, along with stimulating the activity of growth factors. Surgical debridement begins with cleaning and disinfecting the surrounding tissue around the wound. Then, the unhealthy tissue is removed by cutting it off using scalpels, curettes, or scissors. The tissue that is exposed after debridement is treated with antibiotics or antifungal treatments. Surgical debridement has been shown to reset the proper timing of the phases of wound re-epithelialization by reintroducing the initial trauma seen in the hemostatis phase of wound healing, as will be understood by a skilled person (Ref. surgery.ucsf.edu/conditions-procedures/debridement. asp, www.ncbi.nlm.nih.gov/books/NBK507882/).

In embodiments herein described particles according to the disclosure can be delivered with a method and system are described for controlled ballistic delivery of a biologically active cargo to a target region within an identified bilayer of the multilayered tissue of an individual.

In methods and systems of the disclosure, a "target region" within a bilayer of the multilayered tissues is portion of the tissue comprising a segment of at least one of the apical layer and the basal layer, the portion centered around a target penetration distance d from the accessible surface. In the target region, the thickness Lt and the target penetration distance d are selected from

- $L_t$=$L_a$/2, and d=$L_a$/2; when the portion consists of a portion of the apical layer
- $L_t$ equal to the lesser of $L_a$/2 or ($L_a$+$L_b$)/4, and d=$L_a$; when the portion comprises the internal boundary facing the basal layer; and
- Lt is the lesser of $L_a$/2 or $L_b$/2, and d is equal to the lesser of 5$L_a$/4 or ($L_a$+$L_b$/4); when the portion consists of a portion of the basal layer.

Accordingly, in methods and systems of the present disclosure, a target region is a region below an accessible surface of an apical layer and not more than 5 mm from the accessible surface of the apical layer. A target region, typically has a thickness not less than 10 microns and not greater than 1 mm. A target region may be specified anatomically and is not limited to a specified distance from the accessible surface of the apical layer. For example, in a skin wound in which the epidermis is absent, and the remaining dermis has variations in thickness, the target region may be specified to be the hypodermis rather than a specific distance from the exposed surface of the dermis. In embodiments where the cargo is a drug, clinically, such a selection of the target layer would enable sustained release of one or more therapeutic agents into the dermis without the need for removal of a dressing to perform topical application of the therapeutic agents. In this example, the apical layer is the dermis, and the basal layer is the hypodermis. In some embodiments the target region can be selected to have comprise a selected boundary between two layers of a soft tissue.

In embodiments of methods and systems of the disclosure the properties of the particles are selected in function of the selected bilayer and target region within the bilayer since the related features inherently require particles that fit within a layer. Consequently, the particles are interacting with layered soft tissues that generally have at least one layer having thickness comparable to the size of the particle. In this regime, the interaction of the projectile with the soft tissue is sensitive to its layered structure, unlike larger projectiles (pellets, bullets, shrapnel). In preferred embodiments the particles are substantially spherical particles that have a diameter that is less than or approximately 1000 microns and is selected based on the layered structure.

In methods and systems of the present disclosure, particles comprising a cargo alone or in combination with a carrier material can be controllably located within one or more target regions of an identified bilayer through ballistic delivery of the particle.

The term "ballistic delivery" as used herein refers to the delivery of high velocity particles to a target substrate such that they are physically embedded in the target material.

Techniques for accelerating microparticles include using an expanding gas to impart momentum on a microparticle. For biological substrates, a precision pneumatic device that diverts expanding gas away from a treated tissue sample can be preferred.

In embodiments, herein described the impact velocity of ballistically delivered particles of at least 100 m/s.

In exemplary embodiments, the ballistic delivery in the sense of the disclosure can be performed using a pneumatic capillary particle accelerating device. For example, particles can be placed on a mesh substrate inserted in a luer lock tubing connector. Particles are deposited in aqueous solution with a concentration of about 1% w/w. Once the particles are fully dry (lyophilization has been used to fully dry the material), then the luer lock connector is loaded into the ballistic device. When the device is adequately aimed at a biological substrate, then a solenoid valve will be triggered to deliver compressed helium at 50-100 psig. Gas rushes past the mesh substrate, picks up the microparticles, and accelerates them down a capillary. This capillary ejects particles into a proprietary vacuum chamber, that strips away compressed gas shocks, and ejects gas free streams of high velocity microparticles. To detect microparticles in the target substrate, it helps to include a fluorescent compound in the microparticle formulation. This allows the use of confocal microscopy to identify the positioning of particles in the 3D tissue substrate.

Other forms of particle acceleration can also be employed. In additional exemplary embodiments, a PDS1000 gene gun can be used which operates by accelerating particles on a polymeric disc. For example, particles are placed on the disc and typically dried, but liquid payloads can be delivered as well. The disc is accelerated when helium bursts a rupture disc. While the device bursts a rupture disc and discharges it into a vacuum to maximize the velocity of gas expanding through a nozzle, a similar device can be designed that discharges helium into ambient air while diverting most of the harmful gas. After the polymeric disc is accelerated, it is made to collide with a mesh stopping screen. Any particles that are on the polymeric disc leave the substrate and carrying through the mesh stopping screen with the velocity of the polymeric disc at the time of collision. This method benefits by using the low aerodynamic relaxation time of the polymeric disc, meaning that high density microparticles can be accelerated to high velocities without using an impractical, long acceleration tube. Another technique to accelerate microparticles involves using laser induced projectile impact testing. In this method, particles are placed on an elastomer spun-coated on a thin gold layer (several micron thick). When the gold foil is ablated using a high powered YAG laser, a small bubble will form in the elastomer that ultimately bursts. This fast event will cause particles to eject from the surface of the elastomer at velocities as high as kilometers per second.

In preferred embodiments, a device can be configured to deliver particle configured for delivery to target layers into the multilayered tissue. In particular, in some embodiments, a device can be used configure to receives input particles (as a dose or a stream) and accelerates them to a velocity distribution selected to deliver output particles into the wound or tissue to an intended self-regulating depth. In some embodiments, the particles are carried by a carrier gas down a capillary tube.

As used herein, a "capillary tube" refers to a tube with a small inner diameter. The input particles can be a mixture of different particles, such as a combination of drug delivery particles and microdevice particles. The output particles are a subset of the input particles. A substantial fraction of the output particles exits the device with sufficient kinetic energy to embed in a debrided wound at a self-regulating depth. Different particles may be delivered to different depths by design of the density, aspect ratio and size of the particles as described herein. For example, drug delivery particles and microdevice particles may be delivered together and achieving different self-regulating depths by design.

In some embodiments, the particles are delivered by a pneumatic particle accelerating device, such as a gene gun or a pneumatic capillary gun, that delivers the particles by the use of a high velocity jet of gas. However, the high velocity gas can be damaging to the delivery location (e.g. tissue), so it is preferable to use a device that can deliver the particles to the target without having high velocity gas impinge on the target.

As used herein, "particle gun" refers to a device configured to provide a thin jet of particles to a target location. A "pneumatic particle gun" refers to a particle accelerating device that uses a jet of high velocity gas to carry the particles towards the target location. The gas is referred to as a "carrier gas".

In some embodiments, the pneumatic particle accelerating device can be modified/designed to prevent the target site from being damaged by high velocity gas as discussed in Example 48 and FIGS. 52 and 53.

In some embodiments, the pneumatic particle accelerating device includes small orifices (smaller than the inner diameter of the capillary tube, e.g. 200-400 microns across, or larger sizes such as 400-1200 microns) on orifice disks that stand between the capillary tube and the target location. The small orifices restrict the amount of gas travelling to the target while allowing a substantial amount of particles to pass through to the target location. The orifice disks can be made of any relatively stiff material that is strong enough to withstand the impinging gas and particles, such as stainless steel, brass, hard plastic, carbon composites, ceramic, etc. Gas deflected off the orifice disks is excess gas.

In some embodiments, the pneumatic particle accelerating device includes a vent in the outer housing ("tube" if cylindrical) to vent excess gas, where the vent is located near (e.g. 600-900 μm) the exit of the capillary tube inside the housing. In some embodiments, the housing includes a protective cone/shield positioned at the exterior of the vent to divert the escaping gas away from the target.

In some embodiments, the orifice disks are housed in an insert that allows the orifice disks to be adjusted, by swapping them out for different disks with different orifice sizes and/or placing them at different distances from the capillary tube. The insert and disks (collectively called a gas diversion unit, GDU) can also be disassembled for inspection of the interior surfaces to characterize the spatial distribution of particle loss (particles not exiting the particle accelerating device towards the target).

In some embodiments, the orifice disk insert has a plurality of holes around it allowing a vacuum to be generated between two or more of the orifice disks, diverting gas away from the target location and slowing down the gas exiting towards the target location with an applied vacuum, thereby protecting the target location.

As used herein, an "applied vacuum" refers to a lower pressure differential compared to the ambient pressure, such that gas moves towards the lower pressure area.

Having multiple holes surrounding the particle jet allows an even vacuum pressure differential from all directions around the jet major axis, thereby preventing the jet of particles from being diverted in any particular direction. In some embodiments, the even vacuum pressure differential can be generated by using a vacuum chamber surrounding the insert from all sides normal to the jet major axis. The orifice disks can be held in place in the insert by the use of gaskets/locking rings (e.g. 2 mm thick) that are machined to have a slight bevel to keep them centered, placed between the orifice disks to also serve as spacers to independently vary the distance between the disks (e.g. the distance between the first and second disk can be different than the distance between the second and third disk) by varying the number or thickness of spacers between the disks.

In embodiments herein described, the microparticle that can be delivered with method and systems of the present disclosure have a diameter from 1 to 1,000 μm and a density from 1 g/cc up to 20 g/cc.

Methods and systems herein described and related particles and compositions, in several embodiments can be used to deliver a biologically active cargo such as drugs and implants to controlled target regions of the corneal tissues and in particular to deliver particles to the target region of a bilayer with controlled spatial distribution In particular, in embodiments herein described a set of particles ballistically delivered to a target region of the multilayered tissue have an average density $\rho_p$ from 1400 $kg/m^3$ to 20000 $kg/m^3$, an average diameter $D_p$ greater than 1 micron and less than the least of 1000 micron, $D_p$ being $L_a/2$ or $L_b/2$, and a dispersity index PDI from 1 to 2.

The specific set of Dp and $\rho_p$ and conditions for delivery and in particular the related velocity voj that results a distribution of at least 30% of a particle set within a target region in a bilayer of the multilayered tissue can be identified with a determining step which takes into account the properties of the particles but also the properties of the layers and bilayer of the multilayered tissue.

In embodiments of methods and systems of the disclosure the interaction of a penetrating particle with the layered structure is used to achieve localization that is guided by the structure of the tissue, not simply a specified distance from an exposed surface and is accounted for by the selected parameters defining the properties of the tissue and/or of the related bilayer.

In particular, in methods and systems of the present disclosure a combination of particle mean size, substantially spherical particle mean density, and particle mean impact velocity is determined using prescribed sequence of steps. As will be evident in the sequence of steps, more complete and precise information regarding the thickness and properties of the individual layers of the multilayered tissue results in a smaller set of prescribed experiments to find an inventive combination of substantially spherical particle mean size, substantially spherical particle mean density, and substantially spherical particle mean impact velocity.

In embodiments of methods and systems of the present disclosure, the method comprises providing a tissue having features described herein with respect to a multilayered tissue. In particular the provided tissues comprises a bilayer having a bilayer thickness L from 50 microns to 5000 microns, a bilayer width W at least 10*L, a tissue Young's modulus E from 500 Pa to 50 MPa and a tissue density ρ from 850 $kg/m^3$ to 1200 $kg/m^3$.

In embodiments of methods and systems of the present disclosure, in the provided tissue, the bilayer comprises an apical layer and a basal layer underneath the apical layer, the apical layer having thickness $L_a<L$, and a compressive strength $Y_a$; and the basal layer having thickness $L_b=L-L_a$ and a compressive strength $Y_b$. The apical layer is defined by an accessible surface facing an environment external to the tissue and an internal boundary facing the basal layer, the apical layer having an accessible surface area at least ten-times $L^2$.

In embodiments of methods and systems of the present disclosure, the providing can be performed by providing a tissue, in vivo, ex vivo or in vitro depending on the experimental setting and design as will be understood by a skilled person. The providing can comprise preparing the tissue in a form and under condition allowing ballistic delivery in the sense of the disclosure as will also be understood by a skilled person.

In embodiments of methods and systems of the present disclosure, the method also comprises selecting a target region of interest. The target region has a target region thickness Lt and comprises a portion of at least one of the apical layer and the basal layer the portion centered around a target penetration distance d from the accessible surface. wherein the target region thickness Lt and the target penetration distance d are selected from

- $L_t=L_a/2$, and $d=L_a/2$; when the portion consists of a portion of the apical layer
- $L_t$ equal to the lesser of $L_a/2$ or $(L_a+L_b)/4$, and $d=L_a$; when the portion comprises the internal boundary facing the basal layer; and
- Lt is the lesser of $L_a/2$ or $L_b/2$, and d is equal to the lesser of $5L_a/4$ or $(L_a+L_b/4)$; when the portion consists of a portion of the basal layer.

Accordingly, methods and systems of the disclosure can comprise determining a) if a tissue of interest satisfies the definition of a multilayered tissue in the sense of the disclosure, whether a bilayer can be identified in the tissue of interest that has an apical layer and a basal layer in the sense of the disclosure and b) if the desired location for delivery particles satisfies the definition of a target region.

Methods and systems of the disclosure can further comprise obtaining the comprise obtaining L, W, E and ρ of the bilayer of interest within the multilayered tissue, and/or the La, Lb of the apical layer and basal layer and/or Lt of the target region.

As a consequence, in some embodiments of the methods and systems of the disclosure, once the multilayered tissue and the target region are identified, the method can further comprise determining the thickness of the apical layer $L_a$ and the thickness of the basal layer $L_b$. This determining can be performed using in vivo imaging of the multilayered tissue at a specific location in or on the body of an individual to be treated. Alternatively, the determining can be performed based on established anatomy of the multilayered tissue at a specific location in or on the human body. The actual and/or estimated values of the thickness of the apical layer, $L_a$, and the thickness of the basal layer, $L_b$, are used to confirm that each one satisfies the definition of a layer.

In some embodiments of the methods and systems of the disclosure, once the apical layer and the basal layer are provided, the method can further comprise obtaining information allowing determination or estimation of their relevant physical properties. For example, information concerning knowledge to the composition and anatomy of individual layers identifiable by a skilled person can be used to provide the determination or estimation of the tissue properties alone or in combination with experimental detection and/or indications of the present disclosure. In particular Table 3 is provided that lists estimated values of three properties of each layer: mean density $\rho_i$, effective compressive strength $Y_i$, and effective viscosity $\mu_i$, where the subscript i indicates the specific layer, such as apical or basal. Thus, the apical layer has mean density of $\rho_a$, and the effective compressive strength $Y_a$, and effective viscosity $\mu_a$, where the subscript a indicates the apical layer. Similarly, the basal layer has mean density of $\rho_b$, and the effective compressive strength $Y_b$, and effective viscosity $\mu_b$, where the subscript b indicates the basal layer.

TABLE 3

| Tissue Type | For following tissue types, values of layer properties → | mean density $\rho_i$ [kg/m$^3$] | effective compressive strength $Y_i$ [kPa] | effective viscosity $\mu_i$ [Pa · s] |
|---|---|---|---|---|
| I | corneal epithelium, vascular endothelia, mucosal epithelia, hypodermis, adipose layers | 915 | 70 | 1 |
| II | corneal stroma, dermis, mucosal lamina propria | 1050 | 650 | 1 |
| III | smooth muscle, muscularis mucosae | 1100 | 1500 | 10 |
| IV | epidermis, skeletal muscle | 1150 | 4200 | 100 |

In some embodiments of the disclosure the softest layers are further recognizable within the indication of Table 3 by virtue of composition (e.g., rich in adipose) or location within a well-recognized type of tissue (e.g., the surface layer of a mucosal tissue) or by cell type and spatial arrangement (e.g., the corneal epithelium or vascular endothelia). The next softest group can be recognized based on composition (e.g., layers with both high-water content and rich in ECM proteins such as the corneal stroma) and location within a well-recognized type of tissue (e.g., the dermis of the skin). Similar reasoning holds for the successively stiffer layers. Table 3 provides examples of each tissue type (I, II, III or IV) that the skilled person can generalize to layers not to explicitly listed, but having similar structure, composition and properties to one or more of the exemplars of a given tissue type.

In some embodiments herein described, Table 3 provides values of the three parameters that are used to perform the iterative calculation of the impact velocity that provides delivery to a specified target region. The three parameters affect the penetration of particles into tissue due to the inertia of a tissue layer (requiring a value of the density of tissue layer i, denoted $\rho_I$), the mechanical integrity of the tissue that yield for the particle to progress into it (requiring a value of the compressive strength of tissue layer i, denoted $Y_I$) and the drag force exerted by the tissue on the particle (requiring knowledge of an effective viscosity of tissue layer i, denoted $\mu_I$). Thus, the apical layer is identified using knowledge of tissue anatomy of the bilayer tissue and using Table 3 to identify the corresponding tissue type and look up the values of the required parameters. For example, the effective compressive strength for the apical layer is found using the tissue type: $Y_I$=70 kPa, $Y_{II}$=690 kPa, $Y_{III}$=1500 kPa, $Y_1$=4200 kPa is the compressive strength of the apical layer according to its type I, II, III or IV and used as $Y_a$. Likewise, the anatomy of the bilayer tissue to assign the basal layer to one of the four tissue types (I, II, III or IV) and using the effective compressive strength of that tissue type as the compressive strength of the basal layer $Y_b$.

In embodiments of the methods and systems of the disclosure, the obtained value for the physical parameters of the multilayered tissue, the related bilayer, apical and basal layer and target region can be used in performing an iterative calculation of the impact velocity required to deliver some particle of the set of particles to the target region for a selected particle diameter $D_p$ (or simply D) within the definition of a particle in the present disclosure and for a selected density of a particle $\rho_p$ of the present disclosure.

The calculation reveals whether the selected $D_p$ and $\rho_p$ provide an acceptable value of the impact velocity $v_{o,j}$ that will safely deliver particles preferentially to the target region. An acceptable value of $v_{o,j}$ is less than 1500 m/s, so that the present disclosure can be employed safely by remaining below Mach 2, twice the speed of sound in helium (the usual carrier gas) at standard temperature and pressure. If the resulting value of $v_{o,j}$ is greater than 1500 m/s, the skilled person can proceed to increase the selected particle density and diameter to reduce $v_{o,j}$, repeating as needed. If not acceptable value of $v_{o,j}$ is obtained prior to reaching the maximum particle density of the present disclosure (20,000 kg/m$^3$) and reaching an unacceptably large particle diameter (the least of 1000 micron, $L_a/2$ or $L_b/2$), then the target region of the selected tissue cannot be reached using the present disclosure.

The iterative calculation requires that a target region be selected in the bilayer tissue among three options "apical", "boundary" or "basal";

- the target region is said to be "apical" when it occupies the central half of the apical layer. That is, the "apical target region" has a thickness of $L_t$=$L_a/2$, and centered about a target penetration distance d=$L_a/2$ from the accessible surface;
- the "boundary target region" straddles the interior boundary that separates the apical and basal layers and has a thickness that gives it equal penetration into the basal layer when the basal layer is thick enough to do so and extends only $L_b/4$ otherwise. Consequently, the target layer thickness $L_t$ is equal to the lesser of $L_a/2$ or $(L_a+L_b)/4$, and has a target penetration distance located at the interior boundary, at d=$L_a$; and
- the "basal target region" is entirely in the basal layer and therefore has a penetration distance deep enough that the basal target region thickness is entirely on the basal side of the interior boundary; specifically, when the basal layer is thicker than the apical layer, the basal target penetration distance d is placed to the basal side of the boundary by a distance $L_a/4$, i.e., d=$5L_a/4$, paired with a target layer thickness $L_t$=$L_a/2$; and when the basal layer is thinner than the apical layer, d is placed to the basal side of the boundary by a distance $L_b/4$, i.e., d=$(L_a+L_b/4)$, paired with $L_t$=$L_b/2$ In embodiments of the disclosure, by grouping tissues in a way that a skilled person can use based on available imaging and well-established tissue anatomy, one of skill can address challenges with respect to placing particles at a specific target region using an effective penetration distance parameter as will be understood by a skilled person.

The "effective target penetration distance" d* is greater than or equal the "target penetration distance," as it can be visualized the distance the particle would penetrate into a semi-infinite slab of the apical material. The change in compressive strength moving from the apical layer to the basal layer is used to convert the remaining kinetic energy of the particle after the deflection and dissipation due to the boundary into the equivalent distance that the particle would penetrate into the apical material. Doing this enable the iterative calculation to be performed without reference to the basal layer properties. The conversion of the penetration distance d to the effective penetration distance d* also accounts for the energy deflected and dissipated by interaction with the interface. In the case of soft multilayer tissues, this effect proved to be negligible if the target region lies entirely in the apical layer. Therefore, no correction is required and d*=d in the case of an "apical target region". To "bunch up" particles at the boundary required that they have enough kinetic energy to compensate for the deflected and dissipated energy. A surprisingly simple function is capable of approximating this effect: the absolute value of the log of the ratio of compliances provides a correction that neglects the difference between a situation in with the apical layer is stiffer and the basal layer is softer or vice versa. Soft tissue densities are sufficiently close to one another that the contrast in compressive modulus dominates the effect. Lastly, the effect is approximately linear for contrast up to a factor of 100 and then saturates. A functional form that captures this well is the arctangent, leading to the selection of the functional form of the factor that describes in the greater penetrating power required due to interaction with the boundary:

$$f = \arctan\left(\left|\log\left(\frac{Y_a}{Y_b}\right)\right|\right).$$

Thus, the values of $Y_a$ and $Y_b$ are used to convert the target penetration distance d of the selected target region to an effective target penetration distance d* for the target region as follows:

- the "apical" target region has $d^*=d=L_a/2$;
- the "boundary" target region has $d^*=d^*(1+f)=L_a^*(1+f)$, where $$f = \arctan\left(\left|\log\left(\frac{Y_a}{Y_b}\right)\right|\right);$$

and

- the "basal" target region has $d^*=d^*(1+f)+(d-L_a)(\sqrt{Y_b/Y_a})=L_a^*(1+f)+\min(L_a/4, L_b/4)^*(\sqrt{Y_b/Y_a})$;
- providing a particle of density $\rho_p$ from 1400 kg/$m^3$ to 20000 kg/$m^3$, average diameter $D_p$ that is greater than 1 micron and is less than the least of 1000 micron, $L_a/2$ or $L_b/2$, and polydispersity index PDI from 1 to 2.

Accordingly, in embodiments of the present disclosure an simple iterative calculation is provided to determine the impact velocity that delivers a substantial fraction of particle to the target region using physically meaningful parameters with values that are provided in Table 3 or are evaluated as herein described as well as four parameters, k, m, n (herein, $n_0$) and q described in Ye et al. (2022) for the case of small projectiles penetrating into soft tissue without causing injury. In the methods and systems herein described the prefactor k=0.550 provides the correct magnitude of the impact velocity; the parameters m=1.271 and $n_0$=0.826 provide the power-law dependence on the dimensionless particle diameter and the crude approximate of the effect of the dimensionless velocity; q=12.03 provides a valuable correction that is particularly significant in the delicate regime of low impact energy is not adequately described by the Poncelet model. The dimensionless groups identified by Ye et al. (2022) and the scaling exponents that they measured for the effect of each dimensionless group provide the scaling exponents for the dependence of the dimensionless penetration depth on the dimensionless particle diameter, the dimensionless density of the particle relative to the tissue layer and the velocity at impact. Furthermore, the study provides a valuable correction relative to simple scaling exponent for the dependence of dimensionless penetration on dimensionless impact velocity. Thus, in the following expression, the values of n, m and q are provided by Ye at. (2022). The iterative calculation determining a velocity $v_{o,j}$ proceeds by iterating $$v_{o,i} = \sqrt{Y_a/\rho_p}\left((1/k)\left(d^*/D^m\right)\left(\mu_a^{m-1}\right)\left(\sqrt{Y_a\rho_p}\right)^{1-m}\left(\rho_a/\rho_p\right)\right)^{1/n_i}$$

from i=0 to j, where $n_0$=0.826 and $n_i=n_0-q(v_{o,i-1}\sqrt{\rho_a/Y_a})$, until $|(v_{0,i}-v_{0,i-1})/v_{0,i-1}|<0.1$; selecting the $D_p$, $\rho_p$ and when is less than 1,500 m/sec; and In some embodiments of method and systems herein described the method can further comprise ballistically delivering a set of a1 particles having the selected $D_p$ and $\rho_p$ at velocity $v_{o,j}$ to the accessible surface of the apical layer of the bilayer tissue to deliver into the target region at least 30% of the set of particles.

In some embodiments, a method for controlled ballistic delivery of a biologically active cargo to a bilayer tissue of an individual, the method can comprise:

- providing a tissue comprising a bilayer tissue comprising the epidermal and dermal layers of skin, the skin has a Young's modulus E from 0.5 MPa to 2 MPa, the skin has density from 1000 kg/$m^3$ to 1200 kg/$m^3$; the bilayer tissue comprising an apical layer of epidermis having Tissue Type IV and effective compressive strength to the apical $Y_a$=4200 kPa and a basal layer of dermis having Tissue Type II $Y_b$=690 kPa,
- the apical layer having thickness $L_a$ of 75 micron to 100 micron and the basal layer having thickness $L_b$ of 1000 micron to 4000 micron In those embodiments, the method can further comprise selecting a target region in the bilayer tissue that is "apical", "boundary" or "basal";

- the "apical" target region begins $L_a/4$ from the accessible surface, has a target layer thickness $L_t=L_a/2$, and has a target penetration distance $d=L_a/2$;
- the "boundary" target region begins $3L_a/4$ from the accessible surface, has a target layer thickness $L_t$ equal to the lesser of $L_a/2$ or $(L_a+L_b)/4$, and has a target penetration distance $d=L_a$; and
- the "basal" target region begins at a distance from the accessible surface equal to the lesser of $5L_a/4$ and $(L_a+L_b/4)$, has a target layer thickness that is the lesser of $L_a/2$ or $L_b/2$, and has a target penetration distance d equal to the lesser of $5L_a/4$ or $(L_a+L_b/4)$.

In those embodiments, the method can also comprise assigning a tissue type (I, II, III or IV) to the apical layer based on the anatomy of the bilayer tissue and using the tissue type to assign an effective compressive strength to the apical layer of that tissue type ($Y_I$=70 kPa, $Y_{II}$=690 kPa, $Y_{III}$=1500 kPa, $Y_{IV}$=4200 kPa) as the compressive strength of the apical layer $Y_a$; using the anatomy of the bilayer tissue to assign the basal layer to one of the four tissue types (I, II, III or IV) and using the effective compressive strength of that tissue type as the compressive strength of the basal layer $Y_b$; and using the values of $Y_a$ and $Y_b$ to convert the target penetration distance d of the selected target region to an effective target penetration distance d* for the target region, In those embodiments, of the method the "apical" target region has $d^*=d=L_a/2$; the "boundary" target region has $d^*=d^*(1+f)=L_a^*(1+f)$, where $$f = \arctan\left(\left|\log\left(\frac{Y_a}{Y_b}\right)\right|\right);$$

and the "basal" target region has $d^*=d^*(1+f)+(d-L_a)(\sqrt{Y_b/Y_a})=L_a^*(1+f)+\min(L_a/4, L_b/4)^*(\sqrt{Y_b/Y_a})$;

In those embodiments, the method can further comprise providing a particle of density $\rho_p$ from 1400 kg/m3 to 20000 kg/m3, average diameter $D_p$ that is greater than 1 micron and is less than the least of 1000 micron, $L_a/2$ or $L_b/2$, and polydispersity index PDI from 1 to 2;

determining a velocity $v_{o,j}$ by iterating $$v_{o,i} = \sqrt{Y_a/\rho_p}\left((1/k)(d^*/D^m)(\mu_a^{m-1})\left(\sqrt{Y_a\rho_p}\right)^{1-m}(\rho_a/\rho_p)\right)^{1/n_i}$$

from i=0 to j, where $n_0$=0.826 and $n_i=n_0-q(v_{o,i-1}\sqrt{\rho_a/Y_a})$, until $|(v_{o,i}-v_{o,i-1})/v_{o,i-1}|<0.1$;

selecting the $D_p$, $\rho_p$ and $v_{o,j}$ when $v_{o,j}$ is less than 1,500 msec; and ballistically delivering a set of particles having the selected $D_p$ and $\rho_p$ at velocity $v_{o,j}$ to the accessible surface of the apical layer of the bilayer tissue to deliver into the target region at least 30% of the set of particles.

In some embodiments of methods and systems herein described once an appropriate combination of $D_p$, $\rho_p$ and $v_{o,j}$ is selected, the next step is to procure a particle accelerating device that can provide impact velocities v greater than or equal to $v_{lb}$. For illustration, the procedure describes three technologies for particle delivery that currently exist: the BioRad handheld biolistic delivery device (Helios), laser-induced particle impact technology (LIPIT) and the pneumatic particle delivery device (P2D2) of the present disclosure. As additional devices become available, the skilled person will be able to refer to the specifications and determine whether they provide particle velocities $v>v_{lb}$. Once the set of particle-accelerating devices that are capable of producing $v>v_{lb}$ has been identified, the skilled person will choose at least one and use it for the following pre-clinical experiments. The skilled person will follow the use instructions for the particle-accelerating device, including but not limited to providing the proper electrical, optical and pneumatic connections, following the protocols for loading particles, for delivering particles, and for cleaning and maintaining the device.

In some embodiments, once the skilled person has implemented a particle accelerating device that is capable of providing $v>v_{lb}$, the method can further comprise further selecting the selected $D_p$ and $\rho_p$ at velocity $v_{o,j}$ by ballistically delivering a set of particles with the selected Dp ρp and Voi to a tissue surrogate and/or a tissue sample, to identify a further selected set of particle size, particle density and particle impact velocity that span the conditions that will preferentially deliver particles to the target region. In some embodiments in which the properties of the individual layers are already well established, the following experiments are typically optional depending on the experimental design and on a desired percentage of particle to be delivered in the target region.

In some embodiments, the method comprises providing a gelatin having features mimicking the determined or estimated feature of the multilayered tissue and/or related layers comprising the target region (herein also tissue surrogate). A Table 4 that provides the concentration of Bloom 250 ballistic gelatin to be used in experiments to identify the combinations of particle size, mean density and particle delivery parameters that are capable of delivering particles to the target region. Experiments are essential when the impact velocities provided by a selected particle accelerating device are not known. Experiments can be performed that establish the delivery parameters that provide adequate penetration into the tissue surrogate. Penetration into a transparent surrogate can be measured in a laboratory that has access to imaging equipment suitable for characterizing multilayered tissue.

TABLE 4

| Tissue Type | For following tissue types, the gel that serves as a surrogate → | Concentration of Bloom 250 gelatin |
|---|---|---|
| I | corneal epithelium, vascular endothelia, mucosal epithelia, hypodermis, adipose layers | 5% |
| II | corneal stroma, dermis, mucosal lamina propria | 10% |
| III | smooth muscle, muscularis mucosae | 20% |
| IV | epidermis, skeletal muscle | 40% |

In some embodiments, the set of experiments can be specified based on the location of the target region relative to apical and basal layers. If the target region lies within the apical layer, a single gel is used as specified in Table 4 that relates the anatomical identification of a layer to the gel that serves as surrogate for the apical layer. This single-component gel is called an "apical surrogate". If the target region is either near the boundary between the apical and basal layers or in the basal layer, two gels are used, the apical surrogate and a basal surrogate. The composition of the basal surrogate is specified in Table 4 that relates the anatomical identification of the basal layer to the gel that serves as its surrogate. Initial experiments examine penetration into the apical surrogate and, separately, the basal surrogate. Preparation of each surrogate, including determination of the related thickness, proper storage and handling are identifiable by a skilled person upon reading of the present disclosure. The measured penetration depths in each surrogate are used to categorize the prescribed combinations of (particle size, particle density, delivery conditions) as insufficient, sufficient, or excessive using specific criteria that are based on the target region, $L_a$ and $L_b$. If the target region is in the apical layer, this set of experiments in the apical surrogate is sufficient to select the sets of (particle size, particle density, delivery conditions) to test in ex vivo animal tissue, as described in the present disclosure.

In some embodiments wherein testing of delivery to or beyond the boundary between the apical and basal layers is desired, the conditions that satisfy the conditions for "sufficient" but not excessive penetration provide a valuable subset of conditions relative to those tested in individual surrogates. This subset of conditions is examined in a bilayer surrogate. The bilayer surrogate is prepared with a layer of thickness $L_a$ of the apical surrogate on 10 mm thick basal surrogate. In some embodiments, experiments to identify the delivery conditions can be performed using particles that establish the window of particle size, particle density and particle delivery conditions that are capable of reaching the target region.

In embodiments, wherein the method further comprises ballistically delivering to a tissue surrogate a set of particles having the selected $D_p$ and $\rho_p$ at velocity $v_{o,j}$ measurement of resulting $D_p$ and $\rho_p$ at velocity $v_o$ can be performed to obtain a further selected set of $D_p$ and $\rho_p$ at velocity $v_{o,j}$ which result the delivery of an increased controlled percentage of particles with the target region.

In some embodiments of methods and systems of the present disclosure, the method can also comprise ballistically delivering to a tissue sample a set of particles with the selected set of selected $D_p$ and $\rho_p$ at velocity $v_{o,j}$ and/or preferably the further selected set of selected $D_p$ and $\rho_p$ at velocity $v_{o,j}$ For example with at least one of the selected or further selected set of particle size and density and delivery parameters for a specific particle accelerating device, a user can be perform experiments on porcine tissue. The results of the experiments ae expected to enable them to rule out some of the conditions that were not ruled out by experiments in the tissue surrogate (due to the fact that the nonlinear response of actual tissue is not present in the tissue surrogate) and obtain a set of tissue selected $D_p$ and $\rho_p$ at velocity $v_{o,j}$ which can result the delivery of an increased controlled percentage of particles with the target region.

In some embodiments of the methods and systems herein described, in the method the algorithm specifies a limited number of tests to perform with the particle accelerating device. The results of the experiments are used to rule out certain combinations of density, size and operating conditions that were not ruled out by the calculations (due to the fact that the data that would make the model predictive are not available in the literature nor measurable by laboratory instruments that are available to the skilled person).

In some embodiments of methods and systems of the disclosure delivery of the particles to a target region that is specified by proximity to a selected boundary between layers in a multilayered tissue is achieved despite variation in the thickness of one or more overlying layers of soft tissue through which the particles pass. In some embodiments variations in the thickness of one or more overlying layers of soft tissue exist due to injury or disease. In some embodiments, variations in the thickness of one or more overlying layers of soft tissue are modified by debridement during the treatment of an injury or disease.

In some embodiments the properties and thickness of the layers in a soft tissue are known. The present disclosure describes how the known thicknesses and properties of the layers of the soft tissue may be used to select particle properties and delivery parameters to preferentially place particles near a desired boundary in the multilayered tissue.

In some embodiments the properties of individual layers in a multilayered tissue are not known, in view for example of a lack of experimental methods to characterize individual layers of a soft tissue. In those embodiments, methods and systems of the disclosure can provide a set of data provided in view of the determining alone or in combination with provide a set of experiments that a skilled person can perform to efficiently determine the range of particle properties that provide delivery to a desired target region in a selected multilayered tissue. In some cases, the experiments can be performed in a model of the soft tissue that is prepared using materials that approximate the layers of the multilayered tissue. In some cases, the experiments can be performed in an ex vivo animal model of the multilayered tissue of interest.

In some embodiments, the distribution of impact parameters produced by a given particle accelerating device is not known, for example from a lack of measurements of the distribution of impact velocities of particles that have been accelerated by a given particle accelerating device. In those embodiments, methods and systems of the disclosure can provide s set of experiments that a skilled person can perform to efficiently determine the distribution of impact parameter produced by a given particle accelerating device.

In some embodiments, methods and systems herein described can be used in medical applications. For medical applications, the system of delivery preferably includes a technique to protect tissues from materials used to impart momentum to microparticles.

Density boosting additives, including iron oxides and metal nanoparticles can theoretically be added to carrier materials to achieve increased particle density. Another technique to delivery payloads with high density includes using porous metals loaded with therapeutic cargo.

In some embodiments the methods herein described can be performed with combination of components forming a system for controlled ballistic delivery of microparticle to the cornea.

In some embodiments, the system according to the present disclosure comprise a convex microparticle having a diameter from 1 to is less than the least of 1000 micron, $L_a/2$ or $L_b/2$ and a density from 1.4 g/cc up to less 20 g/cc, the microparticle comprising the biologically active cargo within a carrier material.

The system further comprises a device configured to ballistically deliver to a multilayered tissue a particle. Preferably the particle is a substantially spherical microparticle. In some embodiments the device can be used for controlled ballistic delivery of a biologically active cargo to the at target region of the multilayered tissue of an individual according to methods herein described.

For example, a device that can be used comprises devices for the delivery of genetic materials to the cornea using metal microparticles such as the one described in Zhang et al [6].

The systems herein disclosed can be provided in the form of kits of parts. In kit of parts for performing any one of the methods herein described, the related and the reagents can be included in the kit alone or in the presence of device of microparticles compositions. In kit of parts for the treatment of an individual the microparticles and devices for the related application can be comprised together with the reagents formulated for administration to the individual as well as additional components identifiable by a skilled person.

In a kit of parts, the microparticles, devices and the reagents for the related application and additional components identifiable by a skilled person are comprised in the kit independently possibly included in a composition together with suitable vehicle carrier or auxiliary agents. For example, one or more probes can be included in one or more compositions together with reagents for detection also in one or more suitable compositions.

Additional components can include the VOAG, a drying column, and fluorescent compounds to mark the location of microparticles. identifiable by a skilled person upon reading of the present disclosure.

In embodiments herein described, the components of the kit can be provided, with suitable instructions and other necessary reagents, in order to perform the methods here disclosed. The kit will normally contain the compositions in separate containers. Instructions, for example written or audio instructions, on paper or electronic support such as tapes, CD-ROMs, flash drives, or by indication of a Uniform Resource Locator (URL), which contains a pdf copy of the instructions for carrying out the assay, will usually be included in the kit. The kit can also contain, depending on the particular method used, other packaged reagents and materials (e.g wash buffers and the like).

In some preferred embodiments, methods and systems and related particles a biologically active cargo comprises one or more pharmaceutically active agents possibly including one or more drugs in the sense of the disclosure. In those embodiments, methods and systems of the disclosure can be used in connection with therapeutic applications, for the treatment and/or prevention of conditions of the cornea of the individual.

The term "treatment" as used herein indicates any activity that is part of a medical care for, or deals with, a condition, medically or surgically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" indicates a physical status of the body of an individual (as a whole or as one or more of its parts e.g., body systems), that does not conform to a standard physical status associated with a state of complete physical, mental and social well-being for the individual. Conditions herein described comprise disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms in an individual.

In some embodiments method and systems of the disclosure can be used in alternative or in combination with, emulsions, ointments, gels, and polymeric inserts to increase the bioavailability of medicine in the cornea.

In methods and systems of the present disclosure and related particles, which comprise antibiotics, the antibiotics are comprised in a therapeutically effective amounts that can be identified by a skilled person based on the specific agent, tissue and as will be understood by a skilled person.

In methods and systems of the present disclosure and related particles, the administration of a biologically active cargo and in particular of antibiotics antimicrobials, steroid NSAID and other drug in the sense of the disclosure. In methods and systems of the present disclosure and related particles, with one or more antibiotics is known and expected to result in a therapeutic effect on the target tissues/

In some embodiments method and systems of the disclosure can be used in alternative or in combination with nanotechnologies, including dendrimers, cyclodextrins, nanoparticles, liposomes, and polymeric micelles can be combined with the microparticle composition as described. Novasorb®, a cationic emulsion, can be used to deliver latanoprost, a prostaglandin analog used for treating glaucoma. Durasite® is a solution of cross-linked polyacrylamide that can be used to deliver besifloxacin and azithromycin for the treatment of conjunctivitis.

In some embodiments method and systems of the disclosure can be used to obtain the delivery of high-velocity medicinal microparticles to the anterior surface of the eye.

Biolistic delivery of microparticles to the cornea has several advantages compared to standard topological solutions. First, therapeutic microparticles can be delivered to the surface of the cornea in a uniform, quantifiable layer that will not be redistributed due to gravity and the geometry of the anterior ocular surface. This is expected lead to much more even distribution of therapeutic compounds, which can be beneficial for treatments like corneal cross-linking surgery in which cross-linking density is affected by spatial distribution. Second, the use of ballistic microparticles likely allows for instantaneous traversal of the eye's mucin coat. This barrier can lead to rejection of many negatively charged molecules.

Additionally, the medicinal particles embed in the corneal epithelium, remain fixed in place, and slowly dissolve to release therapeutic compounds to surrounding tissue volumes. In particular, embedding a micro particle in corneal tissue allows for bioavailability of compounds for a long duration of time. If particles are embedded in tissue, fixing them in place, they can dissolve over a period of several hours, leading to more effective uptake of medicine.

In some embodiments, the medicinal particles can be used for treatment and/or prevention of conditions on additional multilayered tissues will be understood by a skilled person.

In particular in some embodiments, the methods and systems and related particles of the disclosure can be used in connection with treatment and/or prevention of wounds, by delivery particles comprising antibiotics, antimicrobial, growth factors and/or wound healing agent as will be understood by a skilled person upon reading of the present disclosure.

In those embodiments, suitable antibiotics that can be used include ampicillin, kanamycin, ofloxacin, Aminoglycosides, Carbapenems, Ceftazidime, Cefepime, Ceftobiprole, Fluoroquinolones, Piperacillin, Ticarcillin, tobramycin, aztreonam, coliston, tazobactam, and others (or combinations of these antibiotics) that can be readily recognized by a person skilled in the art.

Additional antibiotics that can be used include Amoxicillin and clavulanic acid (Augmentin®), Methicillin, oxacillin, nafcillin, cloxacillin, dicloxacillin, cabenicillin, ticarcillin, piperacillin, mezlocillin, azlocillin, ticarcillin and clavulanic acid (Timentin®), piperacillin and tazobactam (Zosyn®), cephalexin, cefdinir, cefprozil, cefaclor, cefuroxime, sulfisoxazole, erythromycin/sulfisoxazole, tobramycin, amikacin, gentamicin, erythromycin, clarithromycin, azithromycin, tetracycline, doxycycline, minocycline, tigecycline, ciprofloxacin, levofloxacin, vancomycin, linezolid, imipenem, meripenem, and aztreonam.

As a person of ordinary skill in the art would understand, the antibiotics herein listed can be selected for treating infections and/or reducing inflammation caused by bacteria including *Staphylococcus* (*S. aureus* and *S. epidermidis*), *Pseudomonas* (*P. aeruginosa*), *Burkholderia cepacia, Escherichia coli, Enterococcus* spp., *Corynebacterium* spp., and some mycobacteria. In some embodiments antibiotics can be selected to treat infections and/or reduce inflammation caused by the bacteria listed in Table 5 below.

TABLE 5

Bacteria found in chronic wounds

| Bacteria | References |
|---|---|
| *Acinetobacter* sp. | (Gjødsbøl et al., 2006, 2012; Dowd et al., 2008a; James et al., 2008; Gontcharova, 2010; Wolcott et al., 2016) |
| *Anaerococcus* sp. | (Gardner et al., 2013; Smith et al., 2016; Wolcott et al., 2016) |
| *Bacillus* sp. | (Gjødsbøl et al., 2006; Dowd et al., 2008b, 2008a; Gontcharova, 2010; Wolcott et al., 2016) |
| *Corynebacterium* sp. | (Gontcharova, 2010; Gjødsbøl et al., 2012; Gardner et al., 2013; Scales and Huffnagle, 2013; Smith et al., 2016; Wolcott et al., 2016) |
| *Enterobacter* sp. | (Gjødsbøl et al., 2006; Dowd et al., 2008a; James et al., 2008; Smith et al., 2016; Wolcott et al., 2016) |
| *Enterobacter cloacae* | (Gjødsbøl et al., 2006, 2012) |
| *Enterococcus* sp. | (Dowd et al., 2008a; James et al., 2008; Scales and Huffnagle, 2013; Smith et al., 2016; Wolcott et al., 2016) |
| *Enterococcus faecalis* | (Gjødsbøl et al., 2006, 2012; Wolcott et al., 2016) |
| *Escherichia* sp. | (Dowd et al., 2008a; James et al., 2008; Gontcharova, 2010; Gjødsbøl et al., 2012; Scales and Huffnagle, 2013) |
| *Escherichia coli* | (Gjødsbøl et al., 2006; Dowd et al., 2008a) |
| *Finegoldia* sp. | (Gontcharova, 2010; Gardner et al., 2013; Wolcott et al., 2016) |
| *Finegoldia magna* | (Smith et al., 2016; Wolcott et al., 2016) |
| *Paenibacillus* sp. | (Dowd et al., 2008a) |
| *Peptoniphilus* sp. | (Dowd et al., 2008a; Gardner et al., 2013; Smith et al., 2016; Wolcott et al., 2016) |
| *Porphyromonas* sp. | (Gardner et al., 2013) |
| *Prevotella* sp. | (Gontcharova, 2010; Gardner et al., 2013; Scales and Huffnagle, 2013; Smith et al., 2016; Wolcott et al., 2016) |
| *Propionibacterium* sp. | (Gontcharova, 2010; Wolcott et al., 2016) |
| *Propionibacterium acnes* | (Wolcott et al., 2016a) |
| *Pseudomonas* sp. | (Gjødsbøl et al., 2006; Dowd et al., 2008a; James et al., 2008; Gontcharova, 2010; Scales and Huffnagle, 2013; Smith et al., 2016; Wolcott et al., 2016) |
| *Pseudomonas aeruginosa* | (Gjødsbøl et al., 2006, 2012; Scales and Huffnagle, 2013; Wolcott et al., 2016) |
| *Staphylococcus* sp. | (Dowd et al., 2008a; James et al., 2008; Gontcharova, 2010; Gardner et al., 2013; Smith et al., 2016; Wolcott et al., 2016) |
| *Staphylococcus epidermidis* | (Scales and Huffnagle, 2013; Wolcott et al., 2016) |
| *Streptococcus* sp. | (Dowd et al., 2008a; James et al., 2008; Gontcharova, 2010; Scales and Huffnagle, 2013; Smith et al., 2016; Wolcott et al., 2016) |
| *Turicibacter* sp. | Wolcott et al., 2016b |

In some embodiments, suitable antibiotics comprise antibiotics effective against *Pseudomonas aeruginosa* such as Aminoglycosides, Carbapenems, Ceftazidime, Cefepime, Ceftobiprole, Fluoroquinolones, Piperacillin, Ticarcillin, tobramycin, aztreonam, coliston, and others (alone or in combination) that can be recognized by a skilled person.

Exemplary antibiotics that can be used i for treating chronic wounds include tobramycin, amoxicillin, clavulanic acid, clindamycin, aminoglycosides, ciprofloxacin, cefalosporines, metronidazole and others identifiable to a person skilled in the art.

In preferred embodiments, antibiotics that can be used for treating chronic wounds include Ciprofloxacin, Piperacillin, Ceftazidime, Aztreonam, and Tobramycin: In some embodiments, one or more of Ciprofloxacin: 5 ug/mL, Piperacillin: 320 ug/mL, Ceftazidime: 40 ug/mL, Aztreonam: 160 ug/mL, and Tobramycin: 40 ug/mL can be administered alone or in combination In some embodiments, the effective amount of one or more antibiotics is a therapeutically effective amount which can be obtained according to drug description, FDA guidance, or recommendations by Centers for Disease Control and Prevention (CDC), Infectious Diseases Society of America (IDSA) or other health protection agencies as will be understood by a person skilled in the art.

Exemplary antimicrobials that can be used for treating chronic wounds include sterile saline or hydrogel, povidone-iodine solutions, cadexomer iodine, hypochlorous acid, collagenase and others identifiable to a person skilled in the art.

In some embodiments, methods and systems and related particles herein described can further comprise at least one wound healing agent The wording "wound healing agents" refer to agents that can stimulate and/or accelerate any one of the stages during the wound healing process, including inflammation, proliferation and remodeling as will be understood by a skilled person. In methods and systems and related particles of the present disclosure wound healing agents are comprised in a therapeutically effective amounts that can be identified by a skilled person based on the specific agent, wound and route of administration as will be understood by a skilled person.

In some embodiments, wound healing agents comprise growth factors, which are substance capable of stimulating cell division, migration, differentiation, protein expression and enzyme production and/or cell proliferation, in an organ or tissue of the individual "Growth factor" at Dorland's Medical Dictionary 2011 [43]; [44]). In particular, the wound healing properties of growth factors are typically mediated through stimulation of angiogenesis and cellular proliferation, which affects both the production and the degradation of the extracellular matrix and also plays a role in cell inflammation and fibroblast activity. [45]) and affect the inflammatory, proliferation and migratory phases of wound healing.[46].)

Growth factors typically comprise secreted proteins or steroid hormones, signaling molecules between cells. Examples are cytokines and hormones that bind to specific receptors on the surface of their target cells and promote cell differentiation and maturation. Exemplary target cells re keratinocytes and fibroblasts which are involved in re-epithelialization and collagen deposition, respectively [44]; [47]).)

Exemplary growth factors possibly comprised in wound healing compositions, and related biomimetic matrix, methods and systems comprise epidermal growth factor (EGF), platelet derived growth factor (PDGF), fibroblast growth factor (FGF), transforming growth factor (TGF-b1), insulin-like growth factor (IGF-1), human growth hormone and granulocyte-macro-phage colony-stimulating factor (GM-CSF)[15]; [48] [49].)

Preferred growth factors comprise GM-CSF with particular reference to in full thickness wounds [50]). epidermal growth factor (EGF), [44]) with particular reference to combined treatment with silver sulphadiazine [51]), PDGF with particular reference to treatment where granulation tissue and re-epithelialization is desired (such as) in human patients with diabetic foot ulcers. [44]; [52] [53] [54], [55], [56], [57], fibroblast growth factor (FGF), [44]; [55], [58], [59], [60], [61]) and vascular endothelial growth factor (VEGF). [44]; [62], [63], [64], [65] [66])

A summary of growth factor modified materials and their corresponding strategies for growth factor encapsulation and delivery is reported in Table 1 of [44] enclosed as Appendix I in U.S. provisional 63/012,036 incorporated herein by reference in its entirety, In some embodiments, wound healing agents comprise supplements such as vitamins and mineral supplements [15] [67].including vitamins A, C, E as well as zinc and copper. [15] comprised in an effective amount identifiable by a skilled person in view of the specific supplement as well as timing formulation and route of administration.

In some embodiments, supplements included in methods and systems and related particles herein described, comprise Vitamin A, in particular in embodiments where treatment is directed to promote epithelial cell differentiation, [15] [68]) collagen synthesis and bone tissue development. [15, 69]) normal physiological wound healing as well as reversing the corticosteroid induced inhibition of cutaneous wound healing and post-operative immune depression. [15, 70].

In some embodiments, supplements included in methods and systems and related particles herein described, comprise Vitamin C in particular in embodiments where treatment is directed to promote synthesis of collagen and other organic components of the intracellular matrix of tissues such as bones, skin and other connective tissues. [15] [68]) normal responses to physiological stressors such as in accident and surgical trauma and the need for ascorbic acid increases during times of injury [15] (Pugliese PT. 1998.). immune function particularly during infection. [15] [71]). (Martins-Green and Saeed, 2020) [33] [72], [73]. [74]).

In some embodiments, supplements included in methods and systems and related particles herein described, comprise Vitamin E in particular in embodiments where treatment is directed to promote wound healing. [75]) preservation of important morphological and functional features of biological membranes. [45]. [76]) antioxidant and anti-inflammatory activity [77]) as well as promoting angiogenesis and reduces scarring [78]). (Martins-Green and Saeed 2020) [33] [79].

In some embodiments, supplements included in methods and systems and related particles herein described, comprise Zinc in particular in embodiments where treatment is directed to promote healing of leg ulcers through enhancement of re-epithelialization [80]) upregulation of metallothioneins [81]), rapid healing of wounds retarded by corticosteroid treatment [82]. treatment of deep second-degree burn wounds, preferably in combination with FGF and EGF [83]) decrease of *Staphylococcus* load in the wound [84])

In some embodiments the wound healing agent is an anti-oxidant agent, which, as used herein indicates a compound that inhibits oxidation. In particular, in a biological environment, antioxidants inactivate reactive oxygen species (herein also ROS) by donating their electrons to these species and preventing them from capturing electrons from other important molecules such as DNA, proteins and lipids, thus protecting the environment against excessive oxidative stress (herein also OS) as will be understood by a skilled person. (Martins-Green and Saeed, 2020) [33].

In preferred embodiments, of the wound healing combination compositions biomimetic matrix and related compositions, methods and systems applied to chronic wounds, comprise at least one antioxidant. In some embodiments, the at least one antioxidant comprises an antioxidants operating through enzymatic and/or an antioxidants operating through non-enzymatic reactions that can occur intracellularly in the cytosol and/or in organelles such as the mitochondria or in the extracellular environment. (Martins-Green and Saeed, 2020) [33]. Antioxidants are comprised in wound healing combination compositions biomimetic matrix and related compositions, methods and systems in a therapeutically effective amounts identifiable by a skilled person based on the specific antioxidant as well as formulation, method and route of administration.

Exemplary types of antioxidants, those that perform enzymatic reactions and those that are non-enzymatic in their effects are shown in Table I of (Martins-Green and Saeed 2002) [33] enclosed Appendix VI n U.S. provisional 63/012,036 incorporated herein by reference in its entirety, inclusive these antioxidants targeting reactions occurring in the extracellular microenvironment, others occur intracellularly in the cytosol and/or in organelles such as the mitochondria [85])

In some embodiments, antioxidants included in methods and systems and related particles herein described, comprise one or more of superoxide dismutase (SOD glutathione S-transferases (GSTs), glutathione peroxidases (GPx), NADP(H), catalase, heme-oxygenase 1 (HO-1), peroxiredoxins (Prdx), thioredoxin-1 (Trx-1) and -2 (Trx-2). (Martins-Green and Saeed, 2020 [33]).

In particular, in some embodiments, antioxidants included in methods and systems and related particles herein described, comprise Hemet-oxygenase 1 (HO-1) in particular in embodiments where treatment is directed to promote degradation of heme into CO and/or iron in the presence of $O_2$ and NADPH giving rise to biliverdin that is converted into bilirubin [86] [87],wound closure and angiogenesis resulting in increased wound healing. [86] [87], (Martins-Green and Saeed, 2020) [33].

In particular, in some embodiments, antioxidants included in methods and systems and related particles herein described, comprise peroxiredoxins and thioredoxins in particular in embodiments where treatment is directed to promote reduction of oxidative stress [88] [89] reduction of $H_2O_2$ as well as a broadrange of peroxides [90] [91] detoxification of tissues and cells from peroxynitrite [92] [93] rapid wound [93] [94], reduction of other proteins by cysteine thiol-disulfide exchange and reduction of inflammation [95]. (Martins-Green and Saeed, 2020).

In particular, in some embodiments, antioxidants included in methods and systems and related particles herein described, comprise non-enzymatic antioxidants such as vitamin C (ascorbic), vitamin E (α-tocopherol), Vitamin D, glutathione, N-acetyl cysteine (NAC), alpha lipoic acid (αLA), carotenoids (e.g. lycopenes), bilirubin and uric acid. [96] . . . [97]] [98]. [93]

In some embodiments, antioxidants included in methods and systems and related particles herein described, comprise glutathione in particular in embodiments where treatment is directed to promote strength of the wound tissue. [99] healing of wounds in diabetic individual [100]. Preferably in combination with Vit E(α-tocopherol) [101] [102] [103] [104]. (Martins-Green and Saeed, 2020) [33].

In some embodiments, antioxidants included in methods and systems and related particles herein described, comprise Vitamin D in particular in embodiments where treatment is directed to promote cancer prevention and inhibition of inflammation[105], proliferation and migration of endothelial cells [106].

In some embodiments, antioxidants included in methods and systems and related particles herein described, comprise Alpha-Lipoic Acid (α-LA) in particular in embodiments where treatment is directed to promote chelation of toxic heavymetal ions including $Fe^{2+}$ and $Cu^{2+}$. $Fe^{2+}$ can react with $H_2O_2$ to produce $Fe^{3+}$+OH·+$OH^-$ (Fenton reaction) which can cause protein modification, lipid peroxidation and DNA damage, scavenging of OS [107] regeneration of Vit E, Vit C, coenzyme Q10 and glutathione. (Martins-Green and Saeed, 2020).

In some embodiments, antioxidants included in methods and systems and related particles herein described, comprise N-acetyl-cysteine (NAC): in particular in embodiments where treatment is directed to promote antimicrobial activity in connection with biofilm formation and/or disruption, in particular in wounds infected by *Pseudomonas aeruginosa, Escherichia coli, Staphylococcus epidermidis, Streptococcus pneumoniae, Staphylococcus aureus* and *Klebsiella pneumoniae* [108], [109] [110] (Mohsen et al 2015) [111]. N-acetyl-cysteine (NAC): can also be comprised in in particular in embodiments where treatment is directed to promote modulation of granulocyte function, increase IL-12 secretion, activation NF-κB pathway, decrease of metalloproteinase-9, IL-8, IL-6, and/or inflammatory cytokines and oxidative stress at normal levels [112] [113] [114] [115] [116] [117], burn wound healing[118]. Healing of incisional wound of diabetic and non-diabetic individual [119] faster healing [120] [102] [103] [104] (Martins-Green and Saeed 2020).

In some embodiments, antioxidants included in methods and systems and related particles herein described, comprise other small molecules such as carotenoids (in particular lycopenes), bilirubin, and/or uric acid. (Martins-Green and Saeed 2020}

In some embodiments, antioxidants included in methods and systems and related particles herein described, comprise bilirubin in particular in embodiments where treatment is directed to promote healing, increased neovascularization and improved collagen deposition of diabetic wound [121] and reduction of oxidative stress in wound tissues [122] (Martins-Green and Saeed 2020.

In some embodiments, antioxidants included in methods and systems and related particles herein described, comprise 6,8 dithio-uric acid in particular in embodiments where treatment is directed to promote wound healing protection of cells and in particular neural cells endothelial cells keratinocyte and fibroblasts from oxidative damage [123] [124] [74] . . . (Martins-Green and Saeed 2020).

In some embodiments, antioxidants included in methods and systems and related particles herein described, comprise herbal extracts such as curcumin and honey. (Martins-Green and Saeed 2020.)

In some embodiments, antioxidants included in methods and systems and related particles herein described, comprise curcumin in particular in embodiments where treatment is directed to promote increase in collagen content and wound contraction [125] and/or in treatment of excision wounds. [126] [127] [128]. [129]. (Martins-Green and Saeed 2020).)

In some embodiments, antioxidants included in methods and systems and related particles herein described, comprise honey in particular in embodiments where treatment is directed to promote, antimicrobial treatment [130] anti-inflammatory treatment. [131] early improvement in wound healing process. [132] [133], immunomodulatory treatment. [134] [135]. (Martins-Green and Saeed 2020).

In some embodiments, antioxidants included in methods and systems and related particles herein described, comprise Factor-E2-related factor (Nrf2) in particular in embodiments where treatment is directed to improve healing under oxidative stress conditions in impaired wounds in particular in diabetic wounds [137] [138]]. [136] [139] [140]. (Martins-Green and Saeed 2020).

In some embodiments the wound healing agent is an anti-oxidant agent, such as N-acetyl cysteine, coenzyme Q (ubiquinol), vitamin A, vitamin C, vitamin E, glutathione, lipoic acid, carotenes, flavenoids, phenolics, and ergothioneine, melatonin, ellagic acid, punicic acid, luteolin, catalase, superoxide dismutase, peroxiredoxins, cysteine, or a physiological salt thereof, or a combination thereof. In some embodiments, the wound healing agent can be a free radical scavenger, a lipid peroxidation inhibitor, or a combination thereof.

Exemplary effective amount of anti-oxidant agents comprise 0.1-3.0% NAC, 0.3% bilirubin ointment as well as 10 mg/kg of curcumin to increase collagen and 40 mg/kg for excision wounds (daily application).

In embodiments where the ballistic delivery of the present disclosure delivery of particles and in particular substantially spherical particle into a wound can be used in conjunction with various scaffolds and dressings applied on the exposed surface of the wound.

In embodiments where the ballistic delivery of the present disclosure delivery of particles and in particular substantially spherical particle into a wound major advantage of delivery particles into a multilayered tissue is that it leaves the exposed surface pristine for re-epithelialization and granular tissue formation as will be understood by a skilled person upon reading of the present disclosure.

Further details concerning the identification of the embodiments of methods and systems of the disclosure and related compositions, that can be performed in combination with such devices can be identified by the person skilled in the art upon reading of the present disclosure.

EXAMPLES

The methods and system herein disclosed are further illustrated in the following examples, which are provided by way of illustration and are not intended to be limiting.

The following material and methods were used in performing the experiments reported in the examples 1 to 38 of the present disclosure, which shows ballistic delivery performed with Dp pp and velocity of the particles obtained through different calculations and resulting however in controlled delivery to the identified target region of the cornea of a percentage of particles, with Dp pp and velocity and within target region in accordance with the calculations and determination performed with the method of the disclosure.

Drying Column Used for Microparticle Preparations A drying column was built for the production of solid polymeric microparticles. In particular one-meter-tall 10-cm-diameter drying column was wrapped in heater tape (about 3.6 meters of tape with a width of 5 cm; McMaster Carr). The tape was controlled with a CN142 temperature controller (Omega Engineering) that was used to drive a solid-state relay controlling power to the heater. The temperature controller was receiving input from a K-Type thermocouple attached between the heat tape and the wall of the glass column. This allowed us to have more control over heat tape, preventing overheating. Two T-Type Process Heaters (Omega Engineering; Item #AHP-5052) were used to heat the carrier gas (fed to the top of the column) and the dilution gas (fed to the bottom of the column). The carrier gas was used to dilute the air in the column and to carry the particles gently to the particle trap. The dilution gas was fed directly to the particle trap to dilute vapor in the column and prevent condensation. Another CN142 temperature controller was used to control the temperature of the inline heater feeding the carrier gas to the column. The other inline heater was wired in series with the first heater, giving it indirect temperature control. Three flow control-valves with rotameters were used to control 1) the carrier gas flow, 2) the dilution gas flow, and 3) the dispersion gas flow being sent directly to the VOAG (gases labelled in FIG. 1). The dispersion gas was meant to disperse droplets radially as they enter the column, thus improving drying and hopefully reducing droplet coagulation. Since the column is configured to produce respirable microparticles and vapors from organic solvents, the entire apparatus was placed inside a tent enclosure with a duct connected to the house ventilation system. This setup allowed for containment of hazardous materials, and also kept the column at a workable height. In general, this design of the drying column was made to effectively dry microparticles, to dilute the vapors exiting the bottom of the column, and to fully contain the aerosols produced within.

Monodisperse Aerosol Generator: A Vibrating orifice aerosol generator (VOAG) a device known to create monodisperse droplet described in Berglund, & Liu, (1973) [141] [was used The orifice is made of a precision pinhole laser-drilled into a thin foil disc (Edmund Optics). It is an element that can be interchanged when a different outlet size is required or when the orifice has become obstructed. The piezoelectric element is a 2.5-cm-diameter disc punched out of 75-μm-thick steel shim stock fixed to a piezoelectric ceramic (7×8 mm; Stem Inc.) using silver epoxy. When initiating a jet, the tubing which carries fluid away from the device is capped, introducing a step change in pressure. The piezoelectric ceramic is controlled using a function generator (Agilent 33220a) with sinusoidal waveforms oscillating between positive and negative five volts. There is an input for compressed air on the device that disperses microparticles ejected into the particle drying column.

The mount used to place the VOAG on top of the column centered and helped disperse the aerosol being fed to the drying column. Mounts were built that used a quick, diagnostic test to see if droplets were being produced in a monodisperse manner. With the jet initiated, a stream of gas was directed orthogonally at the droplet-train. If the flow of the gas was laminar and the frequencies being provided to the VOAG were in the range of monodisperse breakup, then the liquid would be deflected as a kinked ray, instead of a spray. This phenomenon is demonstrated in. With no excitation, particles are deflected in a spray because the distribution is polydisperse and droplets have different characteristic aerodynamic relaxation times. When a 19 kHz signal is applied to the microjet, a clean ray of particles is deflected.

Oscillatory Shear Rheology

To measure the viscosity of PEG solutions, a strain-controlled oscillatory shear rheometer was used (ARES 4100). An 80 mm cone-shaped geometry (4° degree cone angle) was used with a 50 μm gap. Samples were tested on the rheometer with low strain rates compared to particle impacts (from 1 to 100 1/s) and n=5 measurements were recorded per solution.

Aerosol Flowrate Measurement

To measure the flowrate of fluid ejected from orifice pinholes, liquid was collected in 1.5 mL conical microcentrifuge tubes for thirty seconds. At the end of collection times, the mass ejected from the pinhole was measured. Using the diameter of the pinhole, the velocity of incompressible fluid exiting the orifice was calculated. Measurements were recorded six times for each viscosity of fluid tested.

Custom High-Speed Imaging System

When imaging aerosols, the a-\ was used to record images of shadows cast by moving droplets. The VOAG was mounted on top of a hollow poly(ethylene) cylinder. Aerosols were illuminated with either a continuous lamp or a bright pulsed-LED (VLP-4830-2S; VAL Electronics). The former was used to measure broad polydisperse size distributions. The pulsed-LED was used to visualize monodisperse size distributions when more resolution was desired. Aerosols were imaged three centimeters from the outlet of the VOAG. A Chronos 2.1-HD high speed camera (Krontech) was used for these studies. It was run at 1024 frames per second to maximize camera resolution (1.3 megapixels). There were two separate microscope objectives used in this study, 2× and 10× magnification lenses (Mitutoyo). The lenses have a 33.5 mm working distance. The 2× objective was used to measure aerosols not being exposed to piezoelectric agitation (with the continuous light source and a 1 μsec exposure time). The 10× objective was used for monodisperse aerosols (with the pulsed light source). The LED flashes for a duration of 10 μsec at the start of every ten milliseconds.

Image Processing Pipeline

To record droplet size distributions from high-speed video, an image processing pipeline was written in Python (Appendix A.2). Binary images were generated that turned camera frames into 2D plots that show information describing what pixels contain outlines of droplets. Since droplet data often had different degrees of background lighting, threshold pixel values were chosen on a video by-video basis. Threshold values were increased until droplet objects no longer increased in size. Once masks were generated from image data, regionprops, an open-source Python function, was used to locate objects and record their major and minor axis dimensions. The major axis was indicated by where the droplet was at its widest and the minor axis was where it was the smallest. Droplet diameters (major axes) were recorded if major:minor axis ratios were less than 1.3 and droplets were not connected. These criteria were included to reject droplets that had not yet relaxed after breaking up from the capillary jet, to reject droplets that had not yet broken up, and to reject droplets colliding. Data from individual frames were saved and plotted. Droplet size-distributions of polydisperse aerosol trains were reduced to whisker plots using bokeh, another open-source Python package.

Assessment of Tissue Damage Using Confocal Microscopy

Confocal microscopy was done on tissue treated with stainless steel microparticles prior to staining with picrosirius red (from Abcam Inc.). Picrosirius red is a fluorescent dye that binds strongly to collagen fibrils and stains epithelial tissue. Sections of tissue were cut to 30 μm thickness and were then stained for 5 minutes. This was sufficient to produce bright fluorescence on the stroma and the epithelium. Tissue was inspected using a Zeiss LSM 710 inverted confocal microscope. Z-stacks were recorded (30 μm depth) to show how the tissue is damaged because of microparticle impact.

Example 1: Preparation of Microparticles Using a Drying Column

Figure 2:
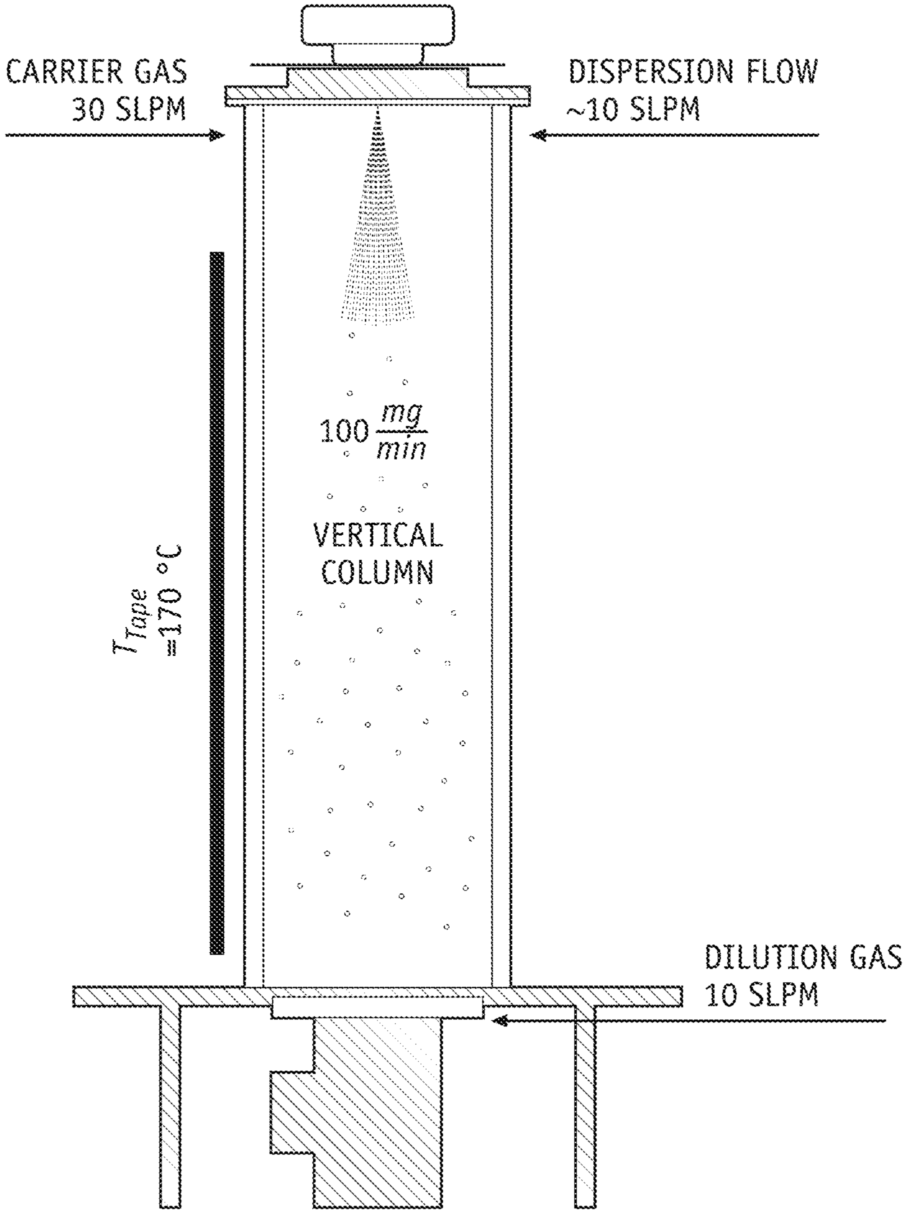
FIG. 2 shows a schematic representation of a dry column for preparation of microparticles according to the present disclosure. The schematics shows how Nitrogen is fed to the VOAG (dispersion gas), to the top of the column (carrier gas), and to the particle trap (dilution gas). The column walls are heated to a certain temperature and the VOAG usually ejects a ~200 mgs of solution a minute, if the 35 μm pinhole is used

Microparticles were prepared using a drying column schematically described in FIG. 2.

In particular, nitrogen was fed to the VOAG (dispersion gas), to the top of the column (carrier gas), and to the particle trap (dilution gas). In particular, the dispersion gas flow was set by monitoring the state of the aerosol jet at the top of the column using a borescope. The flow was increased to 10 SCFH until the jet just started to move with the dispersion gas. A flowrate of 30 SCFH was chosen for the carrier gas. This resulted in an approximate velocity of gas moving through the column of 3 cm/s. Dilution gas was set to 10 SCFH.

The column walls are heated to a certain temperature and the VOAG usually ejects a ~200 mgs of solution a minute, if the 35 μm pinhole is used. A previous drying simulation indicates that if droplets made of ethanol can be aerosolized with diameters less than or equal to 100 μm, then solid microparticles can be formed in the one-meter-tall drying column.

At steady state with a 35 μm pinhole ejecting fluid into the column at 0.1 g/min, the column gas temperature was 100° C. (measured two-thirds of the way up the column with a temperature probe). The inline heaters were set to 250° C., resulting in a steady state gas temperature of 80° C. for the nitrogen going into the column. The VOAG using a 35 μm pinhole was excited at 35 kHz to try and produce droplets that were around 70 μm.

These are the typical conditions at which particle preparations were run at.

Example 2: Flowrate Characterization of Aerosolized Particles

In order to characterize the flow rate used to provide microparticles with a drying column with a procedure exemplified in Example 1, 50 and 75 μm pinholes were used to aerosolize solutions that have viscosities from 1 to 40 centipoise.

Solution viscosity follows the following power law expression, where c is the weight fraction of PEG in solution.

$$\mu=1955.2c^3-368.7c^2+61.0c+0.3. \quad (4)$$

Figure 3:
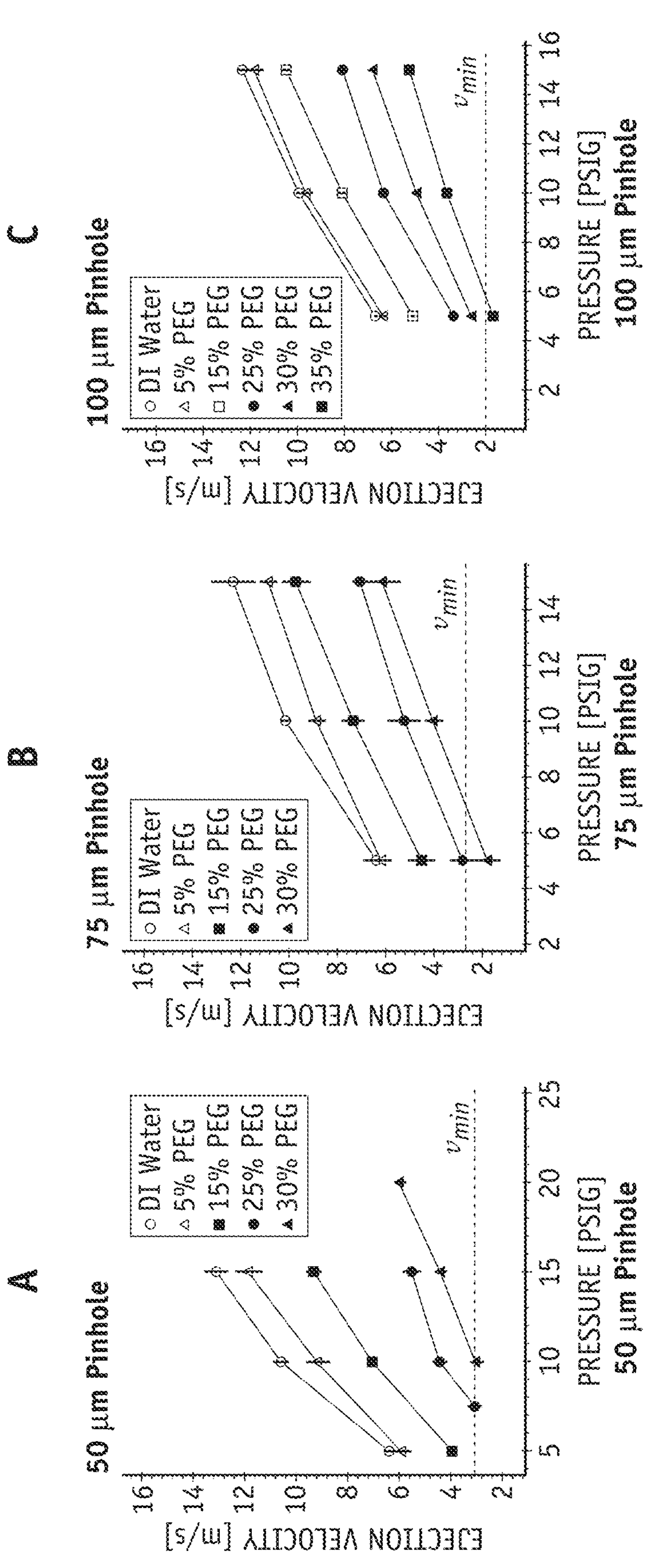
FIG. 3 shows charts illustrating mass flowrate and ejection velocity for different pinholes with PEG solutions of different concentration. The mass flow rate (top) and ejection velocity (bottom) for three pinholes is plotted for a set of different PEG solutions. N=6 measurements. Error bars show 95% confidence intervals. Dotted lines show $v_{min}$, predicted by Equation 2 as reported in Lindblad 1965 [3], wherein that $v_{min}$ scales inversely with jet diameter $D_j$, density ρ, and the liquid's surface tension in ambient air σ, namely, $$v_{min} = \sqrt{\frac{8\sigma}{\rho_l D_j}}. \quad (1)$$
Figure 4:
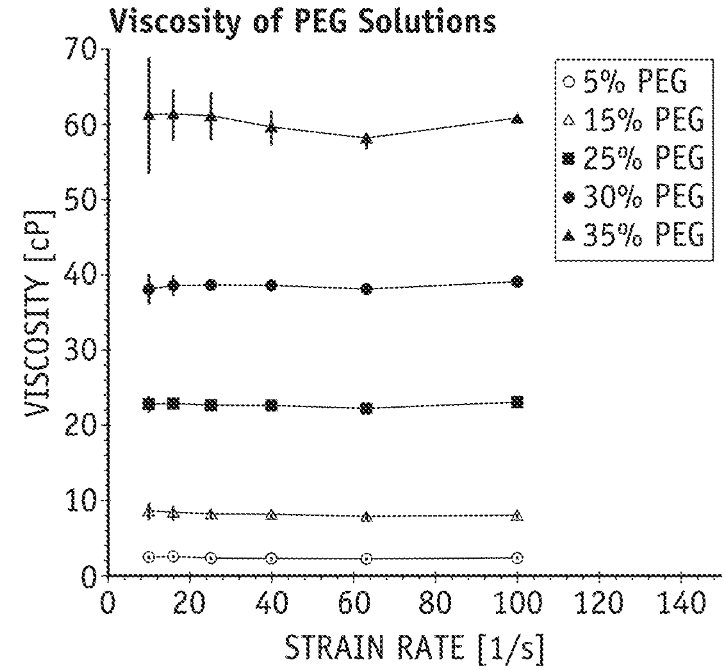
FIG. 4 shows a diagram reporting the oscillatory shear rheology of PEG solutions. Strain sweeps for five different PEG solutions from 10 to 100 1/s. Each point is from n=5 tests. Error bars show 95% confidence intervals.

The results of flow characterization studies are shown in FIG. 3 and the viscosities measured for solutions tested in this study are shown in FIG. 4

The data for the 50 μm pinhole shows that when solution viscosity reaches 20 cP, the lowest aerosolization pressure tested increases slightly from 5 to 7.5 PSI. This is because, at 5 PSI, the aerosol could not be initiated and maintained for more than a few seconds. When testing 30% PEG, the minimum pressure tested increases further to 10 PSI. This behavior suggests that a minimum pressure is needed for aerosol formation. FIG. 3 also plots the ejection velocity.

Ejection velocity for a given pressure is similar between pinholes. Dotted lines indicate the theoretical minimum jet velocity predicted by Equation 2. The theoretical minimum ejection velocity was predicted accurately for the 50 μm pinhole, but jet velocities below the predicted value were measured for data with the 75 and 100 μm pinholes.

Solutions were tested with higher viscosity (60 and 80 cP), but they were found to be exceedingly difficult to form droplet trains. When pinhole size was increased to 100 μm, the VOAG was able to aerosolize a 60 cP solution. The range of viscosities reported represent a range that can be aerosolized reliably with the VOAG used in this study.

Figure 5:
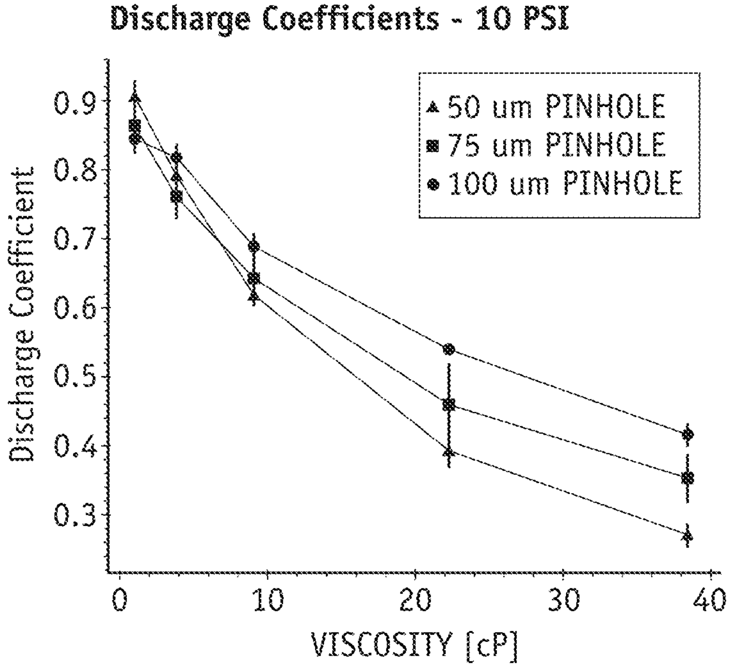
FIG. 5 shows a diagram reporting the discharge coefficient as a function of viscosity. At 10 PSI, the discharge coefficient of each pinhole is recorded. N=6 samples per data point. Error bars show 95% confidence intervals.

Higher pressures were applied (up to 60 PSI; 4.21 bar), and they did not lead to jet initiation when viscosities were greater than 60 cP. FIG. 5 shows how $C_D$ changes in the aerosol generator.

Example 3: Size Distribution. Of Aerosolized Microparticles

Figure 6:
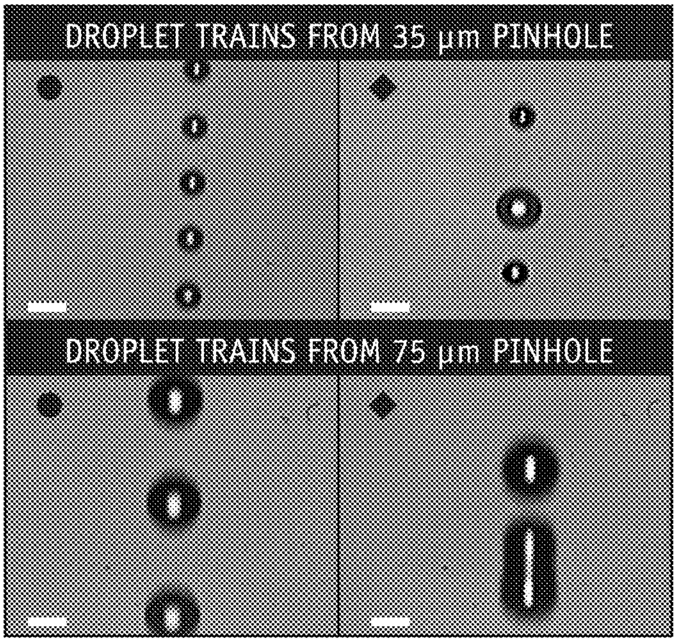
FIG. 6 shows a chart of representative micrographs of aerosols emitted from different pinholes (10× Objective; strobing light—1 msec exposure time). Light exposure is 10 microseconds when recording of trains of ♦ monodisperse and ● polydisperse droplet trains. 100 μm bar shown.
Figure 7:
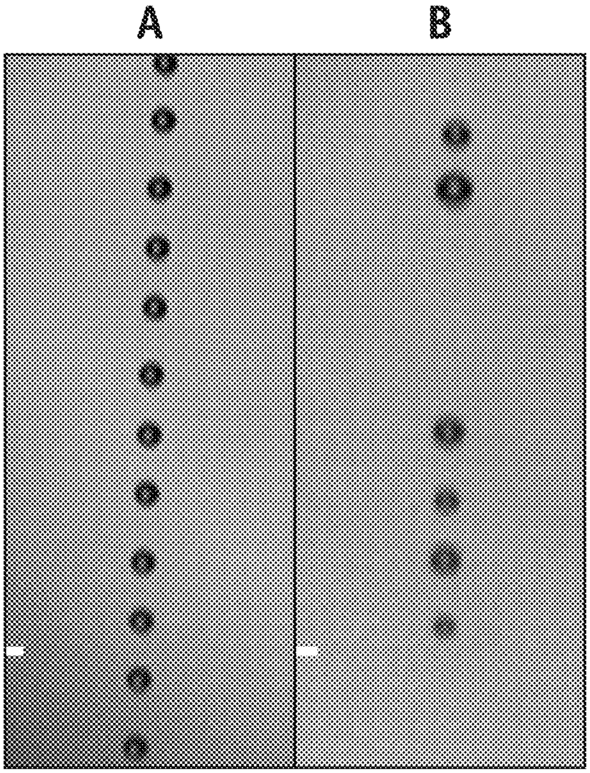
FIG. 7 shows micrographs of aerosols emitted from a 35 μm pinhole (2× Objective; bright continuous light source—1 μsec exposure time). In particular FIG. 7 Panel A) shows monodisperse aerosol excited at 35 kHz and FIG. 7 Panel B) shows polydisperse aerosol excited at 60 kHz. 100 μm error bars shown.

To measure the size distributions of viscous solutions aerosolized by the VOAG, the image processing pipeline (Appendix A.2) went through frames one by one thresholding and acquiring droplet data. Representative images of aqueous aerosols measured with 10× and 2× objectives are shown in FIG. 6 and FIG. 7 respectively and related size distribution are shown in FIG. 8.

These figures indicate the dichotomy between monodisperse and polydisperse aerosol size-distributions. Monodisperse aerosols show identically sized objects with uniform spacing. Polydisperse distributions are characterized by non-uniform spacing between droplets and aspherical shapes, which are formed from insufficient time for drops to relax following droplet breakup or collisions between droplets of different size/characteristic acceleration times. The 10× objective which produced FIG. 6 was used to measure droplet size from monodisperse aerosols (for better size resolution than the 2× objective). Despite slight motion blur in the images, this study was capable of measuring diameters accurately by recording the major axis perpendicular to the velocity vector.

Figure 8:
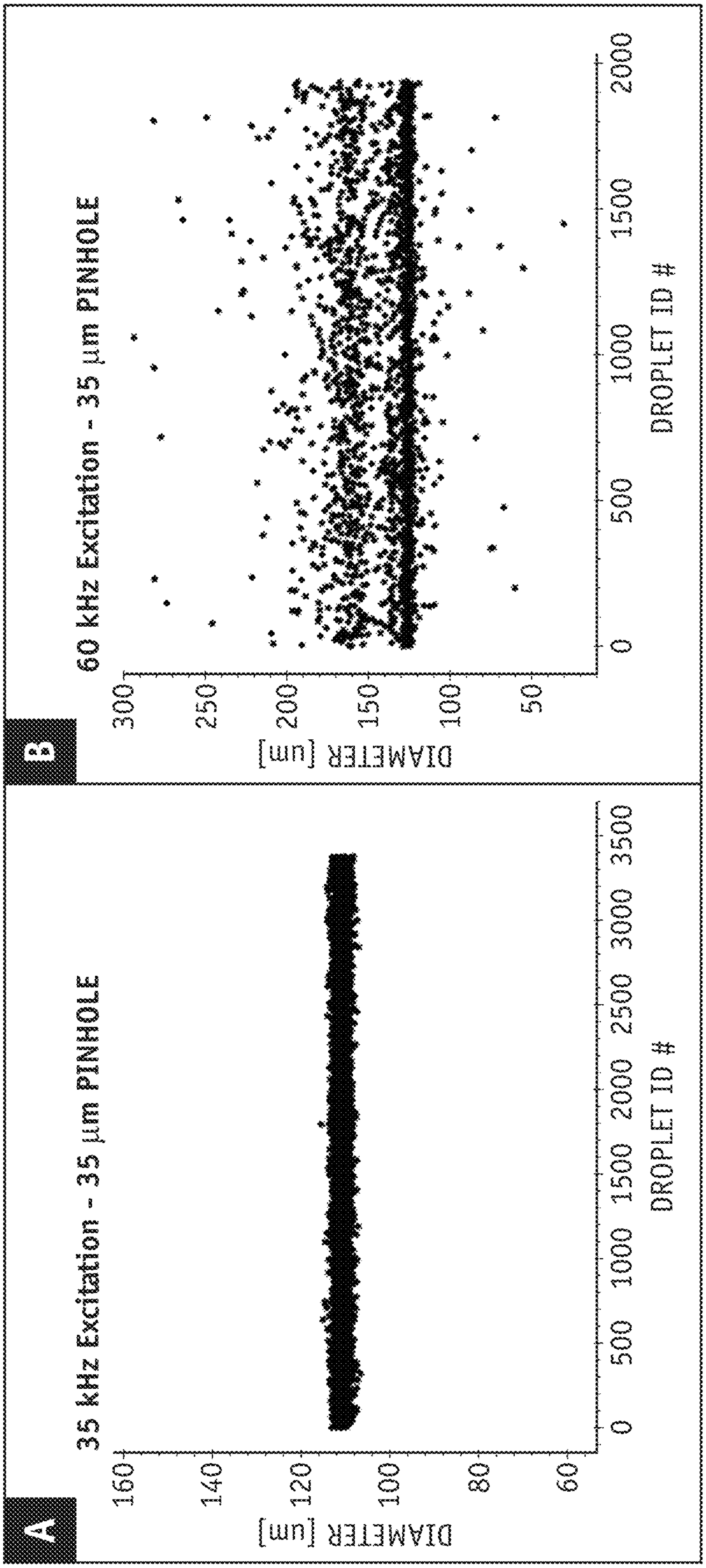
FIG. 8 shows charts illustrating size distribution for aerosol formed from water emitted by a 35 μm pinhole. Size distributions show the droplet-sizes recorded from two separate high-speed videos (three and two seconds long). The x-axis shows the droplet ID number from videos which increases with elapsed time. In particular, FIG. 8 Panel A shows droplets from an aerosol excited at 35 kHz.

Size distributions, like those shown in FIG. 8 were recorded for a range of viscosities using a 75 μm pinhole. These graphs, which show individual droplet size over time (denoted by Droplet ID number—a sequential numerical marker), describe the same monodisperse and polydisperse aerosols shown in FIG. 7 Using Image J on FIG. 7 Panel A droplet size measured around 110 μm, indicating good accuracy of the image processing pipeline. FIG. 7 Panel B shows a polydisperse distribution, with high number density around two different sizes.

Example 4: Effect of Viscosity and Pinhole on Droplet Sizes Produced

Figure 9:
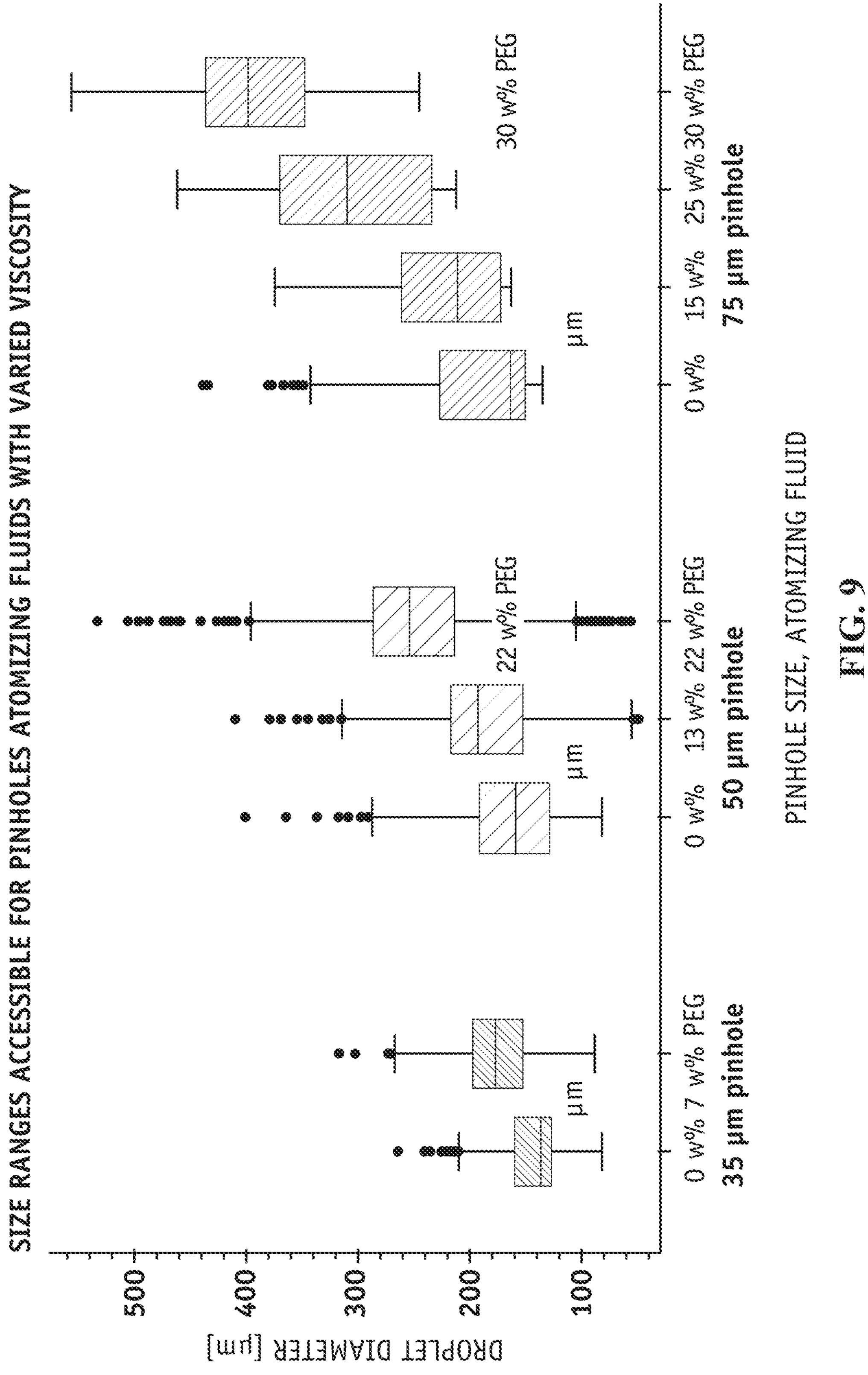
FIG. 9 shows a diagram illustrating size distribution of viscous aerosol droplets from orifice pinholes without piezoelectric excitation. Box-plots summarize the size-distribution of aerosols emitted from three different pinholes with a range of PEG solutions. Driving force for aerosolization was 0.3 bar.

The size distribution of polydisperse, non-excited droplet-trains was recorded. The data is represented using a boxplot in FIG. 9. Boxes show the interquartile range (IQR), and whiskers show the lowest datapoint still within 1.5 times the IQR. Black points on these figures indicate outliers in the dataset. The data shows significant increases in droplet-size as viscosity is increased. Using the power law expression in Equation (5), an increase in viscosity from 1 to 3.4 cP for the 35 μm pinhole (using 7% PEG as the weight fraction) results in a significant increase in droplet size. The mean droplet size increases from 148.3 μm to 173.5 μm and the IQR shifts as well. Thus, an increase in viscosity, which has minimal effect on the mass flowrate of a given pinhole, can still have a significant effect on the breakup of a capillary jet into droplets.

The effects seen in 50 and 75 μm pinholes also show significant changes with increased viscosity. Using a 13% w/w PEG solution (6.3 cP), the mean droplet size shifts from 162 μm to 181 μm. When a 22% w/w solution is used (16.7 cP), the mean droplet size shifts to 241 μm and the IQR shifts from 3 to 4 pinhole diameters to between 4.5 and 5.5 orifice diameters. The 75 μm pinhole showed a large range in droplets produced. Testing the solution that was ~40 cP in viscosity, droplets were made that were five to six times the diameter of the orifice.

These data indicate that the VOAG is sensitive to changes in viscosity and altering solution viscosity can lead to a much wider range of droplet sizes that can be used.

Example 5: Production of 70 to 175 μm Droplets Using Atomization of Alcohols To test low-viscosity, high-volatility liquids like ethanol and isopropanol, a 75 μm pinhole was first used. Isopropanol was filtered and then the flowrate was measured using a pressure of 0.34 bar. The average volumetric flowrate of isopropanol was measured to be 1.49 cc/min. This corresponds to an ejection velocity of $$v = \frac{\dot{Q}}{\frac{\pi}{4}D_o} = \frac{\left(1.49\frac{\text{cm}^3}{\text{min}}\frac{1\text{ min}}{60\text{ sec}}\right)}{\frac{\pi}{4}(.0075\text{ cm})^2}\frac{1\text{ m}}{100\text{ cm}} = 5.6\text{ m/s},$$

where $\dot{Q}$ is the volumetric flowrate and $D_o$ is the orifice diameter.

When comparing this with the data shown in FIG. 3, it can be seen that the expected ejection velocity was 6.0 m/s±0.5 m/s, so the pinhole was considered to be clear and unobstructed. Next, the expected range of frequencies leading to monodispersity was calculated. The high-end range of frequencies is given by $\lambda=3D_j$ in Equation (4), where $D_j$ is the jet diameter, which is approximated using the diameter of the orifice. This disturbance wavelength leads to a frequency of $$f = \frac{v}{3D_o} = 25.0\text{ kHz}.$$

Figure 10:
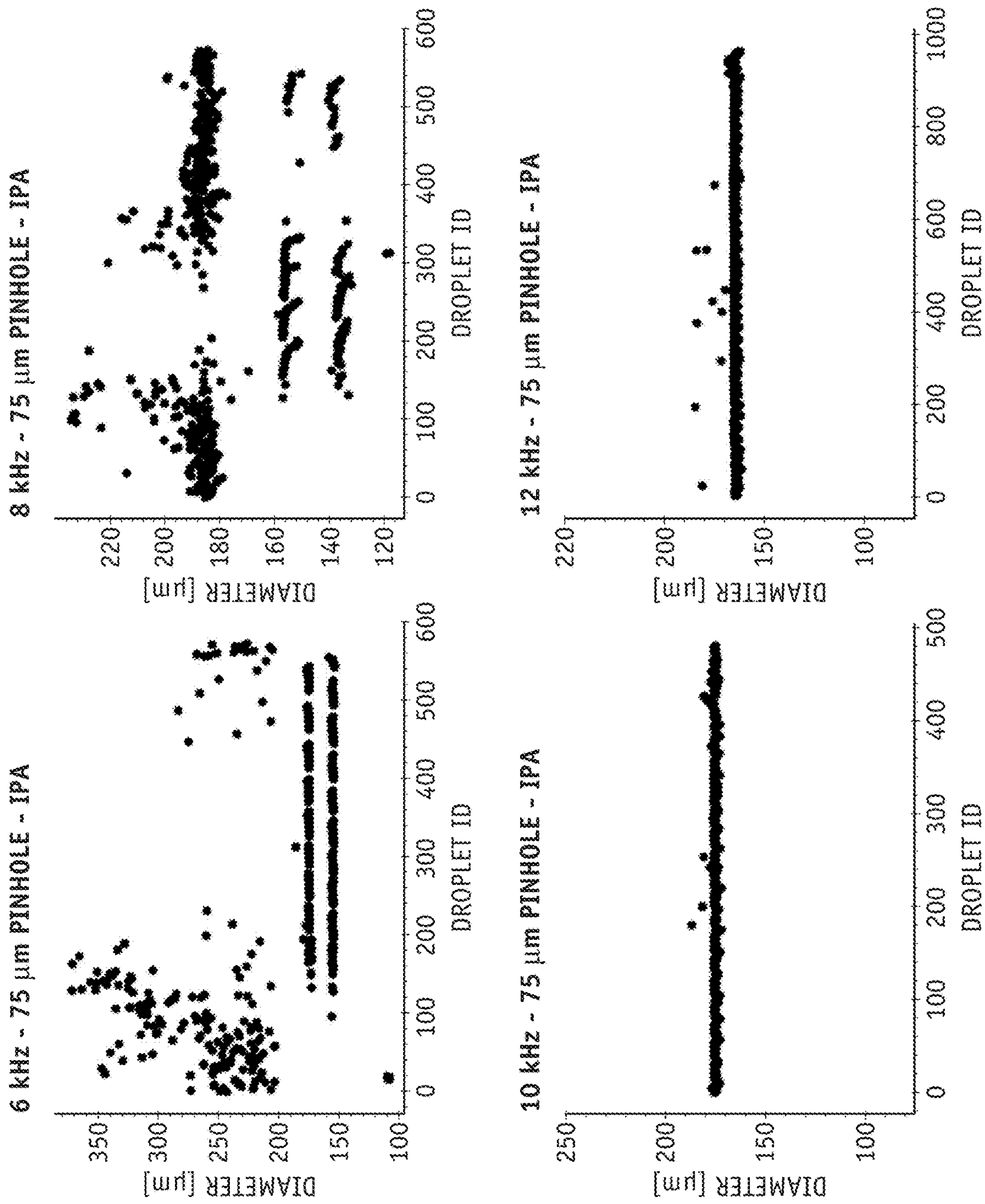
FIG. 10 shows charts illustrating size distribution of isopropanol ejected from a 75 μm pinhole (6 to 12 kHz). Lower frequencies show bimodal and even trimodal distributions of droplet size. Then, when the expected region of monodisperse frequencies is entered, there is a shift to monodisperse droplet production.
Figure 11:
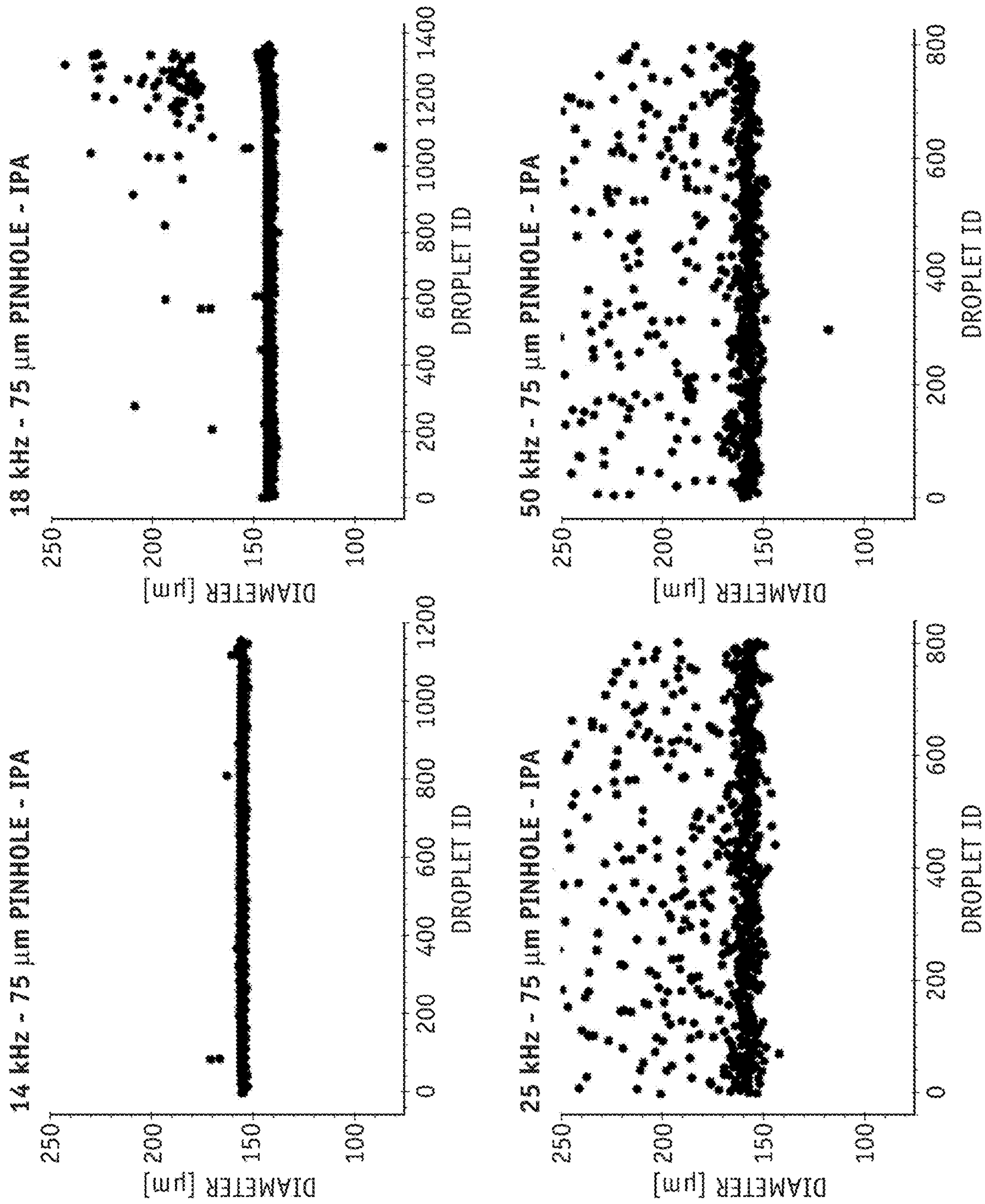
FIG. 11 shows charts illustrating size distribution of isopropanol ejected from a 75 μm pinhole (14 to 50 kHz)—monodisperse production occurs up until 18/19 kHz. Then at 25 kHz and 50 kHz, the production of droplets is essentially the same as if the orifice were not being excited at all.

The low end of expected monodisperse frequencies is 10.7 kHz. Based on these calculations, frequencies were chosen below this range (6 and 8 kHz), within this range (10, 12, 14, and 18 kHz), as well as size distributions greater than this range of frequencies (25 kHz and 50 kHz). The size distributions measured in this analysis are shown in \ FIG. 10 and FIG. 11.

Example 6: Preparation of Monodisperse Microparticles with Controlled Sizes

A 35 μm pinhole was chosen to produce monodisperse aerosols and in particular 70 μm to 120 μm droplets formed with ethanol. If the generator was operated at around 35 kHz, 70 μm droplets could be produced by the VOAG. With this droplet size, an expected final particle diameter can be calculated using the following conservation equation:

$$D_p = C_v^{1/3}D_d \tag{5}$$

where $D_p$ is the diameter of the particle, $D_d$ the diameter of the droplet, and $C_v$ is the volumetric concentration of solute. For a 70 μm droplet with concentration of 1% to 5% w/w, the expected final droplet size comes out to 15 to 26 pm. For a 100 μm particle, the expected final particle size comes out to 21 to 36 μm.

This size range is in the range of previously tested ballistics, so these conditions can be selected for particle preparations.

Microparticles with different sizes and densities can be prepared using a drying column in view of the indications of Examples 1 to 5 as will be understood by a skilled person

Example 7: Description of Microparticles Formed

Figure 12:
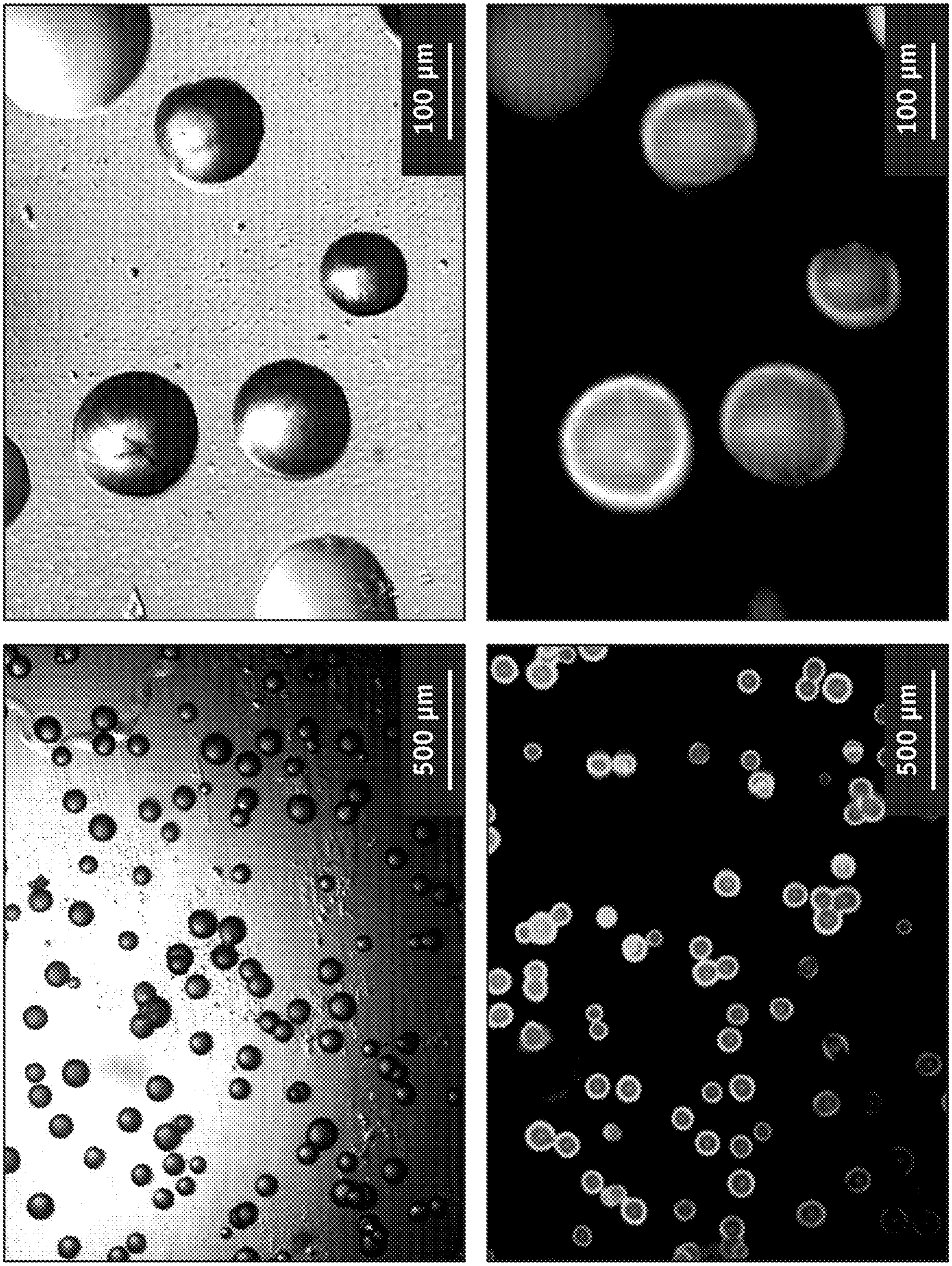
FIG. 12 reports pictures showing PEG microparticles made with 1% w/w Eosin Y using 50 μm pinhole. These microparticles were formed using the protocol described herein. The particles had a flattened morphology from relaxing on the bottom of the petri dish. As seen in the top-right image, particles were not fully dried by passage through the dry column.

Using the drying column, several samples of PEG microparticles were prepared. PEG was used due to its biocompatibility and its relatively high density for a polymer (1.125 g/cc). FIG. 12 shows the particles that are produced using the 50 μm pinhole, which may not be fully dry. The microparticles formed in this particle preparation were made using a 50 μm pinhole receiving excitation at 17.5 kHz. These images show a distribution of particles that is polydisperse. The microbeads that appear dry are 50-80 In methods and systems of the disclosure the density would need to be increased to at least 1.4 g/cc as will be understood by a skilled person upon reading of the disclosure The polydispersity is likely due to a distribution of residence times in the column and potential coagulation of droplets. In addition, while monodispersity is checked at the beginning of runs, it is quite likely that particulate matter builds up on the orifice leading to periods where the aerosol is no longer monodisperse. One other interesting facet of these images is the dark stained ring surrounding particles. In many particle preparations that resulted in wet microparticles, this ring phenomenon is observed. The predominant theory for this observation involves the diffusion of charged solutes in wet droplets to the interface between droplet and air. This can lead to subsequent crystallization on the surface, poor drying, and hollow morphologies.[22]

Figure 13:
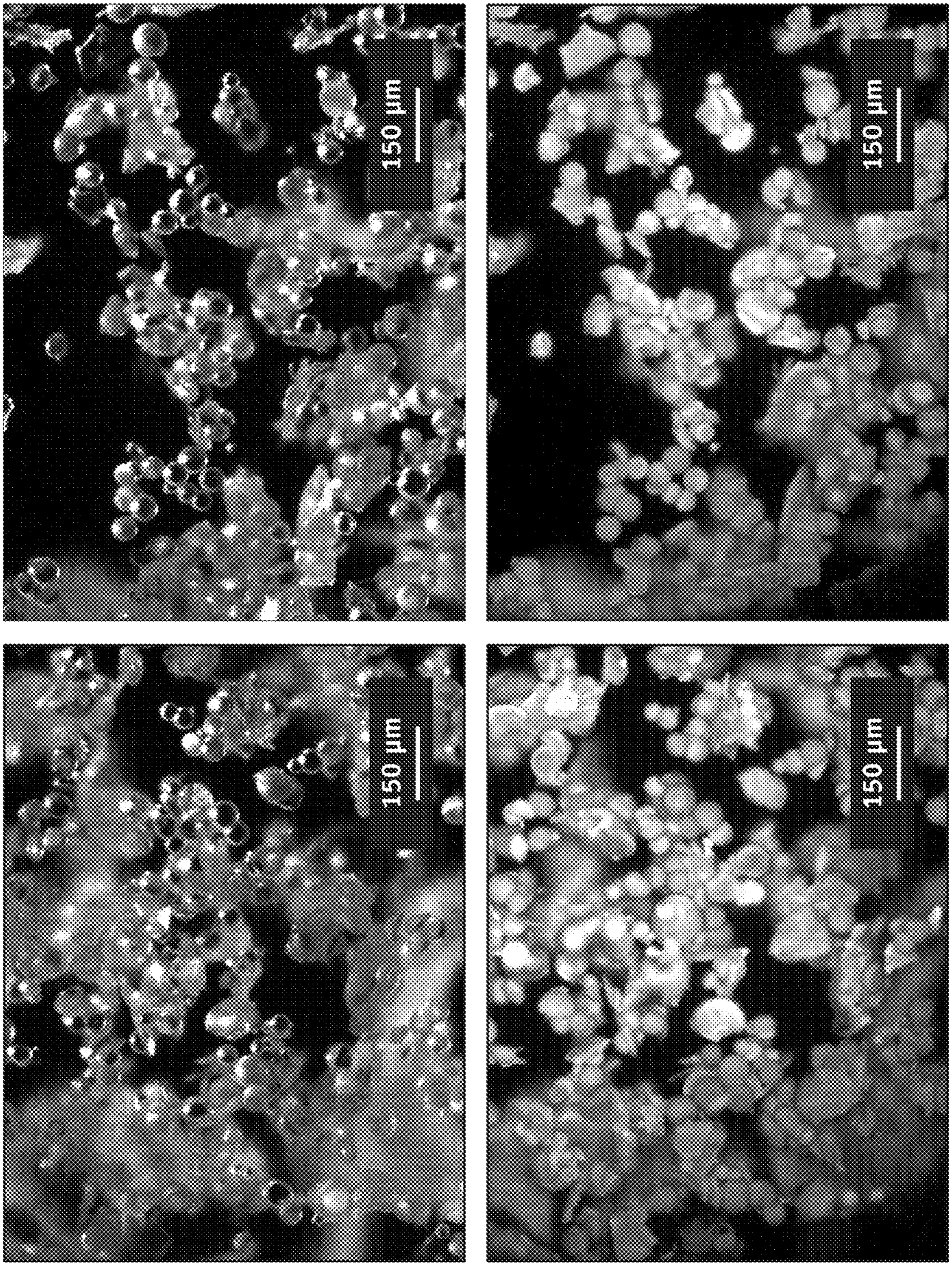
FIG. 13 reports pictures showing PEG microparticles made with 1% w/w Eosin Y using 35 μm pinhole. The particles were smaller than those formed with the 50 μm pinhole. The particles are round, solid, and stick to one another.

When a smaller pinhole was used, particles like those shown in FIG. 13 were formed. In these figures, clusters of particles can be shown sticking together. There is no discernible Eosin Y ring on these particles, possibly because charged solutes do not have enough time to diffuse to the surface of the droplet before drying. The solid microparticles are all under 50 μm. There was also a good amount of PEG that crystallized on the bottom of petri dishes. This material was scraped up with the rest of the microparticles. Nonetheless, this particle preparation was a success, because it achieved essentially dry microparticles that are in the same size range as our previous ballistics testing. With these particles set aside and stored under vacuum, they were ready to be placed on macrocarriers and used in our ex vivo ballistics experiments.

A skilled person will understand that a solution can be aerosolized into the column using tungsten, acoustic agitation, and a larger pinhole, but the heat duty of the column is going to need to be increased to dry the larger droplets.

Example 8: Preparation of Microparticle with Biologically Active Cargo

To form particles in the drying column, the following procedure was developed. A solution of poly(ethylene glycol) (PEG 10 kDa $M_w$; Alpha Aesar) was prepared by heating and stirring in 96% ethanol (VWR) until the solution reached 35° C. and was stirred for another half hour.

A cargo is added by appropriate procedure based on the type and amount of cargo to be included. In the case of 1% w/w Eosin Y microparticles, 3.96 grams of PEG was dissolved in 96 grams ethanol along with 40 mgs of Eosin Y salt (Sigma Aldrich). The solution was cooled to room temperature and filtered with a 0.45 μm cutoff syringe filter. (see Example 8)

The solution can be loaded into the VOAG and a microjet was initiated. After checking monodispersity of the aerosol stream using the impinging jet method of Example 3. (FIG. 7), the VOAG was mounted on top of the column without having engaged any heating. Once the aerosolizer was mounted, temperature controllers were turned on along with gas inputs. While the column was heating up, the bottom of the particle trap was left open so vapor and condensed liquid could drip out.

After one hour of heating and feeding the aerosol jet into the column, the particle trap was connected to the collection chamber and a glass petri dish was inserted to collect settling particles. The column was run for one-hour intervals, at which time dried particles would be collected and a fresh petri dish would be placed in the collection chamber. With low flowrates of 0.1 to 0.2 mL/min, the 50 mL fluid reservoir would last for a few hours. If solution ran out, fresh solution would be refilled, but often this would lead to obstructions building up in the pinhole during column downtime.

The petri dishes were placed in a vacuum oven at ambient temperature and vacuumed down to 125 mmHg. After drying overnight, the particles were scraped up using a razor blade and stored in a scintillation vial. In general, the yields were low. About 40 mgs of particles could be collected over a preparation that lasted four hours and used 100 mL of particle solution (1% yield)

Example 9: Preparation of Microparticles Comprising Eosin Y as Cargo and PEG as Carrier To poly(ethylene glycol) (PEG) microspheres with 1% w/w Eosin Y were prepared using a spray-drying technique.

A vibrating orifice aerosol generator (Berglund et al., 1973[141]) with a 35 μm pinhole ejecting droplets at 5 m/s with a piezoelectric ceramic vibrating at 30 kHz was used to produce droplets of 3.96% w/w PEG with 0.04% w/w Eosin Y in 96% v/v ethanol.

Droplets fell through a 1-meter-tall 10-cm-diameter drying column equipped with ports for heated, dry gas. N2 at 100° C. with a flowrate of 30 standard cubic feet per hour was used to heat and carry the smaller particles through the column. Large (100 μm) droplets had a settling time in the column of around 5 seconds.

Microparticles were collected at the bottom of the drying column and further dried in a vacuum oven overnight (at ambient temperature) before being placed on macrocarriers.

The size distributions of this particle preparation resulted in particles of sizes 30 to 50 μm. In the end, the broad library of microparticle size and composition that was desired could not be produced, due to time constraints and difficulties avoiding pinhole obstruction. With higher heat duties to the column, slightly larger pinholes, and improved dispersion of droplet trains entering the column, it is expected that it will become easier to make dry microparticles. A rich potential research project involves making particles containing density-boosting metal nanoparticles to increase the embedding energy of therapeutic microparticles.

Example 10: Selection of Gel Substrate for Ballistic Experiments

Before testing a Pneumatic Capillary Gun (PCG), a convenient gel target was required that had similar mechanical properties compared to corneal tissue. Agarose gels can be prepared quickly and are transparent, which is a benefit for ballistics experiments. Based on previous work done by Professor Groisman, agarose was selected as the substrate material. Oscillatory shear rheology was performed on a range of agarose gels using an 8 mm diameter geometry. To make gels, agarose was dissolved in DI water by microwaving until boiling. Using a Pasteur pipette, the boiling solution was poured in between two acrylic plates clamped around 0.7 mm spacers with rectangular slots for the solution to flow into. The gels were allowed to set at 4° C. for two hours. The gels were cut into discs using an 8 mm biopsy punch. Tissue samples were prepared by dissecting the cornea from porcine eyes and punching out an 8 mm disc from the center of the tissue using a biopsy punch. When testing tissue, an 8 mm cleated geometry developed by our lab was used to prevent wall slip [142] [143]. To test samples, the rheometer geometry was lowered onto samples until a normal force was registered. Strain sweeps were run on a stress-controlled rheometer (TA Instruments; AR1000) from 1 to 100 1/s with eight points per decade (at 25° C.).

Figure 14:
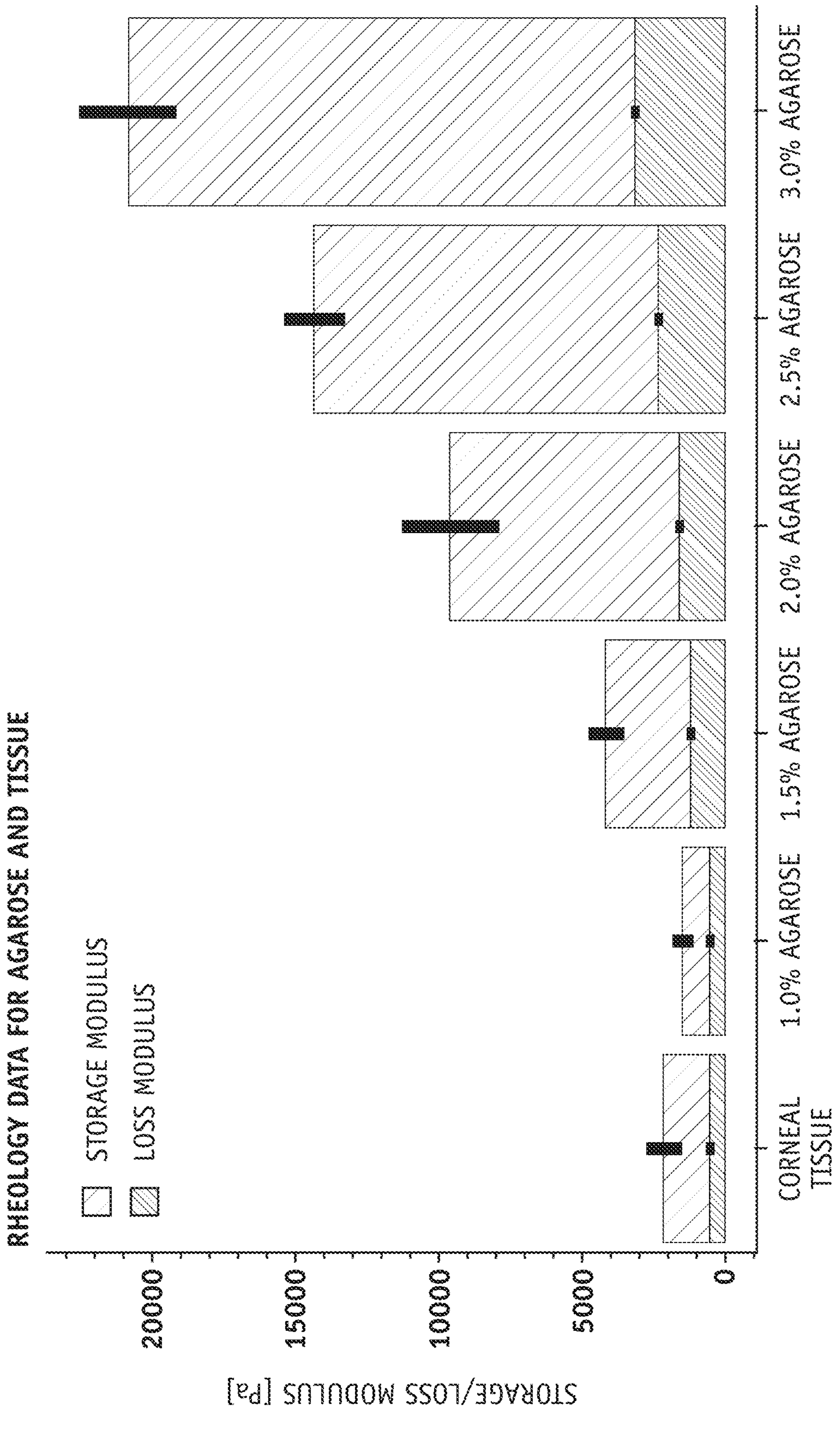
FIG. 14 shows a chart illustrating the rheological data of agarose gels and corneal tissue. Storage and loss modulus taken as the average of reported values when doing frequency sweeps from 1 to 100 1/s. N=6 measurements per sample. 95% confidence intervals shown.

The results of this testing are shown in FIG. 14. The storage and loss modulus for 1.0 to 3.0% w/v agarose gels are plotted along with the data measured from corneal tissue. From this data, it can be found that the 1.0% w/v gels are the most similar compared to the corneal tissue. The outcomes of this experiment are considered along with the testing parameters. The strain rates measured in this experiment are very low. This is problematic, since it has been demonstrated that the mechanical properties of corneal tissue are heavily dependent on strain-rate [144]. Regardless, this data indicated the use of 1% w/v agarose gels for our initial ballistic testing. Agarose was chosen over ballistic gelatin since agarose can be prepared much more quickly than ballistic gelatin. In later experiments, a switch was made to ballistic gelatin so that regressions fit to empirical data could be used to infer particle impact velocity.

Figure 15:
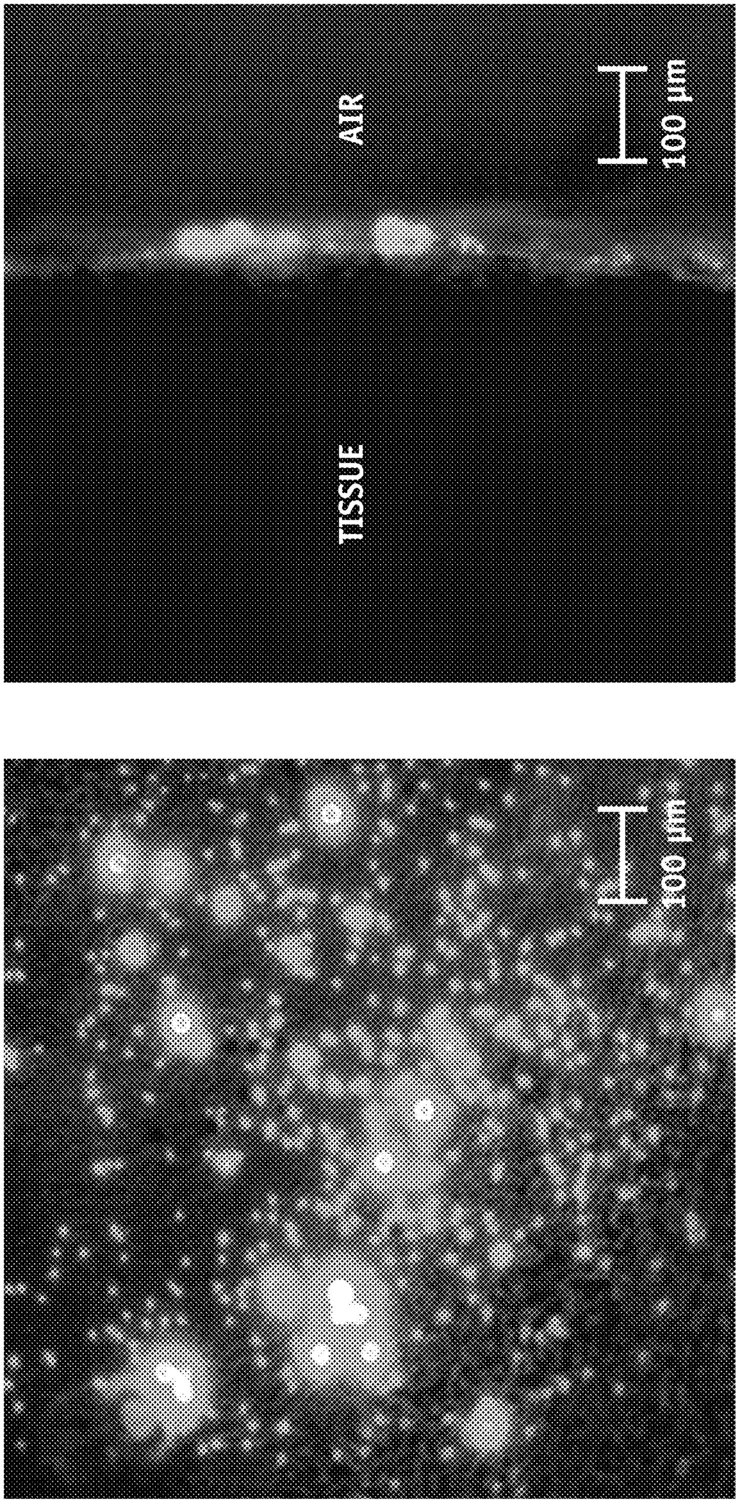
FIG. 15 shows transmission micrographs of corneal tissue treated with 4 and 30 μm poly(styrene) spheres. Top-down view of the cornea shows all microparticles in the same plane (left panel). Cross-section of cornea with particles all on the surface (right panel).

Example 11: Initial Experiments Done with Pneumatic Capillary Gun (PCG) on Corneal Tissue After determining penetration depth statistics in agarose for 10 to 280 μm polystyrene microspheres using the PCG, experiments were done to see if these microspheres would embed in porcine corneal tissue. This testing was done by preparing lure-lock cassettes that contain a solution of 1.5% w/w 30 μm particles with 0.5% w/w 4 μm particles. Each cassette received 2.5 μL of the solution and were dried using the freeze-drying method (Section 2.2.4). 4-μm microparticles were included to mark the surface of the tissue (due to their low impact velocities from fast deceleration rates). Similar solutions were prepared with 10 and 20 μm particles. Once cassettes were prepared, porcine eyes were trimmed of surrounding fat and muscle tunic and their surfaces were dried. Particles were delivered to the anterior surface of the tissue using an acceleration pressure of 4 bar and an injection pressure of 4.5 bar in Alex Groisman's capillary device. To image particles in tissue, transmission microscopy and confocal microscopy were performed to illuminate fluorescent microparticles. Transmission microscopy was performed by dissecting the cornea, placing it on a microscope slide, and tilting it to reveal the cross-section. Transmission microscopy results are shown in FIG. 15. In both the top-down view of the cornea and the view of the cross-section, all microparticles appear on the anterior ocular surface in the same plane. These results indicate that the plastic spheres do not have enough kinetic energy to penetrate the surface of the cornea. FIG. 15 also reveals a dense network of collagen fibrils under the surface of the epithelium. This meshwork leads one to suggest that smaller microparticles may be able to get into the stroma, but these particles do not have enough energy to break through the epithelial layer. In confocal microscopy, all three particle preparations containing 10, 20, and 30 μm particles showed similar results—superficial penetration. These particle samples appeared in the same plane, just barely penetrating the surface from zero to half a diameter.

Figure 16:
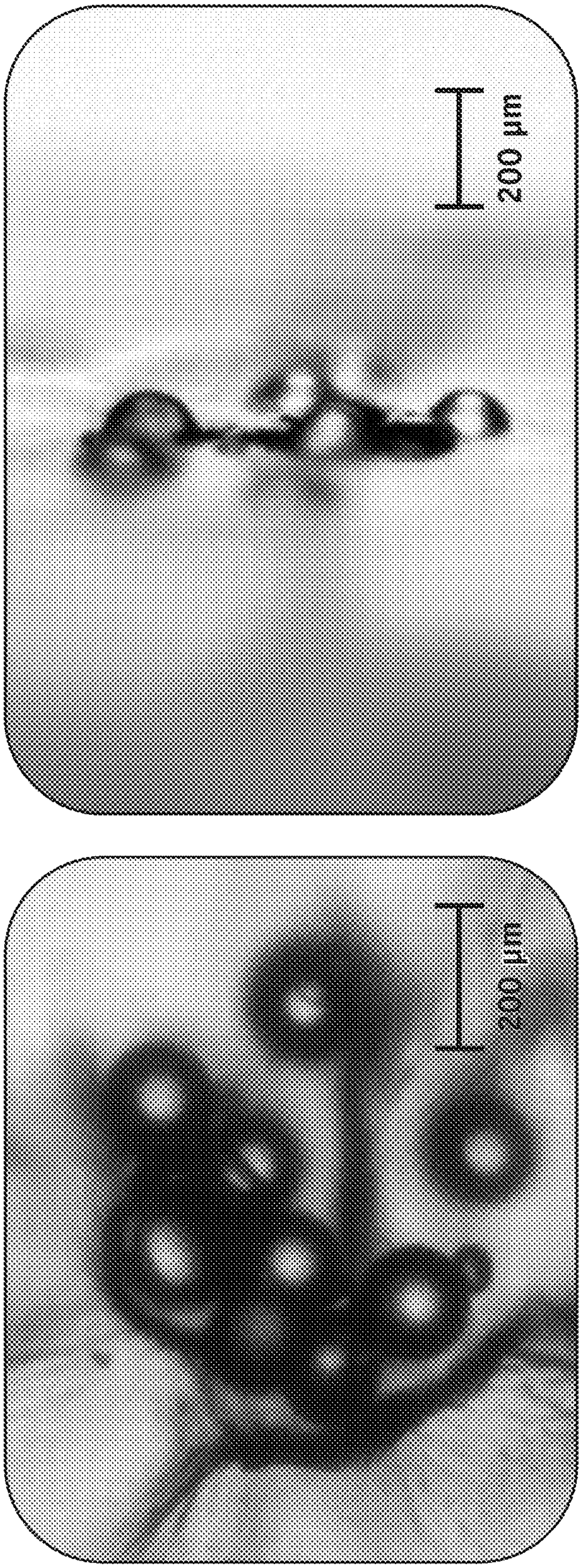
FIG. 16 shows transmission micrographs of corneal tissue treated with 150-180 μm barium titanate spheres (4.2 g/cc), wherein a cluster of particles indents the surface of the cornea instead of penetrating to deeper tissues (left panel) and a group of particles has embedded by about half a particle diameter (right panel).

To increase the amount of kinetic energy of particles, 150-180 μm barium-titanate microspheres were delivered to the cornea. These beads, which had the ability to penetrate 1% w/v agarose gels by over two millimeters, represented the microparticle with the greatest overall kinetic embedding energy accessible with the PCG (at that time). Despite deep penetration in gel, microparticles were again found to be incapable of penetrating the cornea. Two modes of particle arrest are shown in FIG. 16. Some of the microparticles were "caught" by the cornea, making an indentation on the surface of tissue. Other particles are seen embedding in the surface by as much as half a diameter. Since these particles are over three times the thickness of the epithelium, this penetration does possibly suggest penetration to the stroma. However, penetration with such large spheres in which particles may just be indenting the surface is not the kind of particle penetration sought out for (indetectable by the eye). When the PDS1000 gene gun became available, it afforded the opportunity to test smaller, denser materials (see Table 6 for reason the ballistic device is less compatible with dense particles).

Example 12: Preparation of Corneal Tissue Samples

To carry out experiments, porcine eyes were acquired within twelve hours of animal sacrifice (Sierra Medical Products) and were used within two hours. The eyes were stored in antibiotic media and kept moist with phosphate buffered saline (PBS) prior to microparticle treatment until ready for particle delivery, when the eyes were trimmed of surrounding tissue and the surface was lightly dried.

Following particle delivery, porcine eyes were placed in Falcon vortex tubes filled with Davidson's Fixative Solution (DFS, as described in Shariati et al., 2008[145]). Whole eyes were allowed to be fixed for two hours so the cornea would maintain its natural shape, and then corneal tissue was dissected from intact globes, placed in DFS, and refrigerated for 24 hours.

Whole eyes were allowed to be fixed for two hours so the cornea would maintain its natural shape, and then corneal tissue was dissected from intact globes, placed in DFS, and refrigerated for 48 hours.

Tissue was transferred from DFS to 10% w/w sucrose in PBS for eight hours followed by 30% w/w sucrose in PBS overnight. Fixed cornea tissue was trimmed to a 1 cm square and frozen in optimal cutting temperature (OCT) compound for 1 hour at −80° C. Sections were prepared on a microtome in a cryostat to a thickness of 50 μm (larger than the largest particle size) and were imaged immediately to collect data on particle positioning within the tissue. Gel samples were sufficiently stable to section manually using a razor blade in order to photograph particle-field cross-sections.

Example 13: Ballistic Delivery of Microparticles

A BioRad PDS-1000 gene gun (catalog #: 1652257) was used to deliver high-velocity microparticles following protocols described in Sanford et al., 2003. In brief, a payload of microparticles of interest is placed on a Kapton disc (macrocarrier) that is mounted below the gas acceleration tube of the device. A rupture disc that bursts at a prescribed pressure (1350 PSI, 92 bar) is mounted in the gas acceleration tube.

The sample chamber is then pumped down to approximately 23 mm Hg to maximize payload acceleration (the sample is exposed to vacuum for approximately 30s). The gas acceleration tube is pressurized with a desired carrier gas (helium); when the rupture pressure is reached, the gas expands, accelerating the macrocarrier in a reproducible manner. Particles release from the macrocarrier when it is abruptly stopped by a wire mesh that allows microparticles to pass (1 cm flight length).

Five polydisperse microparticle materials were chosen to span the desired density range. The range of tested microparticle composition and density is shown in Table 6.

TABLE 6

Information About Particles Used

| Particle Material | Particle Density | Size (Diameter) Range |
|---|---|---|
| poly (ethylene) | 1.1 g/cc | 10-29 μm |
| soda-lime glass | 2.5 g/cc | 10-22 μm |
| barium-titanate glass | 4.2 g/cc | 5-22 μm |
| stainless steel | 7.8 g/cc | 5-22 μm |
| tungsten | 19.2 g/cc | 20-40 μm |

According to the manufacturers (Cospheric for all particles except ones made of tungsten which come from US Research Nanomaterials Inc), few particles are smaller than the indicated size range and not more than 10% of microparticles are larger than the indicated size range. This accords with the distribution of sizes measured in subsequent data.

The particles were placed in 96% v/v ethanol at a concentration of 3% w/w and vortexed immediately prior to pipetting 20 μL onto macrocarriers. Note that the experiments are analyzed one particle at a time to relate penetration depth to particle size, so the results are not affected by possible differences between the particle size distribution on the macrocarriers (suspension taken from the bottom of the test tube might be enriched in faster-settling larger particles). Ethanol was allowed to evaporate three hours in a desiccator at ambient temperature and pressure before particles were used.

Particles were delivered to the surface of the cornea prepared according to Example 10, using the Bio-Rad PDS-1000, which delivers particles to tissue under rough vacuum. Embedding has also been achieved by a custom-device that works at atmospheric pressure.

Microparticle penetration was characterized in three gels and three cornea samples for all materials tested according to procedures exemplified in the following examples.

Example 14: Corneal Tissue Processing for Penetration Depth Measurements

Following treatment according to Example 13, the corneal tissue was fixed using a paraformaldehyde solution, and then was sectioned to reveal cross-sections. This method allowed reliable measurement of penetration depths. While the microtome blade possibly moves particles, the reproducible depths observed in the research suggest that this effect was low.

Figure 17:
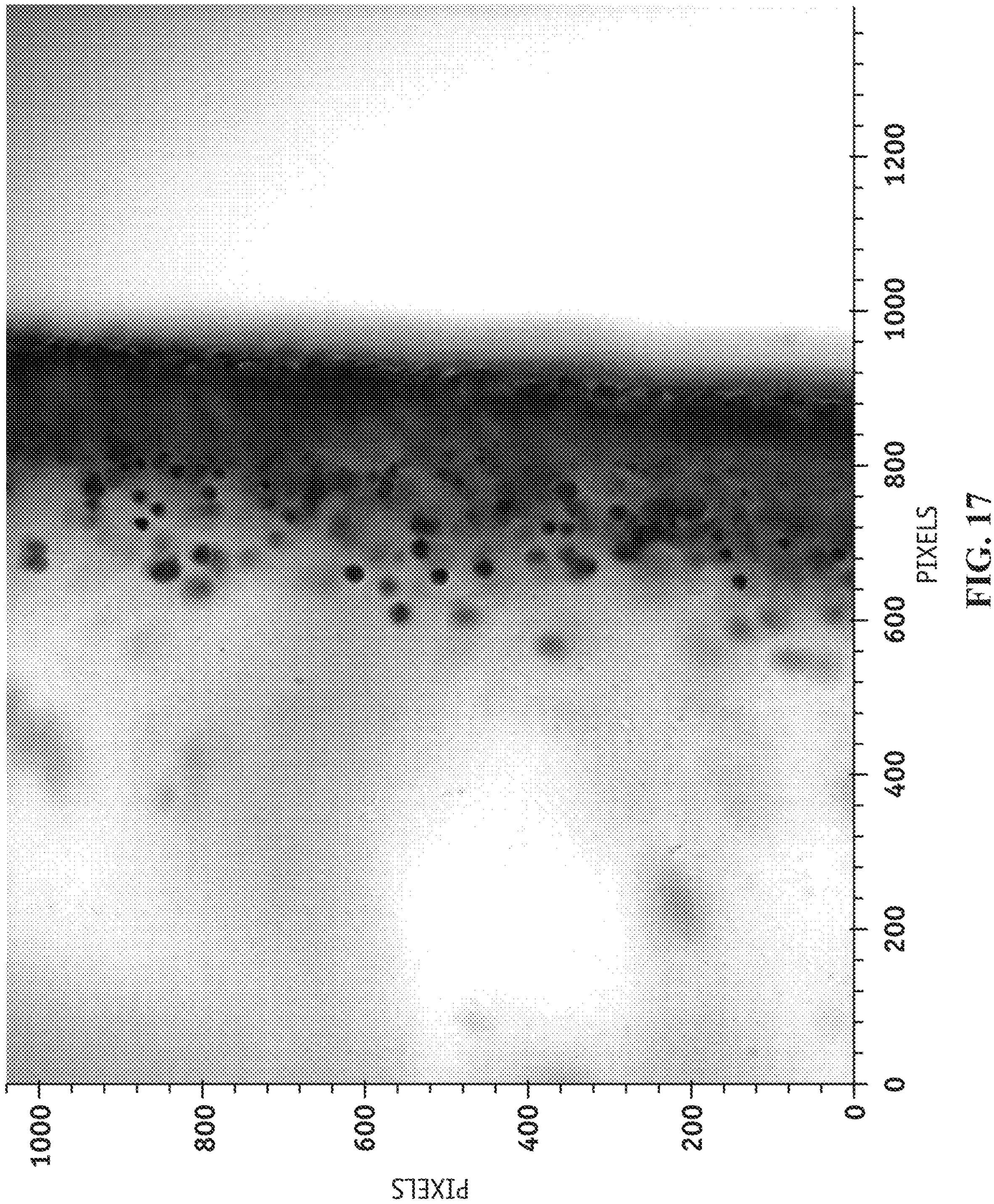
FIG. 17 shows interface used in Jupyter Notebook to click on microparticles in order to record points on each side of the particle as well as points on the surface. These coordinates were fed to the end of the image process pipeline and penetration statistics were generated. Here is shown penetration of stainless-steel microspheres in 10% w/w gelatin.

To collect statistics on particle penetration into gelatin or corneal tissue, an image processing pipeline was developed in which individual particles are selected, particle diameter is measured, and the distance from the surface of the specimen is calculated according to Image Processing Pipeline: FIG. 17 shows a representative Image Interface of microparticles delivered to a cornea tissue sample.

Example 15: Ballistic Delivery of Microparticles Comprising Eosin Y to Corneal Tissue Sample The microparticles of Examples 9, were ballistically delivered to the corneal tissue sample prepared according to Example 10, with a procedure exemplified in Example 11. The related depth was measured according to procedures exemplified in Example 12.

In particular, using a vibrating orifice aerosol generator, droplets were generated with a procedure exemplified in Example 8 and 9, using a solution of 3.96% w/w poly (ethylene glycol) (10 kDa) with 0.04% w/w Eosin Yin ethanol.

Specifically, droplets, which were controlled to have diameters of ~100 μm (using a 35 μm pinhole with 15 kHz excitation, 0.35 cc of solution per minute), were fed into a temperature-controlled 1-metertallcolumn heated to 100° C. 30-50 μm particles were collected in a petri-dish and dried by being placed in a vacuum chamber (125 torr) under ambient temperature overnight.

Figure 18:
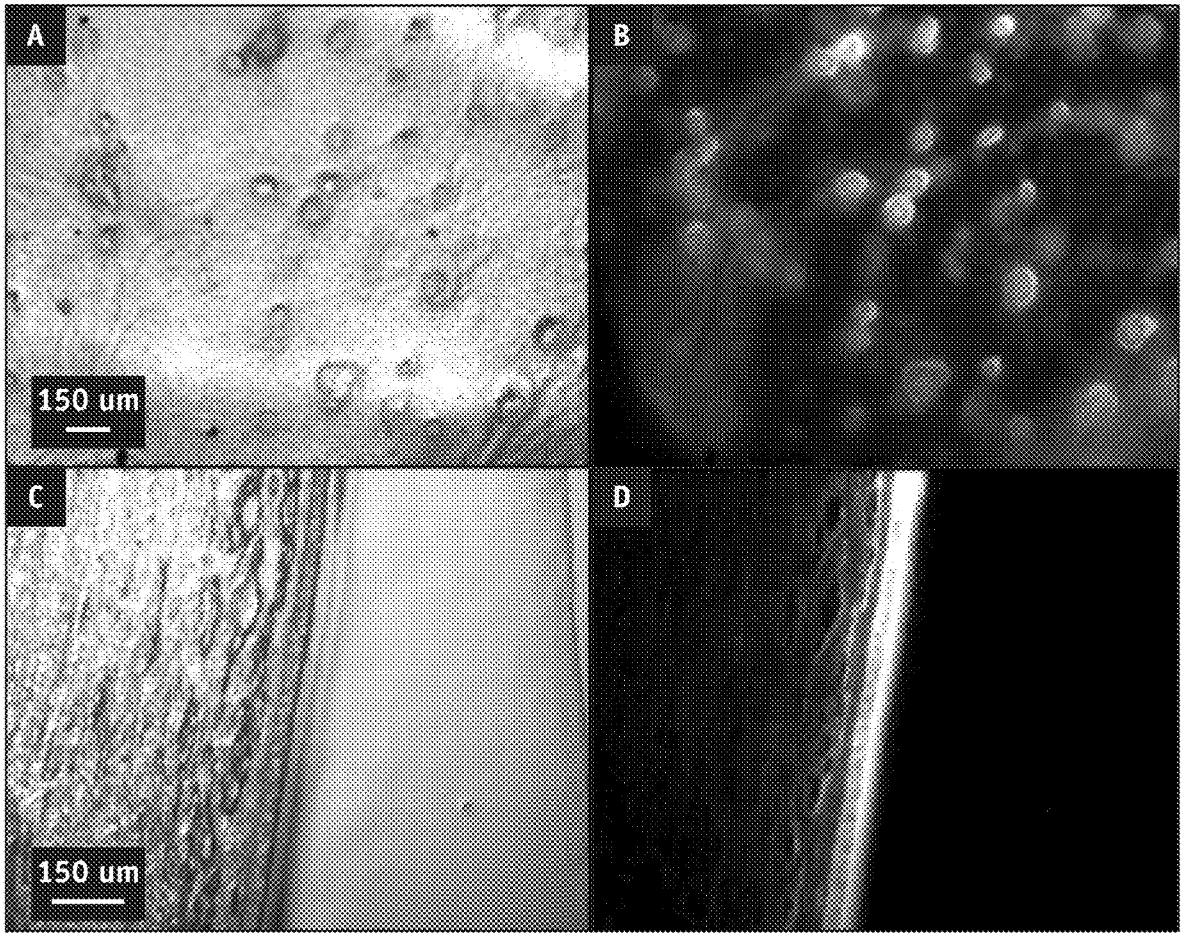
FIG. 18 shows polyethylene glycol microspheres with 1% w/w EY embedded in corneal tissue, wherein in Panel A 10 minutes after particle instillation of anterior surface of the cornea, top down view of the cornea under brightfield microscopy; in panel B cornea under fluorescent excitation under 500 nm light excitation of Eosin Y 10 minutes after instillation; in panel C two days after instillation, 50 μm thick cross-section of cornea tissue under brightfield microscopy; and in panel D two days after instillation exposed to fluorescent excitation of Eosin Y.

The related results are shown in FIG. 18 Panel A and FIG. 18 Panel B which show particles firmly embedded on the surface of the cornea and beginning to dissolve. FIG. 18 Panel C and FIG. 18 Panel D shows tissue brightly stained with the therapeutic Eosin Y, even after sitting in tissue fixation solution for two days.

A confocal image of the dye fluorescence, like that shown in FIG. 18 Panel B, reveals staining from Eosin Y around microparticles. Following the tissue fixation protocol (two days later), FIG. 18 Panels C and D show the staining of the epithelium with Eosin Y. While more images of the tissue closer to the time of delivery were not acquired, microparticles appear to have fully dissolved while being exposed to fixative solutions. Solid microparticles could not be found and there was a strong staining of the corneal epithelium with the fluorescent Eosin dye. As can be seen in the images, staining of the underlying stroma was minimal. There was some evidence of stromal staining. There is impetus to more closely measure the dissolution of these microparticles.

This support the conclusion that release into the tear film is gradual and may indicate that drug enters adjacent tissues over time. First, particles of size ranging from 5-22 μm diameter with density range from that typical of polymer/drug compositions to that of steel were successfully delivered to corneal epithelium. Second, the corneal epithelium appears to close over the particles after they enter the tissue; we did not see a "track" left by the particles.

Example 16: Ballistic Delivery of Microparticles of Different Size and Densities to the Cornea The microparticles of Example 11, including the microparticles of Table 4, were ballistically delivered to the corneal tissue sample prepared according to Example 10, with a procedure exemplified in Example 11. The related depth was measured according to procedures exemplified in Example 13.

By bombarding tissue with a set of microparticles with a broad range of densities and sizes, information about minimum kinetic embedding energies can be deduced. The following protocol for delivering microparticles to tissue was used. Eyes were mounted and placed in the gene gun chamber as close as possible to the macrocarrier containment assembly. To deliver particles to tissue, 1350 PSI (91.8 bar) rupture discs were used.

The gene gun bombardment chamber was evacuated to ~30 mm Hg absolute pressure. To prepare macrocarriers, the particles were placed in 96% ethanol at a concentration of 3% w/w and were vortexed immediately prior to pipetting 20 μL onto macrocarriers. Particles were allowed to dry for two-four hours before delivery to tissue.

Experiments were analyzed one particle at a time to relate penetration depth to particle size, so the results are not affected by possible difference between the particle size distribution on the macrocarriers (suspension taken from the bottom of the test tube might be enriched in faster-settling larger particles). To quantify the impact response of the cornea to particles, three shots of microparticles were delivered to tissue for each particle density used.

Example 17: Penetration Model of Microspheres in Cornea Tissue

A model of ballistic delivery of microparticles in the cornea has been tested in view of the data of the ballistic deliver of microparticles performed according to Example 14 the Soda-lime, Barium and Stainless steel microparticles of Example 11. The related depth was measured according to procedures exemplified in Example 13 and reported in FIG. 19.

Figure 19:
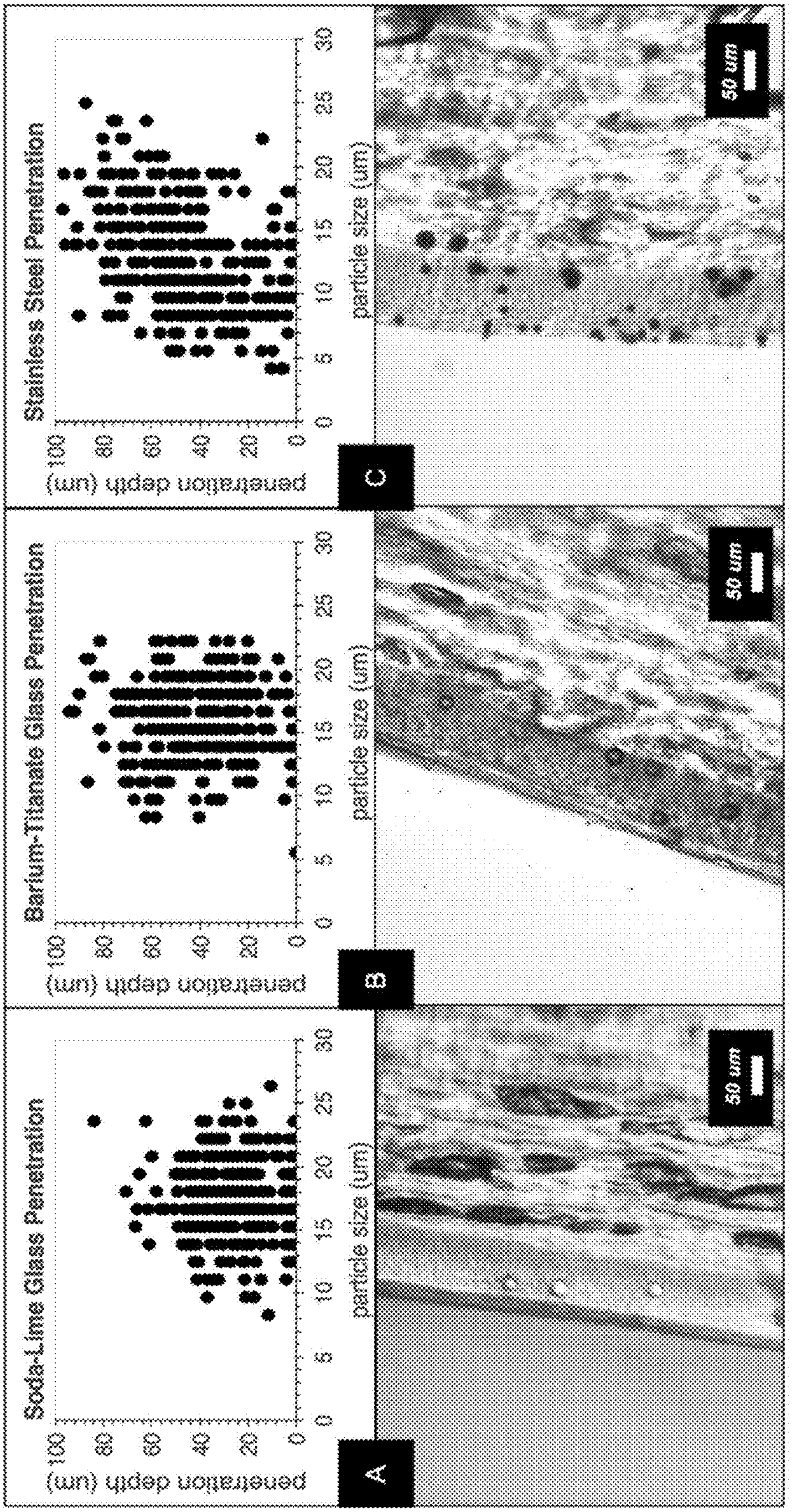
FIG. 19 reports charts and pictures illustrating particle embedding in corneal tissue. Penetration depth of 300 particles from three shots to porcine cornea and representative micrographs for soda-lime glass particles in FIG. 19, Panel A, barium-titanate glass particles in FIG. 19, Panel B, and stainless-steel particles in FIG. 19, Panel C.

In particular the statistics shown in FIG. 19 were recorded by processing image data from sections of corneal tissue exposed to ballistic microparticles.

Each scatter plot shows the result of 300 particles identified in tissue. The particles were identified and their dimensions indicated by a user of the image processing pipeline. This was done instead of thresholding image intensity data because there were defects in the image data that came from reflections off of the tissue which made it difficult to identify objects from thresholding alone. There are slight variations in the thickness of the epithelium. The thickness of the epithelium was measured for 100 images of corneal sections. The average thickness was 63.1 μm (standard deviation of 9.8 μm). Despite areas where the epithelium was thinner, there is little ability for the microparticles tested to carry through the epithelium and embed into the stromal tissue of the cornea.

As shown in the illustration of FIG. 19, all three particle compositions penetrate the cornea the extent of penetration is shown to depend on density more than on size.

In particular, as shown in FIG. 19 both small and large particles embed to similar depths in the corneal epithelium, and most particles can be found between 30 and 60 μm deep (see in particular However, while, the lowest-density microspheres (1.1 g/cc poly(ethylene); PE) did not penetrate the cornea deeply (see FIG. 19 panel A), the particle with higher density tended to accumulate towards the basal layer of the epithelium (see FIG. 19 panels B and C)

Both lower density and high density layer however were able to firmly embed in the apical layer of the cornea as shown by the illustration of FIG. 19 panels A-C.

Example 18: Penetration Model of Microspheres in Cornea Tissue by Probability Density Additional information concerning the behavior of microparticle ballistically delivered in cornea the related probability density of particle was determined To calculate probability density, impact statistics are binned according to their distance from the sample surface. Then, binned penetration depths are divided by the total number of observations for that particle size. Penetration depth is normalized by dividing the penetration distance by particle diameter, so the expected proportionality to particle diameter yields a constant normalized penetration depth.

Figure 20:
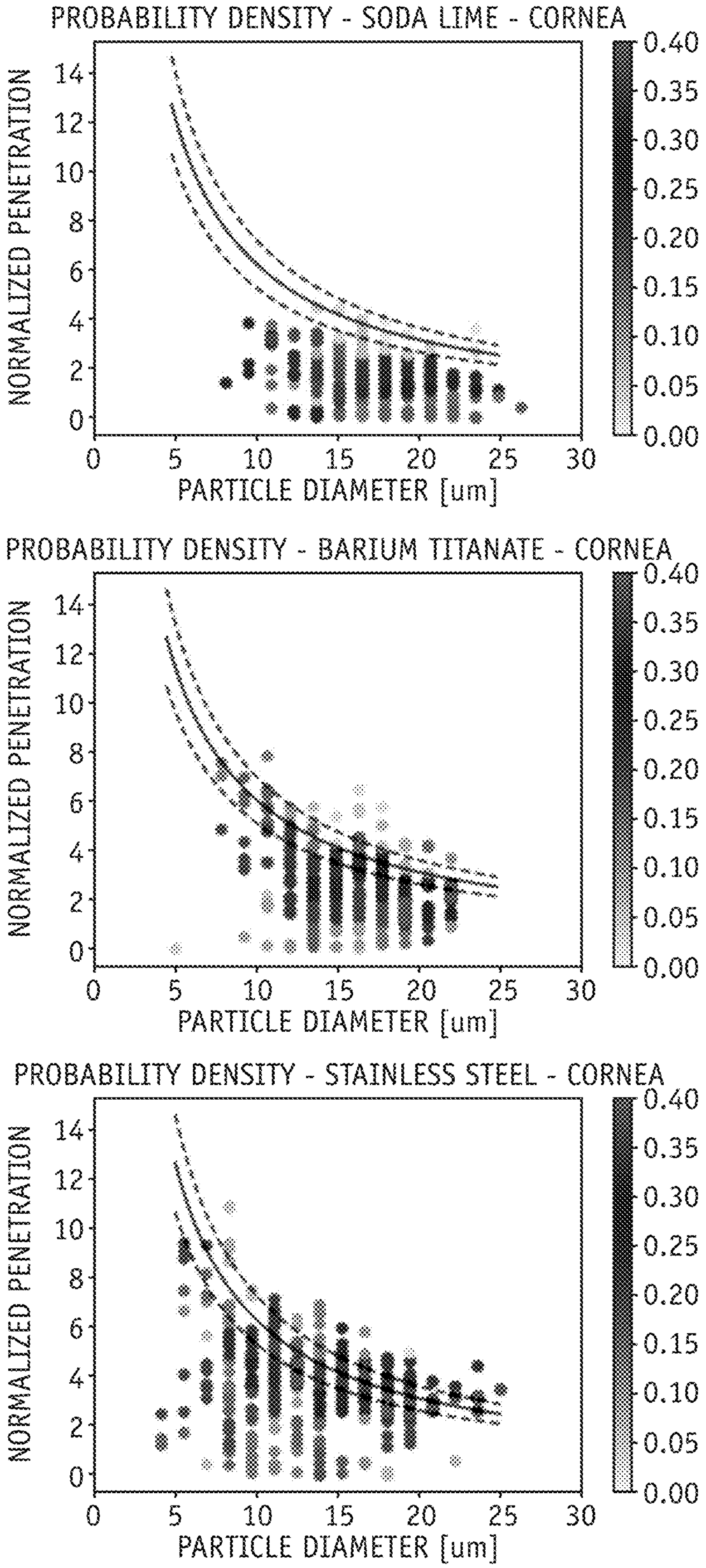
FIG. 20 shows probability densities of soda lime, barium titanate, and stainless-steel impacts in corneal tissue shown with particle penetration normalized by particle diameter. The solid curve represents the measured average thickness of the epithelial layer bounded by dashed curves at a standard deviation above and below the mean value.
Figure 21:
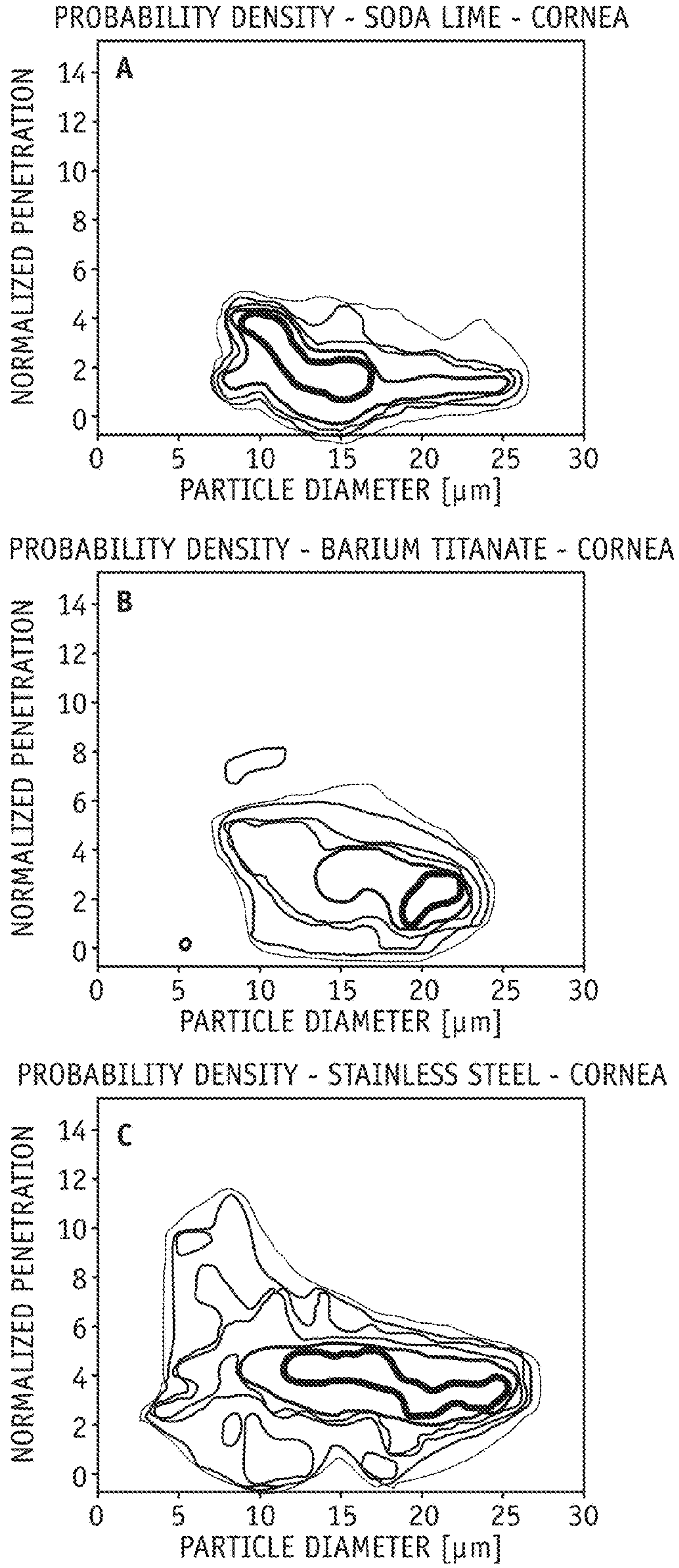
FIG. 21 shows the same penetration depth data as in FIG. 20 in a contour format.
Figure 22:
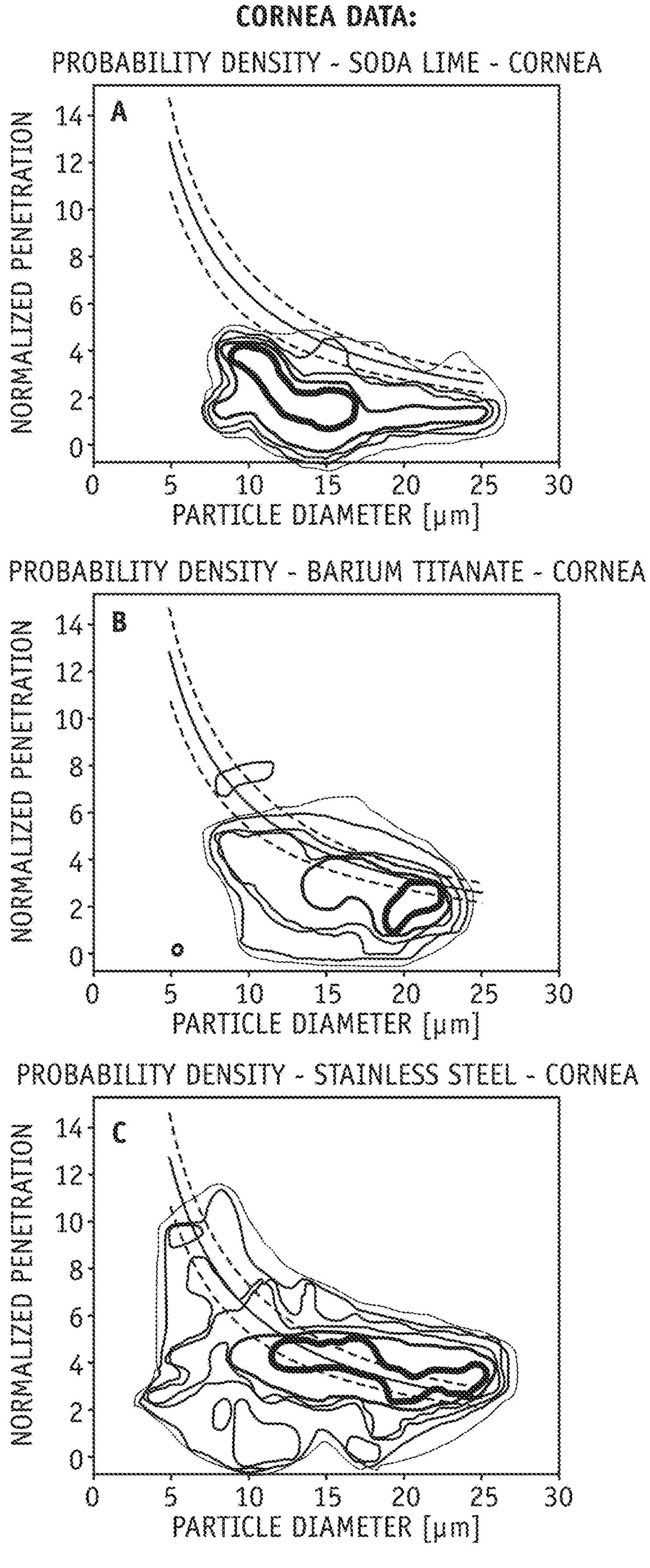
FIG. 22 shows the same penetration depth data as in FIG. 20 in a contour format with average thickness of the epithelial layer bounded by a standard deviation.

The results are shown illustration of FIGS. 20, 21 and 22. In FIG. 20, the "hotter colors" (darker) represent areas where the probability density was greatest. FIG. 21 shows the same penetration depth data of FIG. 20 in a contour format. FIG. 22 shows the same penetration depth data as in FIG. 20 in a contour format with average thickness of the epithelial layer bounded by a standard deviation.

The probability density for the normalized penetration depth in ballistic gelatin is insensitive to particle size, as expected (FIG. 20 Panels A-C). In gelatin, increasing relative density of the particles relative to the sample conforms with the expected proportional increase in normalized penetration. In contrast, normalized penetration into the cornea is not independent of particle size and does not simply increase proportionally with the particles' relative density (FIGS. 20A-C).

In FIG. 20, the curved bands represent the expected location of the interface between the epithelium and the stroma. When the average thickness of the epithelium is divided by the diameter of an expected particle, the solid curve is generated. The dotted lines indicate upper and lower bounds of the epithelium interface calculated by using the standard deviation statistics recorded measuring the thickness of the epithelium.

Peculiar features of the distribution of normalized penetration in the cornea include possible evidence of bimodal probability distributions for small, low-density particles (FIG. 20 Panel A), 12.5±0.7 and 14.0±0.7; for smaller particles, very few entered the epithelium and loss of particles from the surface during handling precluded quantitation). A first peak at very low penetration suggests that there is a threshold impact velocity required to pass through the apical layer of the corneal epithelium (the distribution of impact parameter for small soda lime particles includes some that are so low that the particles come to rest on the epithelium). With increasing size, soda lime particles transition to a unimodal distribution as seen in ballistic gelatin, with the most probable normalized penetration that is insensitive to particle size (FIG. 20 Panel A, for particle diameter >15 μm).

At the opposite extreme, large, high-density particles show a penetration depth that does not increase with particle size and normalized penetration depth actually decreases with increasing particle size (FIG. 20 Panel B for particle diameter >15 μm and FIG. 20 Panel C for particle diameter >8 μm). This behavior is not described by either the Poncelet model or the elastic Froude number scaling rule. The ability to deposit particles to a narrow region relative to the distribution of size and velocity of the particles is clinically useful. It enables clinicians to deliver a biologically active cargo to a controlled depth reproducibly despite variations in the particle size and velocity.

The peak penetration depth appears to be dictated by the thickness of the epithelium (indicated by a shaded band in FIG. 20 Panel A) The limited ability of the microparticles tested to penetrate through the epithelium and embed into the stromal tissue of the cornea suggests that there is a threshold remaining kinetic energy that is exceeded for particles to pass through the boundary between the epithelium-stroma. In accord with this hypothesis, the distribution of penetration depths has a pronounced asymmetry, with an abrupt decrease in probability of penetration into the stroma.

As a result of the probability density determination exemplified in FIGS. 20, FIG. 21 and FIG. 22 it appears that when particles enter the cornea, there is a narrow range of penetration depths in which particles with having the tested diameter and densities can embed, confined to the epithelium and the bowman's layer if present for the range of impact parameter examined here.

Once particles reach the epithelial-stromal boundary, their motion is essentially arrested. Although previously unanticipated, this behavior can be rationalized in hindsight based on corneal mechanical properties in the literature. Atomic force microscopy (AFM, using for example, SiN cantilevers with a borosilicate sphere tip) has been applied to interrogate individual layers, leading to a Young's Modulus of 0.57 kPa for the corneal epithelium, 110 kPa for Bowman's Layer, and 33 kPa for the stroma (Last et al.; 2010 [9]). However, the large contrast in properties reported by Last et al is not found in other studies, such as [11] which reports elastic modulus of the rabbit corneal epithelium, 0.57±0.29 kPa (mean±SD); anterior basement membrane (ABM), 4.5±1.2 kPa; anterior stroma, anterior stroma, 1.1±0.6 kPa (note the 30 fold lower value than Last et al.)

While porcine corneas lack Bowman's Layer, mechanical properties within the stroma can be stiff and vary with depth. Regions where the collagen lamellae are more interwoven (the anterior stroma) are consistently found to be stiffer than the posterior cornea (Blackburn et al., 2019[7]). Such a step up in the stiffness could explain the high probability of particles halting at the boundary between the two layers.

The experimental discovery that particles observed to penetrate to the same depth in ballistic gelatin form a group with respect to their ability to penetrate the cornea provides guidance regarding other combinations of density and velocity that will also deliver particles of diameter from 20 to 30 μm to the posterior half of the epithelium: in addition to particles having dimension 20-30 μm and density of 7.8 g/cc with velocities from 140 to 180 m/s, delivery to the posterior half of epithelium can be achieved using particles having dimension 20-30 μm and a density of 4.2 g/cc by using velocities from 270 to 330 m/s.

Although it would require supersonic velocities, as can be provided by LIPIT, particles having dimension 20-30 μm and a density of 2.5 g/cc can also be delivered to the posterior half of the epithelium by using velocities from 450 to 550 m/s. The penetrating power varies smoothly with velocity and density, such that interpolation between the experimentally observed ranges reliably identifies other combinations of density and velocity that will provide localization of delivery to the posterior half of the epithelium for a selected particle size. This is useful when considerations of a particular formulation of biologically active cargo and carrier places a restriction on the density that can be used. For example, particles of density 3.35 g/cc (midpoint between 4.3 and 7.8 g/cc) having velocity from 360 to 440 m/s.

This conclusion is unexpected as the possible role of the epithelial basement membrane and concluded that for the porcine corneas considered here before the experiments herein summarized was considered unlikely to make a significant contribution to arresting particle penetration: it is quite thin (~100 nm thick) and is continuous with the stroma below (Abhari et al.; 2018[146]).

Nonetheless, the evidence reported in this present disclosure suggests layered heterogeneity in mechanical properties of tissue is what gives rise to the cornea's penetration response.

Example 19: Penetration of Low Density (Less than 2.5 g/cc) Microparticles in Corneal Tissue Lowest-density microspheres (1.1 g/cc poly(ethylene); PE of Example 11 and Table 6 above) did not penetrate the cornea deeply, but they were able to firmly embed in the apical layer of the cornea.

Figure 23:
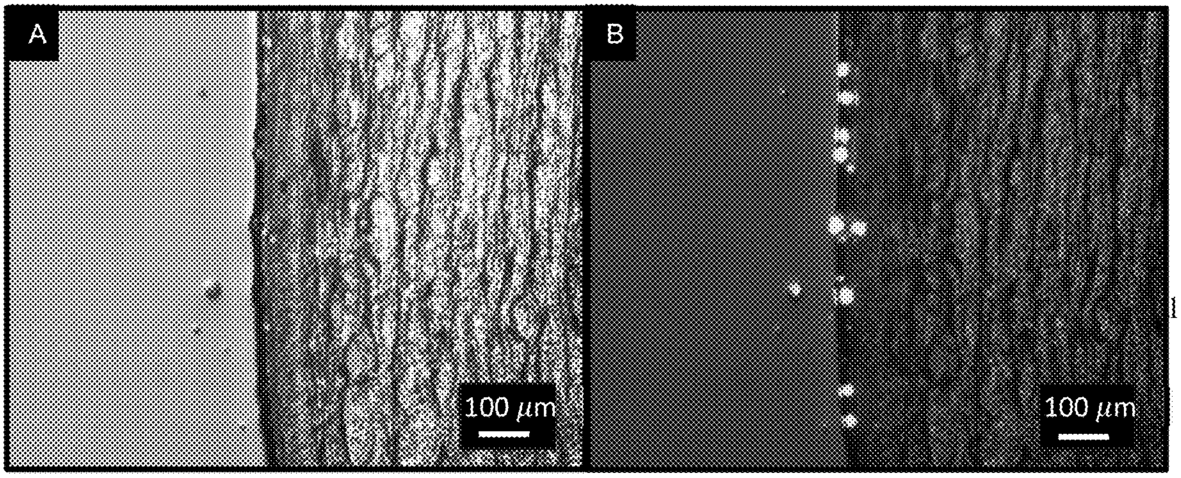
FIG. 23 shows superficial penetration of low-density microspheres in corneal tissue. Poly(ethylene) spheres, which show low penetration in ballistic gelatin, barely penetrate corneal tissue. Fluorescent micrograph shown on the right to highlight microparticles.

When corneal tissue was tested with these particle payloads, penetration was superficial. FIG. 23 Panels A and B show fluorescent microparticles embedded just at the surface of tissue. While penetration was far from reaching stromal tissue, it is promising that particles can be found on tissue after three days of the tissue processing protocol.

These results suggest that microparticles are firmly embedded on the surface of the tissue. In addition, since the densest layer of tight protein-junctions are on the anterior surface of the cornea between stratified epithelial cells, this type of penetration may still enhance drug delivery.

Figure 24:
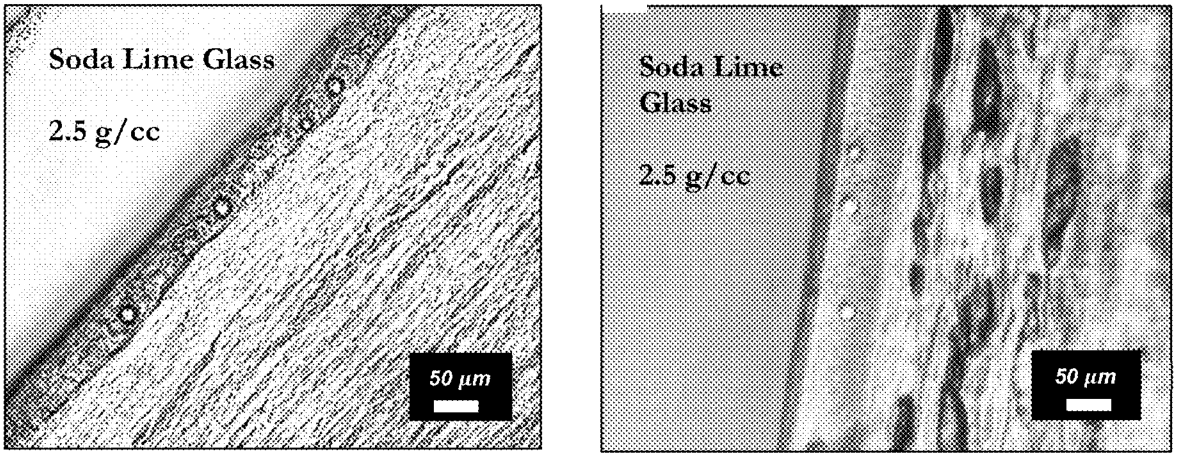
FIG. 24, reports pictures showing Soda-Lime glass spheres embedded in section of corneal tissue. Tissue sections are 50 μm thick. Particles embed throughout the epithelium.
Figure 25:
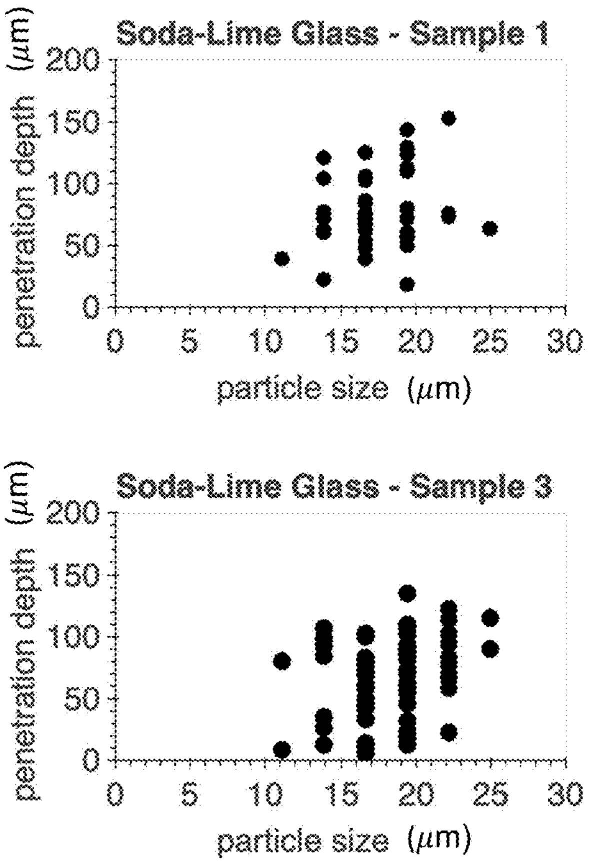
FIG. 25 shows charts illustrating Penetration statistics of soda-lime spheres embedded in corneal tissue. The penetration of spheres in tissue is shown for three separate shots into three different corneal samples. Image processing pipeline was used to go through each image individually.

Example 20: Resulting Penetration of 2.5 to 7.8 g/cc Microparticles in Corneal Tissue The next particles that were tested were soda lime glass spheres (10-22 μm; 2.5 g/cc). These particles showed significant penetration through the corneal epithelium, and they did not penetrate any further. The penetration observed from representative micrographs shown in FIG. 24 indicates particles scattered throughout the epithelium. Penetration statistics for all three cornea samples treated with microparticles, shown in FIG. 25, indicate similar penetration statistics from one particle delivery to another. Sample one shows only 80 particles found in the tissue (as opposed to 100 for all other samples and materials). More images were taken of the third sample to compensate. The range of particles detected by the image processing pipeline is representative of the actual range of particles reported by the vendor. Some particles are slightly larger than the expected size range, potentially due to clicking on larger diameters than actually were seen using the image processing pipeline. It is possible that deceleration of smaller particles led to a pileup at the surface of the tissue. There was a smaller quantity of particles found in the tissue sections than was seen testing higher density microspheres. It is possible that particles are embedding in the apical surface of the cornea and tissue processing is stripping particles from the surface, reducing the number of particles seen in sections. This low number of particles observation was seen with PE spheres as well.

Figure 26:
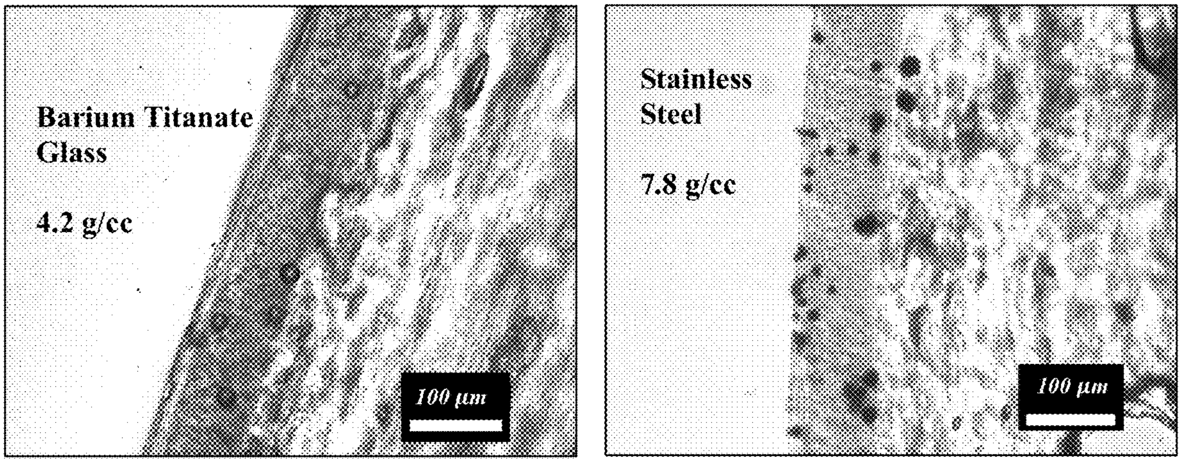
FIG. 26 reports pictures showing penetration of barium-titanate and stainless-steel microparticles in cornea. The penetration of spheres in tissue is shown in 50 μm tissue sections.
Figure 27:
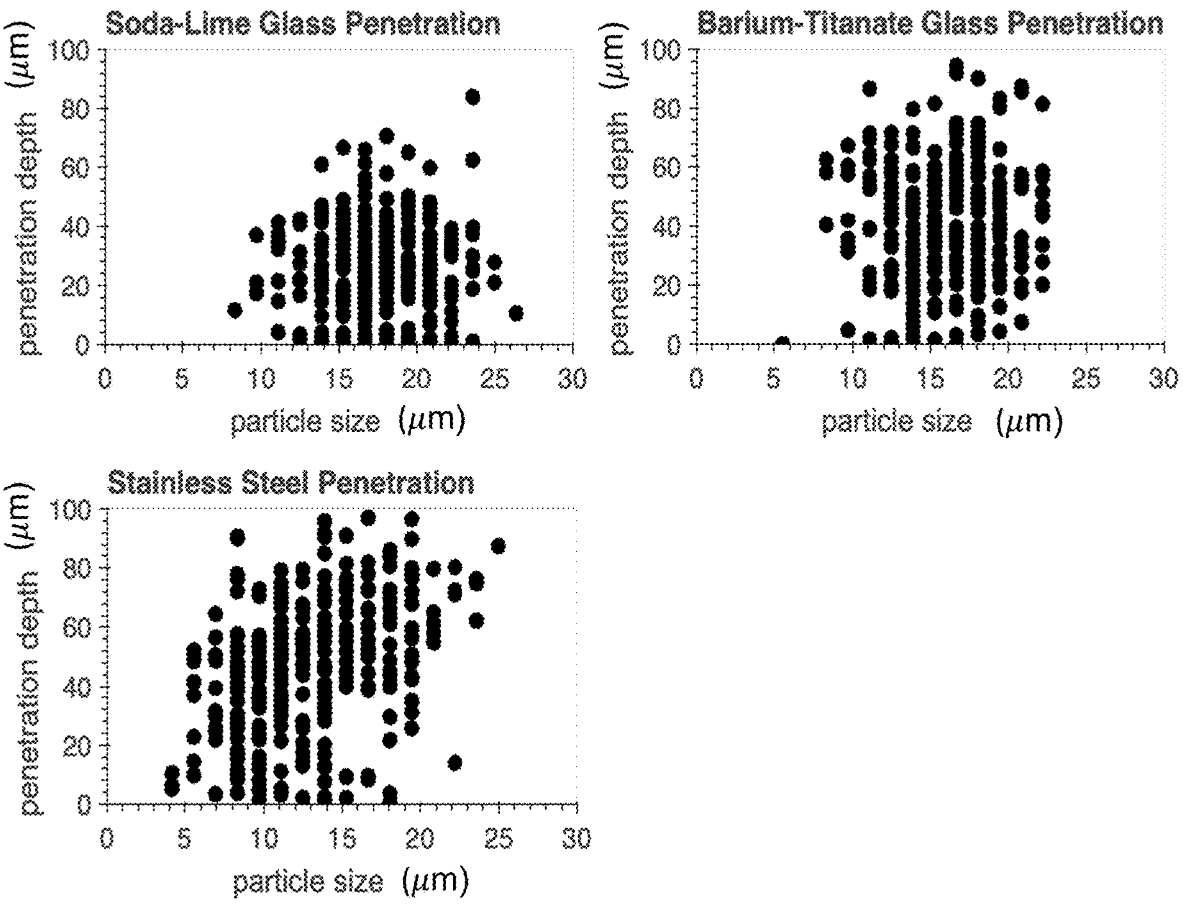
FIG. 27 shows charts reporting penetration statistics for range of particle densities in cornea. The penetration of spheres in tissue is shown for three separate shots of soda-lime glass, barium-titanate glass, and stainless-steel microspheres. Changing particle density only slightly changes particle penetration depth.

When particle density was increased, penetration depth in tissue did not significantly rise, as was expected. Barium-titanate spheres penetrated to the bottom of the corneal epithelium but did not travel any deeper than this. While these particles were able to travel over twice the distance as soda-lime glass spheres in gelatin, FIG. 26 shows the particles getting stuck at the interface between the epithelial layer and stroma. What's more, stainless steel microparticles, which embedded in gelatin up to four times as much as soda-lime glass microparticles, get held back by the same interface. The full penetration statistics of the particles tested, shown in FIG. 27, indicate a slight increase in penetration depth when projectile density is increased, but the penetration is similar for the three sets of particles.

Figure 28:
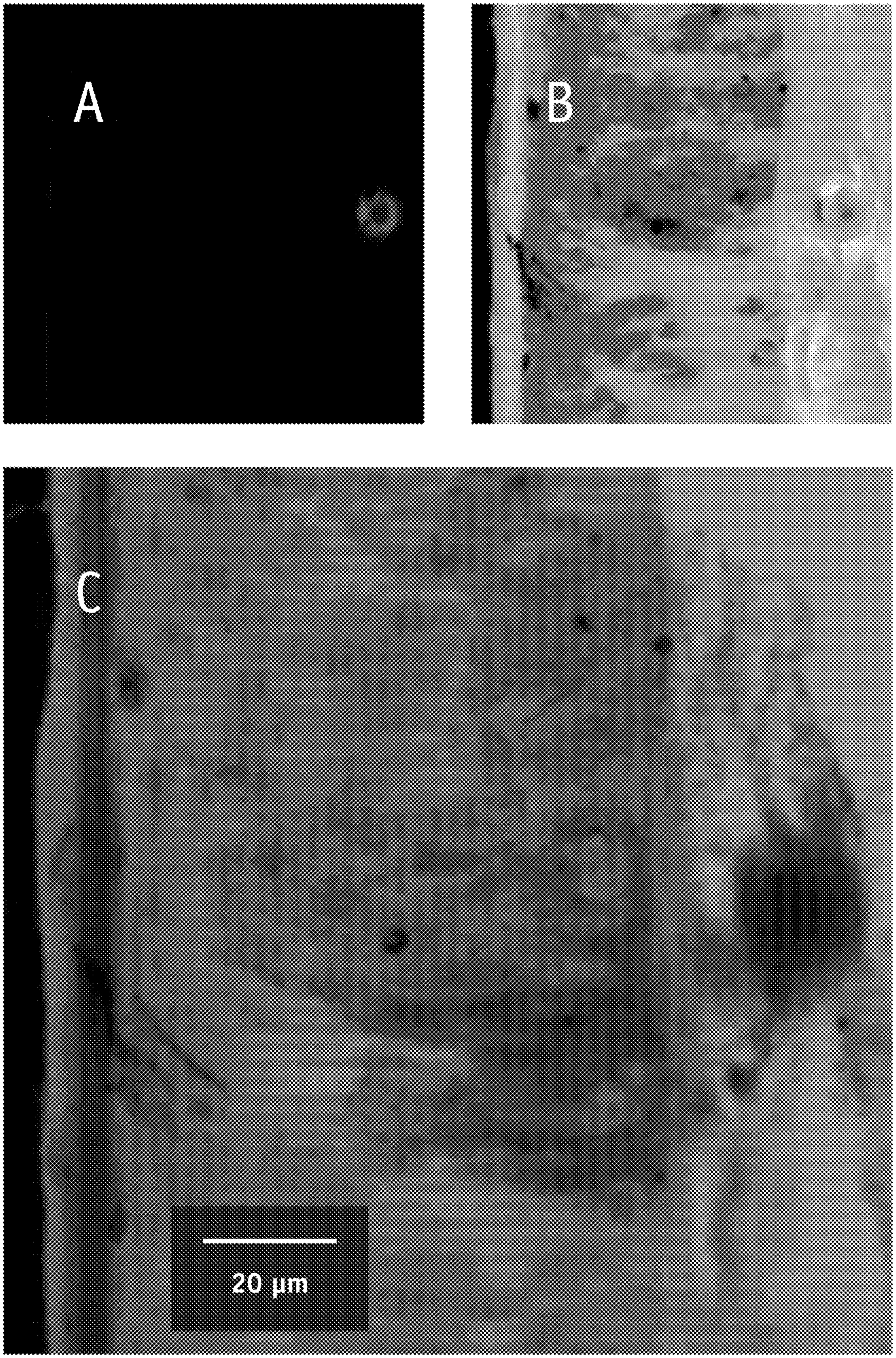
FIG. 28 shows confocal Z-Stack illustrating steel particle embedded in Picrosirius-Red stained corneal tissue. From A to C, depth in the z-stack is increased. The 30 μm thick section was stained for 5 minutes in Picosirius Red.

While embedding depth was shallow, it is interesting to note that penetration into the epithelium did not leave a visible "track." To the extent observable with optical microscopy, no evidence of tissue damage was seen. Confocal microscopy was done on tissue treated with stainless steel microparticles prior to staining with picrosirius red (Abcam Inc.). Picorsirius red is a fluorescent dye that binds strongly to collagen fibrils and is used to determine collagen type, as in Vogel et al.[7] While it was recommended that staining should be done for 1 hour, sections of tissue were stained for 5 minutes. This was sufficient to produce bright fluorescence on the stroma and the epithelium. The tissue was sectioned 30 μm thick to ensure adherence to the microscope slip during staining. When this was done, there were no observed defects in the epithelium that could have been a trail, despite there being many particles that were in the tissue (FIG. 28).

There are slight variations in the thickness of the epithelium. The thickness of the epithelium was measured for 100 images of tissue sections. The mean thickness was 63.1 μm (standard dev. 9.8 μm). Despite areas where the epithelium was thinner, there is little ability for the microparticles tested to carry through the epithelium and embed into the stromal tissue of the cornea.

Figure 29:
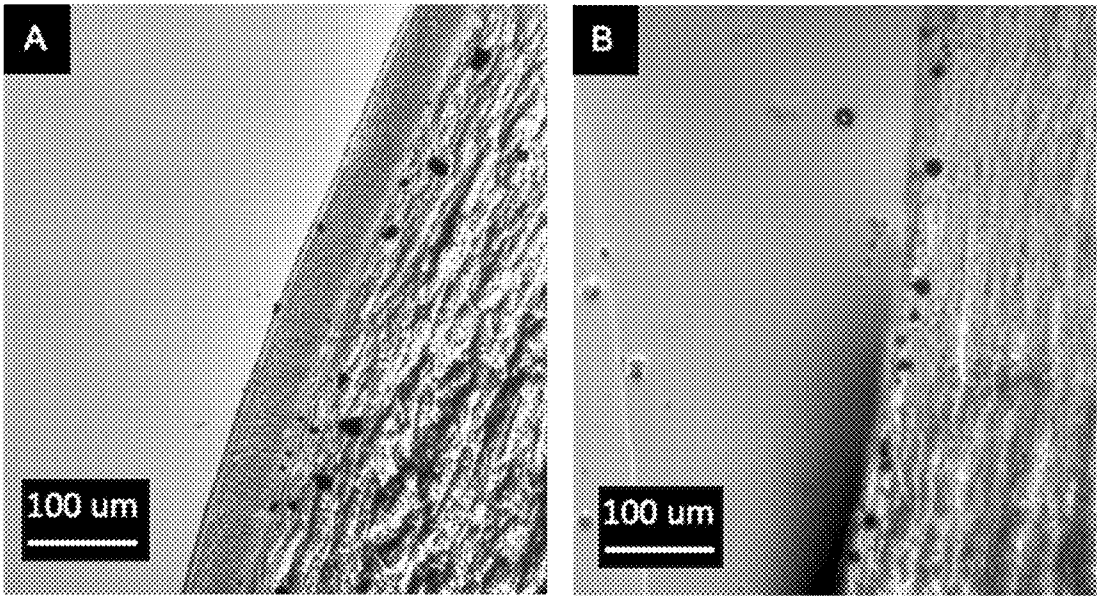
FIG. 29 shows pictures illustrating in panel A tungsten microparticles embedded to shallow depth in stroma and in panel B stainless steel microparticles in tissue with epithelium debrided prior to bombardment.

Example 21: Penetration of Particles Having Density 7.8 g/cc to 20 g/cc and Debrided Corneal Tissue A density was established at which microparticles infiltrate the stroma when tungsten was used as a projectile material. FIG. 29 Panel A \shows the results of bombarding intact corneal tissue with tungsten particles. As can be seen, the tungsten microparticles just enter the superficial layers of stromal tissue. Despite having a density twice that of stainless-steel particles tested, there is only a small increase in the total penetration depth of microparticles. FIG. 29 Panel B shows the results of bombarding corneal tissue that has been debrided (epithelium removed with a razor blade). As can be seen, the stroma is an effective momentum sink that arrests particles on its surface.

Figure 30:
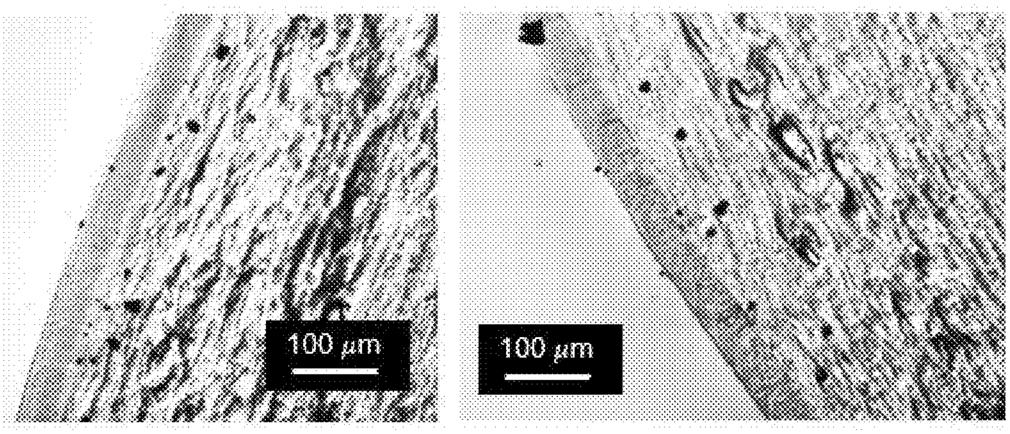
FIG. 30 shows 20 to 40 μm tungsten ballistics embedded in corneal tissue, wherein microparticles of tungsten ballistics, which have 19.2 times the density of the tissue itself, are able to get all the way through the epithelium.

Example 22: Penetration of Particles Having Density 20 g/cc to 40 g/cc in the Cornea As a test to determine minimum kinetic energy needed to break through to the stroma, penetration of tungsten microparticles with a diameter of 20 to 40 μm was investigated. Since these particles had such a high settling velocity, it was difficult to pipette mixtures of ethanol and tungsten particles. As such, tungsten was deposited dry on Kapton macrocarriers. Electrostatic forces between particles and the polymer film were enough to keep the particles in place long enough to be bombarded into tissue. The results of bombardments in corneal tissue using an 1800 PSI rupture disc were recorded. Tungsten particles embedded between 50 and 100 μm into the stroma in the two images are shown in FIG. 30. As is shown, tungsten particles are firmly embedded in the tissue, with little damage or disturbance of the surrounding tissue. This data shows that in order for microparticles to traverse the epithelial layer of the cornea, they need to have exceptionally high density like tungsten.

Example 23: Penetration of Microparticles in Anterior and Posterior Layers of Stromal Tissue Tough mechanical properties of the stroma appear to be the cause of particles getting effectively stopped in corneal tissue. This would explain how small particles are able to travel freely more self-diameters in distance before getting halted at the stroma, but larger particles are halted as soon as they reach the epithelium-stroma interface. To test if the stroma was the main source of resistance to microparticle entry, corneal tissue was prepared for ballistics testing that had been debrided (epithelium removed). If particles were indeed being stopped by the thick anterior layers of the stroma, the spheres should still become arrested at superficial depth. If there is a decelerating effect of the corneal epithelium, then microparticles should travel even further without the layer of tissue intact.

Figure 31:
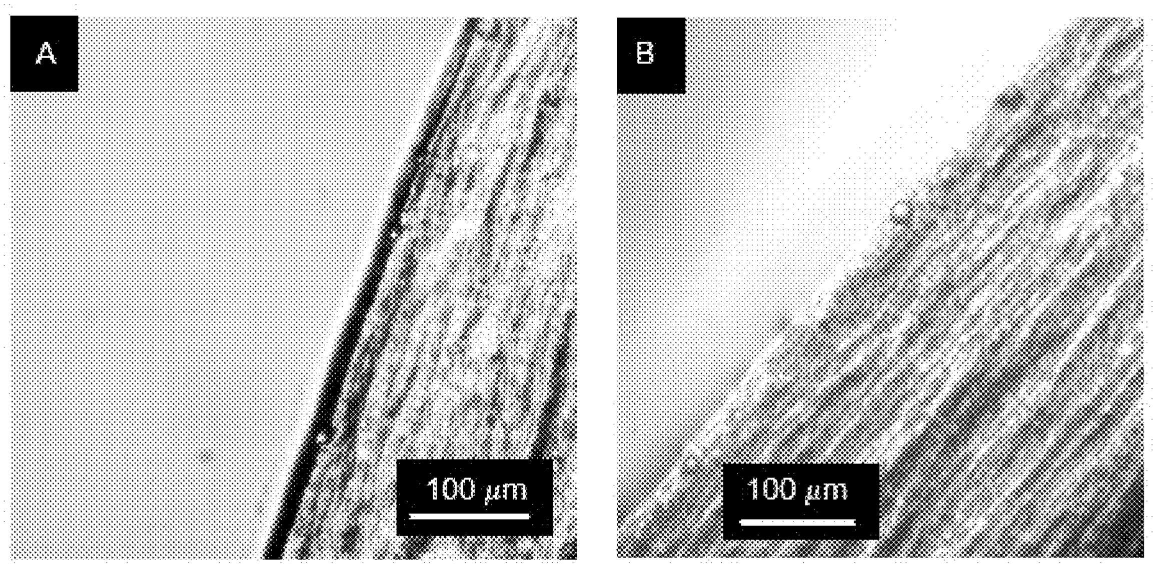
FIG. 31 shows 10-22 μm soda lime spheres embedded in debrided corneal tissue wherein microparticles are embedded in the outermost layer of the stroma and fewer particles are found than with epithelium intact.
Figure 32:
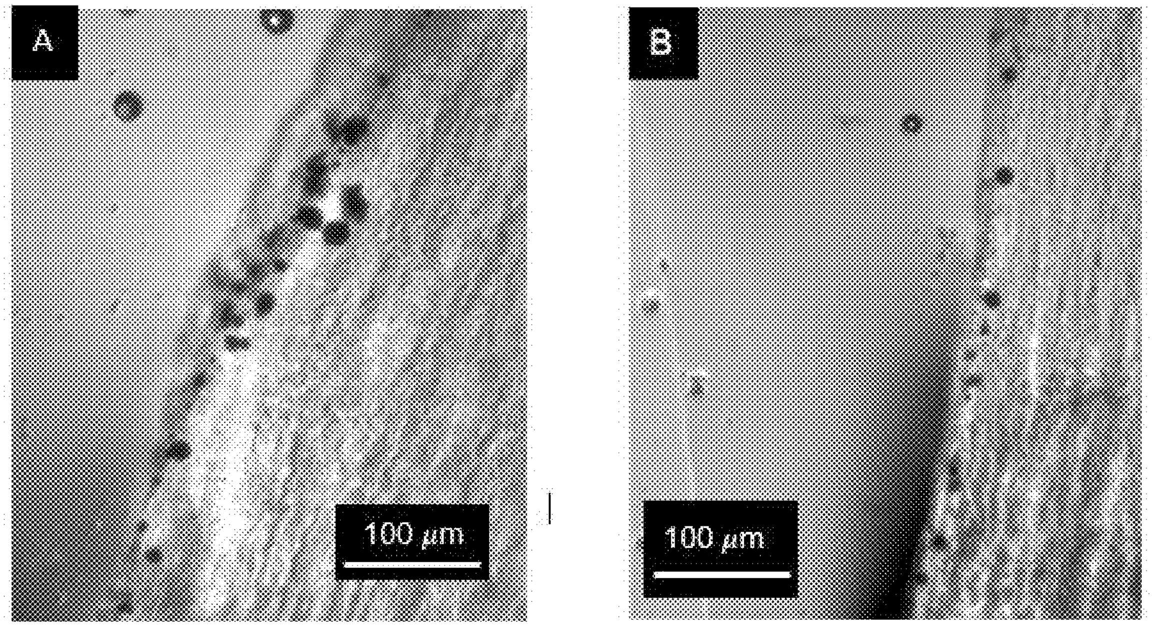
FIG. 32 shows 5-22 μm stainless steel spheres embedded in debrided corneal tissue wherein microparticles are embedded in the outermost layer of the stroma. Particles on the large and small end of the size spectrum show up in the tissue.

The corneal epithelium can be removed by scraping the surface of the cornea with a razor blade. This was done before two preparations of particles were delivered ballistically with the PDS1000 gene gun. Soda-lime and stainless steel microparticles were prepared for the experiment. The results of soda-lime glass spheres embedding in debrided tissue show what was expected: the particles (FIG. 31 are arrested in the outermost layer of the stroma. It was also observed that fewer particles were in the cornea following the tissue processing procedures, as opposed to when the corneal epithelium is in place when particles are embedded. Perhaps this soft layer of tissue keeps particles in the sample while tissue is being fixed and protected. Only the particles that get firmly stuck in the fibers of the stroma remain when the tissue is inspected. Even when the particles are three times as dense as the stainless-steel microspheres are, FIG. 32 shows that microparticles are arrested in the anterior stromal surface. There are fewer microparticles embedded in the tissue than with the epithelium intact, but there are more present than with the soda-lime glass particles. It can be seen that both stainless steel microparticle sizes on the low and high end of the size spectrum show up in the images selected.

Figure 33:
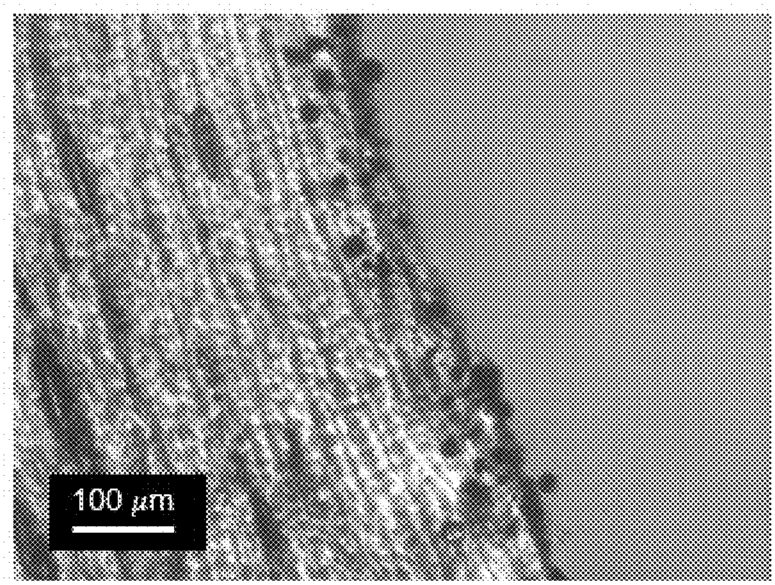
FIG. 33 shows 5-22 μm stainless steel spheres embedded in posterior corneal surface wherein microparticles are embedded in the endothelium and a small distance into the underlying stroma tissue.

In addition to delivering microparticles to the anterior surface of the stroma, particles were also delivered to the posterior surface to assess the ability of the interface to arrest particles (FIG. 33). This was done by dissecting cornea tissue from porcine eyes and using the ballistic device to treat the back surface of each sample. The endothelium is a five micron thick monolayer of cells with hexagonal packing.[12] Since it has such a low thickness, this layer's contribution to the mechanical properties relating to microparticle entry are likely small (compared to underlying posterior layers of the stroma). When posterior corneal tissue was treated with microparticles, there was a similar particle arresting response observed compared to particles embedding at the anterior surface. Particles embed in the stroma by one to two diameters, but none go deeper than this. AFM data from the literature reports that the posterior stroma has a lower Young's Modulus than the anterior stroma. Penetration observed was a bit deeper than in experiments done on the anterior stroma.

Example 24: Microparticles Ballistically Delivered to the Cornea Stay in Place in the Target Tissue Layer where they are Delivered To assess the ability for tissue to seal up as ballistic particles embed in the material, picrosirius red was used to stain the epithelium and stroma and confocal microscopy was used to image individual layers of the tissue surrounding a single particle.

Figure 34:
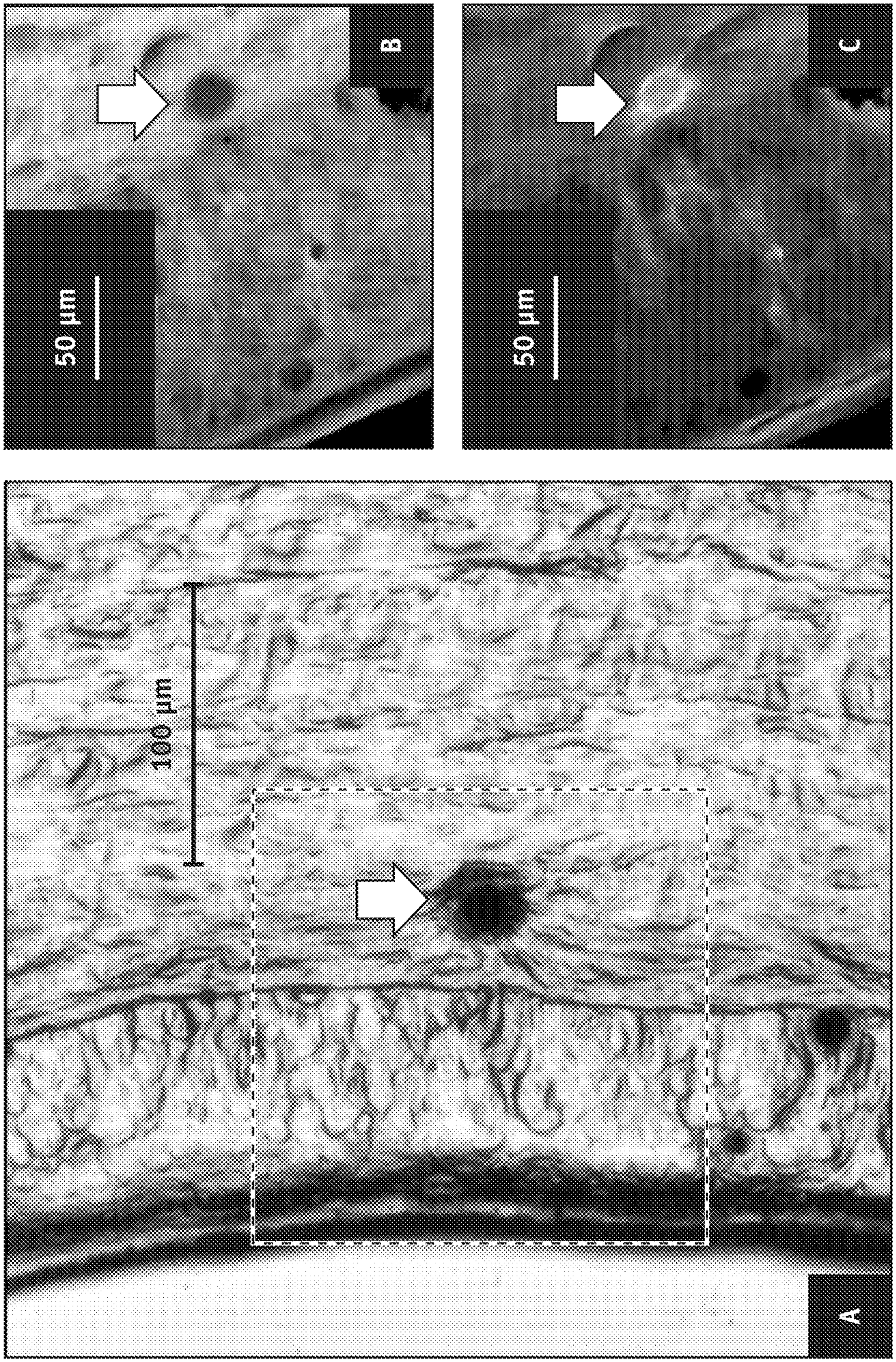
FIG. 34 shows particles create low damage as the embed in tissue, wherein in panel A transmission micrograph of a stainless steel microparticle embedded in the stroma, arrow indicates a single 20 μm particle, in panel B confocal micrograph of picrosirius red stained, 30-μm-thick tissue section, arrow indicates same particle as in panel A, image is 20 μm deep in the z-stack, and in panel C confocal micrograph from 10 μm deep in the z-stack.

A transmission micrograph indicating a single particle is shown in FIG. 34 Panel A. Images in FIG. 34 Panels B and C show individual frames from a z-stack measured around the same stainless-steel particle in FIG. 34 Panel A.

While embedding was shallow, it is interesting to note that penetration into the epithelium did not leave a visible "track." To the extent observable with optical microscopy, no evidence of tissue damage was seen. When tissue was examined using confocal microscopy, there also was no evidence of noticeable tracks left in tissue. The results show the particle firmly embedded in collagen fibrils in FIG. 34 panel C. There is a local compression of the fibers surrounding the particles and a bright fluorescent signal. The integrity of the epithelium can be seen clearly in FIG. 34 panel B. This frame shows that there are no clear tracks left by the particle in the epithelial layer. This suggests that the ballistic treatment is non-destructive—as particles travel through tissue in the embedding process, the material has the ability to reseal behind the particle. This elastic response is akin to the formation and subsequent collapse of smooth cavities that form when ballistics penetrate homogeneous materials, like ballistic gelatin. This result is promising and indicates that while there may be local compression of tissue, there are no visible channels left behind penetrating particles.

Example 25: Microparticles Penetration in the Cornea Appears to be Density Dependent Observation of the probability density of microparticles shot to the porcine cornea samples prepared according to Example 10.

Penetration of lowest density microparticles (polyethylene; 1.1 g/cc) was superficial in corneal tissue. Accordingly, when target and particle density are equivalent, significant penetration is prevented. A similar result was observed when custom, therapeutic microparticles are delivered to corneal tissue. Despite low penetration depth of projectiles, there was still efficient distribution of therapeutic compound to the cornea. While the epithelium shows most of the staining, there was some staining of the underlying stroma as well. Perhaps having small particles that embed in the apical surface of the cornea that slowly dissolve is a preferable mode of drug-delivery compared to topical administration of drug solution.

In contrast by using tungsten microparticles (density is 19.2 g/cc), there was effective embedment of microparticles in the corneal stroma.

To the best of Applicant's knowledge, this is the first example of ballistic microparticles traversing the epithelium and accessing underlying stromal tissue. However, this result highlights how effective of a momentum sink the corneal stroma is—only with exceptional high density can embedment in the tough fibers of the stroma be achieved. Even with the epithelium completely removed, stainless-steel microparticles still only embed in the stroma to a superficial distance. The stroma does appear to be an effective stopping medium for ballistic microparticles. While the corneal epithelium appears to be able to slow particles down slightly (especially smaller particles), it is likely, considering these experiments, that the primary barrier to microparticle uptake is the stromal interface.

These observations support the conclusion that microparticles with a density lower than 7.8 g/cc embed in the epithelium of a cornea and in particular that density between 2.5 g/cc and 7.8 g/cc will embed in the basal layer of the epithelium. Microparticle with a density higher than 7.8 g/cc and in particular from 7.8 g/cc to 20 g/cc instead are expected to be able to be delivered in corneal tissue layer beyond the epithelium and in particular to Bowman's layer of an eye if present.

The results summarized in Examples 8 to 20 also support the conclusion that the cornea is protected from high velocity microparticles in a different if not better way than gelatin like tissue, and in skin tissue as a stopping medium (Kendal et. al, 2000[147]; Kendal[148]).

Reference is made in this connection the Examples 26 to 33 below which show different models for ballistic delivery in gelatin and skin tissues.

Toughness demonstrated by the cornea is even more surprising, considering the cornea has a higher water constant than skin tissue. The cornea has a reported water content of 76% by mass (Hedbys et al.; 1966[149]), much higher than the exposed surface of the skin's stratum corneum, which contains 40% water at the surface and increases to 70% water by the stratum granulosum (Warner et al. 1988[150]).

Example 26: Preparation of Ballistic Gelatin Samples

Ballistic gelatin is a material with consistent mechanical properties used in ballistics research. [151, 152] Gels were prepared using the standard protocol (Jusilla et al., 2004 [153]) at three concentrations of 2.5, 5.0 and 10.0% w/w. Gelatin samples were allowed to solidify for 24 hours at room temperature and then for 24 hours at 4° C.

Specification of ballistic gelatin: the term bloom with regard to gelatin may be used in two different contexts.

One refers to the process of softening the gelatin in liquid prior to melting it (e.g., "bloom the gelatin in cold water for 5-10 minutes"). The other use of Bloom refers to the firmness of gelatin. When the rigidity of the gel is measured by the method established by Oscar T. Bloom to the resulting value is called the Bloom Strength. A higher value indicates a stiffer product. Ballistic gels are made using "250 Bloom gelatin", (gelatin that has Bloom Strength of 250).

A procedure for preparing 10% ballistic gelatin is as the following. Using 250 Bloom gelatin (purchased in powder form from a reliable source and stored so that it does not deteriorate), 2 g of gelatin powder was mixed with 4 g of filtered water. Then 14 g of hot water (at 60° C.) was added to the mix. The entire mixture was then stirred at regular intervals of 3 min for 15 s each until the powder was fully dissolved. The mixture was then poured into plastic molds and placed in a refrigerator for 2 h at 5 C. When a sample is removed from the refrigerator, care is taken so that water does not condense on the gelatin and so that water does not evaporate from the gelatin. The gelatin should be used within 20 minutes after removing it from the refrigerator so that its properties do not degrade.

Example 27: Microparticles Penetration 2.5% to 10.0% w/w Ballistic Gelatin

To show the effect of substrate toughness on particle penetration, microparticles were delivered to gels made with different concentrations. 2.5% and 10% w/w gels were made so that penetration models in Veysset et al. [154] could be used to interpret the data.

Three concentrations of ballistic gelatin were examined (2.5, 5 and 10% w/w) for comparison with prior literature.

The image processing pipeline used processes individual frames, isolates objects with an intensity below a certain threshold, and generates the statistics reported. Each scatterplot shows the result of 300 impacts into the homogeneous material. Data from impacts in 5% w/w gelatin are described in FIG. 35. Statistics were generated based on data from impacts in 5% w/w gelatin, and data in FIG. 36 qualitatively describes penetration in 2.5% w/w and 10.0% w/w ballistic gelatin.

The image processing pipeline measured microparticles that are within the expected size distribution. Some microparticles are larger than the expected range, which is expected since the vendor reports 10% of particles have sizes larger than the reported range.

Figure 37:
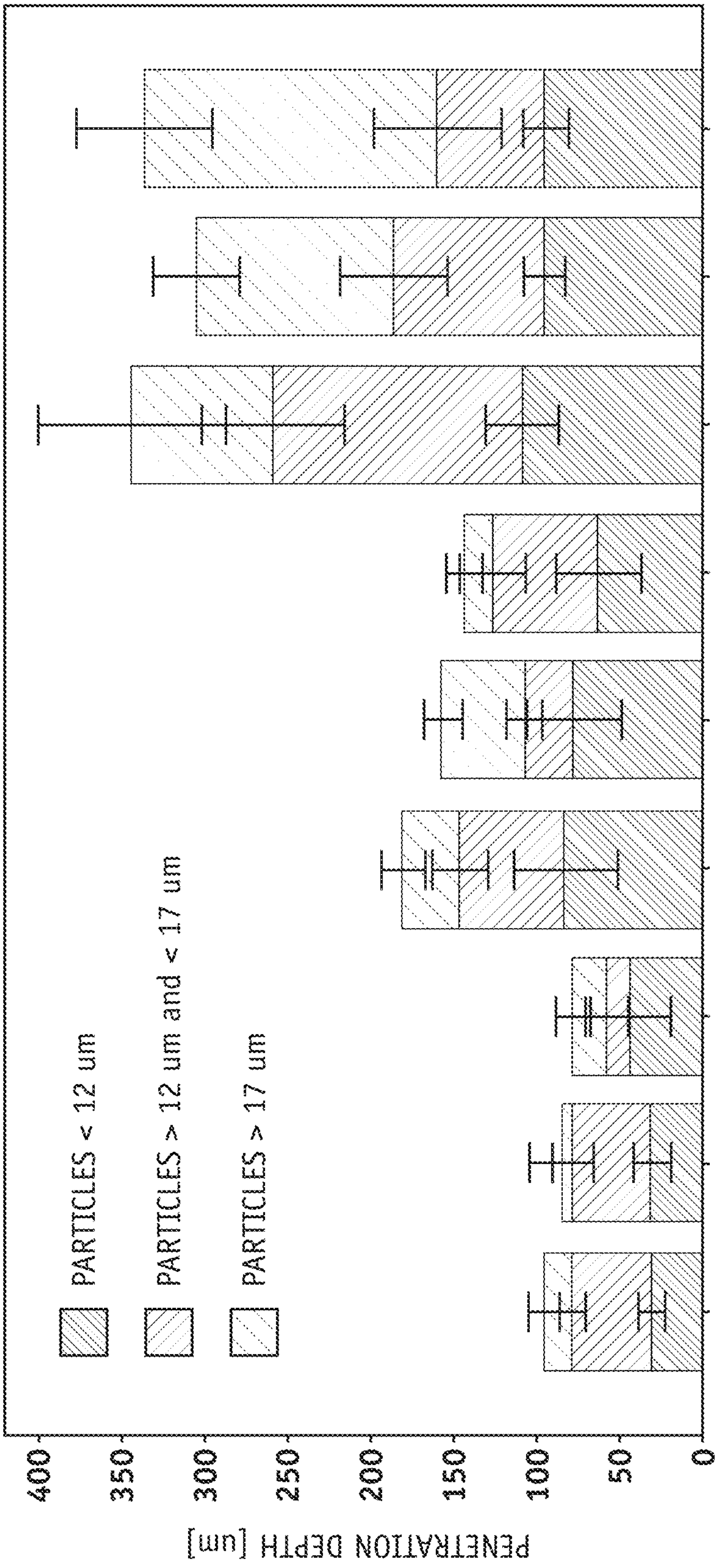
FIG. 37 shows average penetration depth for each of three replicate doses of polydisperse particles delivered into gelatin. The overall bar is the average over relatively large particle diameters; the intermediate bar is the average over particles of intermediate diameter, and the lowest bar is the average over relatively small particles. Error bars show 95% confidence intervals of the penetration depth distribution. SL1=soda-lime glass shot #1, BT2=barium-titanate glass shot #2, and SS3=stainless steel shot #3.

To show the consistency of the ballistic device, mean penetration depths are reported for three different size groupings for soda-lime glass, barium-titanate glass, and stainless steel microparticles. The results of this analysis are shown in FIG. 37.

The mean and standard deviation of penetration computed for each of three replicate experiments shows good reproducibility (FIG. 37): with the exception of the middle-size range for stainless steel, the mean penetration depth for each of three particle diameter groupings are indistinguishable (no statistically significant difference from experiment-to-experiment).

This indicates that particle penetration data is comparable each time the ballistic device is actuated.

Figure 35:
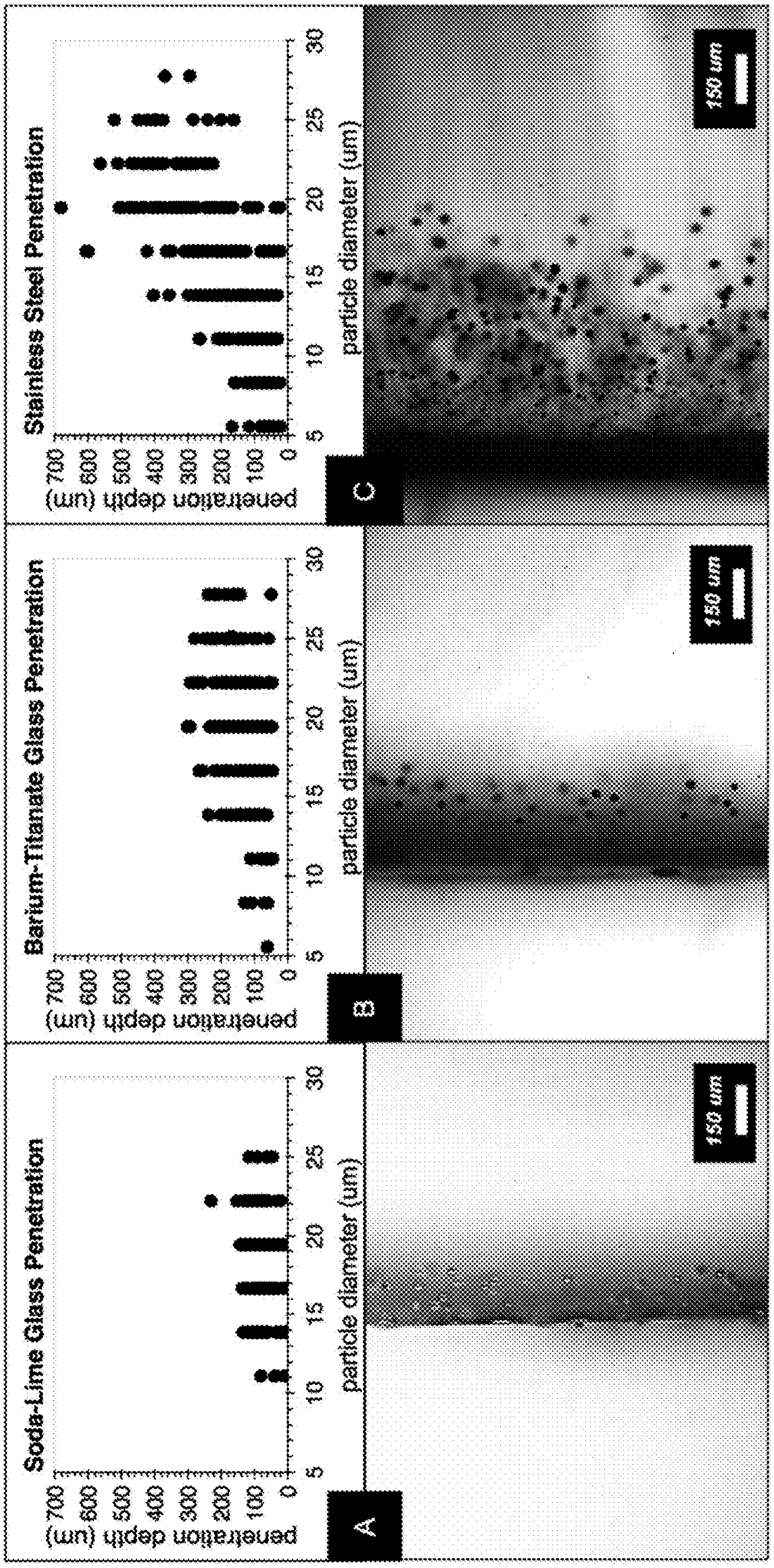
FIG. 35 shows demonstration of particle embedding energies in 5% w/w gelatin. Penetration depth of particles from three shots to gelatin and representative images for soda-lime glass particles in panel A, barium-titanate particles in panel B, and stainless-steel particles in panel C.
Figure 36:
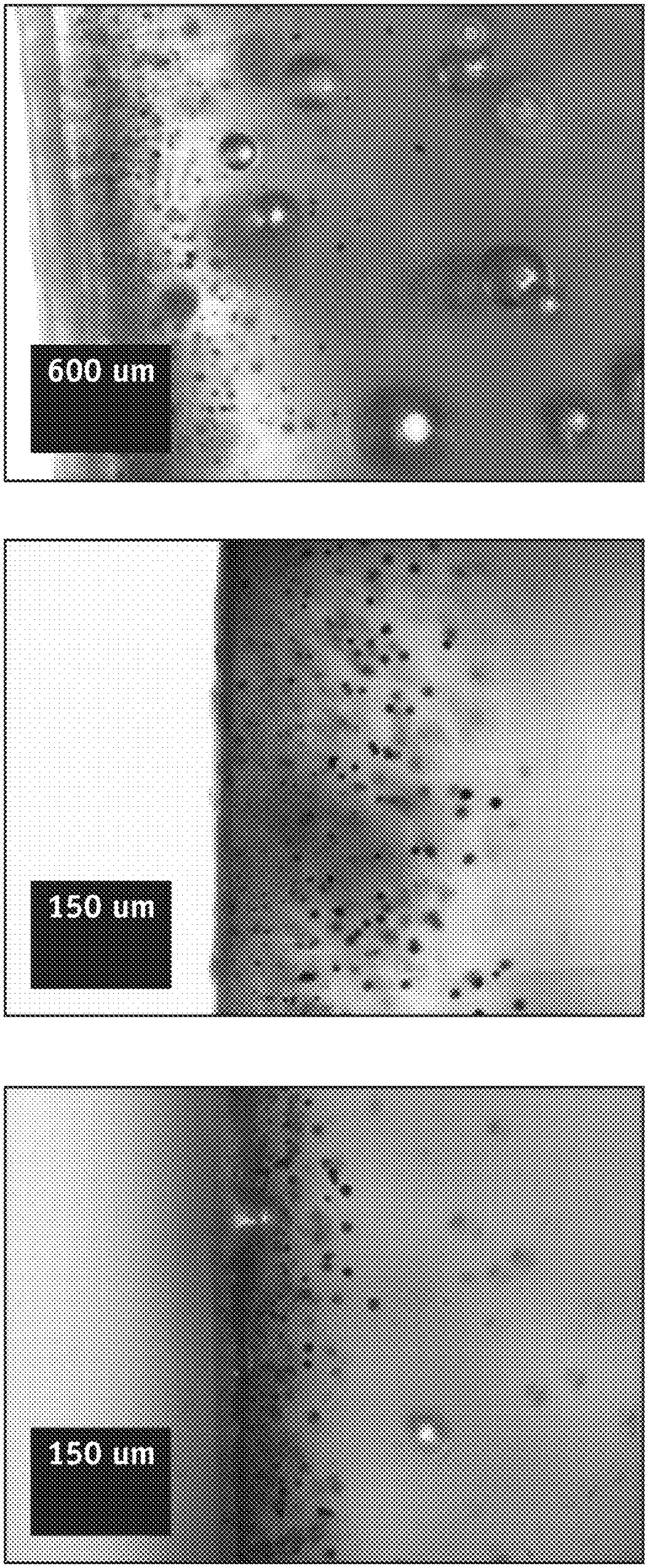
FIG. 36 shows pictures illustrating representative penetration depth of stainless-steel microspheres in 2.5% w/w gelatin (top panel), 5.0% w/w gelatin (middle panel), and 10.0% w/w gelatin (bottom panel).

The statistics generated from data of FIG. 35 and FIG. 36 are presented in FIGS. 38-41. From the image of 2.5% w/w gelatin, it can be seen that some particles penetrate the gel by over a millimeter. The 5% w/w gelatin, penetrates by up to 600 μm. Last, the 10% gelatin penetrates by only 150 to 200 μm. As can be seen, penetration of the steel microparticles was progressively attenuated as the concentration of gelatin was increased.

Figure 38:
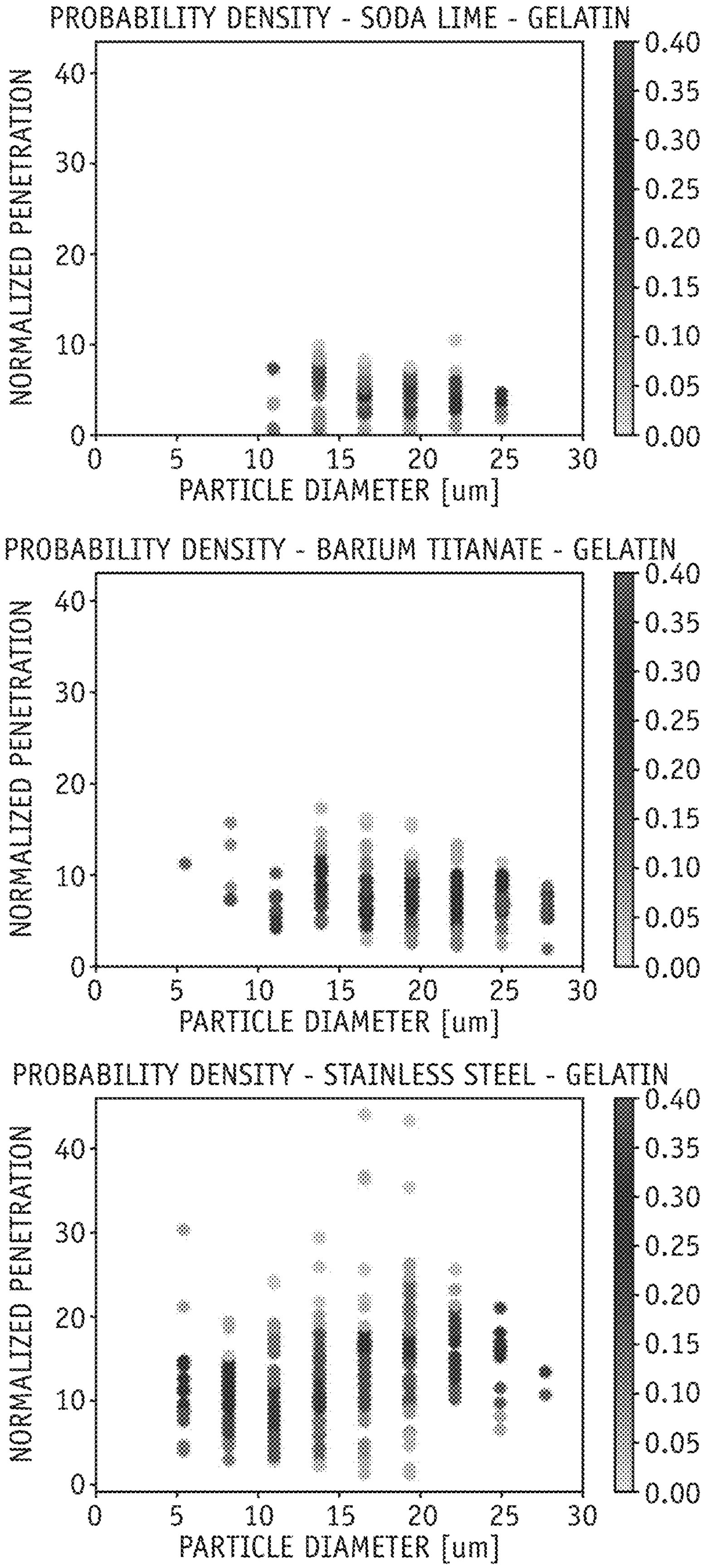
FIG. 38 shows charts illustrating probability densities of soda lime, barium titanate, and stainless-steel impacts in 5% w/w ballistic gelatin shown with particle penetration normalized by particle diameter. Probability density for the colormap was calculated by binning data into discreet groups along the x and y axes.
Figure 39:
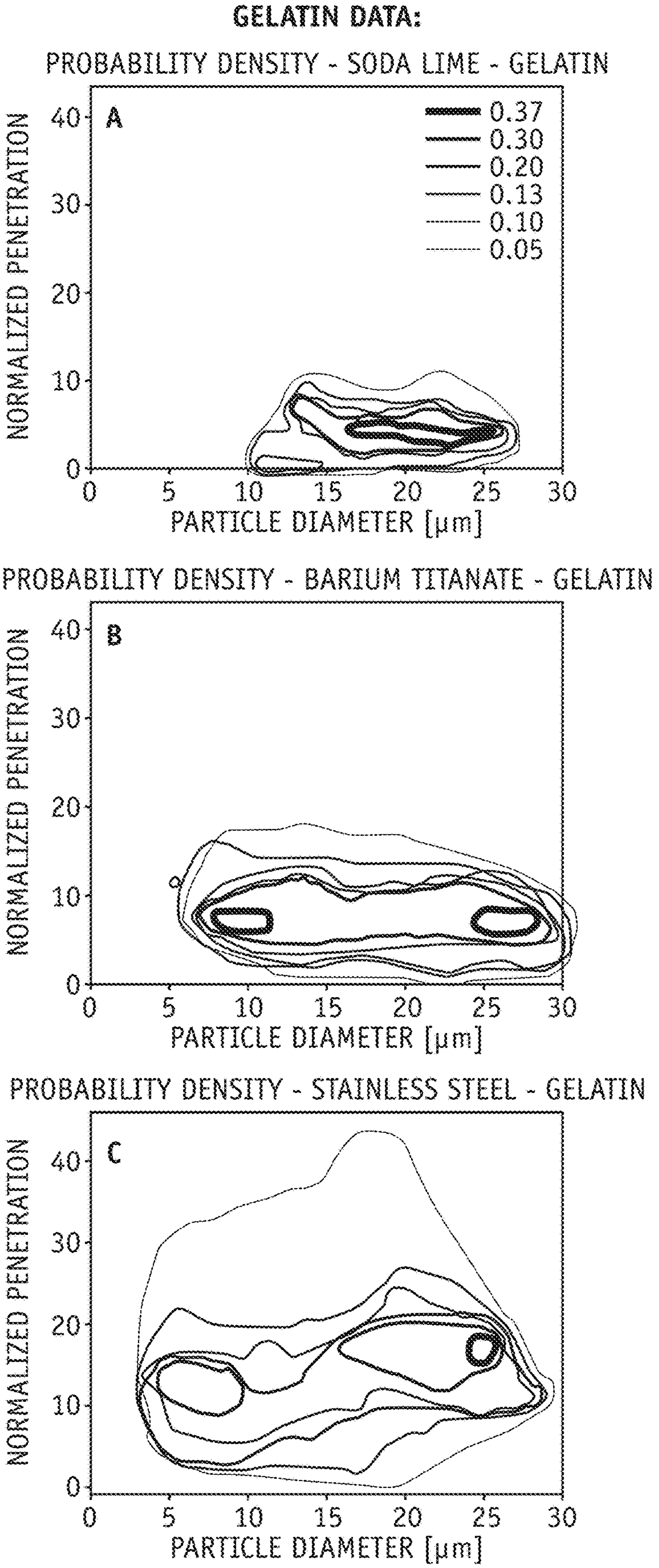
FIG. 39 shows the same data as in FIG. 38 in a contour format.
Figure 40:
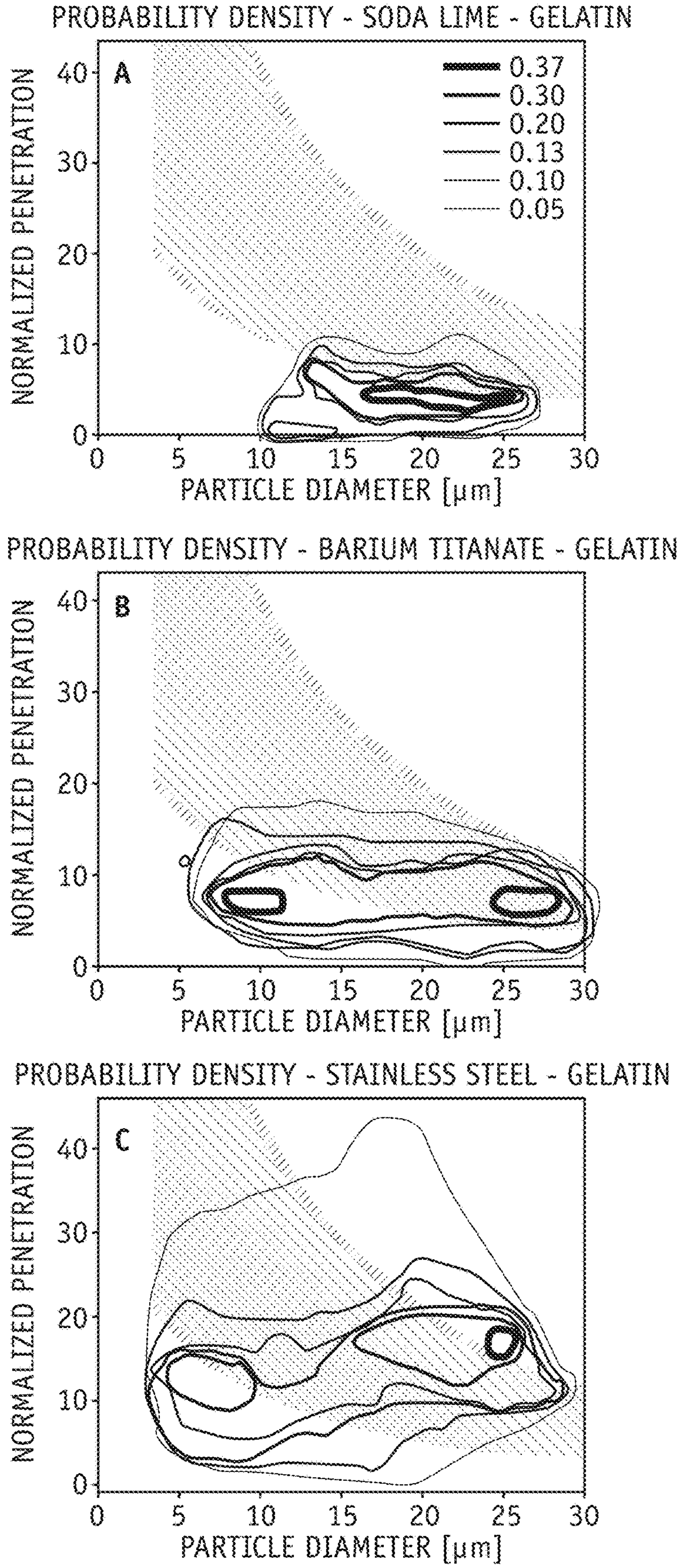
FIG. 40 shows the same data as in FIG. 38 in a contour format with average thickness of the epithelial layer bounded by a standard deviation in the shadowed area.

Using the results of Veys set et al., who show penetration of microparticles into ballistic gelatin conforms to the Poncelet Model (loss of kinetic energy predominantly due to work of fracture) and provide resistance values for the three concentrations examined in this work, we can infer the distribution of impact velocities (FIGS. 38-40). The results indicate the velocity of most microparticles is in the range 150 to 300 m/s, with some particles having impact velocity inferred to be as high as 500 m/s.

Penetration depth $z_\infty$ in the uniform, isotropic gelatin is known to scale with the Elastic Froude Number $$\frac{z_\infty}{2r_p} \sim \left[\frac{\Delta\rho v^2}{E}\right]^\gamma,$$

where Δρ indicates density difference relative to the target material, v is the impact velocity, E is the shear storage modulus of the substrate, $r_p$ is the particle radius, and γ is an exponent empirically found to be close to one half for projectiles orders of magnitude larger than what is used here (Swain et al.; 2014 [155]).

In Swain et al., this dimensionless group included a difference between the impact velocity and a threshold velocity for embedment, which was proportional to the contact pressure. The estimated impact velocity was used alone in this analysis, due to insufficient knowledge of particle velocity. Direct measurement of particle velocity was not performed, due to the ballistic embedment process being enclosed in a sealed vacuum chamber that made it difficult to film embedment with high-speed imaging. Penetration in this dataset is observed to scale with the Elastic Froude Number to a power of 0.8±0.2 (see Example 5 Table 7 below).

Example 28: Elastic Froude Number Based Scaling Relationship for Penetration in Gel In previous ballistics research, penetration of millimeter-sized projectiles has been shown to scale with the Elastic Froude Number to some power. One can write the following generalized expression for penetration in homogeneous materials:

$$\frac{z_\infty}{D_p} \sim \left[\frac{\Delta\rho u_o^2}{G}\right]^\gamma \tag{6}$$

where $z_\infty$ is the final penetration depth, $D_p$ is the diameter of the particle, and γ is a power which is usually found to be around ½ in gel materials.

In Akers and Belmonte[156], spheres penetrating a viscoelastic, micellar fluid were shown to display maximum penetration depth scaling with $$\frac{z_\infty}{2r_p} \sim \left[\frac{\Delta\rho U^2}{E}\right]^{1/3}.$$

In Swain et al, the penetration of steel spheres in ballistic gelatin was shown to scale with $$\frac{z_\infty}{2r_p} \sim \left[\frac{\Delta\rho U^2}{E}\right]^{1/2}.$$

In Table 6 as described above, the ratio of density differences between target and substrate is compared to the ratio of penetration depths. This was done for small particles (<12 μm), medium sized particles (12 μm≤Particles≤17 μm), and large particles (17 μm<Particles). The value of γ in $$\Delta\rho_1^\gamma / \Delta\rho_2^\gamma$$

that fit the data best was 0.79±0.19.

TABLE 7

Comparing Ratio of Mean Penetration Depths to Ratio of Densities with Exponent γ

| | Particles < 12 um | | | 12 um ≤ Particles ≤ 17 um | | | Particles > 17 um | | |
|---|---|---|---|---|---|---|---|---|---|
| | $\Delta\rho_{BT}/\Delta\rho_{SL}$ | $\Delta\rho_{SS}/\Delta\rho_{BT}$ | $\Delta\rho_{SS}/\Delta\rho_{SL}$ | $\Delta\rho_{BT}/\Delta\rho_{SL}$ | $\Delta\rho_{SS}/\Delta\rho_{BT}$ | $\Delta\rho_{SS}/\Delta\rho_{SL}$ | $\Delta\rho_{BT}/\Delta\rho_{SL}$ | $\Delta\rho_{SS}/\Delta\rho_{BT}$ | $\Delta\rho_{SS}/\Delta\rho_{SL}$ |
| experimental - $z_{\infty 1}/z_{\infty 2}$ | 2.10 | 1.34 | 2.81 | 1.77 | 1.59 | 2.81 | 1.85 | 2.05 | 3.81 |
| theoretical - $\Delta\rho_1^\gamma/\Delta\rho_2^\gamma$ | 2.10 | 1.33 | 2.79 | 1.77 | 1.59 | 2.79 | 1.86 | 2.05 | 3.84 |
| Abs(experimental-theoretical) | 0.00 | 0.00 | 0.01 | 0.00 | 0.00 | 0.02 | 0.01 | 0.00 | 0.02 |
| $\gamma_{min}$ | 0.96 | 0.39 | 0.68 | 0.74 | 0.99 | 0.68 | 0.8 | 0.97 | 0.89 |
| | | | | | | | | $\bar{\gamma}_{min}$ | 0.79 |
| | | | | | | | | Standard deviation | 0.19 |

Example 29: Poncelét Model of Veysset[154]

For a microparticle penetrating tissue, there are three main forces experienced: 1) friction, 2) inertial resistance from acceleration of tissue around a particle, and 3) resistance of the material to cracking/deformation. The Poncelét model assumes that friction is negligible compared to inertial and resistance terms. The resulting kinematic equation is shown below:

$$m_p \frac{dv}{dt} = B_2 v^2 + B_o \tag{7}$$

$$B_1 = \frac{1}{2} C_D \rho_s A \text{ and } B_2 = AR$$

where A is the area of a particle, $\rho_s$ is the target density, and R is a gel resistance term that is typically correlated to yield stress. Integrating this equation twice, using the impact speed and the relation between distance and velocity, yields the following expression:

$$z(t) = \frac{m_p}{B_1}\left[\ln\cos\left(\frac{\sqrt{B_1B_2}}{m_p}(t_f - t)\right) - \ln\cos\left(\frac{\sqrt{B_1B_2}}{m_p}t_f\right)\right] \quad (8)$$

Where $t_f$ is the time that it takes for the particle to come to rest, given by:

$$t_f = \frac{m_p}{\sqrt{B_1B_2}}\tan^{-1}\left(v_o\sqrt{\frac{B_1}{B_2}}\right) \quad (9)$$

Finally, the max penetration depth is given by the following expression:

$$z_{max} = \frac{2}{3}\frac{\rho_pD_p}{\rho_sC_D}\ln\left(\frac{\rho_sC_Dv_o^2}{2R} + 1\right) \quad (10)$$

where $z_{max}$ is the maximum penetration depth, $\rho_p$ is the density of the particle, R is the resistance of the material to penetration, and $C_D$ is a drag coefficient. This maximum penetration is not always the final resting depth of a particle. In elastic media like gelatin, research has shown that microparticles can spring backward after forming long cavities. This elastic recoil results in shallower penetration than is ultimately measured in gelatin for a given impact velocity, but this equation is still helpful in estimating a lower bound for impact velocity.

Using our normalized penetration depth data, the penetration observed in ballistic gelatin can be compared with the Poncelet Model to estimate impact velocity. To do this, the mean particle penetration was calculated as well as the maximum penetration depth. By plotting the data in FIGS. 38-41 on curves showing the expected penetration in 5% w/w gelatin (as predicted by the model), a range of impact velocities can be inferred using data from soda lime glass and barium titanate glass penetration. In both figures, the mean penetration of the sample shows up with normalized penetration depth indicating a velocity of a little over 200 m/s. Standard deviation of the penetration depth data set indicates that most particles have velocities from 150 to 300 m/s.

Figure 41:
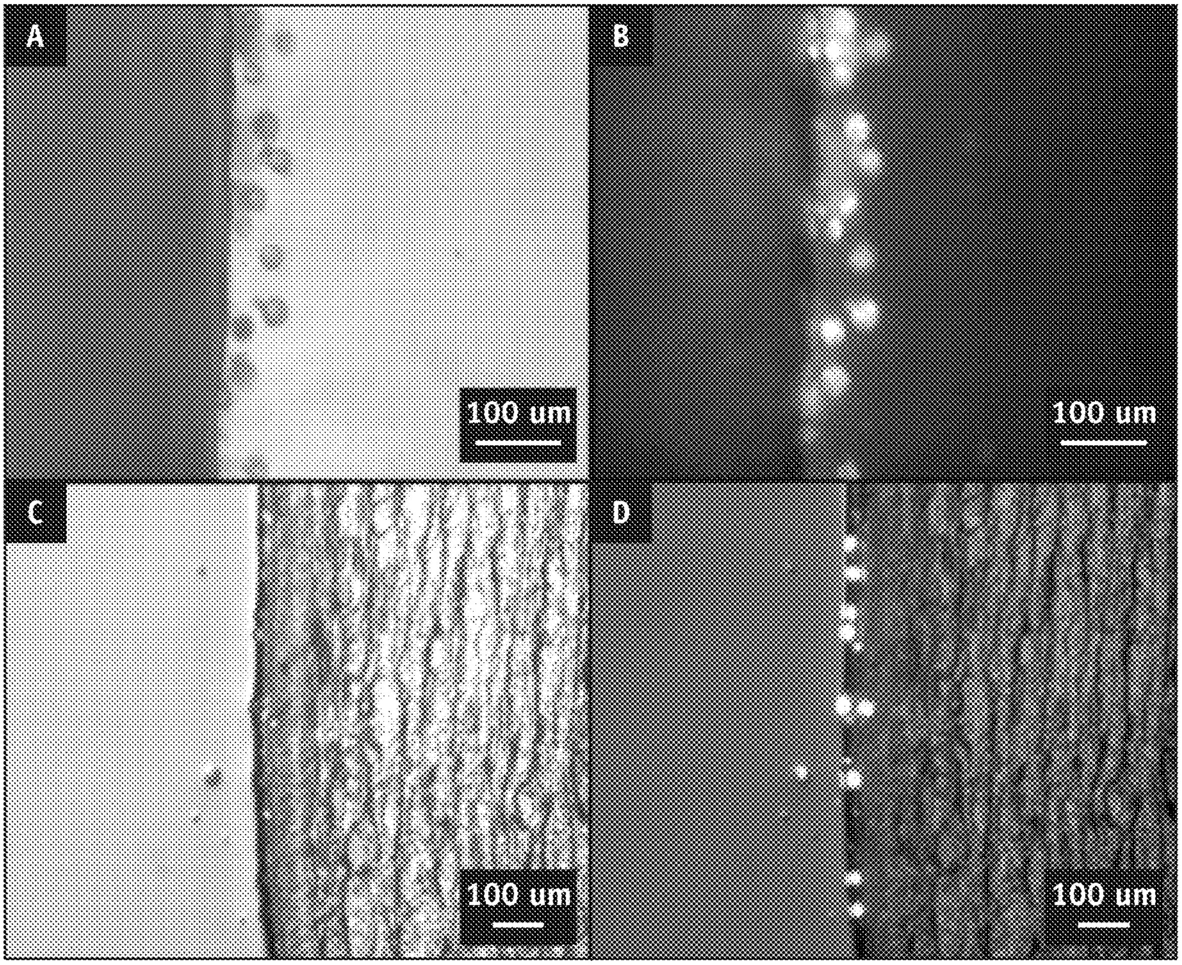
FIG. 41 shows pictures illustrating penetration of 1.1 g/cc polyethylene spheres in gelatin and corneal tissue, wherein in panel A bright-field microscopy of 5% w/w gelatin, in panel B fluorescent micrograph of gelatin, in panel C PE spheres in corneal tissue (brightfield), and in panel D PE spheres in corneal tissue.

The maximum penetration depth in the figures corresponds to an impact velocity around 500 m/s. Data from stainless steel impacts in 5% and 10% w/w ballistic gelatin shown in FIG. 41 indicates slightly different penetration depths. The data from 5% w/w gelatin compared to the Poncelet Model indicates an impact velocity of around 200 m/s, but the data from impacts in 10% w/w gelatin indicates an impact velocity for the mean penetration depth of 300 m/s. The maximum penetration for both datasets indicate a maximum impact velocity of around 500 m/s. The reason that the 10% w/w gelatin compares differently to the Poncelet Model may have to do with using a lower number of penetration statistics to calculate mean values. The actual data used to calculate these values is shown in FIG. 41 and there are only 75 points in the dataset as opposed to 300.

Based on this analysis, a range of microparticle velocities is expected to be between 150 and 500 m/s, with most microparticles having a velocity of 150 to 300 m/s. This range is not only broad, it is likely an underestimation due to the elastic recoil in gel. The fact that the three different sets of penetration data for soda-lime, barium-titanate, and stainless-steel microparticles show similar predicted impact velocities suggests that The Poncelet Model fits the data well. While the prediction of velocity at least indicates that the microparticles tested as described herein had impact velocities on the order of hundreds of meters per second.

Example 30: Probability Density of Microparticle Ballistic Delivery in Gelatin

Figure 42:
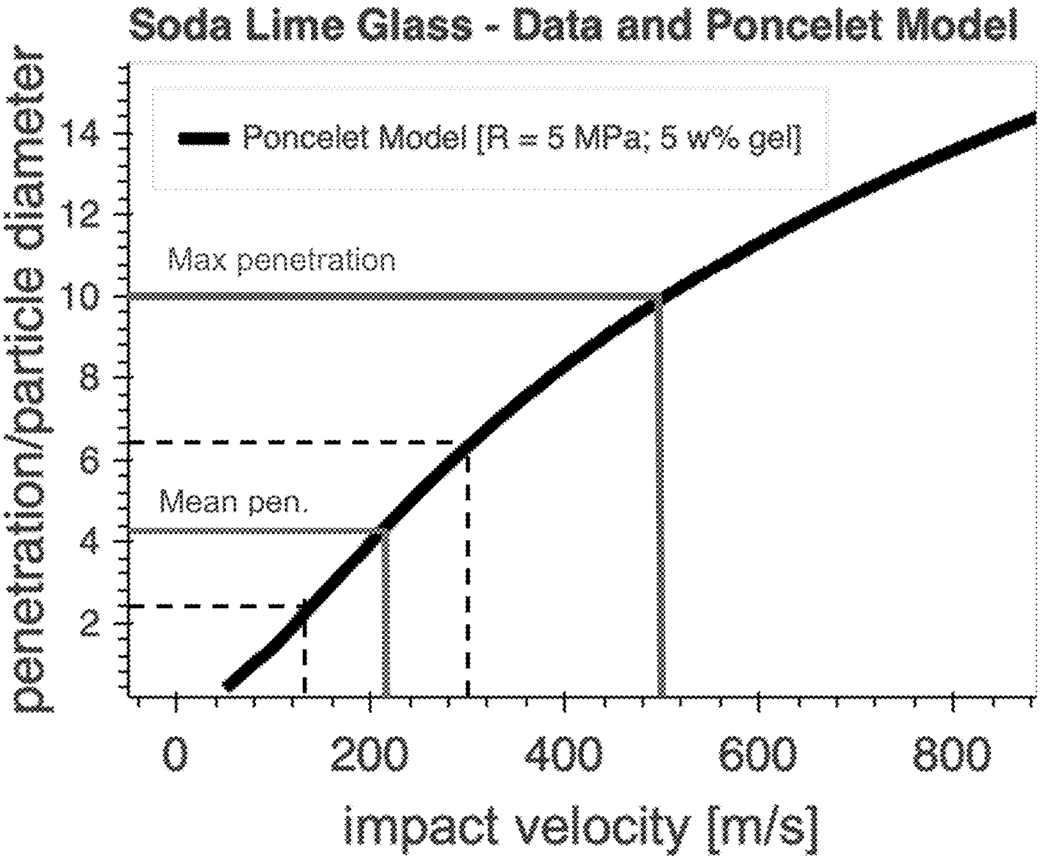
FIG. 42 shows a chart illustrating the Poncelet model for maximum penetration of spheres with density of 2.5 g/cc. Blue intercept line shows average measured penetration depth of soda-lime spheres embedded in 5% w/w gelatin. Dotted lines show one standard deviation above and below the mean. Dash-dot intercept line shows the penetration depth and the corresponding impact velocity of a microparticle embedding at the maximum recorded normalized penetration.
Figure 43:
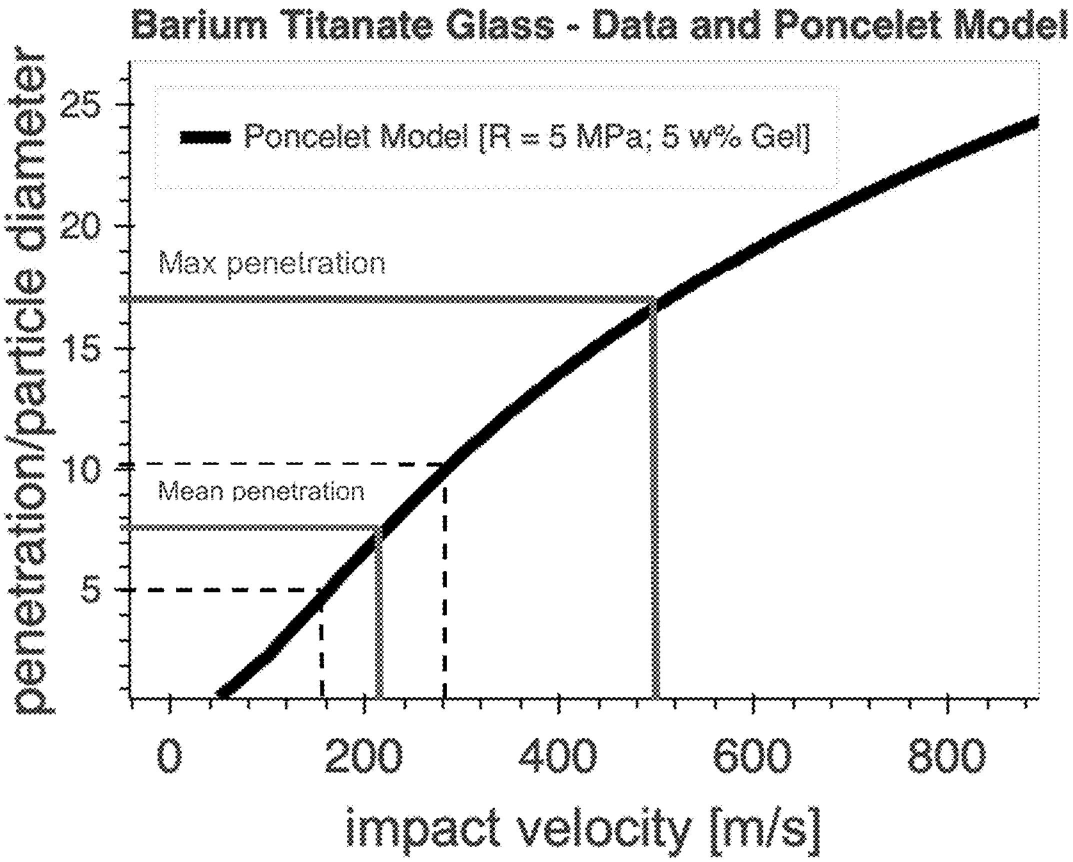
FIG. 43 shows a chart illustrating the Poncelet model for maximum penetration of spheres with density of 4.2 g/cc. Solid intercept line shows average measured penetration depth of barium titanate spheres embedded in 5% w/w gelatin. Dotted lines show one standard deviation above and below the mean. Dash-dot intercept line shows the penetration depth and the corresponding impact velocity of a microparticle embedding at the maximum recorded normalized penetration.
Figure 44:
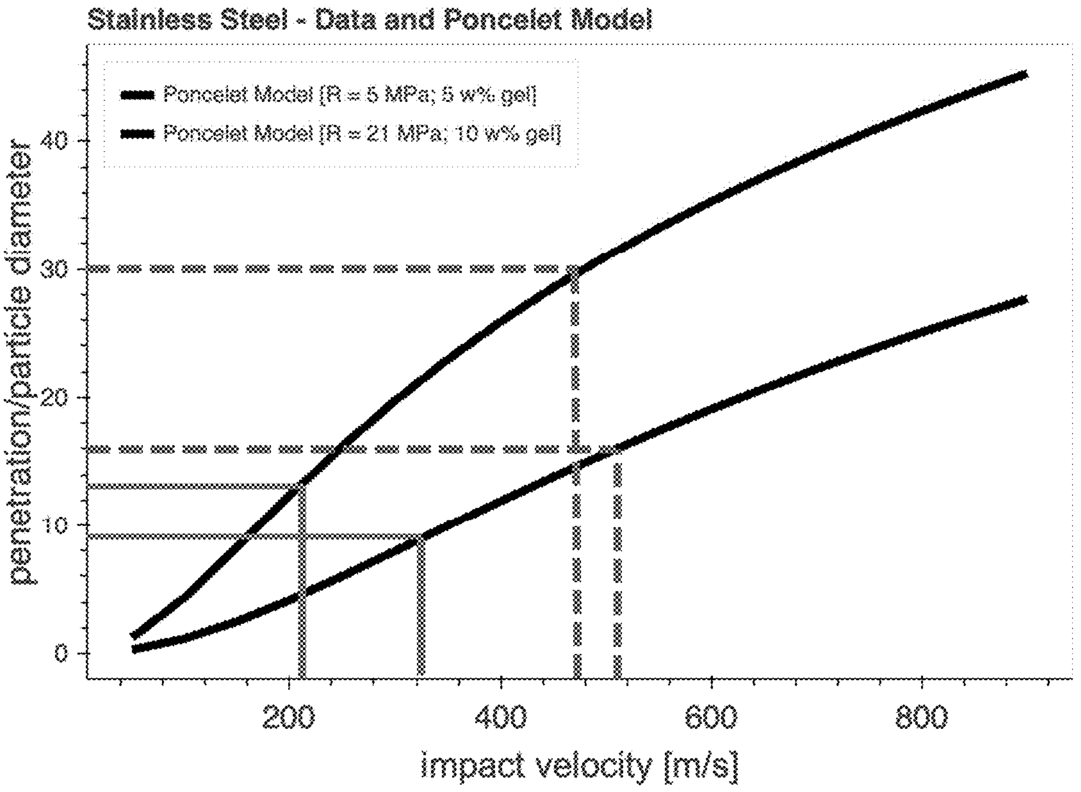
FIG. 44 shows a chart illustrating the Poncelet model for maximum penetration of spheres with density of 7.8 g/cc.

The results in gelatin lay the foundation for interpreting the particle penetration observed in the cornea, which is dramatically different. Both small and large particles embed to similar depths in the corneal epithelium. Like the images shown in FIG. 41, most particles can be found between 30 and 60 μm deep. The probability density for the normalized penetration depth in ballistic gelatin is insensitive to particle size, as expected (FIGS. 42-44). In gelatin, increasing relative density of the particles relative to the sample conforms with the expected proportional increase in normalized penetration. In contrast, normalized penetration into the cornea is not independent of particle size and does not simply increase proportionally with the particles' relative density (FIG. 20 Panels A-C).

Example 31: Inference of Impact Velocities from Penetration Depth Data in Ballistic Gelatin The resistance values as referred to in Veysset allows inference of impact velocities from penetration depth data in ballistic gelatin. In FIG. 45, predicted penetration depths are shown for two different particle compositions, using the Poncelét Model. The curves show expected penetration depth in three concentrations of gelatin, 2.5% w/w, 5.0% w/w, and 10.0% w/w. The data is produced by dividing Equation (4) by particle diameter and graphing the results. From experimental data in Veysset et al., resistances of 1.5 MPa, 6.0 MPa, and 21 MPa are used in the penetration equation for the previously mentioned respective concentrations of gelatin, 2.5% w/w, 5.0% w/w, and 10.0% w/w.

The results of this analysis reinforce the importance of projectile density. In FIG. 45, the expected penetration of a polymer particle with density of 1.1 g/cc and a stainless-steel particle are shown. At low density, particles require velocities of several hundred meters per second in order to achieve just a few diameters of penetration. In fact, the model equation predicts the maximum depth reached in gel and does not consider elastic rebounding of particles, which can further attenuate penetration depth. As gelatin concentration increases, it becomes harder and harder for the spheres to embed. When the particle is made of stainless steel, the minimum velocity needed to achieve significant penetration is much lower, and the penetration that is possible for the projectile is considerably higher. These figures show that by changing particle density, a broad range of penetration in gel substrates can be achieved.

Example 32: Penetration of Low-Density Microparticles and Medicinal Microparticles in Gelatin and Cornea (Comparative)

Lowest-density microspheres (1.1 g/cc poly(ethylene)) failed to demonstrate any significant embedding depth in gelatin or in corneal tissue. In FIG. 41 panel A and FIG. 41 panel B, it can be seen that these projectiles only embed in 5% w/w gelatin by one to three diameters. The embedding depth is much shallower than all other materials tested.

Not surprisingly, when corneal tissue was tested with these particle payloads, penetration was superficial. FIG. 46 panel C and FIG. 46 panel D show fluorescent microparticles embedded just at the surface of tissue.

This is in line with the description of FIG. 18 panel A and FIG. 18 panel B show PEG microparticles with 1% w/w Eosin Y embedded in the anterior surface of the cornea. These images were taken 10 minutes after ballistic delivery, and it can be seen that microparticles are dissolving into the surrounding tissue.

Following the tissue fixation protocol two days later, FIG. 18 panel C and FIG. 18 panel D show the staining of the epithelium with Eosin Y. Microparticles have fully dissolved, and there is a strong staining of the corneal epithelium with the fluorescent Eosin dye. There is also considerable staining of the stroma below.

Example 33: Model for Shallow Penetration in Tough Materials

For shallow penetration in tough materials (e.g. microparticles embedding in skin), the cavity strength model is used. In this model, the impact pressure is assumed to be equal to the cavity strength during impact, which is about 3 times the yield strength [157]. Therefor, the cavity strength model is written:

$$dE=Fdx \rightarrow dE=3Y_M A_p dx \tag{11}$$

where E is the energy of the particle, F is the force from impact, $Y_M$ is the material yield strength, and $A_p$ is the area of the projectile. This expression can be integrated and arranged into a predictive equation for penetration depth, which is proportional to $$\rho r u_o^2,$$

a value that is used to plot shallow penetration of ballistics (the kinetic energy per unit cross-section):

$$z_\infty = \frac{\frac{1}{2} m_p u_o^2}{3 Y_M A_p} = \frac{\rho_p R_p u_o^2}{6 Y_M} \tag{12}$$

where $z_\infty$ is penetration depth, $u_o$ is the impact velocity, $m_p$ is projectile mass, $\rho_p$ is its density, and $R_p$ is its radius. In Kendall-Wright Smith et al. [147], it is shown that penetration in human cadaver skin fits well to a similar model, the fracture toughness model, for different particles sizes, densities, and impact velocities [147]. Skin is a useful tissue to compare the cornea to, because it is a heterogeneous material composed of tissue layers with different mechanical properties, similar to the corneal epithelium and the underlying stroma.

Example 34: Preparation of Microparticles Using PLA as Carrier Material the preparation of poly(lactic acid) microparticles with varying amounts of L and D stereoisomer content. It is thought that by changing the ratio of these monomers, then the rate of particle hydrolysis can be controlled. The particles were prepared using an emulsion-based preparation. Polymer was dissolved in dimethyl sulfoxide and this solution, which is immiscible in water, was mixed in a solution of 1% PVA. Once DMSO evaporates from the immiscible phase, solid, PLA microparticles are left behind. The process of preparing microparticles this way is described in . . . . In addition to using PLA, $CuSO_4$ was dissolved in methanol and quickly mixed with the DMSO solution. $CuSO_4$ was added to the PVA solution as well to try and load the microparticles with $CuSO_4$. The goal is to have microparticles that leech copper ions, which can act as a cofactor for lysyl oxidase, an enzyme that cross-links collagen fibrils. The purpose of this work was to try and enable light-free cross-linking of the cornea facilitated by therapeutic, ballistic microparticles.

Example 35: Biolistic Microparticles to Deliver Applied Ophthalmic Medicines

The results reported in the previous example support the use of high velocity microparticle bombardment as a means of embedding drugs in the cornea's epithelial barrier.

Drug delivery to the cornea is limited by several mechanisms. Natural lacrimation and blinking remove hydrophilic drugs, and the corneal epithelium (a lipophilic tissue layer) has tight junctions between stratified epithelial cells that prevent many drugs from diffusing into the tissue (Ableson et al., 2009) [158]. Enhancing drug uptake into the cornea has the potential to improve treatments for diseases of the eye. For example, Novosorb, a cationic emulsion which binds to the mucin layer on the eye's anterior surface (made by PolyNovo), has had success in delivering latanoprost, a prostaglandin analog which lowers intraocular pressure for patients with glaucoma (Daull et al., 2017) [159].

An exemplary use of the particles and method of the disclosure that illustrates the range of particle size and corresponding number of particles to deliver a relevant dose of drug is delivery of cross-linking therapeutic to treat corneal ectasias.

Corneal cross-linking surgery (CXL), a procedure in which photosensitizing cross-linking agents are used to reinforce the mechanical properties of the cornea (Gordon-Shaag et al., 2015) [160], requires delivery of cross-linking agents (e.g. riboflavin and Eosin Y) to the stroma. Slow transport through the epithelium is usually overcome by removing the epithelium to access the stromal layer. Techniques to improve the flux of cross-linker are under development, like the use of iontophoresis and proteins that disrupt epithelial tight junctions, but in the US epithelium-off CXL remains the standard of care for keratoconus, despite a reduction in post-operative complications (Cifariello et al., 2018 [161]; Jia et al., 2018 [162], Bidwell et al., 2014 [163]). If particles with a large volume fraction of drug were used, a sufficient dose might be provided biolistically to deliver 6,000 particles of 30 μm diameter distributed across 1 $cm^2$ of corneal tissue, potentially in the blink of an eye (Huynh 2011 [164]).

Example 36: Ballistic Devices

In the preceding Examples A BioRad PDS-1000 gene gun (catalog #: 1652257) was used. Additional device can be used to deliver the microparticles of the disclosure to be selected based on the indications herein provided concerning type of particles related dimensions and density, target regions, as will be understood by a skilled person upon reading of the present disclosure.

For example, devices for the delivery of genetic materials to the cornea using metal microparticles such as the one described in Zhang et al. [6] can be used. They observed that particle delivery using an unmodified BioRad Helios device resulted in injury: all of the corneas that received particles from the unmodified BioRad Helios were positive for fluorescein eye drops, indicating that the epithelium was ruptured allowing fluorescein to pass from the tear film into the stroma.

To minimize corneal epithelial defects and to maintain a constant distance between the gene gun and the cornea, a device was developed that can be mounted in front of the Helios gene gun and put firmly on the orbital rim. For application to the present disclosure, calibration experiments for a specific particle size distribution, and for specific particle shape and density. The calibration can be performed following the procedure described in Example 31. The measured profile of penetration depth as a function of particle size in the specific particle size distribution provide a size-dependent velocity delivered at the constant distance provided by the improvements of Zhang et al. relative to the unmodified Helios. Another example of a delivery device that can be used comprises the particle accelerating device developed by Groisman as illustrated by the procedure in Example 10.

For conditions in which the calculated velocity required to achieve delivery to a selected target region for a selected particle size distribution, shape and density is in excess of Mach 1 (approximately 344 m/s in air at ambient pressure and temperature), a device that can be used comprises the particle delivery device laser-induced particle impact test (LIPIT) platform, in which an intense short laser pulse is used to accelerate microparticles to supersonic velocities [154]. Calibration of the device for use in the present disclosure is performed and follows the literature protocol to observe particle impact events with a high-frame-rate camera and analyze the time sequence of images to determine the velocity that is provided for a specific particle size, shape and density.

Example 37: Microparticle Biolistic Delivery

Polylactide (PLA) is an exemplary carrier for copper minerals as an exemplary biologically active cargo to address the clinical need to provide sustained release of $Cu^{2+}$ in the cornea. Sustained release of $Cu^{2+}$ in the cornea is therapeutically used to enhance lysyl oxidase activity and thereby increase enzymatic crosslinking and halt progressive thinning and bulging of the cornea in keratoconus. The use of $Cu^{2+}$ for treatment of keratoconus has been demonstrated by Dr. Bala Ambati. The clinical results dictate the copper dose and time-course of release. Copper minerals that dissolve over days to weeks. Polylactide (PLA) is a vehicle that can delay release relative to a mineral delivered without a carrier. PLA also has the desirable feature that it tends to lower the pH as it is hydrolytically cleaved to lactic acid, which will mitigate increases in pH as the basic copper minerals dissolve.

Keratoconus (KCN) is a progressive disorder that leads to corneal thinning and bulging with typical onset at approximately 15-16 years of age[165]. Mild KCN can be corrected with glasses or soft contact lenses; as the disease progresses, large, irregular refractive errors become difficult to correct and ultimately 1 in 5 patients require a corneal transplant, [166] with associated risk of intraoperative and post-operative complications (bleeding, scarring, cataract formation, etc.).[167] Over the past decade, a surgical method to slow or halt progression of KCN, Corneal Collagen Crosslinking (CXL), has reached the clinic. In the US, the approved procedure requires epithelial scraping, application of riboflavin drops and prolonged exposure to UV-A to generate singlet oxygen that leads to formation of protein crosslinks that stabilize the cornea.[168] Because the procedure involves stripping the epithelium, it is associated with severe pain, temporary visual loss, stromal haze and infections. [169-173] In addition, the CXL therapy cannot be used in patients with thin corneas due to the risk of permanent damage to the cornea.

Dr. Bala. Ambati developed the concept of treating KCN by enhancing corneal crosslinking without the need for photoactivation. Insufficient physiologic corneal crosslinking plays an important role in KCN, particularly crosslinking mediated by lysyl oxidase (LOX),[174-176] which converts lysine to allysine that spontaneously conjugates to lysine or hydroxylysine, forming lysinonorleucine (LNL) or hydroxy-LNL (HLNL) crosslinks. These adducts render collagen and elastin insoluble, providing a stable extracellular matrix. Ambati performed in vitro and in vivo preclinical experiments which showed that increasing [$Cu^{2+}$] can restore LOX activity, increase crosslinking as measured by LNL in rabbit cornea treated topically, and increase biomechanical strength of human cadaver corneas and rabbit corneas ex vivo. In clinical trials, the treatment involves topical application of a copper sulfate solution, IVMED-80 eye drops, morning and evening. IVMED-80 has the potential to become the standard of care as it would be the first purely pharmacologic intervention for KCN. Efficacy relies on patient compliance and transport of $Cu^{2+}$ across the epithelium. Copper has a narrow therapeutic range (100 μM to 1 mM) above which it is toxic, creating a situation in which sustained release could be particularly beneficial. Therefore, a method to provide sustained release of $Cu^{2+}$ in the cornea is needed.

Biolistic delivery will quickly deliver Cu(II) in a sustained release vehicle to maintain a therapeutic [$Cu^{2+}$] for weeks, eliminating variability associated with patient compliance and transport across the corneal epithelium. Based on the formulation of IVMED-80 currently in a Phase 1/2a clinical trial, we estimate that the corneal stroma receives $1.6\times10^{-9}$ g of $CuSO_4$ per topically applied eye drop, corresponding to $2\times10^{-11}$ mol Cu(II)/day. This estimate is consistent with observations during the first 4 months of the current clinical trial that patient's eyes have no visible blue color and color vision is not affected (patients received eye drops twice daily for 16 weeks in three groups: vehicle, IVMED-80, and 6 weeks IVMED-80 followed by 10 weeks vehicle). Effective treatment duration is at least 6 weeks. The present disclosure is used with combinations of selected copper minerals that have shown promise for sustained release and PLA carrier that will delay their exposure to biological fluids.

Based on their release profiles of $Cu^{2+}$ from alginate gels, the copper minerals atacamite ($Cu_2Cl(OH)_3$) and hydroxy cupric phosphate heptahydrate ($(Cu_8(PO_3OH)_2(PO_4)_4\cdot7H_2O)$),[Bassett et al.] abbreviated CuC and CuP, are selected for sustained release from polylactide (PLA) composite particles. Basset et al. showed that the rate of $Cu^{2+}$ release from alginate hydrogel can be tuned from a half-time less than 1 day to more than 14 days by control of crystal perfection, crystal size, mineral form and dissolution medium (dissolution is relatively rapid in biological media). Prior results suggest that release from 30 μm diameter <1%-D PLA nanocomposite particles can extend release for more than 30 days. Some experimentation is required to finalize the selection of stereoregularity of PLA (D-content), CuC:CuP ratios, total mineral loading and PLA-composite particle size to provide overlapping release kinetics that combine to approximate linear release profiles for up to 6 weeks in corneal stroma in vitro.

Delivery of a 2-week dose requires {$2\times10^{-11}$ mol Cu(II)/day} {14 days}=$2.8\times10^{-10}$ mol Cu(II) which can be provided using approximately 180 composite particles of 10 μm diameter containing 40 vol % mineral (1:1 CuC:CuP by mass). This particle size is of particular interest because it is not expected to be perceptible by the patient; and the total number of particles is small enough that the particles would occlude less than 0.04% of the area of the cornea. Mineral particles will are synthesized following literature protocols that provide pure atacamite[Pollard 1989] [177] or pure hydroxy cupric phosphate heptahydrate[Chen 2009] [178]. Both of these minerals tend to form platelet-shaped crystals that are 20-40 nm thick and 500-1000 nm across. Rigorously dry particles are dispersed in chloroform using sonication and the suspension of particles is then mixed with a 10% w/w PLA solution in chloroform. The presence of PLA stabilizes the mineral dispersion. Spray drying is used to synthesize substantially spherical particles that have dimension 10 to 20 μm.

The density of the particles is calculated using $vf_{PLA}$=60% vol fraction PLA (dry solid), vf_CuC=20% vol fraction CuC, vf_CuP=20% vol fraction CuP and using the densities $\rho_{PLA}$, $\rho_{CuC}$, and $\rho_{CuP}$. The density of the particles is thus $vf_{PLA}\ \rho_{PLA}+vf_{CUC}\ \rho_{CuC}+vf_{CUP}\ \rho_{CuP}$. The resulting density and the desired particle size range 10 to 20 μm is used with the example above that provides experimental results a higher and a lower particle density. Interpolating between the two densities and their corresponding velocity ranges for delivery to the posterior epithelium provides velocities that would be suitable for size 20 to 30 μm. Smaller particles will need to have faster velocity. Based on the example that describes the probability density of penetration depth for individual sizes, the velocity is increased by a factor of 25/15, the middle values of the two size ranges, 20 to 30 μm and 10 to 20 μm. The resulting combination of particle density, particle size range and velocity range will deliver more than 50% of the particles to the posterior half of the epithelium.

Example 38 Characteristics of Skin Wounds

Features of the skin and of skin wounds are illustrated in the schematics of FIG. 47. From www.phoenix-society.org/resources/understanding-the-healing-stages-of-a-burn-wound.

In the illustration of FIG. 47, First-Degree Burns (Superficial) are schematically shown. This type of burn affects the top layer of skin, or epidermis, and causes minor damage to the skin. The skin can be red or tender. Common first-degree burns include mild peeling sunburns or a short contact cooking injury. These burns can usually be treated at home. Healing usually takes a few days and doesn't typically show scarring.

In the illustration of FIG. 47, Superficial Second-Degree Burns (Partial Thickness) are schematically shown. This burn type penetrates the skin's second layer, the dermis. This type of burn often forms blisters, and can generally heal in 10 to 14 days with mild to moderate scarring.

In the illustration of FIG. 47, Deep Second-Degree Burns (Partial Thickness) are schematically shown This type of burn is a deep, partial thickness burn that goes further into the skin and involves both the epidermal and deeper dermal layers of the skin. Scarring for this type of wound can be severe, and these types of wounds can need skin grafting. A skin graft is a surgery that removes injured skin and replaces it with healthy skin from another body location. These deep burns can leave raised scars.

In the illustration of FIG. 47, Third-Degree Burns (Full Thickness) are schematically shown. Third-degree and more severe burns, sometimes referred to as full-thickness burns, damage both layers of skin and can go into the underlying tissue. Burned skin may feel dry and leathery and turn white, black, or gray. You may not have initial pain as nerve endings under the skin can be destroyed, which affects the body's ability to feel pain. As the nerves regrow, your sense of touch may be affected. These burns have a high risk of infection and often require additional treatment. The care team will involve a surgeon using skin grafts to help heal the area.

In the illustration of FIG. 47, Fourth-Degree Burns are shown. This is the most severe and potentially life-threatening type of burn. Fourth-degree burns are the highest degree, and affect all layers of skin, muscles, tendons, and bones.

Progress is being made to guide wound healing after skin injury to provide recovery of sensory function (regenerate nerves and hair follicles) and thermal regulation (regenerate sweat glands).

For example, Messersmith and co-workers demonstrated healing of skin with regeneration of hair follicles in a mouse model; multiple peripheral subcutaneous injections of a hydrogel containing 1,4-DPCA (1,4-dihydrophenonthrolin-4-one-3-carboxylic acid), a drug that inhibits degradation of hypoxia-inducible factor 1α (HIF-1α) by prolyl hydroxylases (PHDs), were performed over a 10-day period and led to regenerative wound healing in Swiss Webster mice after ear hole punch injury. (Ref [Zhang] Zhang, Y., Strehin, I., Bedelbaeva, K., Gourevitch, D., Clark, L., Leferovich, J., Messersmith, P. B., & Heber-Katz, E. (2015). Drug-induced regeneration in adult mice. *Science translational medicine,* 7(290), 290ra92. doi.org/10.1126/scitranslmed.3010228.

Example 39: Stages of Skin Wound Healing and Involvement of Cells and Active Agents It is increasingly clear that the time sequence of delivery of multiple active agents will be required to achieve full recovery after injury. The wound healing process has three phases (after hemostasis).

First is the inflammatory phase, then the proliferative phase followed by the remodeling phase. During the first phase, the inflammatory phase begins at the time of injury and lasts approximately 48-96 hours. Platelets arrive and release PDGFs and TGFs to attract neutrophils and macrophages. Neutrophils arrive and aid in removing bacteria and debris from the wound. Macrophages, one of the most important mediators of wound healing, produce a variety of growth factors including TGF, FGF, PDGF, and IL, as well as recruit fibroblasts to the wound (see Table 8 below).

The proliferative phase begins approximately 72 hours after the initial wound or debridement. Fibroblasts are recruited and begin the process of angiogenesis, epithelization and collagen formation. Fibroblasts begin producing type III collage in this phase.

When collagen synthesis and breakdown become equal then the wound healing transitions into the final stage, which is the remodeling phase. Increased collage production occurs for up to a year after injury. The collagen type changes from type III to type I and fibroblasts transition into myofibroblasts, allowing for the tissue to contract. The collagen reorganizes and gains tension and strength.

An exemplary illustration of the timing of involvement of the cells in the wound healing and the timing of the wound healing phases is reported in FIG. 48A and FIG. 48B respectively.

A list of the main factors involved in wound healing is reported in the following Table 8 from (Ref. Allen Gabriel, MD. "Wound Healing and Growth Factors." *Overview, Types of Wound Healing, Phases of Wound Healing*, Medscape, 27 Aug. 2021, emedicine.medscape.com/article/1298196-overview#a3.

TABLE 8

| Growth Factors | Produced by | Time (days) |
|---|---|---|
| Endothelial Growth Factor (EGF) | Platelets, macrophages | 0-2 |
| Transforming Growth Factor (TGF) | Platelets, macrophages, lymphocytes, hepatocytes | 0-2 from platelets<br>2-5 from macrophages<br>3-7 from lymphocytes |
| Vascular Endothelial Growth Factor (VEGF) | Endothelial Cells | During tissue hypoxia |
| Fibroblast Growth Factor (FGF) | Macrophages, mast cells, T-lymphocytes | 2-5 from macrophages<br>3-7 from lymphocytes |
| Platelet-Derived Growth Factor (PDGF) | Platelets, macrophages and endothelial cells | 0-2 from platelets<br>2-5 from macrophages |
| Interleukins (IL) | Macrophages, keratinocytes, endothelial cells, lymphocytes, fibroblasts, osteoblasts, basophils, mast cells | 2-5 from macrophages |
| Colony-Stimulating Factors (CSF) | Stromal cells, fibroblasts, endothelial cells, lymphocytes | 3-7 from lymphocytes<br>4-10 from fibroblasts |
| Keratinocyte Growth Factor (KGF) | Fibroblasts | 4-10 |

Example 40 Particles for Sequential Sustained Release

Methods and systems of the disclosure can be used with a variety of particles that achieve sequential sustained release, including, but not limited to, layer-by-layer structured particles, particles composed of biocompatible porous glass loaded with a sequence of active agents, composite particles that contain drug crystal or glass inclusions in a polymer matrix and multilayered core-shell particles in which the successive shells contain the active agents in the order of sustained release, and so on. The particles are designed to have sufficient mechanical integrity that they survive delivery into the exposed tissue.

One type of active agent, growth factors, stimulate wound healing and cell growth and are widely studied in the re-epithelization of the skin. It is desirable to deliver them in a sustained release vehicle due to the instability of growth factors in vivo and their relatively short half-life.

Growth factors and cytokines are critical in the wound healing process that includes tissue regeneration and the regrowth of the epithelium. The studies of growth factors paired with a variety of carrier materials have been studied extensively in the past decade. The growth factors include but are not limited to epidermal growth factor (EGF), fibroblast growth factor (FGF), platelet-derived growth factor (PDGF), transforming growth factor-beta (TGF-β), and vascular endothelial growth factor (VEGF).

Carrier materials are being developed to aid in the delivery and to prolong the action time of growth factors. The materials that are used as carriers can be divided into bio-derived and synthetic materials. Bio-derived materials provide advantages such as increased biocompatibility and high biodegrability. Some examples of bio-derived materials used include gelatin-based hydrogels, photocrosslinked alginic acid and hyaluronic acid and chitosan-based membranes and microspheres. Synthetic materials offer better control in their mechanical, physical and chemical properties. Such examples include PLLA membranes and PLGA microspheres.

Relative particles have dimensions 10-100 microns), mode of delivery (ballistic) and placement at a depth of 100-1000 micros in exposed tissue that is actively healing:

The following Table 9 reports materials with relevant active agents known to promote wound healing is from Nurkesh et al 2020 (Ref. [Nurkesh, Ayan, et al. "Recent advances in the controlled release of growth factors and cytokines for improving cutaneous wound healing." *Frontiers in Cell and Developmental Biology* 8 (2020): 638.]).

TABLE 9

| Material | Growth factor/cytokine | Effect | References |
|---|---|---|---|
| Hydrogel | bFGF | Increased fibroblast proliferation in vitro, enhanced wound closure in the scratch assay, and promoted wound healing in vivo | Zhang et al., 2018 |
| | bFGF | Enhanced wound closure, organized collagen depostion, vascularization, granulation, myofibroblast formation, and reduced inflammation | Xu et al., 2017, 2018 |
| | bFGF | Enhanced the formation of granulation tissue, increased angiogenesis, and inhibited inflammation and activity of the pro-inflammatory factors, TNFα and IL-6 | Chen G. et al., 2017 |
| | bFGF | Enhanced wound closure, collagen deposition, vascularization, re-epithelialization, granulation, keratinocytes migration, and reduced inflammation | Xuan et al., 2020 |
| | aFGF | Accelerated cell proliferation, neo-vascularization, and wound healing | Hui et al., 2018b |
| | aFGF or bFGF | Improved wound healing | Wu et al., 2016b |
| | EGF and bFGF | Increased rate of wound closure, decreased number of pro-infammatory cells, enhanced re-epithelialization, and granulation tissue formation | Yoo et al., 2018 |
| | SDF-1 | Accelerated wound healing and increased vascularization | Yao et al., 2020 |
| | VEGF | Enhanced wound healing, granulation, collagen deposition, angiogenesis, and reduced inflammation | Chi et al., 2020 |
| | EGF-like growth factor | Enhanced wound healing in an organ culture model of the porcine skin | Thönes et al., 2019 |
| | ELP-KGF and ELP-ARA290 | Improved wound healing by facilitating blood vessel formation, epithelialization, and granulation tissue formation | Devalliere et al., 2017 |
| | Substance-P and TGF-β1 | Enhanced wound healing, thicker *panniculus adiposus* and carnosus layers | Park et al., 2018 |
| Nanoparticle | KGF | Enhanced wound closure and cell migration | Muhamed et al., 2019 |
| | KGF | Enhanced wound healing and re-epithelialization, accelerated keratinocyte migration and proliferation | Pan et al., 2018 |
| | KGF | Enhanced wound healing, bioactivity, and increased levels of collagen I, α-SMA and TGF-β1 | Li et al., 2019 |
| | EGF | Accelerated migration of inflammatory cells during the inflammation phase, enhanced wound healing | Kang et al., 2017 |
| | EGF | Enhanced wound closure, collagen deposition, angiogenesis, and reduced inflammation and number of myofibroblasts | Gainza et al., 2015a |
| | VEGF 164 | Enhanced wound closure accompanied by increased re-epithelialization and granulation but not wound contraction | Chereddy et al., 2015 |
| Nanofiber | G-CSF | Improved wound closure, scar reduction, fibroblast maturation, as well as increased collagen density and decreased amount of neutrophils | Tanha et al., 2017 |
| Biofilm | bFGF | Enhanced healing, reduced pro-inflammatory cell accumulation, promoted granulation layer formation | Liu et al., 2017 |
| | EGF | Accelerated wound healing via stimulating keratinocyte differentiation and reducing inflammation | Kim et at., 2016 |
| | VEGF and PDGF-BB | Enhanced angiogenesis, granulation, and keratinocyte proliferation | Almquist et al., 2015 |
| Concentrate | bFGF | Enhanced wound closure, angiogenesis, collagen deposition, granulation, cell proliferation in the wound area, re-epithelialization, and hair follicle formation | Wu et al., 2016a |
| | IL-10 and TGF-β3 | Accelerated wound closure, enhanced re-epithelialization, angiogenesis, collagen I distribution, and reduced hypertophic scar formation | Park et al., 2019 |
| Fibrin matrix | VEGF-A165 and PDGF-BB | Enhanced vascularization, suppressed migration of the neutrophils to the wounded area, and attracted Ly6C$^+$ CD11b$^+$ monocytes | Ishihara et al., 2018 |
| Collagen matrix | EGF or bFGF | Accelerated wound healing, re-epithelialization, neovascularization, and collagen deposition | Choi et al., 2018 |
| Lyotropic liquid crystal | EGF | Reduced inflammation, increased wound closure and re-epithelialization | Zhou et al., 2019 |
| | VEGF | Enhanced vascularization | Wang B. et al., 2019 |
| Cryogel | IL-10 TGF-β1, VEGF and bFGF | Improved the regenerative process on a murine internal splint wound model, including neovascularization, wound closure, granulation, and re-epithelialization | Jimi et al. (2020) |

Example 41: Exemplary Procedure to Identify Particle Features to Deliver to a Target Layer This example reports an exemplary procedure to deduce the approximate (impact velocity, size) distribution of particles of a specified density accelerated using specified operating conditions of a specified particle-accelerating device.

Use ballistic gelatin at 5% w/w prepared as directed as a target material for a limited set of experiments using the sustained release particles of interest. to infer the impact velocity from the observed penetration depth and particle size. Despite the uncertainty in the measured depth and particle diameter (see for example Veysset et al.), results prove valuable for the purpose of identifying operating conditions of a specified particle accelerating device that will produce adequate penetrating power to deliver specified sustained release particles into tissue.

Using the particle accelerating device of interest and a representative batch of sustained release particles (or particle surrogates that have the same density and distribution of size and shape), accelerate particles into ballistic gelatin of the selected concentration. Characterize the resulting three-dimensional distribution of particles in the ballistic gelatin using an optical microscope. For example, three dimensional images using optical coherence tomography or confocal microscopy. Perform image analysis to extract for each particle its penetration depth and diameter; tabulate the resulting pairs of values. For each individual particle, calculate the ratio of these two observables (the normalized penetration depth).

This example describes a method using a graph; note that a skilled person could use the description given here to implement a numerical procedure to evaluate $v_o$. in connection with the illustration of FIG. 49A, FIG. 49B and FIG. 49C.

For the effective density of the sustained release particles of interest, $\rho_p$, prepare a graph of normalized penetration depth vs impact velocity, $v_o$, according to the Poncelet model with the parameter values established by Veysset et al. for 5% w/w ballistic gelatin: resistance R=6.0e6 Pa, $C_D$=0.4, gel density $\rho_s$=1,010 kg/m$^3$. That is, plot the theoretical (penetration depth)/(diameter), $z/d=\{(⅔)(\rho_p/\rho_s)(1/C_D)\} \ln \{(\rho_s C_D v_o^2)/(2R)+1\}$ as a function of $v_o$. and use it to identify the vertical axis value for that particle; trace a horizontal line across until it intersects the curve for the specific ballistic gelatin that was used (2.5% w/w or 5% w/w) and trace a vertical line down to read off the approximate velocity that particular particle had at impact. This enables us to use a readily available material (ballistic gelatin) and a readily available instrument (light microscope) to obtain a useful estimate of the ability of the particles to penetrate without requiring an ultrahigh speed camera or laser doppler instrument.

In the methods and systems and devices of the disclosure, a layered soft tissue that has a soft exposed layer on an underlying tougher tissue layer enables self-localizing delivery of sustained release particles. Specifically, Pailler-Mattei et al. deduced from integrated measurements and modelling that the elastic modulus, E, of the dermis and hypodermis (E ca. 35 kPa and 2 kPa respectively) are soft relative to the underlying muscle (E ca. 80 kPa). Particles that exhibit a tight range of normalized penetration in gelatin (broad range of penetration depth), will self-localize when the ballistic microparticles are delivered to a broad, shallow wound in skin (epidermis and some of the dermis are absent). Such delivery of active agents will be beneficial for treatment of second degree thermal, chemical, radiation or electrical burns (and beneficial for some portion of a more severe burn) and serious abrasions. In this broad class of wounds, delivery of sustained release vehicles into the dermis/hypodermis, but not into the underlying muscle, will provide the appropriate location and stable embedment to guide wound healing for a period of several days to weeks. The methods and systems of the disclosure scales to large area wounds much in the manner of air brush painting: a continuous flow of therapeutic sustained release particles can be swept over the area of the wound to deliver a uniform dose per area for arbitrarily large area wounds.

The methods and systems and related devices of the present disclosure can also be used to treat deep, chronic wounds; however, particles with higher density and size than in this example would be required to meet the needs for sustained delivery in in that case, as penetration into muscle tissue is desired.

For the specific particle density in this example ($\rho_p$=2.5 g/cc), the Poncelet model with the parameters for 5% w/w ballistic gelatin from Veysset et al. give the curve shown in the middle graph. The graph on the left shows the probability density of the measurements of penetration depth and particle diameter for a particle delivery experiment into 5% w/w ballistic gelatin for specific operating conditions of a specific device. In this experiment, the normalized penetration depth is peaked in the range 3-6. On the graph with the Poncelet model, this band of normalized penetration values correlates with impact velocity in the range 170 to 230 m/s.

More detailed information on the distribution of impact velocity and possible correlations with particle size (depending on the accelerating device used) can be obtained by using the data for each individual particle to draw a horizontal line at their specific normalized penetration to intersect the Poncelet curve and read off the corresponding impact velocity that particle had when it hit the gelatin surface.

When delivered to a broad, shallow wound, the particles will not exhibit a narrow range of normalized penetration; rather they will exhibit the desired localization in the remaining dermis and hypodermis, but the particles will not appreciably enter the skeletal muscle beneath the skin. Consequently, they will qualitatively follow a constant penetration depth contour (normalized penetration decreasing as the inverse particle diameter) as shown in the graph on the right.

Example 42: Preparation of Agarose Gel

Before testing a Pneumatic Capillary Gun (PCG), a convenient gel target was required that had similar mechanical properties compared to corneal tissue. Agarose gels can be prepared quickly and are transparent, which is a benefit for ballistics experiments. Based on previous work done by Professor Groisman, (see Rinberg 2005) agarose was selected as the substrate material. To make 1% agarose w/v gels, agarose was dissolved in DI water by microwaving until boiling. The boiling solution was poured in between onto a 100 mm petri dish, adding 10 mL of agarose solution per dish to ensure full coverage yielding a gel thickness of approximately 1.5 mm thickness. The dishes are then covered and wrapped in Parafilm and were allowed to set at 4° C. for two hours.

Example 43: Preparation of Gelatin Gel

Ballistic gelatin is a material with consistent mechanical properties used in ballistics research. [151, 152] Gels were prepared using the standard protocol (Jusilla et al., 2004 [153]) at three concentrations of 5.0 and 10.0% w/w. Gelatin samples were allowed to solidify for 4 hours at 4° C.

The procedure for preparing 5% w/w gelatin is as follows. Using gelatin (Sigma Aldrich), the dry amount of gelatin is mixed with half the amount of deionized water needed to achieve the desired concentration at room temperature and stirred continuously. The other half of deionized water is heated to 80° C. for 30 minutes. The heated water is then added slowly to the stirring mixture of gelatin and water to form the final solution. A heat plate is used to keep the mixture heated at 80° C. and stirred for an additional 30 minutes. The solution was poured in between into a 100 mm petri dish, adding 10 mL of agarose solution per dish to ensure full coverage yielding a gel thickness of approximately 1.5 mm thickness. The dishes are then covered and wrapped in Parafilm and were allowed to set at 4° C. for two hours. When a sample is removed from the refrigerator, care is taken so that water does not condense on the gelatin and so that water does not evaporate from the gelatin. The gelatin should be used within 10 minutes after removing it from the refrigerator so that its properties do not degrade.

Example 44: Preparation of Multilayered Gels

To investigate the effect of multilayered gels, we combine the process of making agarose and gelatin from above. 1% w/v agarose gels were poured into 100 mm petri dishes following the instructions above and stored in 4° C. for 2 hours to gel. The agarose gel is removed and allowed to warm to room temperature for 30 minutes. 5% or 10% gelatin solutions were prepared following the protocol from above. 500 mL of either 5% or 10% gelatin solution was pipetted onto the 1% agarose gel and spread to produce a uniform layer of gelatin. This yielded a layer of approximately 20 to 40 μm layer of gelatin on top of the agarose. This multilayered gel is then replaced back into the refrigerator at 4° C. for 2 more hours to allow to gel.

Example 45: Preparation of Microparticles

Polydisperse soda lime glass particles (Cospheric, 2.85 g/cc conductive silver-coated soda lime glass microspheres) ranging from 5 to 22 μm are mixed in solution of distilled water (0.1% w/v) and deposited onto luer-lock cassettes that contain a mesh screen for particle deposition. Each cassette received 1.0 μL of the solution and were allowed to dry at room temperature overnight.

Example 5DK: Microparticles Penetration to 5% to 10% w/w Gelatin

Microparticles were delivered using our ballistic delivery device, as shown above, using 100 psi of Helium as the carrier gas and approximately −10 to −11 psi of vacuum. (Need to add information on the orifice sizes).

A puff of Helium is released via a solenoid for 50 ms, delivering the particles into the gels.

The particles are entrained in a stream of helium air (at gauge pressure of 100 psi/689 kPa) and delivered through our delivery device with the exit orifice 10 mm away from the surface of the gel.

The exit of the orifice of the ballistic device was set to be 10 mm away from the gel surface.

Multilayered gels with 10% gelatin on top of a 1% agarose and 5% gelatin on top of 1% agarose were examined for comparison with single layer gels of 10% gelatin, 5% gelatin and 1% agarose.

Example 46: Imaging Particle Delivery in Gels Using Optical Coherence Tomography The resulting gels were imaged using optical coherence tomography with a Thorlabs OCT (GAN210 base unit: 930 nm central wavelength, 6/4.5 μm axial resolution in air/water, 2.9/2.2 mm imaging depth (air/water), OCTP-900 scan head, OCT-LK3-BB scan lens: 36 mm FL, 8 μm lateral resolution). A-Scan/Line Rate was 15 kHz for all measurements. A 3D stack of images was taken of the area surrounding the particles within the gel. The 3D stack was exported as .tiff files to be analyzed in ImageJ or Fiji (Fiji is Just ImageJ).

Example 47: Image Processing to Measure Penetration Depths

Within ImageJ/FIJI (Fiji is just ImageJ), the OCT images are converted to 8-bit and a threshold is set on the image (240). All pixels above the threshold will be considered as part of the particle, while all other pixels will be considered as being part of the background. This stack is then run through the 3D Object Counter in Fiji, which produced a list of objects and their X, Y, Z coordinates within the image stack. Given the position of the particle, the penetration depth was measured using the measure line tool in Fiji.

Particle depths from each sample are collected from multiple samples to generate a histogram of the penetration depths in single layer agarose, gelatin, and the bilayer gels. The number of particles is normalized to a 1000 particle basis, (how many particles would impact each specific range/bin if the total number of particles delivered was 1000).

The penetration observed between the 1% agarose and the 5% gelatin single layer gels indicate a similar penetration depth distribution out to approximately 200 μm, shown in FIG. 50.

There are variations in the thickness of the top layer of gelatin in the multilayered gel. The thickness was measured for each individual sample of the multilayered gel. The thickness varied from 15 μm to 45 pm. At each boundary, the section of interest is the bounded by 10 μm above the boundary and 10 μm below the boundary. Using this 20 μm window, the number of particles in this region within the multilayered is counted.

A comparison is made to the single layer in agarose and gelatin (if the multilayered comprises of 10% gelatin on top of 1% agarose, then the comparison is made to single layer 10% gelatin, and similarly for 5% gelatin on top of 1% agarose, compared to 5% gelatin). Using the same 20 μm window surrounding the boundary, the number of particles expected in a 1% agarose gel or the corresponding gelatin gel can be determined by looking at the particle distributions from the figures above (see FIG. 50 and FIG. 51). Then a comparison is made to determine whether the number of particles observed in the bilayer is greater than or less than the expected particles in the single layer given the boundary. A percentage of the expected (bilayer particles/expected particles×100%) is then reported in Tables 10 and 11 below.

TABLE 10

| Estimate number of particles expected | | | 1% Agarose | 5% gelatin | | |
|---|---|---|---|---|---|---|
| top layer thickness | Boundary − 10 um | Boundary + 10 um | number in range | number in range | Percent of expected | Conclusion |
| 26.2 | 16 | 36 | 283 | 282 | 86 to 86 | # observed in bilayer is less than either |
| 30.7 | 21 | 41 | 235 | 205 | 108 to 125 | # observed in bilayer is greater than either |
| 31.8 | 22 | 42 | 235 | 205 | 74 to 85 | # observed in bilayer is less than either |

TABLE 10-continued

| Estimate number of particles expected | | | 1% Agarose | 5% gelatin | | |
|---|---|---|---|---|---|---|
| top layer thickness | Boundary − 10 um | Boundary + 10 um | number in range | number in range | Percent of expected | Conclusion |
| 44.8 | 35 | 55 | 115 | 84 | 145 to 198 | # observed in bilayer is greater than either |

TABLE 11

| Estimate number of particles expected | | | 1% Agarose | 10% gelatin | | |
|---|---|---|---|---|---|---|
| top layer thickness | Boundary − 10 um | Boundary + 10 um | number in range | number in range | Percent of expected | Conclusion |
| 15.7 | 6 | 26 | 302 | 363 | 149 to 178 | # observed in bilayer is greater than either |
| 20.1 | 10 | 30 | 330 | 356 | 145 to 156 | # observed in bilayer is greater than either |
| 27 | 17 | 37 | 283 | 312 | 49 to 54 | # observed in bilayer is less than either |
| 29.7 | 20 | 40 | 235 | 268 | 60 to 65 | # observed in bilayer is less than either |

For relevance in delivery, the particles carry enough penetrating power to enter the material.

Particles need to also carry enough penetrating power to reach the boundary.

In order for particles to accumulate at the boundary, they need to have enough penetrating power that they would normally penetrate much deeper than the distance if they were moving in a single-component medium; the influence of the boundary dissipates energy so that they do not proceed beyond the boundary.

The extent to which particles can be preferentially deposited near the boundary depends on the distribution of penetrating power: the "low energy" tail stops before reaching the boundary; the "high energy" tail represents particles that can go beyond the boundary.

Examining the data, when the particles observed in the bilayer gel greatly exceeds the particles in the single component gel (highlighted in yellow in the above tables), it infers that few particles would not stop at the boundary depth in the single component gel.

Example 48: Device for Multilayered Ballistic Delivery

FIG. 52, panel A shows an example of an example compact pneumatic particle accelerating device designed for the methods herein. The design is similar to a delivery device of Alexander Groisman (Ref. arxiv.org/pdf/physics/0502080.pdf and in U.S. Pat. No. 7,892,836), but with some modifications to improve performance. Carrier gas and particles (DVC05) enter the inner capillary tube ("ICT", DVC10) housed in an outer tube ("OT", DVC15) that has gas diversion openings ("GDO", DVC20) diverting the excess gas into the gas diversion cone ("GDC", DVC25) configured to divert the excess gas/particles away from the patient. Examples of particles are described herein in other sections.

An example of a carrier gas includes helium, nitrogen, air or other gases alone or in combinate. A series of orifice disks ("OD-1", "OD-2", "OD-3", DVC30) held by an orifice disk insert ("ODI", DVC35) direct the particles to the patient, while a vacuum chamber ("VC", DVC40) diverts the gas through a vacuum outlet ("VO", DVC45) by a plurality of vacuum channels (DVC50), 24 in this example, between two of the orifice disks evenly distributed around the orifice disk insert.

A cartridge or mesh loaded with particles is in the upper portion (not shown and as known in the art), where the carrier gas accelerates them down the ICT. An electronic solenoid can control the flow of the carrier gas that enters the ICT, varying the pulse length between, for example, 1 ms to 1000s. Prior to entering the ICT, a luer lock cassette with a mesh screen is placed, where the particles are deposited. High speed gas and particles emerge from the ICT and produce a high-pressure zone above OD-1 that causes most of the gas and some of the particles to flow out laterally through the GDO, where the GDC directs them away from the patient (see FIG. 52, panel B). Only particles travelling on-axis pass through OD-1. The space between OD-1 and OD-2 is connected to an evacuated chamber VC by multiple vacuum channels (DVC50) equidistantly surrounding the orifice disk opening (DVC31), an improvement on the previous design that had only one vacuum channel, pulls a vacuum in one direction. The multiple channels pull the vacuum in all normal directions equally.

When vacuum is applied, no perceptible gas leaves through OD-3; instead, it leaves through the VOs, along with some of the particles. For an example scale, a 1 cm bar is shown for panels A and C. The size of the device can be adjusted by design depending on budget and intended specific use. As an additional improvement, the orifice disks are adjustable in the insert, to allow different distancing and orifice sizing as needed for the method.

In this example, the ICT has an outer dimeter of 2.109 mm and an inner diameter of 1.6 mm. The OCT has an outer diameter of 30.5 mm and an inner diameter of 22.9 mm. The GDC has an outer diameter of 25.4 mm. The orifice disks have varying orifice diameters of 200, 250, 300, 350, 400, 600, 800, 1000, 1200, 1400, and 1600 microns.

FIG. 52, panel C shows the vacuum chamber (DVC40) surrounding the disk insert (DVC35), which holds disks in place by a gasket (DVC36). Although the vacuum is applied in one direction from the vacuum outlet (DVC45), the evenly spaced and distanced vacuum channels (DVC50) allow a vacuum around the jet passing through the disk orifice (DVC31) without diverting the major direction of the particles (note that some particles will be diverted radially by the vacuum, but most will stay generally on the major axis set by the ICT).

FIG. 53 shows an example layout for the device. An air/gas input (DVCX05) pushes compressed air/gas into a cassette (DVCX10) containing a mesh (DVCX15) with the microparticles embedded on it. These get pushed through the capillary tube (DVCX25) into the particle accelerating device (DVCX20). A solenoid (DVCX30) controls the air/gas flow.

Example 49: Fabrication of Sequential Growth Factors Di-Layer Polydopamine (PDA) Coated PLDA Particle A pool of PLGA particle of diameter of 10 microns with an L/G ratio of 50/50 and an L/G ratio of 75/25 (e.g. from CD Bioparticles, www.cd-bioparticles.com/product/poly-lactic-co-glycolic-acid-plga-list-214.html) (50 mg) was incubated in a dopamine (DA) solution (300 μL of 40 mg/mL DA in TRIS #1) containing VEGF and FGF each at a concentration of 1 μg/mL at room temperature for 2 h. The sample was then rinsed 3× in TRIS #2 to remove PDA excess and the unreacted DA.

To adsorb a second PDA layer, the sample was immersed in a 1, 9-nonanedithiol solution (1 mg/mL in TRIS #1) for 1 h. The sample was then rinsed 3× in TRIS #2 and incubated in a DA solution containing IL-10 and TGF-β each at a concentration of 1 μg/mL for 2 h (300 μL of a 40 mg/mL DA solution in TRIS #1) to create the second PDA layer. (Ref Maria Godoy-Gallardo, et al. Int. J. Mol. Sci. 2020, 21, 6418; doi:10.3390/ijms21176418).

A schematic representation of the resulting particle is provided in FIG. 54.

Example 18: Penetration of Particles into an Apical Target Region and into a Boundary Target Region The inventive method to place a set of substantially spherical particles preferentially into the target region of a tissue comprising a bilayer is illustrated by application for the case that the tissue is specified to be the cornea, the clear tissue located in the anterior of the eye (FIG. 1A). Reported values of the density of corneal tissue as a whole are available and include 1087 kg/$m^3$ for human cornea and 1062 kg/$m^3$ for rabbit cornea, within the required density range from 850 kg/$m^3$ to 1200 kg/$m^3$. A wide range of values have been reported for the Young's modulus of the cornea as a whole, ranging from 16 MPa and 15.3 MPa obtained using uniaxial tensile testing and elastography to 0.34 MPa and 0.54 MPa for quasi-static measurements under loads similar to the intraocular pressure. The entire range of values complies with the specified range of Young's modulus values of the tissue from 500 Pa to 50 MPa.

The specified tissue comprises a bilayer specified to be the corneal epithelium and stroma. The well established anatomy of the bilayer tissue (FIG. 1B) shows that the bilayer has a thickness of L=550 microns. The bilayer comprises an apical layer that is the epithelium, which has an accessible surface of the apical layer that coincides with the boundary between the tissue and the exterior environment. The accessible surface of the epithelium satisfies the requirement that it have a width W in at least one lateral direction (which follows the curved accessible surface of the epithelium) that is substantially greater than 10 L. For the corneal epithelium the width in any lateral direction is at least 6 mm, which is greater than 10L=5500 micron. And the accessible surface of the epithelium satisfies the requirement that its area, which is substantially greater than 36 $mm^2$, be greater than $10(L^2)=3.0$ $mm^2$. Further, the epithelium has an interior boundary between the apical layer and the basal layer, which is the corneal stroma.

Notice that neither the epithelial basement membrane nor Bowman's layer satisfies the minimum thickness requirement for an anatomical feature to qualify as a layer: neither one, nor the two together meets the requirement that the thickness be greater than 5 microns.

The well established anatomy of the corneal also provides the thickness of the apical layer, the corneal epithelial layer having thickness $L_a$=50 microns, and the thickness of the basal layer, the corneal stroma, which has thickness $L_b$=500 microns. Table 3 includes the corneal epithelium as a example of a Type I tissue, providing the value of the apical layer mean density $\rho_a$=915 kg/$m^3$, compressive strength $Y_a$=70 kPa, and effective viscosity $\mu_a$=1 Pa·s; and Table 3 also include the corneal stroma as an example of a Type II tissue, providing the basal layer mean density $\rho_b$=1050 kg/$m^3$, compressive strength $Y_b$=650 kPa, and effective viscosity $\mu_b$=1 Pa·s. These values provide all the input needed to perform the calculation of the present method.

The utility of the method is illustrated first for an "apical target region": the apical layer thickness $L_a$=50 micron, leads to a thickness of the apical target region $L_t=L_a/2=25$ microns and a target depth $d=L_a/2=25$ microns. Further, for an apical target layer, the effective target penetration distance according to the method is $d^*=d=L_a/2=25$ microns. Knowing d*, along with all of the other values above and selecting a particle density $\rho_p$—of 2500 kg/m3 and a mean diameter $D_p$ of 15 microns, the interactive calculation provided $v_{o,j}$=340 m/s. Therefore, the set of values $\rho_p$, $D_p$, and $v_{o,j}$ were used successfully, providing the results shown in FIG. 20A.

The utility of the method is further illustrated by a "boundary target region": given the apical layer thickness $L_a$=50 micron, the thickness of the apical target layer is $L_t=L_a/2=25$ microns and the target depth $d=L_a/2=25$ microns. Further, for an apical target layer, the effective target penetration distance $d^*=d=L_a/2=25$ micron.

The use of the method to iterate to a successful solution is illustrated in FIGS. 20B and C. The selection of parameters used for the experiment in FIG. 20B was shown by the algorithm to require a velocity was not achieved in practice. Using the observed velocity as a criterion, the density was increased, the calculation repeated predicting that the velocity provided by the available device would deliver particles of a particle density $\rho_p$- of 8000 kg/m3 and a mean diameter $D_p$ of 15 microns, to the boundary region using $v_{o,j}$=320 m/s, which the available device could provide. This set of values $\rho_p$, $D_p$, and $v_{o,j}$ was used successfully, providing the result in FIG. 20C.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including webpages patents, patent applications, journal articles, abstracts, laboratory manuals, books, or other disclosures) in the Background, Summary, Detailed Description, and Examples is hereby incorporated herein by reference. All references cited in this disclosure, including references cited in any one of the Appendices indicated herein, are incorporated by reference to the same extent as if each reference had been incorporated by reference in its entirety individually. However, if any inconsistency arises between a cited reference and the present disclosure, the present disclosure takes precedence. The hyperlinks incorporated by reference are incorporated for the content at the fling date of the present disclosure.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure.

Whenever a range is given in the specification, for example, a temperature range, a frequency range, a time range, or a composition range, all intermediate ranges and all subranges, as well as all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations, which is not specifically disclosed herein.

"Optional" or "optionally" means that the subsequently described circumstance may or may not occur, so that the description includes instances where the circumstance occurs and instances where it does not according to the guidance provided in the present disclosure. For example, the phrase "optionally substituted" means that a non-hydrogen substituent may or may not be present on a given atom, and, thus, the description includes structures wherein a non-hydrogen substituent is present and structures wherein a non-hydrogen substituent is not present. It will be appreciated that the phrase "optionally substituted" is used interchangeably with the phrase "substituted or unsubstituted." Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned can be identified in view of the desired features of the compound in view of the present disclosure, and in view of the features that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Ahmed, I., *The noncorneal route in ocular drug delivery*, in *Ophthalmic drug delivery systems*. 2003, CRC Press. p. 356-385.
2. Ehlers, N. and J. Hjortdal, *The cornea: epithelium and stroma*. Advances in organ biology, 2005. 10: p. 83-111.
3. Lindblad, N. R. and J. Schneider, *Production of uniform-sized liquid droplets*. Journal of Scientific Instruments, 1965. 42(8): p. 635.

4. Jackson, C. M., et al., *Defining and measuring biological activity: applying the principles of metrology*. Accreditation and quality assurance, 2007. 12(6): p. 283-294.
5. Pelikan, E. W., *Glossary of terms and symbols used in pharmacology*. University School of Medicine, Department of Pharmacology and Experimental Therapeutics, Boston, 2004.
6. Xiong, C., et al., *Mass, size, and density measurements of microparticles in a quadrupole ion trap*. Analytical chemistry, 2019. 91(21): p. 13508-13513.
7. Blackburn, B. J., et al., *A review of structural and biomechanical changes in the cornea in aging, disease, and photochemical crosslinking*. Frontiers in bioengineering and biotechnology, 2019. 7: p. 1-16.
8. Marchini, M., et al., *Differences in the fibril structure of corneal and tendon collagen. An electron microscopy and X-ray diffraction investigation*. Connective tissue research, 1986. 15(4): p. 269-281.
9. Last, J. A., et al., *Compliance profile of the human cornea as measured by atomic force microscopy*. Micron, 2012. 43(12): p. 1293-1298.
10. Gouveia, S. M. and J. M. Tiffany, *Human tear viscosity: an interactive role for proteins and lipids*. Biochimica et Biophysica Acta (BBA)-Proteins and Proteomics, 2005. 1753(2): p. 155-163.
11. Thomasy, S. M., et al., *Elastic modulus and collagen organization of the rabbit cornea: epithelium to endothelium*. Acta biomaterialia, 2014. 10(2): p. 785-791.
12. Gaudana, R., et al., *Ocular drug delivery*. The AAPS journal, 2010. 12(3): p. 348-360.
13. *The Annual UK Drug Tariff*, in *The Stationary Office*. 1988 (November), 1998 (May), 2007 (February) The UK Drug Tariff: London, UK.
14. Lazarus, G. S., et al., *Definitions and guidelines for assessment of wounds and evaluation of healing*. Arch Dermatol, 1994. 130(4): p. 489-493.
15. Boateng, J. S., et al., *Wound healing dressings and drug delivery systems: a review*. Journal of pharmaceutical sciences, 2008. 97(8): p. 2892-2923.
16. Gilliland, E. L., et al., *Bacterial colonisation of leg ulcers and its effect on the success rate of skin grafting*. Annals of the Royal College of Surgeons of England, 1988. 70(2): p. 105-108.
17. Armstrong, S. and C. Ruckley, *Use of a fibrous dressing in exuding leg ulcers*. Journal of Wound Care, 1997. 6(7): p. 322-324.
18. Hareendran, A., et al., *Measuring the impact of venous leg ulcers on quality of life*. Journal of Wound Care, 2005. 14(2): p. 53-57.
19. Naradzay, F. and R. Alson, *Burns, thermal*. Web MD, 2005.
20. Bolton, L. and L. Van Rijswijk, *Wound dressings: meeting clinical and biological needs*. Dermatology nursing, 1991. 3(3): p. 146-161.
21. Krasner, D., et al., *The ABCs of wound care dressings*. wound management, 1993. 66: p. 68-69.
22. Strodtbeck, F., *Physiology of wound healing*. Newborn Infants Nurs Rev, 2001. 1: p. 43-52.
23. Russell, L., *Understanding physiology of wound healing and how dressings help*. British journal of nursing, 2000. 9(1): p. 10-21.
24. BA, M., *The Skin* Wound healing: biochemical and clinical aspects, ed. D.-m.R. Choen I K, Lindblad W., 1999, Philadelphia, PA: Saunders.
25. GS, S., *Molecular regulation of wound healing*. Acute and chronic wounds: Nursing management. 2nd edition, ed. B. RA. 1999, St. Louis, MO: Mosby.
26. Rothe, M. and V. Falanga, *Growth factors: their biology and promise in dermatologic diseases and tissue repair*. Archives of dermatology, 1989. 125(10): p. 1390-1398.
27. Shakespeare, P., *Burn wound healing and skin substitutes*. Burns, 2001. 27(5): p. 517-522.
28. D M, C., *Wound healing: New understandings*. Nurs Pract Forum 1999. 10: p. 74-86.
29. Martin, P., *Wound healing—aiming for perfect skin regeneration*. Science, 1997. 276(5309): p. 75-81.
30. Percival, N. J., *Classification of wounds and their management*. Surgery (Oxford), 2002. 20(5): p. 114-117.
31. Harding, K., H. Morris, and G. Patel, *Clinical review Healing chronic wounds*. Br Med J, 2002. 324: p. 160-163.
32. Moore, K., et al., *Prediction and monitoring the therapeutic response of chronic dermal wounds*. International wound journal, 2006. 3(2): p. 89-98.
33. Martins-Green, *Wound Healing, Tissue Repair, and Regeneration in Diabetes* 9780128164136. 2020.
34. Schreml, S., et al., *Luminescent dual sensors reveal extracellular pH-gradients and hypoxia on chronic wounds that disrupt epidermal repair*. Theranostics, 2014. 4(7): p. 721.
35. Ferreira, M. C., et al., *Complex wounds*. Clinics, 2006. 61(6): p. 571-578.
36. Chen, W. J., A. A. Rogers, and M. J. Lydon, *Characterization of biologic properties of wound fluid collected during early stages of wound healing*. Journal of Investigative Dermatology, 1992. 99(5): p. 559-564.
37. Hemilä, H. and R. M. Douglas, *Vitamin C and acute respiratory infections*. The international journal of tuberculosis and lung disease, 1999. 3(9): p. 756-761.
38. Rojas, A. I. and T. J. Phillips, *Patients with chronic leg ulcers show diminished levels of vitamins A and E, carotenes, and zinc*. Dermatologic Surgery, 1999. 25(8): p. 601-604.
39. Patel, G. K., *The role of nutrition in the management of lower extremity wounds*. The international journal of lower extremity wounds, 2005. 4(1): p. 12-22.
40. Pierce, G. F., et al., *Transforming growth factor beta reverses the glucocorticoid-induced wound-healing deficit in rats: possible regulation in macrophages by platelet-derived growth factor*. Proceedings of the National Academy of Sciences, 1989. 86(7): p. 2229-2233.
41. Beck, L. S., et al., *One systemic administration of transforming growth factor-beta* 1 *reverses age-or glucocorticoid-impaired wound healing*. The Journal of clinical investigation, 1993. 92(6): p. 2841-2849.
42. Chedid, M., et al., *Glucocorticoids inhibit keratinocyte growth factor production in primary dermal fibroblasts*. Endocrinology, 1996. 137(6): p. 2232-2237.
43. *Growth factor*" at *Dorland's Medical Dictionary*. 2011; Available from: https://web.archive.org/web/20110607011425/http://www.mercksource.com/pp/us/cns/cns_hl_dorlands_split.jsp?pg=/ppdocs/us/common/dorlands/dorland/three/000038554.htm
44. Mandla, S., L. Davenport Huyer, and M. Radisic, *Multimodal bioactive material approaches for wound healing*. APL bioengineering, 2018. 2(2): p. 021503.
45. Komarcević, A., *The modern approach to wound treatment*. Medicinski pregled, 2000. 53(7-8): p. 363-368.
46. Ten Dijke, P. and K. K. Iwata, *Growth factors for wound healing*. Bio/Technology, 1989. 7(8): p. 793-798.
47. Mayet, N., et al., *A comprehensive review of advanced biopolymeric wound healing systems*. Journal of pharmaceutical sciences, 2014. 103(8): p. 2211-2230.

48. Steenfos, H. H., *Growth factors and wound healing*. Scandinavian journal of plastic and reconstructive surgery and hand surgery, 1994. 28(2): p. 95-105.
49. Greenhalgh, D. G., *The role of growth factors in wound healing*. Journal of Trauma and Acute Care Surgery, 1996. 41(1): p. 159-167.
50. Mann, A., et al. *Granulocyte-macrophage colony-stimulating factor is essential for normal wound healing*. in *Journal of Investigative Dermatology Symposium Proceedings*. 2006. Elsevier.
51. Lee, A.-R. C., et al., *Reversal of silver sulfadiazine-impaired wound healing by epidermal growth factor*. Biomaterials, 2005. 26(22): p. 4670-4676.
52. Fang, R. C. and R. D. Galiano, *A review of becaplermin gel in the treatment of diabetic neuropathic foot ulcers*. Biologics: targets & therapy, 2008. 2(1): p. 1-12.
53. Miller, M. S., *Use of topical recombinant human platelet-derived growth factor-BB (becaplermin) in healing of chronic mixed arteriovenous lower extremity diabetic ulcers*. The Journal of foot and ankle surgery, 1999. 38(3): p. 227-231.
54. Pierce, G., et al., *Platelet-derived growth factor-BB and transforming growth factor beta 1 selectively modulate glycosaminoglycans, collagen, and myofibroblasts in excisional wounds*. The American journal of pathology, 1991. 138(3): p. 629.
55. Greenhalgh, D. G., et al., *PDGF and FGF stimulate wound healing in the genetically diabetic mouse*. The American journal of pathology, 1990. 136(6): p. 1235-1246.
56. Judith, R., et al., *Application of a PDGF-containing novel gel for cutaneous wound healing*. Life sciences, 2010. 87(1-2): p. 1-8.
57. Smiell, J. M., et al., *Efficacy and safety of becaplermin (recombinant human platelet-derived growth factor-BB) in patients with nonhealing, lower extremity diabetic ulcers: a combined analysis of four randomized studies*. Wound Repair and Regeneration, 1999. 7(5): p. 335-346.
58. Choi, S. M., et al., *Development of stabilized growth factor-loaded hyaluronate-collagen dressing (HCD) matrix for impaired wound healing*. Biomaterials research, 2016. 20(9): p. 1-7.
59. Choi, S. M., et al., *Effects of structurally stabilized EGF and bFGF on wound healing in type I and type II diabetic mice*. Acta biomaterialia, 2018. 66: p. 325-334.
60. Garcia-Orue, I., et al., *Novel nanofibrous dressings containing rhEGF and Aloe vera for wound healing applications*. International journal of pharmaceutics, 2017. 523(2): p. 556-566.
61. Lin, Y.-J., et al., *Stimulation of wound healing by PU/hydrogel composites containing fibroblast growth factor-2*. Journal of Materials Chemistry B, 2015. 3(9): p. 1931-1941.
62. Bao, P., et al., *The role of vascular endothelial growth factor in wound healing*. Journal of Surgical Research, 2009. 153(2): p. 347-358.
63. Lord, M. S., et al., *Perlecan and vascular endothelial growth factor-encoding DNA-loaded chitosan scaffolds promote angiogenesis and wound healing*. Journal of Controlled Release, 2017. 250: p. 48-61.
64. Elgin, Y. M., V. Dixit, and G. Gitnick, *Extensive in vivo angiogenesis following controlled release of human vascular endothelial cell growth factor: implications for tissue engineering and wound healing*. Artificial organs, 2001. 25(7): p. 558-565.
65. Long, D. W., et al., *Controlled delivery of platelet-derived proteins enhances porcine wound healing*. Journal of Controlled Release, 2017. 253: p. 73-81.
66. Gu, D.-l., et al., *Adenovirus encoding human platelet-derived growth factor-B delivered in collagen exhibits safety, biodistribution, and immunogenicity profiles favorable for clinical use*. Molecular therapy, 2004. 9(5): p. 699-711.
67. Wallace, E., *Feeding the wound. nutrition and wound care*. British Journal of Nursing, 1994. 3(13): p. 662-667.
68. Linder, M. C., *Nutritional biochemistry and metabolism: with clinical applications,* 2nd edition. collagen synthesis and bone tissue development. 1991, East Norwalk, CT: Appleton & Lange
69. Flanigan, K. H., *Nutritional aspects of wound healing*. Advances in wound care: the journal for prevention and healing, 1997. 10(3): p. 48-52.
70. Ehrlich, H. P., H. Tarver, and T. K. Hunt, *Effects of vitamin A and glucocorticoids upon inflammation and collagen synthesis*. Annals of surgery, 1973. 177(2): p. 222-227.
71. Eaglstein, W. H., et al., *Optimal use of an occlusive dressing to enhance healing: Effect of delayed application and early removal on wound healing*. Archives of dermatology, 1988. 124(3): p. 392-395.
72. Taylor, T., et al., *Ascorbic acid supplementation in the treatment of pressure-sores*. The Lancet, 1974. 304(7880): p. 544-546.
73. ter Riet, G., A. G. Kessels, and P. G. Knipschild, *Randomized clinical trial of ascorbic acid in the treatment of pressure ulcers*. Journal of clinical epidemiology, 1995. 48(12): p. 1453-1460.
74. Fitzmaurice, S., R. K. Sivamani, and R. R. Isseroff, *Antioxidant therapies for wound healing: a clinical guide to currently commercially available products*. Skin pharmacology and physiology, 2011. 24(3): p. 113-126.
75. da Rocha, R. P., et al., *Effects of a vitamin pool (vitamins A, E, and C) on the tissue necrosis process: experimental study on rats*. Aesthetic plastic surgery, 2002. 26(3): p. 197-202.
76. Baumann, L. S. and J. S. Md, *The effects of topical vitamin E on the cosmetic appearance of scars*. Dermatologic Surgery, 1999. 25(4): p. 311-315.
77. H, O., *Nutrients in profile.* 2nd edition. Bioconcepts. 1995, Queensland: Kelvin Grove.
78. Kirschmann G, K. J., *Nutrition almanac,* 4th edition. 1996, New York, NY: McGraw-Hill.
79. Rasik, A. M. and A. Shukla, *Antioxidant status in delayed healing type of wounds*. International journal of experimental pathology, 2000. 81(4): p. 257-263.
80. Ågren, M. S., *Studies on zinc in wound healing*. Acta Derm Venereol Suppl 1990. 154: p. 1-36.
81. Kietzmann, M. and M. Braun, *Effects of the zinc oxide and cod liver oil containing ointment Zincojecol in an animal model of wound healing*. DTW. Deutsche tierarztliche Wochenschrift, 2006. 113(9): p. 331-334.
82. Lansdown, A. B., *Metallothioneins: potential therapeutic aids for wound healing in the skin*. Wound repair and regeneration, 2002. 10(3): p. 130-132.
83. Yang, H., J. Chai, and Z. Guo, *Effect of improved topical agents on healing time of deep second-degree burn wound*. Zhongguo xiu fu chong jian wai ke za zhi=Zhongguo xiufu chongjian waike zazhi=Chinese journal of reparative and reconstructive surgery, 2001. 15(3): p. 162-164.
84. Ågren, M. S., et al., *A randomized, double-blind, placebo-controlled multicenter trial evaluating topical zinc*

*oxide for acute open wounds following pilonidal disease excision*. Wound repair and regeneration, 2006. 14(5): p. 526-535.

85. Marczin, N., et al., *Antioxidants in myocardial ischemia-reperfusion injury: therapeutic potential and basic mechanisms*. Archives of Biochemistry and Biophysics, 2003. 420(2): p. 222-236.
86. Tenhunen, R., H. S. Marver, and R. Schmid, *The enzymatic conversion of heme to bilirubin by microsomal heme oxygenase*. Proceedings of the National Academy of Sciences of the United States of America, 1968. 61(2): p. 748-755.
87. Barañano, D. E., et al., *Biliverdin reductase: a major physiologic cytoprotectant*. Proceedings of the national academy of sciences, 2002. 99(25): p. 16093-16098.
88. Lu, J. and A. Holmgren, *The thioredoxin antioxidant system*. Free Radical Biology and Medicine, 2014. 66: p. 75-87.
89. Hanschmann, E.-M., et al., *Thioredoxins, glutaredoxins, and peroxiredoxins—molecular mechanisms and health significance: from cofactors to antioxidants to redox signaling*. Antioxidants & redox signaling, 2013. 19(13): p. 1539-1605.
90. Hofmann, B., H.-J. Hecht, and L. Flohé, *Peroxiredoxins*. Biological chemistry, 2002. 383(3-4): p. 347-364.
91. Wood, Z. A., et al., *Structure, mechanism and regulation of peroxiredoxins*. Trends in biochemical sciences, 2003. 28(1): p. 32-40.
92. Peshenko, I. V. and H. Shichi, *Oxidation of active center cysteine of bovine* 1-*Cys peroxiredoxin to the cysteine sulfenic acid form by peroxide and peroxynitrite*. Free Radical Biology and Medicine, 2001. 31(3): p. 292-303.
93. Kümin, A., et al., *Peroxiredoxin 6 is a potent cytoprotective enzyme in the epidermis*. The American journal of pathology, 2006. 169(4): p. 1194-1205.
94. Schäfer, M. and S. Werner, *Oxidative stress in normal and impaired wound repair*. Pharmacological research, 2008. 58(2): p. 165-171.
95. Yoshida, T., et al., *The involvement of thioredoxin and thioredoxin binding protein*-2 *on cellular proliferation and aging process*. ANNALS-NEW YORK ACADEMY OF SCIENCES, 2005. 1055: p. 1-12.
96. Cano Sanchez, M., et al., *Targeting oxidative stress and mitochondrial dysfunction in the treatment of impaired wound healing: a systematic review*. Antioxidants, 2018. 7(8): p. 98.
97. Vervaart, P. and K. Knight, *Oxidative stress and the cell*. Clinical Biochemist Reviews, 1996. 17: p. 3-16.
98. Shukla, A., A. M. Rasik, and G. K. Patnaik, *Depletion of reduced glutathione, ascorbic acid, vitamin E and antioxidant defence enzymes in a healing cutaneous wound*. Free Radical Research, 1997. 26(2): p. 93-101.
99. Adamson, B., et al., *Delayed repair: the role of glutathione in a rat incisional wound model*. Journal of Surgical Research, 1996. 62(2): p. 159-164.
100. Mudge, B. P., et al., *Role of glutathione redox dysfunction in diabetic wounds*. Wound Repair and Regeneration, 2002. 10(1): p. 52-58.
101. Musalmah, M., et al., *Comparative effects of palm vitamin E and α-tocopherol on healing and wound tissue antioxidant enzyme levels in diabetic rats*. Lipids, 2005. 40(6): p. 575-580.
102. Wlaschek, M. and K. Scharffetter-Kochanek, *Oxidative stress in chronic venous leg ulcers*. Wound Repair and Regeneration, 2005. 13(5): p. 452-461.
103. Loo, A. E. K., et al., *Effects of hydrogen peroxide on wound healing in mice in relation to oxidative damage*. PloS one, 2012. 7(11): p. e49215.
104. Taylor, R. and T. James, *The role of oxidative stress in the development and persistence of pressure ulcers*, in *Pressure ulcer research*. 2005, Springer. p. 205-232.
105. Wiseman, H., *Vitamin D is a membrane antioxidant Ability to inhibit iron-dependent lipid peroxidation in liposomes compared to cholesterol, ergosterol and tamoxifen and relevance to anticancer action*. FEBS letters, 1993. 326(1-3): p. 285-288.
106. Grandjean, E. M., et al., *Efficacy of oral long-term N-acetylcysteine in chronic bronchopulmonary disease: a meta-analysis of published double-blind, placebo-controlled clinical trials*. Clinical therapeutics, 2000. 22(2): p. 209-221.
107. Petersen Shay, K., et al., *Is α-lipoic acid a scavenger of reactive oxygen species in vivo? Evidence for its initiation of stress signaling pathways that promote endogenous antioxidant capacity*. IUBMB life, 2008. 60(6): p. 362-367.
108. Kundukad, B., et al., *Mechanistic action of weak acid drugs on biofilms*. Scientific reports, 2017. 7(1): p. 1-12.
109. Marchese, A., et al., *Effect of fosfomycin alone and in combination with N-acetylcysteine on E. coli biofilms*. International journal of antimicrobial agents, 2003. 22: p. S95-S100.
110. Gomes, F., et al., *Farnesol in combination with N-acetylcysteine against Staphylococcus epidermidis planktonic and biofilm cells*. Brazilian Journal of Microbiology, 2012. 43(1): p. 235-242.
111. Khalaf, A., et al., *Antibacterial, anti-biofilm activity of some non-steroidal anti-inflammatory drugs and N-acetyl cysteine against some biofilm producing uropathogens*. American Journal of Epidemiology, 2015. 3(1): p. 1-9.
112. Cotgreave, I., P. Moldéus, and I. Schuppe, *The metabolism of N-acetylcysteine by human endothelial cells*. Biochemical pharmacology, 1991. 42(1): p. 13-16.
113. Hart, A., et al., *Sensory neuroprotection, mitochondrial preservation, and therapeutic potential of N-acetyl-cysteine after nerve injury*. Neuroscience, 2004. 125(1): p. 91-101.
114. Raftos, J. E., et al., *Kinetics of uptake and deacetylation of N-acetylcysteine by human erythrocytes*. The international journal of biochemistry & cell biology, 2007. 39(9): p. 1698-1706.
115. Bernard, G., et al., *Effect of N-acetylcysteine on the pulmonary response to endotoxin in the awake sheep and upon in vitro granulocyte function*. The Journal of clinical investigation, 1984. 73(6): p. 1772-1784.
116. Aihara, M., et al., *Effects of N-acetylcysteine and ambroxol on the production of IL*-12 *and IL*-10 *in human alveolar macrophages*. Respiration, 2000. 67(6): p. 662-671.
117. Paterson, R. L., H. F. Galley, and N. R. Webster, *The effect of N-acetylcysteine on nuclear factor-κB activation, interleukin*-6, *interleukin*-8, *and intercellular adhesion molecule*-1 *expression in patients with sepsis*. Critical care medicine, 2003. 31(11): p. 2574-2578.
118. Yang, C., et al., *Rapamycin and mTOR inhibitors probably have therapeutic effects for post-operative cognitive dysfunction*. Medical hypotheses, 2013. 81(3): p. 487-488.
119. Tsai, M.-L., et al., *Topical N-acetylcysteine accelerates wound healing in vitro and in vivo via the PKC/Stat*3 *pathway*. International journal of molecular sciences, 2014. 15(5): p. 7563-7578.

120. Sen, C. K. and S. Roy, *Redox signals in wound healing*. Biochimica et Biophysica Acta (BBA)—General Subjects, 2008. 1780(11): p. 1348-1361.

121. Ram, M., et al., *Antioxidant potential of bilirubin-accelerated wound healing in streptozotocin-induced diabetic rats*. Naunyn-Schmiedeberg's archives of pharmacology, 2014. 387(10): p. 955-961.

122. Ram, M., et al., *Bilirubin modulated cytokines, growth factors and angiogenesis to improve cutaneous wound healing process in diabetic rats*. International immunopharmacology, 2016. 30: p. 137-149.

123. Chigurupati, S., et al., *A synthetic uric acid analog accelerates cutaneous wound healing in mice*. PLoS One, 2010. 5(4): p. e10044.

124. Nery, R. A., et al., *Uric acid and tissue repair*. ABCD. Arquivos Brasileiros de Cirurgia Digestiva (São Paulo), 2015. 28(4): p. 290-292.

125. Jagetia, G. C. and G. Rajanikant, *Role of curcumin, a naturally occurring phenolic compound of turmeric in accelerating the repair of excision wound, in mice whole-body exposed to various doses of γ-radiation*. Journal of Surgical Research, 2004. 120(1): p. 127-138.

126. Panchatcharam, M., et al., *Curcumin improves wound healing by modulating collagen and decreasing reactive oxygen species*. Molecular and cellular biochemistry, 2006. 290(1): p. 87-96.

127. Mohanty, C. and S. K. Sahoo, *Curcumin and its topical formulations for wound healing applications*. Drug Discovery Today, 2017. 22(10): p. 1582-1592.

128. Hussain, Z., et al., *Exploring recent developments to improve antioxidant, anti-inflammatory and antimicrobial efficacy of curcumin: A review of new trends and future perspectives*. Materials science and engineering: C, 2017. 77: p. 1316-1326.

129. Calabrese, V., et al., *Curcumin and the cellular stress response in free radical-related diseases*. Molecular nutrition & food research, 2008. 52(9): p. 1062-1073.

130. Alvarez-Suarez, J. M., et al., *The composition and biological activity of honey: a focus on Manuka honey*. Foods, 2014. 3(3): p. 420-432.

131. Khan, R. U., S. Naz, and A. M. Abudabos, *Towards a better understanding of the therapeutic applications and corresponding mechanisms of action of honey*. Environmental Science and Pollution Research, 2017. 24(36): p. 27755-27766.

132. Lindberg, T., et al., *A systematic review and meta-analysis of dressings used for wound healing: the efficiency of honey compared to silver on burns*. Contemporary nurse, 2015. 51(2-3): p. 121-134.

133. Mukai, K., et al., *Effectiveness of Changing the Application of Japanese Honey to a Hydrocolloid Dressing in Between the Inflammatory and Proliferative Phases on Cutaneous Wound Healing in Male Mice*. Wounds: a compendium of clinical research and practice, 2016. 29(1): p. 1-9.

134. Niaz, K., et al., *Health benefits of manuka honey as an essential constituent for tissue regeneration*. Current drug metabolism, 2017. 18(10): p. 881-892.

135. Jull, A. B., et al., *Honey as a topical treatment for wounds*. Cochrane Database of Systematic Reviews, 2015 (3): p. Art. No.: CD005083.

136. Long, M., et al., *An essential role of NRF2 in diabetic wound healing*. Diabetes, 2016. 65(3): p. 780-793.

137. Zheng, H., et al., *Therapeutic potential of Nrf2 activators in streptozotocin-induced diabetic nephropathy*. Diabetes, 2011. 60(11): p. 3055-3066.

138. Suzuki, T. and M. Yamamoto, *Stress-sensing mechanisms and the physiological roles of the Keap1-Nrf2 system during cellular stress*. Journal of Biological Chemistry, 2017. 292(41): p. 16817-16824.

139. Uruno, A., Y. Yagishita, and M. Yamamoto, *The Keap1-Nrf2 system and diabetes mellitus*. Archives of biochemistry and biophysics, 2015. 566: p. 76-84.

140. Jiang, T., et al., *Nrf2 suppresses lupus nephritis through inhibition of oxidative injury and the NF-κB-mediated inflammatory response*. Kidney international, 2014. 85(2): p. 333-343.

141. Berglund, R. N. and B. Y. Liu, *Generation of monodisperse aerosol standards*. Environmental Science & Technology, 1973. 7(2): p. 147-153.

142. Mattson, M., D. Schwartz, and J. Kornfield, *Mechanical measurements of sclera for screening myopia treatments*. Investigative Ophthalmology & Visual Science, 2005. 46(13): p. 1991-1991.

143. Nickerson, C. S. and J. A. Kornfield, *A "cleat" geometry for suppressing wall slip*. Journal of Rheology, 2005. 49(4): p. 865-874.

144. Sharma, A., et al., *Strain-controlled criticality governs the nonlinear mechanics of fibre networks*. Nature Physics, 2016. 12(6): p. 584-587.

145. Shariati, A., et al., *The Effects of Davidson's Fixative Solution in Preserving the Rabbit Eye*. Investigative Ophthalmology & Visual Science, 2008. 49(13): p. 5207-5207.

146. Abhari, S., et al., *Anatomic studies of the miniature swine cornea*. The Anatomical Record, 2018. 301(11): p. 1955-1967.

147. Kendall, M., P. W. Smith, and B. Bellhouse. *Transdermal ballistic delivery of micro-particles: investigation into skin penetration*. in *BS EMBS Int. Conf.* 2000. IEEE.

148. Kendall, M., T. Mitchell, and P. Wrighton-Smith, *Intradermal ballistic delivery of micro-particles into excised human skin for pharmaceutical applications*. Journal of biomechanics, 2004. 37(11): p. 1733-1741.

149. Hedbys, B. O. and S. Mishima, *The thickness-hydration relationship of the cornea*. Experimental eye research, 1966. 5(3): p. 221-228.

150. Warner, R. R., M. C. Myers, and D. A. Taylor, *Electron probe analysis of human skin: determination of the water concentration profile*. Journal of Investigative Dermatology, 1988. 90(2): p. 218-224.

151. Wikipedia. *Ballistic gelatin*, accessed at https://web.archive.org/web/20181222100214/https://en.wikipedia.org/wiki/Ballistic_gelatin. 2018.

152. Segletes, S. B., *Modeling the penetration behavior of rigid into ballistic gelatin*. 2008, Army Research Lab Aberdeen Proving Ground Md.

153. Jussila, J., *Preparing ballistic gelatine—review and proposal for a standard method*. Forensic science international, 2004. 141(2-3): p. 91-98.

154. Veysset, D., et al., *High-velocity micro-particle impact on gelatin and synthetic hydrogel*. Journal of the mechanical behavior of biomedical materials, 2018. 86: p. 71-76.

155. Swain, M., et al., *Projectile penetration into ballistic gelatin*. Journal of the mechanical behavior of biomedical materials, 2014. 29: p. 385-392.

156. Akers, B. and A. Belmonte, *Impact dynamics of a solid sphere falling into a viscoelastic micellar fluid*. Journal of Non-Newtonian Fluid Mechanics, 2006. 135(2-3): p. 97-108.

157. Campbell, L., *Under the hood. The physics of projectile ballistics*. http://panoptesv.com/RPGs/Equipment/Weapons/Projectile_physics.php.

158. Ableson, M. B., Maffei, C. & Howe, A. J., *Why Doesn't the Ocular Drug Work? A look at the various barriers and aids to the efficacy of ocular medications.* Review of Opthalmology 2009.

159. Daull, P., M. Amrane, and J. Garrigue, *Novasorb® Cationic Nanoemulsion and Latanoprost. The ideal combination for glaucoma management.* J Eye Dis Disord, 2017. 2: p. 1.

160. Gordon-Shaag, A., et al., *The genetic and environmental factors for keratoconus.* BioMed research international, 2015. 2015: p. 24-32

161. Cifariello, F., et al., *Epi-off versus epi-on corneal collagen cross-linking in keratoconus patients: a comparative study through 2-year follow-up.* Journal of ophthalmology, 2018. 2018.

162. Jia, H.-Z. and X.-J. Peng, *Efficacy of iontophoresis-assisted epithelium-on corneal cross-linking for keratoconus.* International journal of ophthalmology, 2018. 11(4): p. 687.

163. Bidwell, G., et al., *A corneal penetrating drug delivery system based on elastin-like polypeptide* (1053.4). The FASEB Journal, 2014. 28: p. 1053.4.

164. Huynh, J., *Factors governing photodynamic cross-linking of ocular coat.* 2011: California Institute of Technology.

165. Olivares Jimenez, J. L., et al., *Keratoconus: age of onset and natural history.* Optom Vis Sci, 1997. 74(3): p. 147-51.

166. Kasbekar, S. A., et al., *Corneal transplant surgery for keratoconus and the effect of surgeon experience on deep anterior lamellar keratoplasty outcomes.* Am J Ophthalmol, 2014. 158(6): p. 1239-46.

167. Rebenitsch, R. L., et al., *The lifetime economic burden of keratoconus: a decision analysis using a markov model.* Am J Ophthalmol, 2011. 151(5): p. 768-773 e2.

168. Gore, D. M., A. J. Shortt, and B. D. Allan, *New clinical pathways for keratoconus.* Eye (Lond), 2013. 27(3): p. 329-39.

169. Caporossi, A., et al., *Long-term results of riboflavin ultraviolet a corneal collagen cross-linking for keratoconus in Italy: the Siena eye cross study.* Am J Ophthalmol, 2010. 149(4): p. 585-93.

170. Mazzotta, C., et al., *Stromal haze after combined riboflavin-UVA corneal collagen cross-linking in keratoconus: in vivo confocal microscopic evaluation.* Clin Experiment Ophthalmol, 2007. 35(6): p. 580-2.

171. Vinciguerra, P., et al., *Refractive, topographic, tomographic, and aberrometric analysis of keratoconic eyes undergoing corneal cross-linking.* Ophthalmology, 2009. 116(3): p. 369-78.

172. Vinciguerra, R., et al., *Corneal cross-linking as a treatment for keratoconus: four-year morphologic and clinical outcomes with respect to patient age.* Ophthalmology, 2013. 120(5): p. 908-16.

173. Zamora, K. V. and J. J. *Males, Polymicrobial keratitis after a collagen cross-linking procedure with postoperative use of a contact lens: a case report.* Cornea, 2009. 28(4): p. 474-6.

174. Bykhovskaya, Y., et al., *Variation in the lysyl oxidase (LOX) gene is associated with keratoconus in family-based and case-control studies.* Invest Ophthalmol Vis Sci, 2012. 53(7): p. 4152-7.

175. Shetty, R., et al., *Attenuation of lysyl oxidase and collagen gene expression in keratoconus patient corneal epithelium corresponds to disease severity.* Mol Vis, 2015. 21: p. 12-25.

176. Dudakova, L. and K. Jirsova, *The impairment of lysyl oxidase in keratoconus and in keratoconus-associated disorders.* J Neural Transm (Vienna), 2013. 120(6): p. 977-82.

177. Pollard, A., R. Thomas, and P. Williams, *Synthesis and stabilities of the basic copper (II) chlorides atacamite, paratacamite and botallackite.* Mineralogical magazine, 1989. 53(373): p. 557-563.

178. Chen, X. H., et al., *Direct growth of hydroxy cupric phosphate heptahydrate monocrystal with honeycomb-like porous structures on copper surface mimicking lotus leaf.* Crystal Growth and Design, 2009. 9(6): p. 2656-2661.

The invention claimed is:

1. A method for controlled ballistic delivery of a biologically active cargo to a bilayer tissue of an individual, the method comprising:

providing a tissue comprising a bilayer having a bilayer thickness L from 50 microns to 5000 microns, a bilayer width W at least 10*L, a tissue Young's modulus E from 500 Pa to 50 MPa and a tissue density p from 850 $kg/m^3$ to 1200 $kg/m^3$;

the bilayer comprising an apical layer and a basal layer underneath the apical layer, the apical layer having thickness $L_a$<L, and a compressive strength $Y_a$; and the basal layer having thickness $L_b$=L−$L_a$ and a compressive strength $Y_b$;

the apical layer defined by an accessible surface facing an environment external to the tissue and an internal boundary facing the basal layer, the apical layer having an accessible surface area at least ten-times $L^2$, selecting a target region having a target region thickness Lt and comprising a portion of at least one of the apical layer and the basal layer the portion centered around a target penetration distance d from the accessible surface, wherein the target region thickness Lt and the target penetration distance d are selected from:

$L_t$=$L_a$/2, and d=$L_a$/2; when the portion consists of a portion of the apical layer, $L_t$ equal to the lesser of $L_a$/2 or ($L_a$+$L_b$)/4, and d=$L_a$; when the portion comprises the internal boundary facing the basal layer, and $L_t$ is the lesser of $L_a$/2 or $L_b$/2, and d is equal to the lesser of 5$L_a$/4 or ($L_a$+$L_b$/4); when the portion consists of a portion of the basal layer;

determining an effective target penetration distance d* for the target region, wherein d*=d/2=$L_a$/2 when the target region consists of a portion of the apical layer;

d*=d*(1+f)=$L_a$*(1+f), where $$f = \arctan\left(\left|\log\left(\frac{Y_a}{Y_b}\right)\right|\right)$$

when the target region consists of the internal boundary facing the basal layer; and d*=d*(1+f)+(d−$L_a$)($\sqrt{Y_b/Y_a}$)=$L_a$*(1+f)+min ($L_a$/4, $L_b$/4) *($\sqrt{Y_b/Y_a}$)

when the target region consists of a portion of the basal layer providing a set of particles each comprising the biologically active cargo, the set of substantially spherical particles having an average density $\rho_p$ from 1400 kg/$m^3$ to 20000 kg/$m^3$, an average diameter $D_p$ greater than 1 micron and less than 1000 microns, $L_a/2$ or $L_b/2$, and a dispersity index DI from 1 to 2, determining a velocity $v_{o,j}$ of the set of substantially spherical particles by iterating $$v_{o,i} = \sqrt{Y_a/\rho_p}\left(\left(1/k\right)\left(d^*/D^m\right)\left(\mu_a^{m-1}\right)\left(\sqrt{Y_a\rho_p}\right)^{1-m}\left(\rho_a/\rho_p\right)\right)^{1/n_i}$$

from i=0 to j, where $n_0$=0.826 and $n_i=n_0-q(v_{0,i-1}\sqrt{\rho_a/Y_a})$, until $|(v_{0,i}-v_{0,i-1})/v_{0,i-1}|<0.1$;

selecting the $D_p$, Pp and $v_{o,j}$ when $v_{o,j}$ is less than 1,500 m/sec; and ballistically delivering a set of particles having the selected $D_p$ and $\rho_p$ at velocity $v_{o,j}$ to the accessible surface of the apical layer of the bilayer tissue to deliver into the target region at least 30% of the set of substantially spherical particles.

2. The method of claim 1, wherein:

the bilayer tissue comprises the epidermal and dermal layers of skin, the skin has a Young's modulus E from 0.5 MPa to 2 MPa, the skin has a tissue density from 1000 kg/$m^3$ to 1200 kg/$m^3$; the apical layer is of epidermis and having Tissue Type IV and effective compressive strength to the apical layer $Y_a$=4200 kPa and the basal layer is of dermis and having Tissue Type II $Y_b$=690 kPa, the apical layer having thickness $L_a$ of 75 microns to 100 microns and the basal layer having thickness $L_b$ of 1000 microns to 4000 microns, the selecting the target region in the bilayer tissue includes selecting one of apical target region, boundary target region, or basal target region, wherein:

the apical target region begins $L_a/4$ from the accessible surface, has a target layer thickness $L_t=L_a/2$, and has a target penetration distance $d=L_a/2$;

the boundary target region begins $3L_a/4$ from the accessible surface, has a target layer thickness $L_t$ equal to the lesser of $L_a/2$ or $(L_a+L_b)/4$, and has a target penetration distance $d=L_a$; and the basal target region begins at a distance from the accessible surface equal to the lesser of $5L_a/4$ and $(L_a+L_b/4)$, has a target layer thickness that is the lesser of $L_a/2$ or $L_b/2$, and has a target penetration distance d equal to the lesser of $5L_a/4$ or $(L_a+L_b/4)$;

using the values of $Y_a$ and $Y_b$ to convert the target penetration distance d of the selected target region to an effective target penetration distance d* for the target region, the apical target region has $d^*=d/2=L_a/2$;

the boundary target region has $d^*=d^*(1+f)=L_a{}^*(1+f)$, where $$f = \arctan\left(\left|\log\left(\frac{Y_a}{Y_b}\right)\right|\right);$$

and the basal target region has $d^*=d^*(1+f)+(d-L_a)(\sqrt{Y_b/Y_a})=L_a{}^*(1+f)+\min(L_a/4, L_b/4)^*(\sqrt{Y_b/Y_a})$;

the particle has density $\rho_p$ from 1400 kg/$m^3$ to 20000 kg/$m^3$, having average diameter $D_p$ that is greater than 1 micron and is less than 1000 microns, $L_a/2$ or $L_b/2$, and dispersity index DI from 1 to 2.

3. The method of claim 1, wherein the biologically active cargo comprises at least one growth factor selected from the group consisting of endothelial growth factor (EGF), transforming growth factor (TGF), TGF-b1, TGF-b3, fibroblast growth factor (FGF), platelet-derived growth factor (PDGF), elastin-like peptide (ELP), keratinocyte growth factor (KGF), vascular endothelial growth factor (VEGF), interleukins (IL), IL-10, EGF-like growth factor, ELP-KGF, ELP-ARA290, Substance-P, granulocyte colony-stimulating factor (G-CSF), and stromal cell-derived factor-1 (SDF-1) or any combination thereof.

4. The method of claim 1, wherein the biologically active cargo comprises at least one antibiotics selected from the group consisting of penicillin, amoxicillin, co-amoxiclav, flucloxacillin, phenoxymethylpenicillin, cephalosporin, cefalexin, aminoglycoside, gentamicin, tobramycin, tetracycline, doxycycline, lymecycline, macrolide, azithromycin, erythromycin, clarithromycin, fluoroquinolones, ciprofloxacin, levofloxacin or any combination thereof.

5. The method of claim 1, wherein the biologically active cargo comprises at least one corticosteroid selected from the group consisting of cortisone, hydrocortisone, fludrocortisone acetate, prednisolone, prednisone, methylprednisolone, triamcinolone, dexamethasone sodium phosphate (Decadron), betamethasone, triamcinolone acetonide, and fluorometholone.

6. The method claim 1, wherein the biologically active cargo comprises at least one NSAID selected from the group consisting of celecoxib, refecoxib, etoricoxib, valdecoxib, parecoxib, aspirin, diflunisal, ibuprofen, dexibuprofen, naproxen, fenoprofen, ketoprofen, indomethacin, tolmetin, diclofenac, sulindac, etodolac, ketorolac, piroxicam, meloxicam, tenoxicam, droxicam, mefenanmic acid, meclofenanmic acid, clonixin, and licofelone.

7. The method of claim 1, wherein the substantially spherical particles comprises at least one biocompatible polymer selected from the group consisting of polydopamine, poly(D,L-lactic acid) (PDLLA), poly(L-lactic acid) (PLLA), poly(D-lactic acid) (PDLA), poly (lactic-co-glycolic acid) (PLGA), polycaprolactone (PCL), poly(ethylene argininylaspartatediglyceride) (PEAD), poly-3-hydroxybutyrate (P3HB), poly-4-hydroxybutyrate (P4HB), polyhydroxyvalerate (PHV), polyhydroxyhexanoate (PHH), and polyhydroxyoctanoate (PHO).

8. The method of claim 1, wherein the substantially spherical particles comprise at least one bio-derived polymer selected from the group consisting of gelatin-based hydrogels, alginic acid, hyaluronic acid, photo-crosslinked alginic acid, photo-crosslinked hyaluronic acid and chitosan.

9. The method of claim 1, wherein the substantially spherical particles comprise a core particle and one to five layers of polymers wherein each layer of polymer independently carries the biologically active cargo.

* * * * *